US012577567B2

(12) United States Patent
Zhao et al.

(10) Patent No.: US 12,577,567 B2
(45) Date of Patent: *Mar. 17, 2026

(54) ALTERING GENE EXPRESSION IN MODIFIED T CELLS AND USES THEREOF

(71) Applicant: THE TRUSTEES OF THE UNIVERSITY OF PENNSYLVANIA, Philadelphia, PA (US)

(72) Inventors: Yangbing Zhao, Lumberton, NJ (US); Jiangtao Ren, Philadelphia, PA (US); Xiaojun Liu, Wallingford, PA (US); Carl H. June, Merion Station, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 1043 days.

This patent is subject to a terminal disclaimer.

(21) Appl. No.: 17/456,436

(22) Filed: Nov. 24, 2021

(65) Prior Publication Data

US 2022/0145306 A1 May 12, 2022

Related U.S. Application Data

(62) Division of application No. 15/516,052, filed as application No. PCT/US2015/055780 on Oct. 15, 2015, now Pat. No. 11,208,661.

(60) Provisional application No. 62/073,651, filed on Oct. 31, 2014.

(51) Int. Cl.

| | |
|---|---|
| *C12N 15/113* | (2010.01) |
| *A61K 35/17* | (2025.01) |
| *A61K 35/26* | (2015.01) |
| *A61K 39/00* | (2006.01) |
| *A61K 40/11* | (2025.01) |
| *A61K 40/22* | (2025.01) |
| *A61K 40/31* | (2025.01) |
| *A61K 40/32* | (2025.01) |
| *A61K 40/36* | (2025.01) |
| *A61K 40/41* | (2025.01) |
| *A61K 40/42* | (2025.01) |
| *A61K 40/50* | (2025.01) |
| *A61P 35/00* | (2006.01) |
| *A61P 37/06* | (2006.01) |
| *C12N 5/0783* | (2010.01) |
| *C12N 15/85* | (2006.01) |

(52) U.S. Cl.
CPC .......... *C12N 15/1138* (2013.01); *A61K 35/17* (2013.01); *A61K 35/26* (2013.01); *A61K 39/001102* (2018.08); *A61K 40/11* (2025.01); *A61K 40/22* (2025.01); *A61K 40/31* (2025.01); *A61K 40/32* (2025.01); *A61K 40/36* (2025.01); *A61K 40/416* (2025.01); *A61K 40/418* (2025.01); *A61K 40/4211* (2025.01); *A61K 40/4269* (2025.01); *A61K 40/4274* (2025.01); *A61P 35/00* (2018.01); *A61P 37/06* (2018.01); *C12N 5/0636* (2013.01); *C12N 15/85* (2013.01); *A61K 2039/5156* (2013.01); *A61K 2039/5158* (2013.01); *A61K 40/50* (2025.01); *C12N 2310/10* (2013.01); *C12N 2310/20* (2017.05); *C12N 2501/48* (2013.01); *C12N 2501/515* (2013.01); *C12N 2501/599* (2013.01); *C12N 2501/998* (2013.01); *C12N 2510/00* (2013.01)

(58) Field of Classification Search
CPC ...... A61K 40/32; A61K 40/418; A61K 40/50; C12N 5/0636; C12N 2510/00
See application file for complete search history.

(56) References Cited

U.S. PATENT DOCUMENTS

| | | | |
|---|---|---|---|
| 4,444,887 | A | 4/1984 | Hoffmann |
| 4,694,778 | A | 9/1987 | Learn |
| 4,716,111 | A | 12/1987 | Osband et al. |
| 4,816,567 | A | 3/1989 | Cabilly |
| 5,199,942 | A | 4/1993 | Gillis |
| 5,225,539 | A | 7/1993 | Winter |

(Continued)

FOREIGN PATENT DOCUMENTS

| | | |
|---|---|---|
| CA | 2945335 | 10/2015 |
| CN | 101854949 A | 10/2010 |

(Continued)

OTHER PUBLICATIONS

Liu Y, Tian X, Leitner WW, Aldridge ME, Zheng J, Yu Z, Restifo NP, Weiss R, Scheiblhofer S, Xie C, Sun R, Cheng G, Zeng G. Polymeric structure and host Toll-like receptor 4 dictate immunogenicity of NY-ESO-1 antigen in vivo. J Biol Chem. Oct. 28, 2011; 286(43):37077-84. (Year: 2011).*

(Continued)

*Primary Examiner* — Fereydoun G Sajjadi
*Assistant Examiner* — Qinhua Gu
(74) *Attorney, Agent, or Firm* — Saul Ewing LLP; Alireza Behrooz; Kathryn Doyle

(57) ABSTRACT

The present invention relates to compositions and methods for generating a modified T cell with a nucleic acid capable of downregulating endogenous gene expression selected from the group consisting of TCR α chain, TCR β chain, beta-2 microglobulin and FAS further comprising a nucleic acid encoding a modified T cell receptor (TCR) comprising affinity for a surface antigen on a target cell or an electroporated nucleic acid encoding a chimeric antigen receptor (CAR). Also included are methods and pharmaceutical compositions comprising the modified T cell for adoptive therapy and treating a condition, such as an autoimmune disease.

19 Claims, 153 Drawing Sheets

Specification includes a Sequence Listing.

(56) References Cited

U.S. PATENT DOCUMENTS

| | | | |
|---|---|---|---|
| 5,229,275 | A | 7/1993 | Goroff |
| 5,350,674 | A | 9/1994 | Boenisch |
| 5,413,923 | A | 5/1995 | Kucherlapati |
| 5,530,101 | A | 6/1996 | Queen |
| 5,545,806 | A | 8/1996 | Lonberg |
| 5,565,332 | A | 10/1996 | Hoogenboom |
| 5,567,610 | A | 10/1996 | Borrebaeck |
| 5,569,825 | A | 10/1996 | Lonberg |
| 5,573,905 | A | 11/1996 | Lerner |
| 5,585,089 | A | 12/1996 | Queen |
| 5,585,362 | A | 12/1996 | Wilson |
| 5,625,126 | A | 4/1997 | Lonberg |
| 5,626,561 | A | 5/1997 | Butler |
| 5,633,425 | A | 5/1997 | Lonberg |
| 5,661,016 | A | 8/1997 | Lonberg |
| 5,766,886 | A | 6/1998 | Studnicka |
| 5,787,900 | A | 8/1998 | Butler |
| 5,814,318 | A | 9/1998 | Lonberg |
| 5,843,069 | A | 12/1998 | Butler |
| 5,902,745 | A | 5/1999 | Butler |
| 5,913,998 | A | 6/1999 | Butler |
| 5,939,598 | A | 8/1999 | Kucherlapati |
| 5,980,889 | A | 11/1999 | Butler |
| 5,993,434 | A | 11/1999 | Dev |
| 6,080,840 | A | 6/2000 | Slanetz |
| 6,120,766 | A | 9/2000 | Hale |
| 6,143,291 | A | 11/2000 | June |
| 6,181,964 | B1 | 1/2001 | Hofmann |
| 6,233,482 | B1 | 5/2001 | Hofmann |
| 6,241,701 | B1 | 6/2001 | Hofmann |
| 6,331,415 | B1 | 12/2001 | Cabilly |
| 6,407,213 | B1 | 6/2002 | Carter |
| 6,516,223 | B2 | 2/2003 | Hofmann |
| 6,548,640 | B1 | 4/2003 | Winter |
| 6,567,694 | B2 | 5/2003 | Hayakawa |
| 6,678,556 | B1 | 1/2004 | Nolan |
| 7,171,264 | B1 | 1/2007 | Hofmann |
| 7,173,116 | B2 | 2/2007 | Fewell |
| 8,623,642 | B2 | 1/2014 | Wang |
| 8,697,359 | B1 | 4/2014 | Zhang |
| 8,906,682 | B2 | 12/2014 | June |
| 8,911,993 | B2 | 12/2014 | June |
| 8,916,381 | B1 | 12/2014 | June |
| 8,975,071 | B1 | 3/2015 | June |
| 9,101,584 | B2 | 8/2015 | June |
| 9,102,760 | B2 | 8/2015 | June |
| 9,102,761 | B2 | 8/2015 | June |
| 10,934,336 | B2 | 3/2021 | Zhao |
| 2004/0014645 | A1 | 1/2004 | Draghia-Akli |
| 2004/0059285 | A1 | 3/2004 | Mathiesen |
| 2004/0092907 | A1 | 5/2004 | Mathiesen |
| 2005/0042664 | A1 | 2/2005 | Wu |
| 2005/0048617 | A1 | 3/2005 | Wu |
| 2005/0052630 | A1 | 3/2005 | Smith |
| 2005/0070841 | A1 | 3/2005 | Mathiesen |
| 2007/0036773 | A1 | 2/2007 | Cooper |
| 2007/0128708 | A1 | 6/2007 | Gamelin |
| 2009/0304657 | A1 | 12/2009 | Morgan |
| 2010/0145026 | A1 | 6/2010 | De Romeuf |
| 2011/0158957 | A1 | 6/2011 | Bonini |
| 2012/0321667 | A1 | 12/2012 | Sentman |
| 2013/0217117 | A1 | 8/2013 | Thomson |
| 2013/0266551 | A1 | 10/2013 | Campana |
| 2013/0315884 | A1 | 11/2013 | Galetto |
| 2014/0068797 | A1 | 3/2014 | Doudna |
| 2014/0120622 | A1 | 5/2014 | Gregory |
| 2014/0134195 | A1 | 5/2014 | Russell |
| 2014/0219975 | A1 | 8/2014 | June |
| 2014/0271579 | A1 | 9/2014 | Hyde |
| 2014/0301990 | A1 | 10/2014 | Gregory |
| 2015/0037304 | A1 | 2/2015 | Gregory |
| 2015/0056705 | A1 | 2/2015 | Conway |
| 2015/0353905 | A1 | 12/2015 | Weiss |
| 2016/0009813 | A1 | 1/2016 | Themeli |
| 2016/0120906 | A1 | 5/2016 | Galetto |
| 2016/0243258 | A1 | 8/2016 | Scharenberg |
| 2016/0272999 | A1 | 9/2016 | Duchateau |
| 2016/0348073 | A1 | 12/2016 | Meissner |
| 2017/0016025 | A1 | 1/2017 | Poirot |
| 2017/0175128 | A1 | 6/2017 | Welstead |
| 2017/0274014 | A1 | 9/2017 | Brogdon |
| 2017/0290858 | A1 | 10/2017 | Zhao |
| 2021/0155667 | A1 | 5/2021 | Zhao |

FOREIGN PATENT DOCUMENTS

| | | | | |
|---|---|---|---|---|
| CN | 106103475 | | 11/2016 | |
| EP | 239400 | A2 | 9/1987 | |
| EP | 519596 | A1 | 12/1992 | |
| EP | 592106 | A1 | 4/1994 | |
| JP | 2013535215 | | 9/2013 | |
| JP | 2017535261 | | 11/2017 | |
| WO | 9109967 | A1 | 7/1991 | |
| WO | 9110741 | A1 | 7/1991 | |
| WO | 9317105 | A1 | 9/1993 | |
| WO | 9633735 | A1 | 10/1996 | |
| WO | 9634096 | A1 | 10/1996 | |
| WO | 9816654 | A1 | 4/1998 | |
| WO | 9824893 | A2 | 6/1998 | |
| WO | 9846645 | A2 | 10/1998 | |
| WO | 9850433 | A2 | 11/1998 | |
| WO | 2005113595 | A2 | 12/2005 | |
| WO | 2006031221 | A1 | 3/2006 | |
| WO | 2007131092 | A2 | 11/2007 | |
| WO | 2007150054 | A2 | 12/2007 | |
| WO | 2008037943 | A1 | 4/2008 | |
| WO | 2008039818 | A2 | 4/2008 | |
| WO | 2008121420 | A1 | 10/2008 | |
| WO | 2011059836 | A2 | 5/2011 | |
| WO | 2012019002 | | 2/2012 | |
| WO | 2012038055 | A1 | 3/2012 | |
| WO | 2013019615 | A2 | 2/2013 | |
| WO | 2013074916 | A1 | 5/2013 | |
| WO | 2013126712 | A1 | 8/2013 | |
| WO | 2013158292 | | 10/2013 | |
| WO | 2013166051 | A1 | 11/2013 | |
| WO | 2013176915 | A1 | 11/2013 | |
| WO | 2013176916 | A1 | 11/2013 | |
| WO | 2013177247 | A1 | 11/2013 | |
| WO | 2014011988 | A2 | 1/2014 | |
| WO | 2014039523 | A1 | 3/2014 | |
| WO | 2014059173 | A2 | 4/2014 | |
| WO | 2014153470 | A2 | 9/2014 | |
| WO | 2014160030 | A2 | 10/2014 | |
| WO | 2014165177 | A1 | 10/2014 | |
| WO | 2014165707 | A2 | 10/2014 | |
| WO | 2014184741 | A1 | 11/2014 | |
| WO | 2014184744 | A1 | 11/2014 | |
| WO | 2014186585 | A2 | 11/2014 | |
| WO | 2014191128 | A1 | 12/2014 | |
| WO | WO-2015136001 | A1 * | 9/2015 | .............. A61P 35/00 |
| WO | 2015155341 | A1 | 10/2015 | |
| WO | WO-2015161276 | A2 * | 10/2015 | ........... C12N 15/113 |
| WO | 2016054086 | A1 | 4/2016 | |
| WO | 2016069282 | A1 | 5/2016 | |

OTHER PUBLICATIONS

Extended European Search Report issued Jul. 31, 2023 in European Patent Application No. 23156585.4. 9 pages.

Dotti, G., et al., "Human cytotoxic T lymphocytes with reduced sensitivity to Fas-induced apoptosis", Blood 105 (12):4677-4684, 2005.

Torikai, et al., "A foundation for universal T-cell based immunotherapy: T cells engineered to express a CD19-specific chimeric-antigen-receptor and eliminate expression of endogenous TCR", Blood, 119(24):5697-5705, 2012.

Zhao et al. "Primary Human Lymphocytes Transduced with NY-ESO-1 Antigen-Specific TCR Genes Recognize and Kill Diverse Human Tumor Cell Lines", The Journal of Immunology; vol. 174, No. 7, pp. 4415-4423, Apr. 1, 2005 (Year: 2005).

(56) References Cited

OTHER PUBLICATIONS

Stadtmauer et al. (CRISPR-engineered T cells in patients with refractory cancer; Science, vol. 367, eaba7365, pp. 1-12, published online Feb. 28, 2020, and supplementary materials (Year: 2020).
Chinese Patent Application No. 201580071634.9—First Office Action dated Mar. 19, 2020.
Chinese Patent Application No. 201580071678.1—First Office Action dated Mar. 19, 2020.
European Patent Application No. 15855146.5—Office Action dated May 26, 2020.
European Patent Application No. 15855440.2—First Office Action dated May 8, 2020.
Zhao et al., "Multiple injections of electroporated autologous T cells expressing a chimeric antigen receptor mediate regression of human disseminated tumor", Cancer Research, 2010, 70, 9053-9061.
Eurasian Patent Application No. 201790953—Office Action issued Nov. 22, 2019.
Japanese Patent Application No. 2017-523279—Office Action dispatched Nov. 8, 2019.
Japanese Patent Application No. 2017-523296—Office Action dispatched Nov. 27, 2019.
Li, et al., "Inhibition of HIV-1 infection of primary CD4+ T-cells by gene editing of CCR5 using adenovirus-delivered CRISPR/Cas9." Jorunal of General Virology (2015), 96:2381-2393.
Liao , et al., "Activation of lyphocytes by anti-CD3 single-chain antibody dimers expressed on the plasma membrane of tumor cells", 2000, Gene Therapy 7(1):339-347.
Nakagawa, et al., "Development of next-generation adoptive immunotherapy using cytotoxic T-lymphocyte (CTL) expressing chimeric antigen-rectpor (CAR)", Drug Delivery System, 2013, vol. 28, pp. 35-44 (partial translation provided).
Eurasian patent application No. 201790953/28—Office Action issued on Dec. 20, 2018.
European Patent Application No. 15855440.2—Extended European Search Report dated Oct. 31, 2018.
Maus, et al., "Adoptive Immunotherapy for Cancer or Viruses", 2014, Annu Rev Immunol 32:189-225.
European Patent Application No. 15/855,146—European Search Report dated Jul. 17, 2018.
Kuball et al. "Increasing functional avidity of TCR-redirected T cells by removing defined N-glycosylation sites in the TCR constant domain", The Journal of Experimental Medicine; vol. 206, No. 2, pp. 463-475, published Jan. 26, 2009 (Year: 2009).
Robbins, et al., "Single and Dual Amino Acid Substitutions in TCR CDRs Can Enhance Antigen-Specific T Cell Functions", J Immunol 2008; 180:6116-6131.
Roder, et al., "The EBV-hybridoma technique", Methods Enzymol., 121:140-167 (1986).
Roguska, et al., "A comparison of two murine monoclonal antibodies humanized by CDR-grafting and variable domain resurfacing", Protein Eng., 9(10):895-904 (1996).
Roguska, et al., Humanization of murine monoclonal antibodies through variable domain resurfacing, PNAS, 91:969-973 (1994).
Rosenberg, et al., "Use of Tumor-Infiltrating Lymphocytes and Interleukin-2 in the Immunotherapy of Patients with Metastatic Melanoma", New Eng. J. of Med. 319:1676-1680, 1988.
Sandhu , "A rapid procedure for the humanization of monoclonal antibodies", Gene, 150(2):409-10(1994).
Schenborn, et al., "A novel transcription property of SP6 and T7 RNA polymerases: dependence on template structure", Nuc. Acids Res., 13:6223-36 (1985).
Sims, et al., "A humanized CD18 antibody can block function without cell destruction", J. Immunol., 151:2296-2308 (1993).
Skerra, et al., "Assembly of a Functional Immunoglobulin Fv Fragment in Escherichia coli", Science, 240,1988, 1038-1041.
Smits, et al., "RNA-based gene transfer for adult stem cells and T cells", Leukemia (2004) 18, 1898-1902.
Stepinski, et al., "Synthesis and properties of mRNAs containing the novel "anti-reverse" cap analogs 7-methyl(3'-0-methyl)GpppG and 7-methyl(3'-deoxy)GpppG", RNA, 7:1468-95 (2001).

Studnicka, et al., "Human-engineered monoclonal antibodies retain full specific binding activity by preserving non-CDR complementarity-modulating residues", Protein Engineering, 7(6):805-814 (1994).
Tan, et al., ""Superhumanized" antibodies: reduction of immunogenic potential by complementarity-determining region grafting with human germline sequences: application to an anti-CD28", J. Immunol., 169:1119-25 (2002).
Vaughan, et al., "Human antibodies by design", Nature Biotechnology, vol. 16, No. 6, pp. 535-539, 1998. Abstract.
Verhoeyen, et al., "Reshaping human antibodies: grafting an antilysozyme activity", Science, 239:1534-1536 (1988).
Ward, et al., "Binding activities of a repertoire of single immunoglobulin variable domains secreted from Escherichia coli." Nature 341:544-546 (1989).
Wu, et al., "Humanization of a murine monoclonal antibody by simultaneous optimization of framework and CDR residues", J. Mol. Biol., 294:151-162 (1999).
Yotnda, et al., "Efficient infection of primitive hematopoietic stem cells by modified adenovirus", 2001, Gene Therapy, 8:930-937.
Zhao, et al., "High-Efficiency Transfection of Primary Human and Mouse T Lymphocytes Using RNA Electroporation", Molecular Therapy, vol. 13, No. 1, Jan. 2006.
International Search Report and Written Opinion for PCT/US2015/055780 dated Feb. 2, 2016.
Baca, et al., "Antibody Humanization Using Monovalent Phage Display", 1997, J Biol Chem, 272(16): 10678-10684.
Bargou, et al., "Tumor Regression in Cancer Patients by Very Low Doses of a T Cell-Engaging Antibody", Science 321,974-77 (2008).
Barrett, et al., "Regimen-Specific Effects of RNA-Modified Chimeric Antigen Receptor T Cells in Mice with Advanced Leukemia", Human Gene Therapy 24:717-727 (Aug. 2013).
Barrett, et al., "Treatment of Advanced Leukemia in Mice with mRNA Engineered T Cells", Human Gene Therapy 22:1575-1586 (Dec. 2011).
Bierer , et al., "Cyclosporin A and FK506: molecular mechanisms of immunosuppression and probes for transplantation biology", Curr. Opin. Immun. 5:763-773,1993.
Bird, et al., "Single-Chain Antigen-Binding Proteins", 1988, Science 242(4877):423-426.
Bruggermann , et al., "Designer Mice: The Production of Human Antibody Repertoires in Transgenic Animals.", Year in Immunol., 7:33-40 (1993).
Caldas, et al., Design and synthesis of germline-based hemi-humanized single-chain Fv against the CD18 surface antigen, Protein Eng., 13(5):353-60 (2000).
Carpenito et al., "Control of large, established tumor xenografts with genetically retargeted human T cells containing CD28 and CD137 domains." 2009 Proc. Natl. Acad. Sci. U.S.A. 106:3360-3365.
3095, et al., "Humanization of an anti-p185HER2 antibody for human cancer therapy", 1992, Proc Natl Acad Sci USA 89:4285-4289.
Chang, et al., "A general method for facilitating heterodimeric pairing between two proteins: Application to expression of alpha and betaT-Cell receptor extracellular segments", 1994, Proc Natl Acad Sci USA 91:11408-11412.
Chen, et al., "Structural and kinetic basis for heightened immunogenicity of T cell vaccines", 2005, The Journal of Experimental Medicine 201(8):1243-1255.
Chothia, et al., "Canonical structures for the hypervariable regions of immunoglobulins", J Mol Biol. Aug. 2, 19870; 196(4):901-17. (Abstract).
Clackson, et al., "Making antibody fragments using phage display libraries", 1991, Nature 352:624-628.
Cougot, et al., "Cap-tabolism", 2001, Trends in Biochem. Sci., 29:436-444 (Abstract).
Couto, et al., Anti-BA46 Monoclonal Antibody Mc3: Humanization Using a Novel Positional Consensus and in Vivo and in Vitro Characterization., Cancer Res., 55(8):1717-22 (1995).
Couto, et al., Designing Human Consensus Antibodies with Minimal Positional Templates, Cancer Res., 55 (23 Supp):5973s-5977s (1995).

(56)                    References Cited

OTHER PUBLICATIONS

Davodeau, et al., "Secretion of Disculfide-linked Human T-cell Receptor gamma-delta Heterodimers", 1993, J. Biol Chem 268(21):15455-15460.

Duchosal, et al., "Immunization of hu-PBL-SCID mice and the rescue of human monoclonal Fab fragments through Combinatorial libraries", 1992, Nature 355:258-262.

Elango, et al., "Optimized transfection of mRNA transcribed from a d(A/T)100 tail-containing vector", Biochem Biophys Res Commun. May 13, 2005; 330(3):958-66. (Abstract).

Garboczi, et al., "Assembly, specific binding, and crystallization of a human TCR-alphabeta with an antigenic Tax Peptide from human T lymphotropic virus type 1 and the class I MHX molwxulw HLA-A2", 1996, The Journal of Immunology 157(12):5403-5410.

Garboczi, et al., "Structure of the complex between human T-cell receptor, viral peptide and HLA-A2", 1996, Nature 384:134-141 (Abstract).

Golden, et al., "High-level production of a secreted heterodimeric alpha-beta murine T-cell receptor in *Escherichia coli*", 1997, Journal of Immunological Methods 206(1-2): 163-169 (Abstract).

Griffiths , et al., "Human anti-self antibodies with high specificity from phage display libraries.", The EMBO Journal vol. 12, No. 2, pp. 725-734, 1993.

Henderson , et al., "Comparison of the effects of FK-506, cyclosporin A and rapamycin on IL-2 production.", Immun 73:316-321, 1991.

Hoogenboom , et al., "By-passing immunisation. Human antibodies from synthetic repertoires of germline VH gene Segments arranged in vitro.", J Mol Biol Sep. 2, 19920;227(2):381-8. (Abstract).

Huston et al., "Protein engineering of antibody binding sites: recovery of specific activity in an anti- digoxin single-chain Fv analogue produced in *Escherichia coli*." 1988, Proc. Natl. Acad. Sci. USA 85:5879-5883.

Jakobovits, et al., "Analysis of homozygous mutant chimeric mice: Deletion of the immunoglobulin heavy-chain joining region blocks B-cell development and antibody production", Proc. Natl. Acad. Sci. 90, 1993, 2551-2555.

Jakobovits, et al., "Germ-line transmission and expression of a human-derived yeast artificial chromosome", Nature, 362:255-258 (1993).

Johnson, et al., "Human antibody engineering", Current Opinion in Structural Biology 3:564-571 (1993).

Jones, et al., "Replacing the complementarity-determining regions in a human antibody with those from a mouse", Nature, 321:522-525 (1986).

Klinger, et al., "Immunopharmacologic response of patients with B-lineage acute lymphoblastic leukemia to Continuous infusion to T cell-engaging CD19/CD3-bispecific BiTE antibody blinatumomab", Blood, 2012, 119: 6226-6233.

Kochenderfer, et al., "Adoptive transfer of syngeneic T cells transduced with a chimeric antigen receptor that recognizes murine CD19 can eradicate lymphoma and normal B cells", Blood, 116(9), 2010, 3875-3886.

Liu, et al., "Calcineurin is a common target of cyclophilin-cyclosporin A and FKBP-FK506 complexes", Cell 66:807-815, 1991.

Lonberg, et al., "Human antibodies from transgenic mice", Int. Rev. Immunol., 13:65-93 (1995).

Louis, et al., "Antitumor activity and long-term fate of chimeric antigen receptor-positive T cells in patients with heuroblastoma", Blood 2011, 118: 6050-6056.

Marks , et al., "By-passing immunization. Human antibodies from V-gene libraries displayed on phage", J. Mol. Biol. 222:581-597 (1991).

Mccafferty, et al., "Phage antibodies: filamentous phage displaying antibody variable domains", Nature 348, 1990, 552-554.

Mitchell, et al., "Selective Modification of Antigen-Specific T Cells by RNA Electroporation", Hum Gene Ther. May 2008; 19(5): 511-521.

Morea, et al., "Antibody modeling: implications for engineering and design", Methods, 20(3):267-79 (2000).

Nacheva, et al., "Preventing nondesired RNA-primed RNA extension catalyzed by T7 RNA polymerase", Eur. J. Biochem., 270:1485-65 (2003).

Nishikawa, et al., "Nonviral vectors in the new millennium: delivery barriers in gene transfer", Hum. Gene Ther., 12(8):861-70 (2001) (abstract).

Padlan, et al., "A possible procedure for reducing the immunogenicity of antibody variable domains while preserving their ligand-binding properties", Molecular Immunology 28(4/5), 1991,489-498.

Pedersen, et al., "Comparison of surface accessible residues in human and murine immunoglobulin Fv domains, Implication for humanization of murine antibodies", J. Mol. Biol., 235(3):959-73 (1994).

Porter , et al., "Chimeric Antigen Receptor-Modified T Cells in Chronic Lymphoid Leukemia", 2011, N Engl J Med 365:725-733.

Presta, et al., Antibody engineering., Current Opinion in Biotechnology 1992, 3:394-398.

Presta, et al., "Humanization of an antibody directed against IgE", J. Immunol., 151:2623-32(1993).

Rethi, et al., "Priming of T cells to Fas-mediated proliferative signals by interleukin-7", Blood, 2008, 112:1195-1204.

Riechmann, et al., "Reshaping human antibodies for therapy", Nature, 332:323-327 (1988).

International Search Report and Written Opinion dated Mar. 2, 2016—PCT/US2015/055799.

Sakuma, et al., "Multiplex genome engineering in human cells using all-in-one CRISPR/Cas9 vector system." Scientific Reports, Jun. 23, 2014, vol. 4, 5400 (pp. 1-6), ISSN 0004325722.

Kershaw et al, Gene-engineered T cells for cancer therapy, Nature, 2013, pp. 525-541.

Niu, et al., "Generation of Gene-Modified Cynomolgus Monkey via Cas9/RNA-Mediated Gene Targeting in One-Cell Embryos." Cell, Feb. 13, 2014, vol. 156, pp. 836-843, ISSN 0004325723.

Wang, et al., "One-Step Generation of Mice Carrying Mutations in Multiple Genes by CRISPR/Cas-Mediated Genome Engineering." Cell, 2013, vol. 153, pp. 910-918, ISSN 0004325724.

Saff, et al., "Activation-Induced Cell Death Limits Exector Function of CD4 Tumor-Speci{c T Cells", J Immunol (2004) 172 (11): 6598-6606.

Themeli, et al., "Generation of tumor-targeted human T lymphocytes from induced pluripotent stem cells for cancer therapy", Nat Biotechnol. Oct. 2013 ; 31(10): 928-933.

Torikai, H., et al., "Toward eliminating HLA class I expression to generate universal cells from allogeneic donors", Blood. 2013, 122(8):1341-1349.

Zhou, P., et al., "In vivo Discovery of Immunotherapy Targets in the Tumor Microenvironment", Nature. Feb. 6, 2014, 506(7486):52-57.

Mandal, P.K., et al., "Efficient ablation of genes in human hematopoietic stem and effector cells using CRISPR/Cas9", Cell Stem Cell, Nov. 6, 2014;15(5):643-652.

* cited by examiner

CRISPRs

TRBV ×52  TRBD1 TRBJ1 ×6  TRBC1  TRBD2 TRBJ2 ×7  TRBC2

CRISPRs

TRAV  TRAJ  TRAC

T7 promoter + target RNA + guide RNA scaffold

TTAATACGACTCACTATAGGCCACCAAGCTCCCTTACC

GTTTTAGAGCTAGAAATAGCAAGTTAAAATAAGGCTAGT

CCGTTATCAACTTGAAAAAGTGGCACCGAGTCGGTGCTT

TTTTT

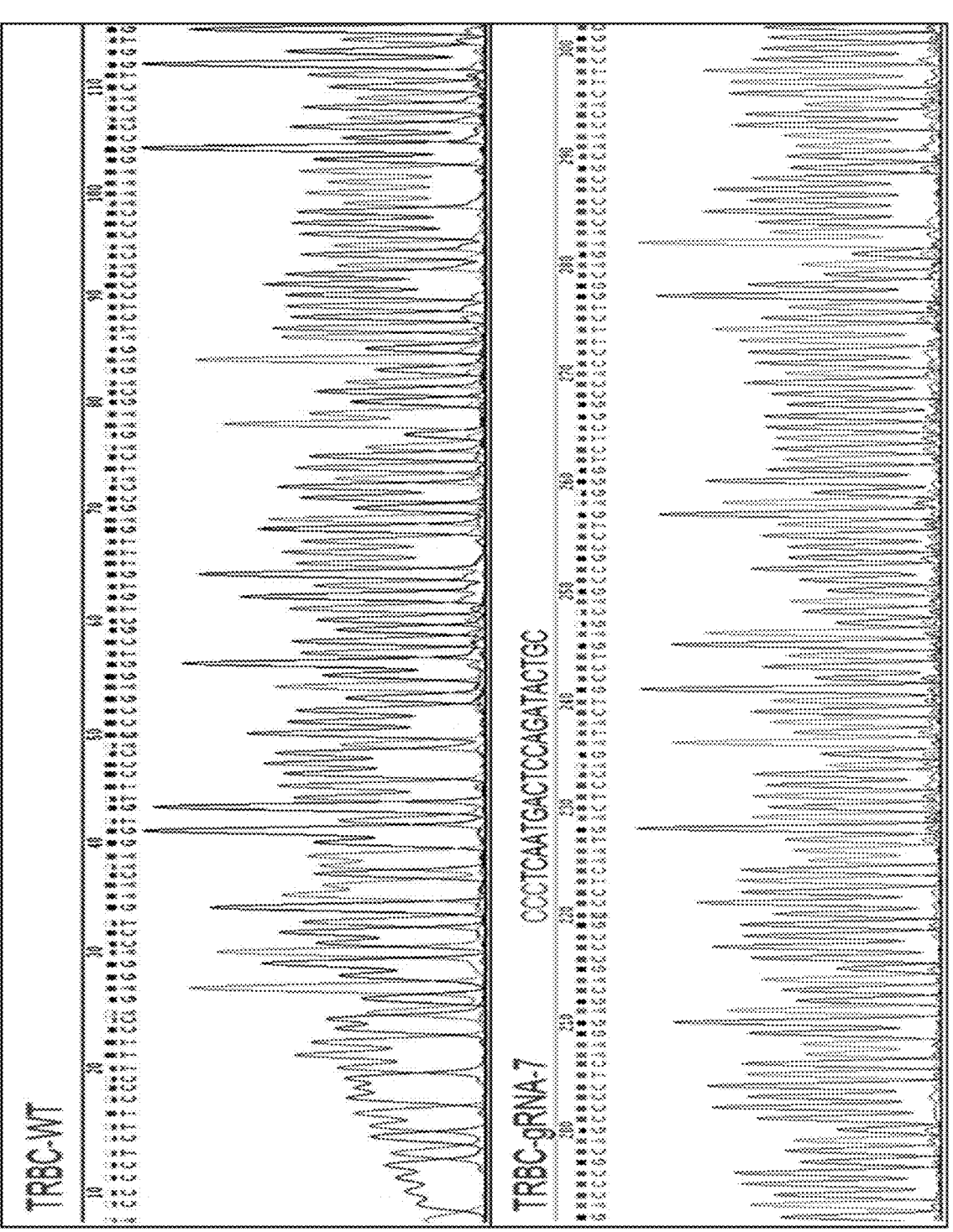
Figure 1C, continued

| | %GFP | MFI | % Viability | um3 |
|---|---|---|---|---|
| 200V/20ms | 61.4 | 151806 | 31 | 300 |
| 200V/10ms | 87.7 | 165419 | 37 | 280 |
| 300V/10ms | 95.4 | 168023 | 23 | 250 |
| 360V/5ms | 65.5 | 76453 | 40 | 320 |
| 360V/1ms | 98.3 | 100755 | 82 | 600 |
| 400V/0.7ms | 97.5 | 81368 | 87 | 610 |
| 500V/0.7ms | 97.8 | 89314 | 80 | 600 |

Figure 2A

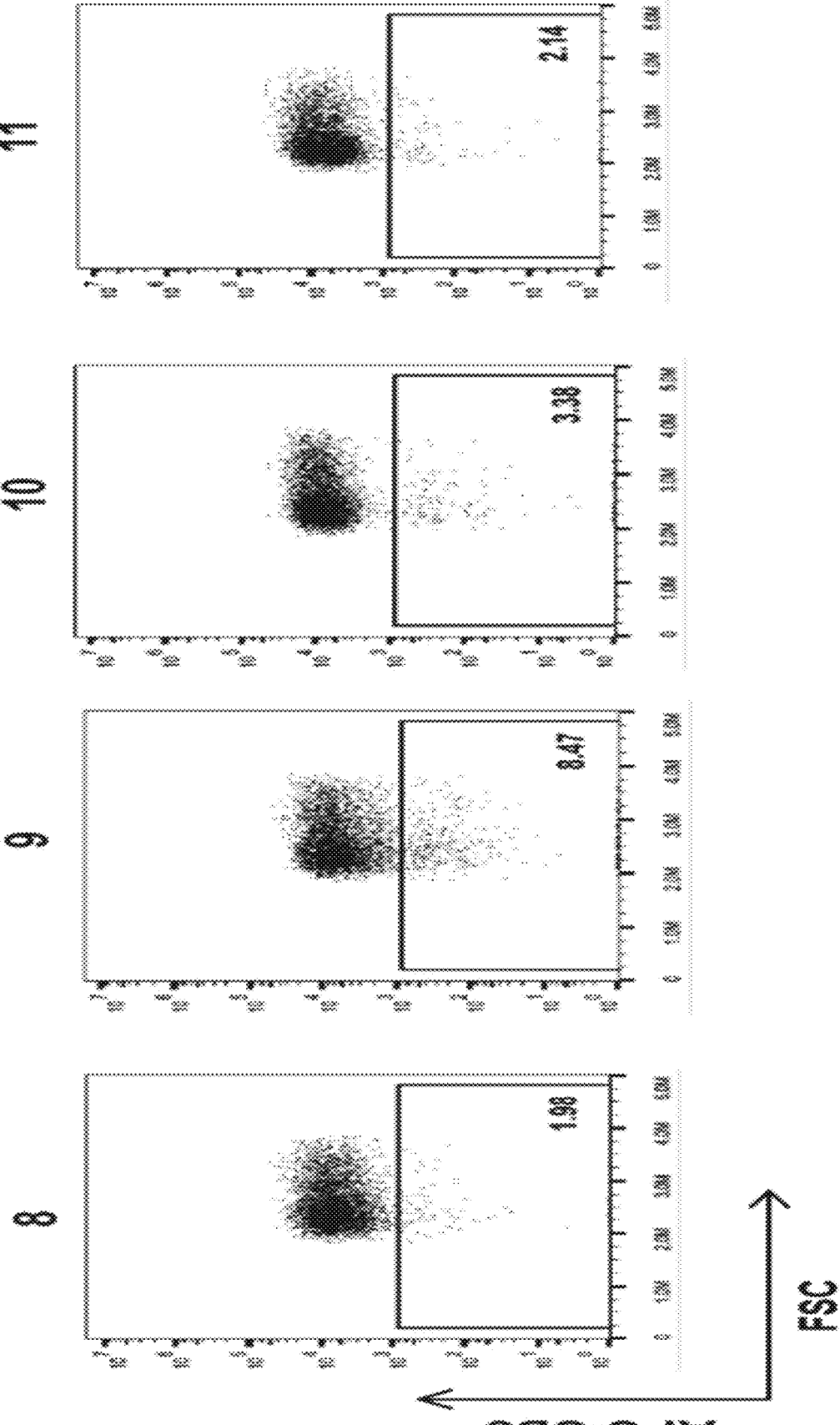
Figure 2E, continued

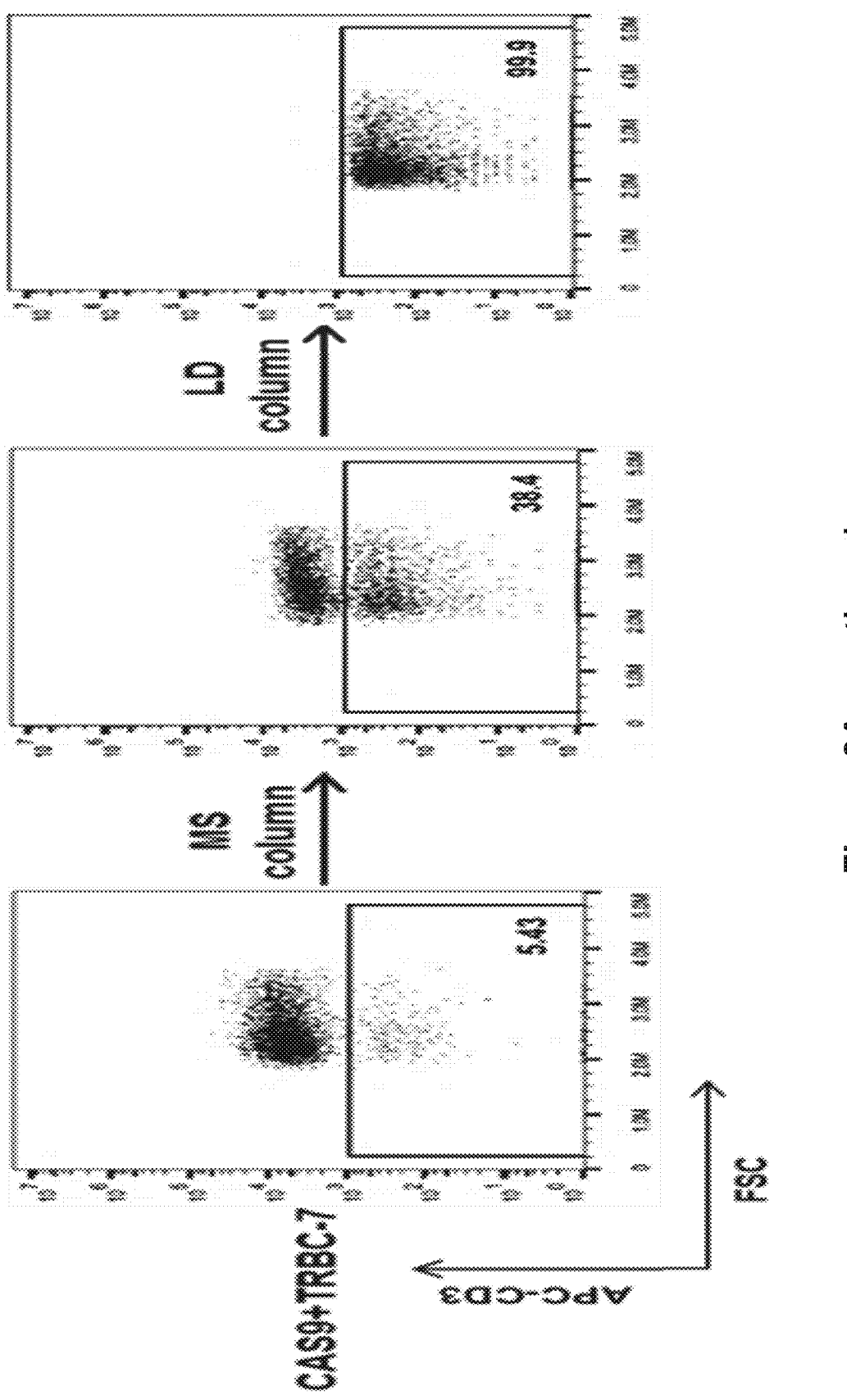
Figure 3A, continued

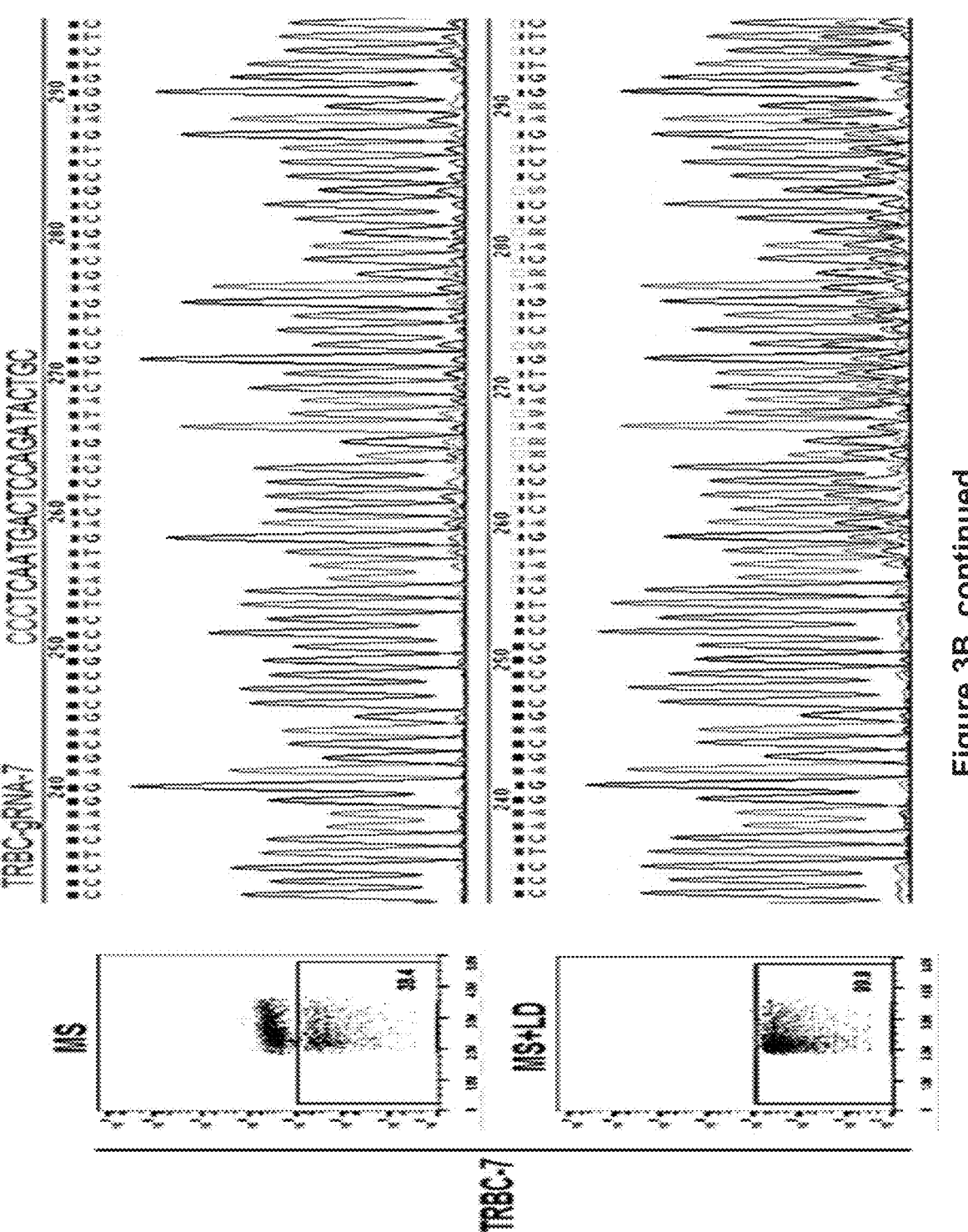
Figure 3B, continued

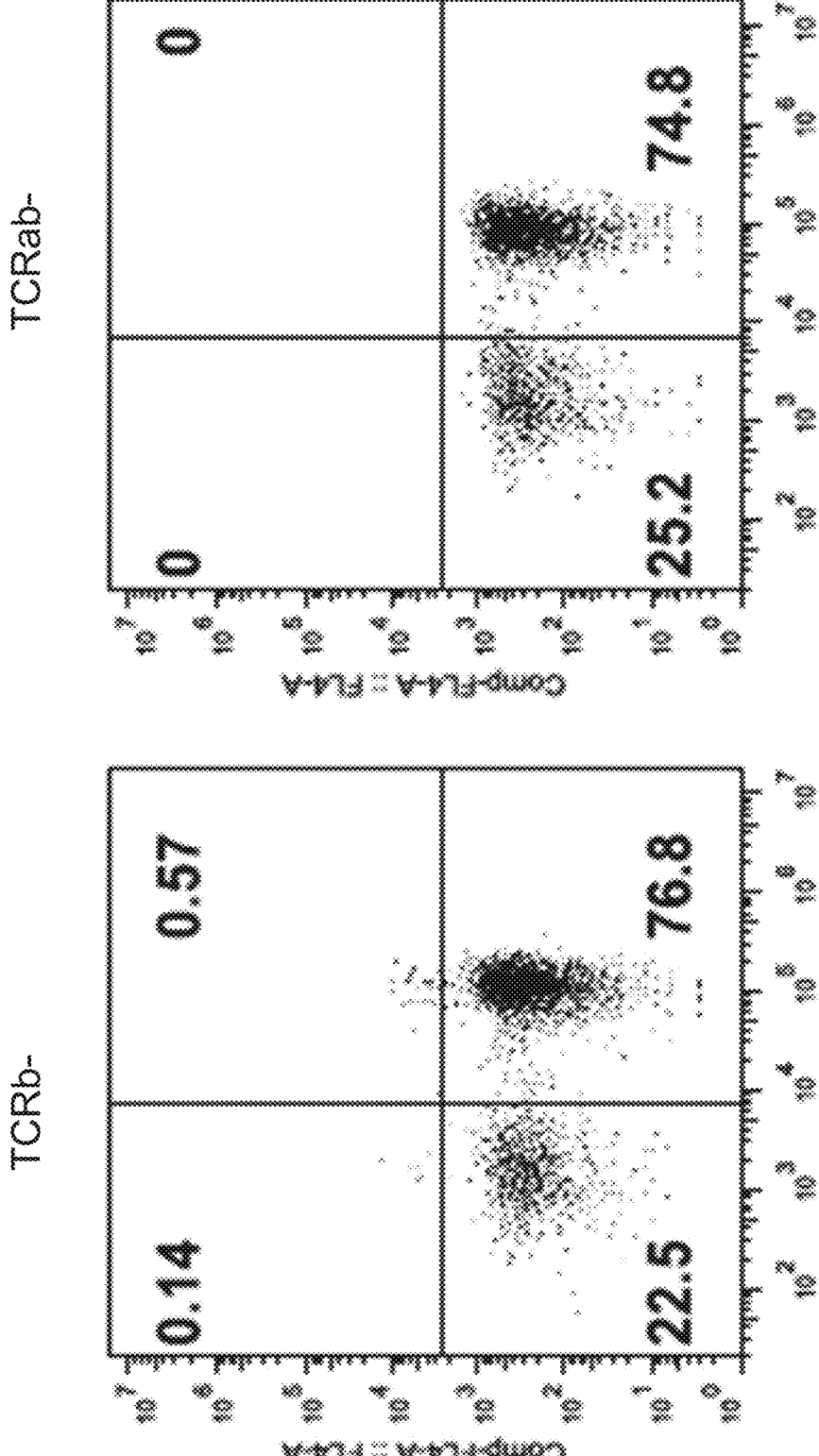
Figure 3C, continued

Figure 3D

| | 0 hrs | 16 hrs | 24 hrs | 36 hrs |
|---|---|---|---|---|
| 1 | CAS9 20ug, gRNA 10ug | | | |
| 2 | CAS9 20ug, gRNA 20ug | | | |
| 3 | CAS9 20ug, gRNA 40ug | | | |
| 4 | CAS9 20ug, gRNA 10ug | | | |
| 5 | CAS9 20ug, gRNA 10ug | gRNA 10ug | | |
| 6 | CAS9 20ug, gRNA 10ug | gRNA 10ug | gRNA 10ug | |
| 7 | CAS9 20ug, gRNA 10ug | | gRNA 10ug | gRNA 10ug |
| 8 | CAS9 20ug, gRNA 10ug | gRNA 10ug | gRNA 10ug | gRNA 10ug |

Figure 4A

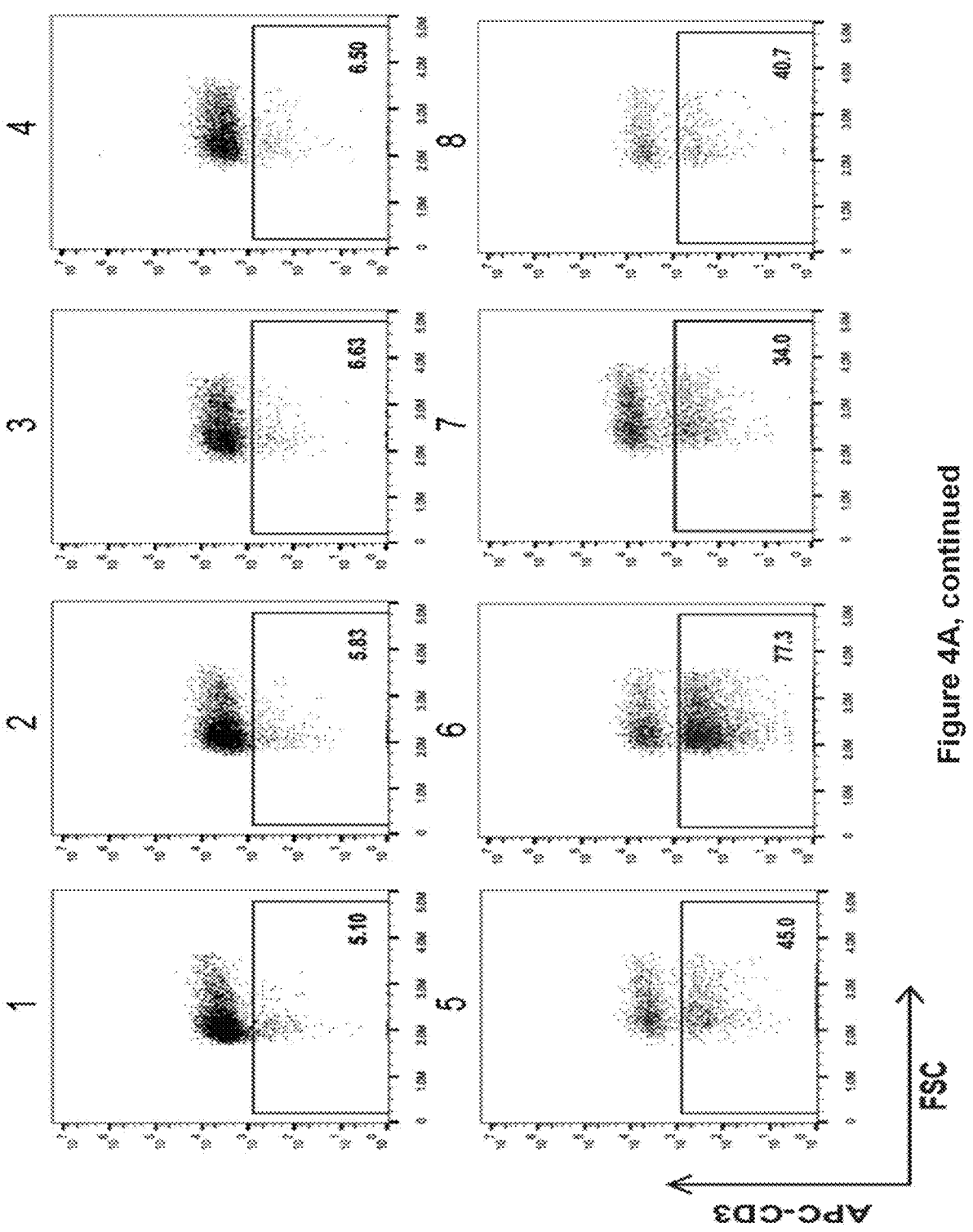
Figure 4A, continued

| CAS9 20 ug | | first time | | second time | |
|---|---|---|---|---|---|
| | | 0 hrs | 16 hrs | 24 hrs | |
| 1 | TRAC13 | C AS9 20ug gRNA10 ug | | | |
| 2 | TRAC13 | C AS9 20ug gRNA10 ug | gRNA 10 ug | | |
| 3 | TRAC13 | C AS9 20ug gRNA10 ug | | gRNA 10 ug | |
| 4 | TRBC4 | C AS9 20ug gRNA10 ug | | | |
| 5 | TRBC4 | C AS9 20ug gRNA10 ug | gRNA 10 ug | | |
| 6 | TRBC4 | C AS9 20ug gRNA10 ug | | gRNA 10 ug | |
| 7 | Capped TRAC13 | C AS9 20ug gRNA10 ug | | | |
| 8 | Capped TRAC13 | C AS9 20ug gRNA10 ug | gRNA 10 ug | | |
| 9 | Capped TRAC13 | C AS9 20ug gRNA10 ug | | gRNA 10 ug | |
| 10 | Capped TRBC4 | C AS9 20ug gRNA10 ug | | | |
| 11 | Capped TRBC4 | C AS9 20ug gRNA10 ug | gRNA 10 ug | | |
| 12 | Capped TRBC4 | C AS9 20ug gRNA10 ug | | gRNA 10 ug | |

Figure 4B

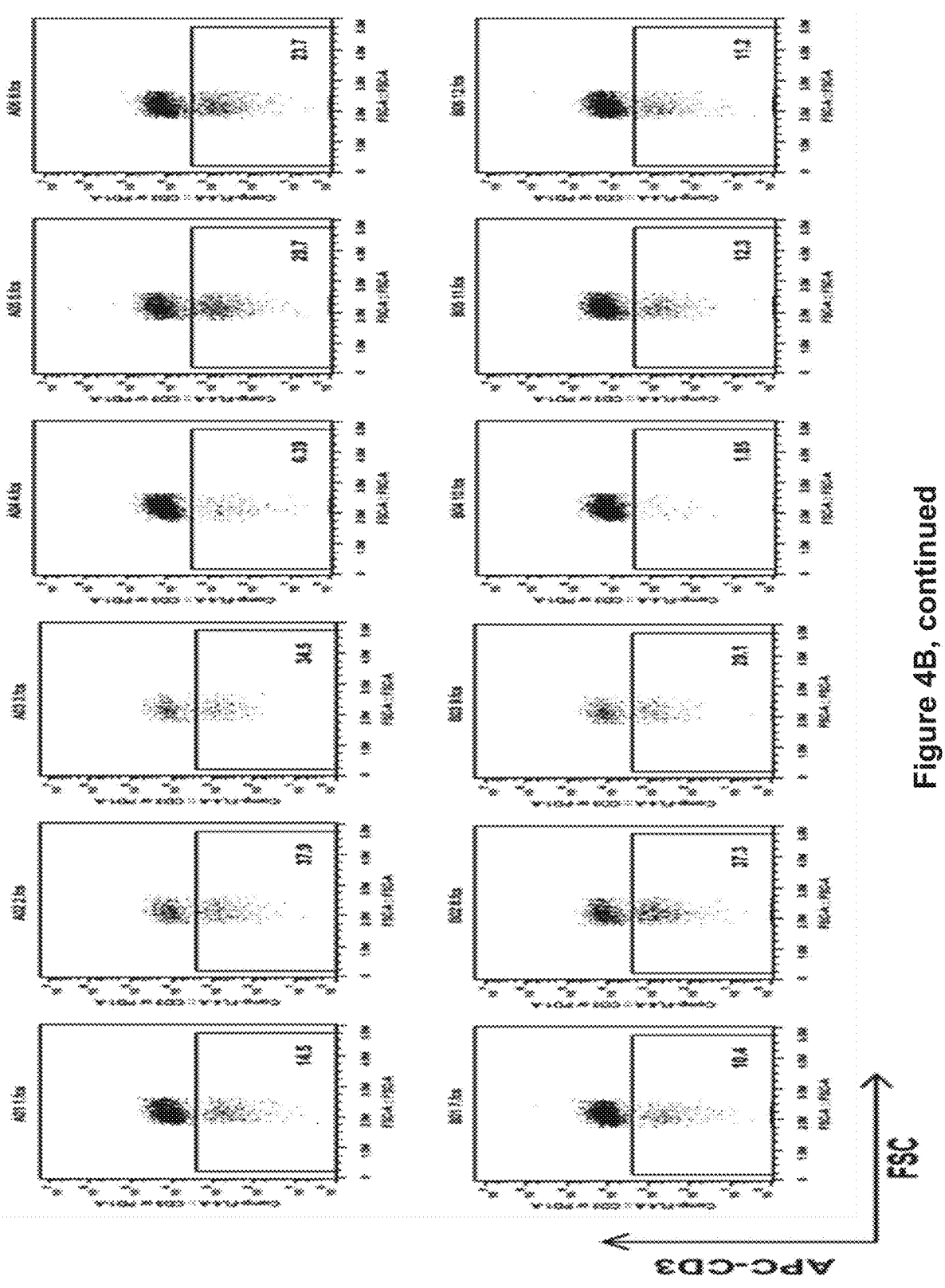
Figure 4B, continued

Fold Expansion

| Groups | Day 0 | Day 3 | Day 5 | Day 7 | Day 9 | Day 11 |
|---|---|---|---|---|---|---|
| REP | 1 | 15 | 100 | 198 | 335 | 507 |
| CD3/CD28 Beads | 1 | 2 | 7 | 14 | 17 | 25 |
| KT/OKT3 | 1 | 2 | 5 | 18 | 29 | 40 |
| KT/K19 | 1 | 3 | 7 | 24 | 36 | 52 |
| KT/K19/TCR-CLEAR | 1 | 3 | 8 | 25 | 42 | 58 |

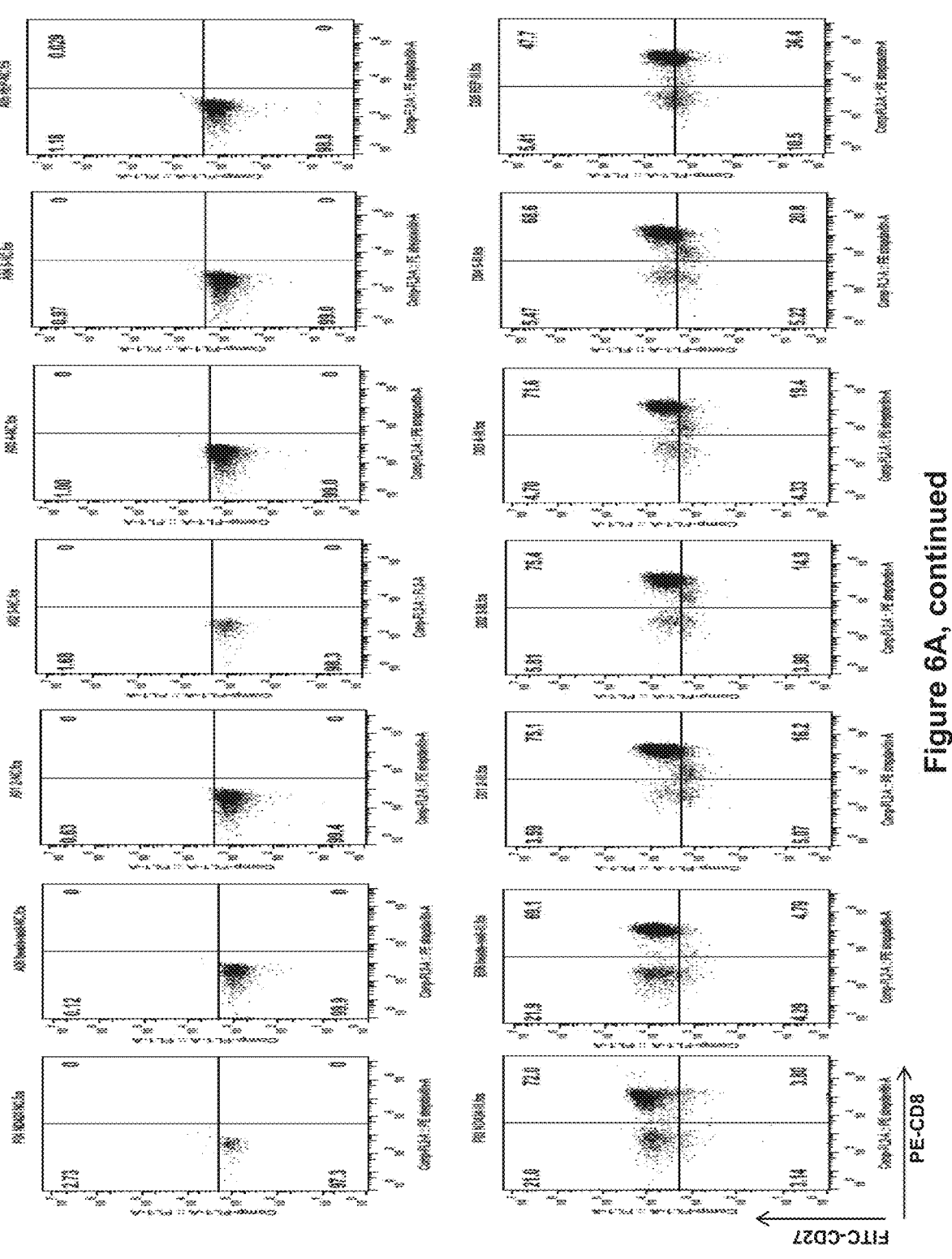
Figure 6A, continued

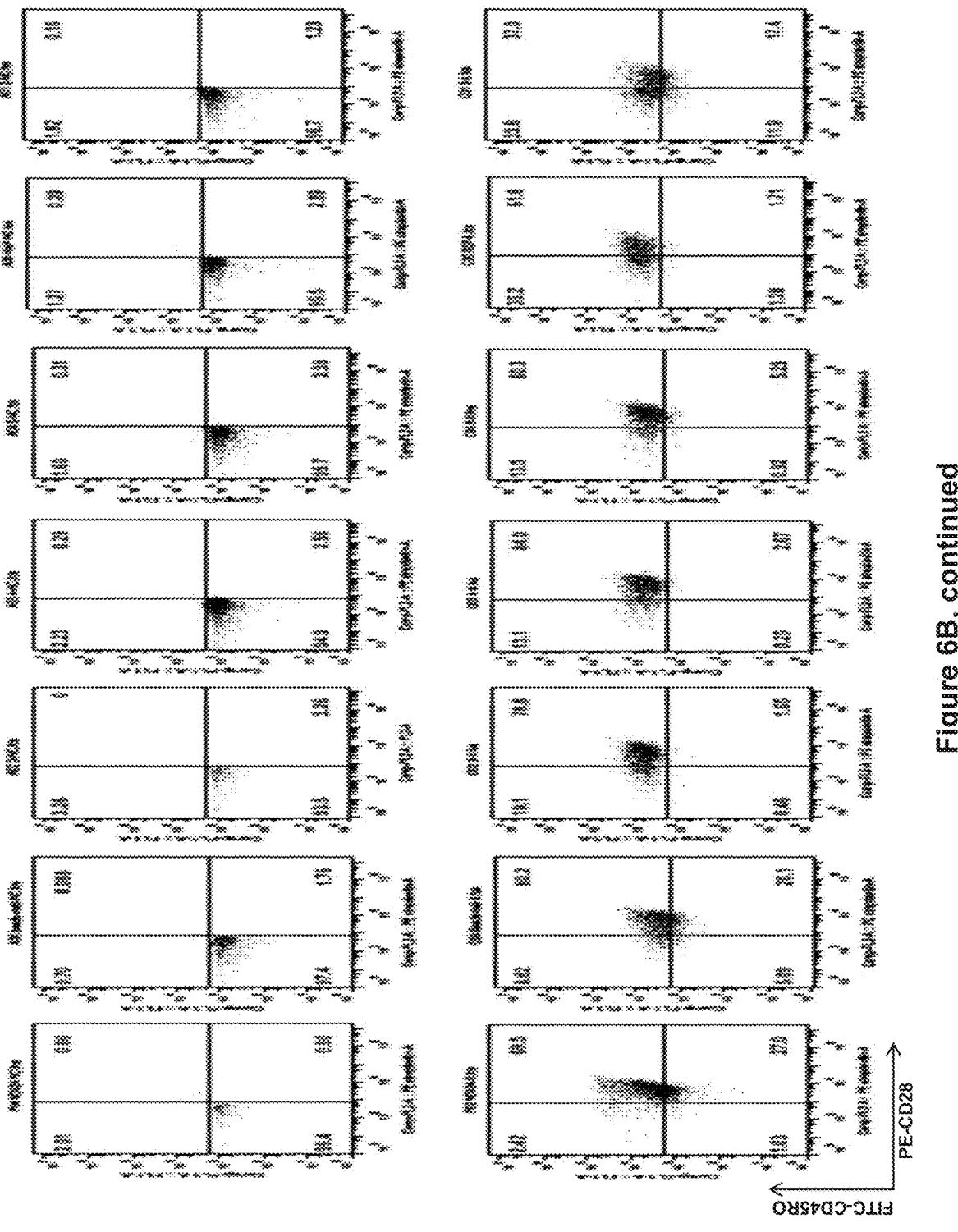
Figure 6B, continued

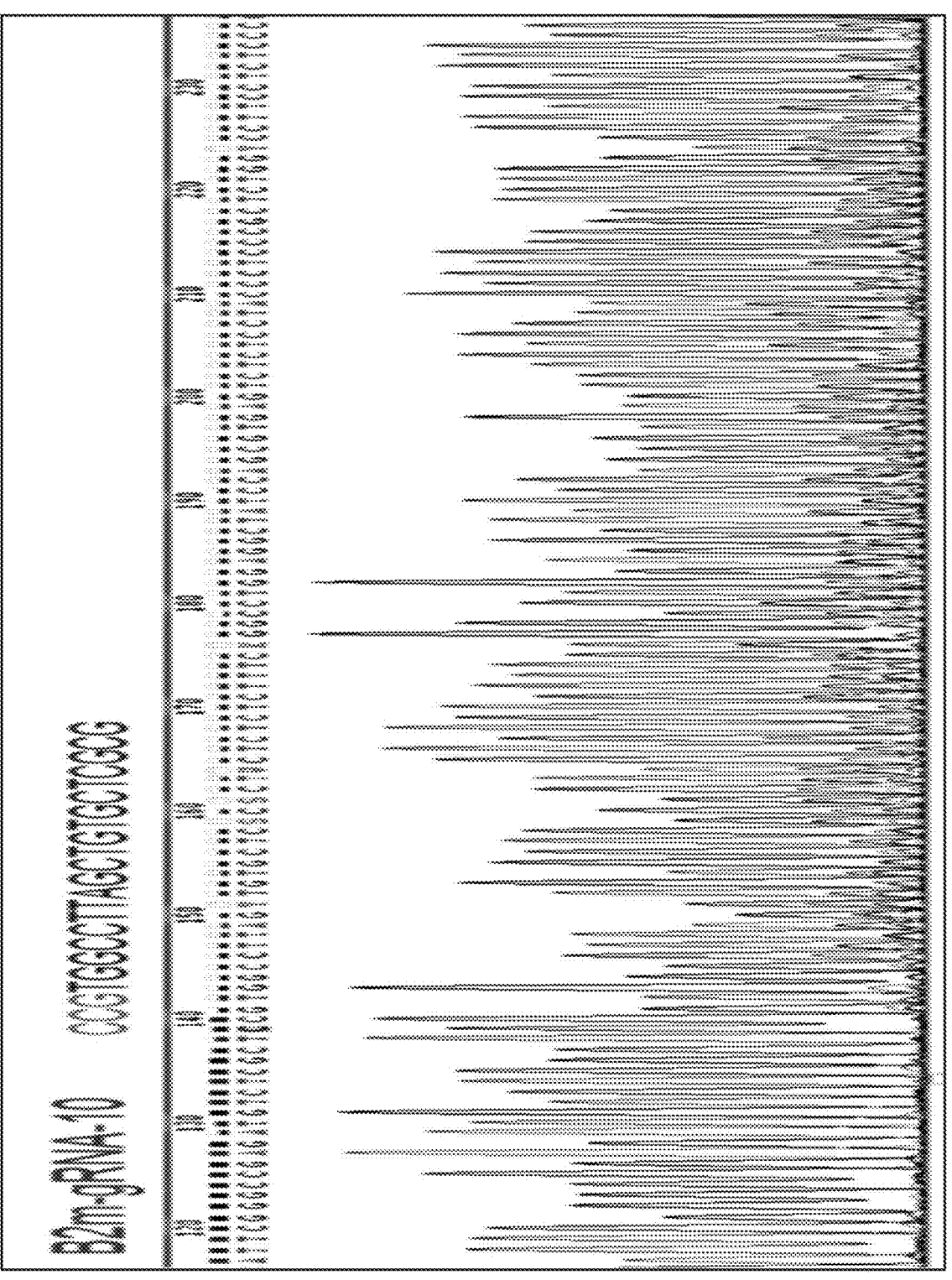
Figure 9A, continued

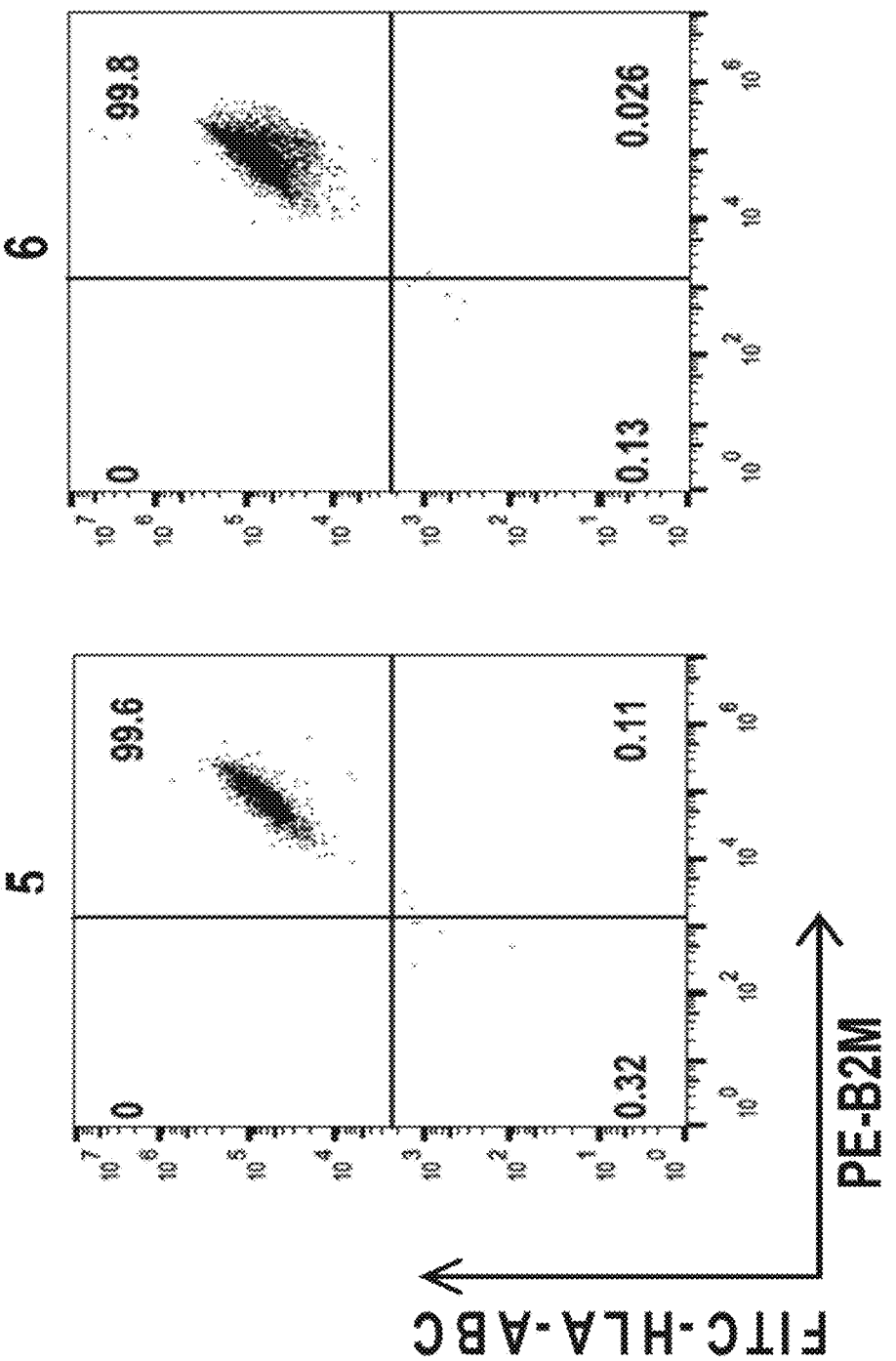
Figure 9B, continued

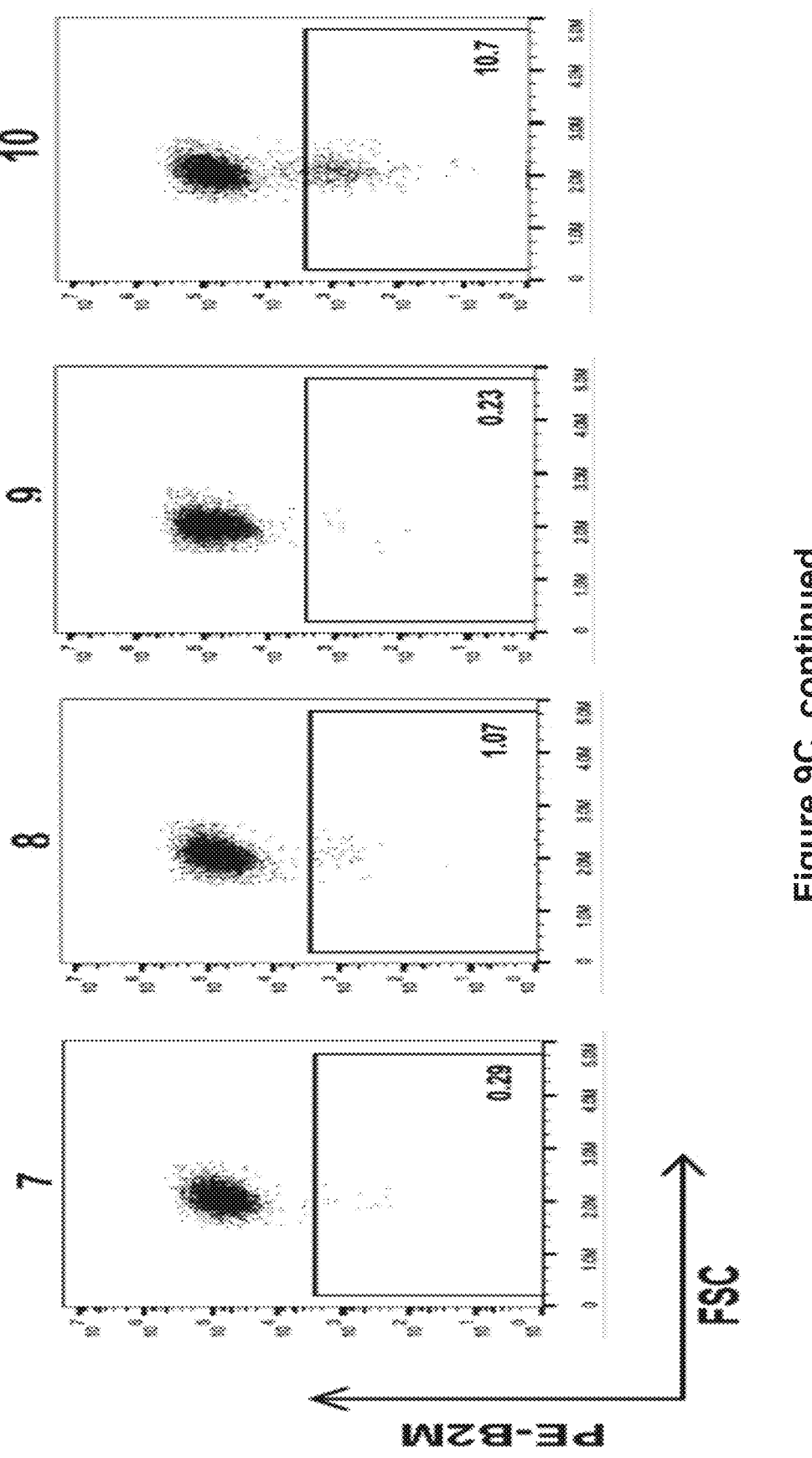
Figure 9C, continued

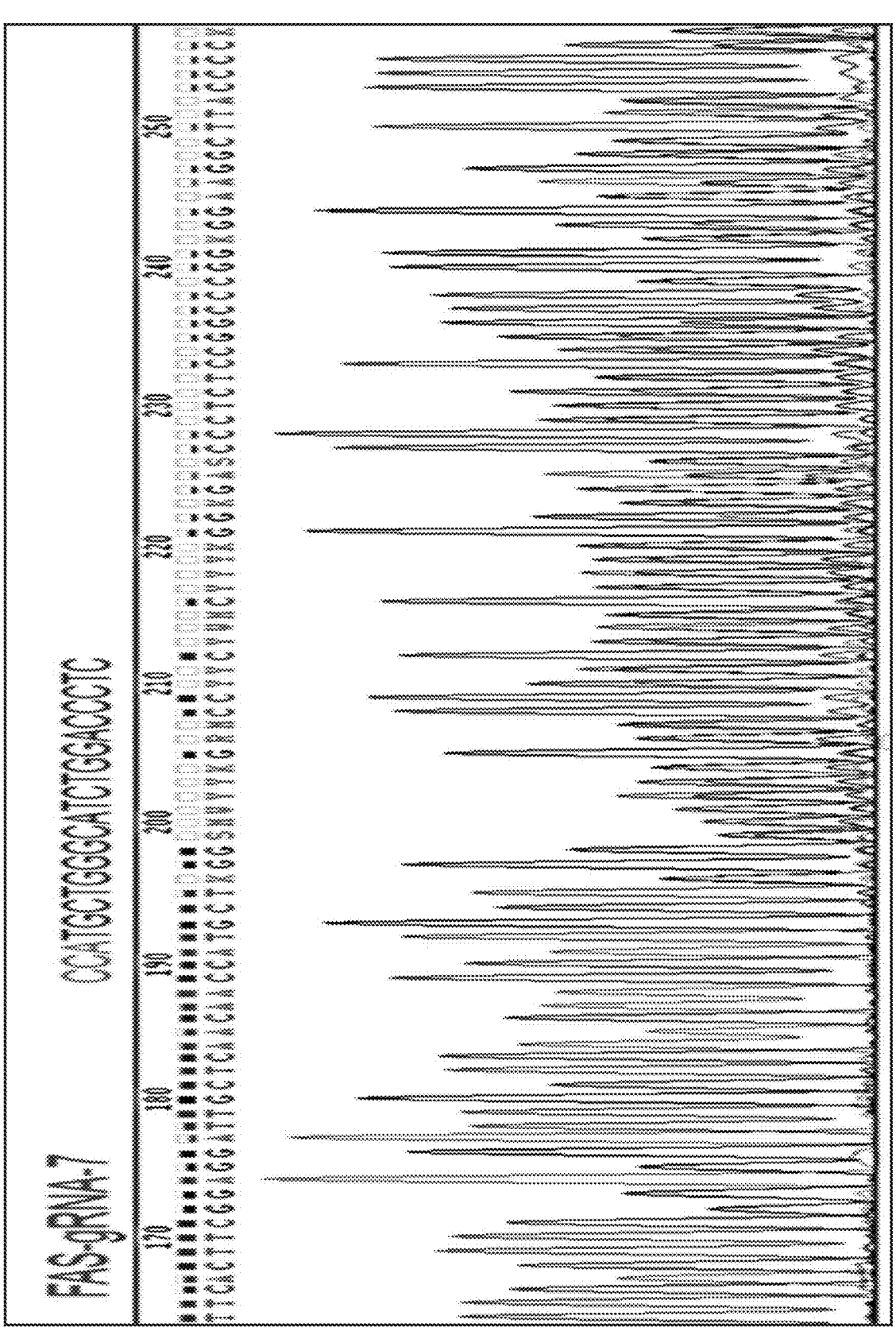
Figure 12A, continued

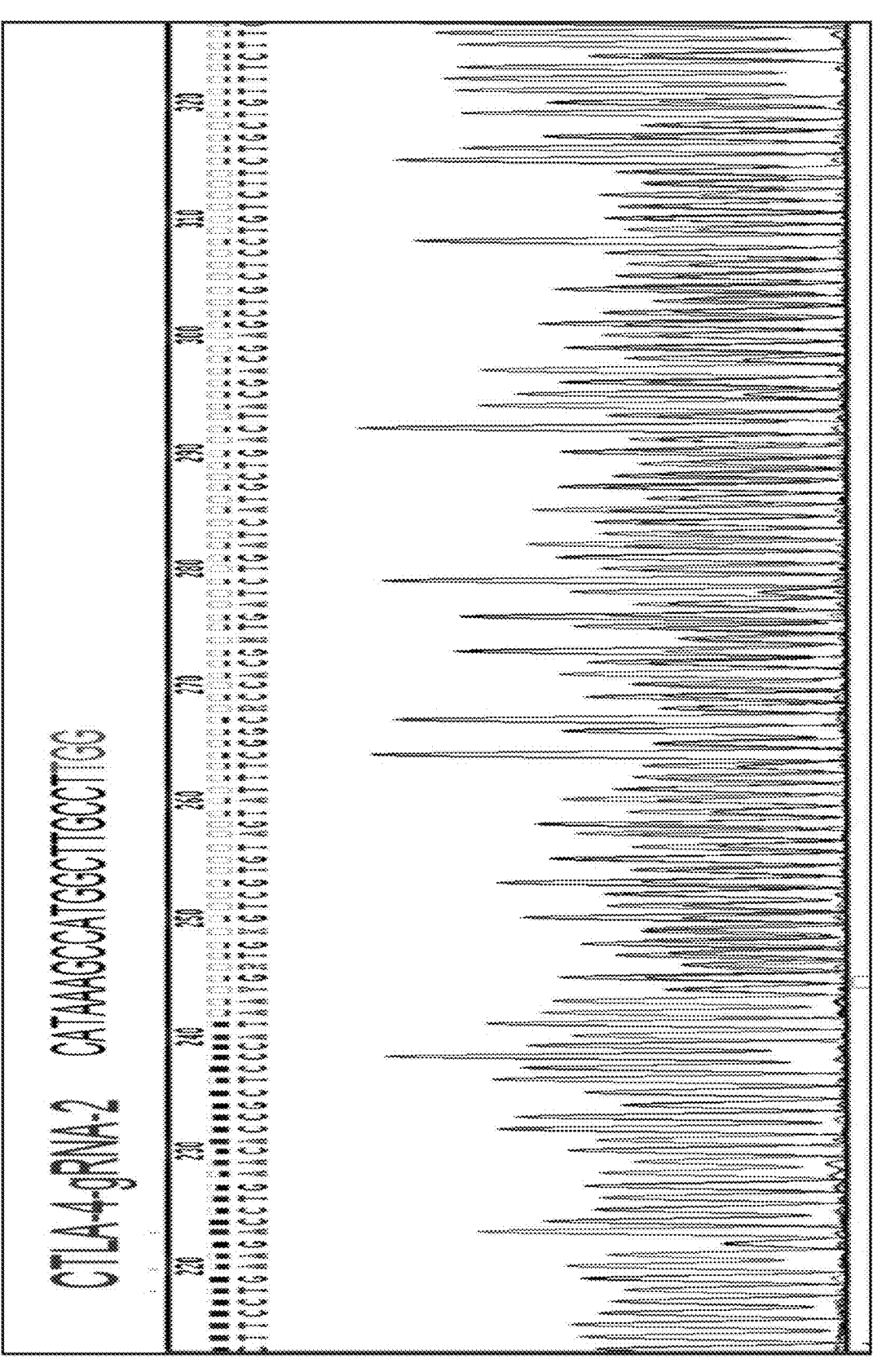
Figure 15A, continued

```
WT       AACACCGCTCCCATAAAGCCATGGCTTGCCTTGGATTTCAGCGGCACAAGGCTCAGCTGAACCT
1   -5   AACACCGCTCCCATAA-----TGGCTTGCCTTGGATTTCAGCGGCACAAGGCTCAGCTGAACCT
1   -2   AACACCGCTCCCATAA--CCATGGCTTGCCTTGGATTTCAGCGGCACAAGGCTCAGCTGAACCT
2   -2   AACACCGCTCCCATAA--CCATGGCTTGCCTTGGATTTCAGCGGCACAAGGCTCAGCTGAACCT
2   +1   AACACCGCTCCCATAAAGTCCATGGCTTGCCTTGGATTTCAGCGGCACAAGGCTCAGCTGAACC
3   -1   AACACCGCTCCCATAAA-CCATGGCTTGCCTTGGATTTCAGCGGCACAAGGCTCAGCTGAACCT
3   -14  AACACCGCTCCCATAAAG----------GGATTTCAGCGGCACAAGGCTCAGCTGAACCT
7   -5   AACACCGCTCCCATAA-----TGGCTTGCCTTGGATTTCAGCGGCACAAGGCTCAGCTGAACCT
7   -5   AACACCGCTCCCATAA-----TGGCTTGCCTTGGATTTCAGCGGCACAAGGCTCAGCTGAACCT
10  -1   AACACCGCTCCCATA-CCATGGCTTGCCTTGGATTTCAGCGGCACAAGGCTCAGCTGAACCT
10  -3   AACACCGCTCCCATAA----CCATGGCTTGCCTTGGATTTCAGCGGCACAAGGCTCAGCTGAACCT
11  -5   AACACCGCTCCCATAA-----TGGCTTGCCTTGGATTTCAGCGGCACAAGGCTCAGCTGAACCT
11  -0   AACACCGCTCCCATAAAGCCATGGCTTGCCTTGGATTTCAGCGGCACAAGGCTCAGCTGAACCT
```

Figure 15B

Ppp-trans-3,4-gRNA-2 CATCAAGCCTGCTAACATGGAGG
Figure 16, continued

Wt: wildtype TCR

S/SD: Second disulfide bond alpha/ Second disulfide bond+ De-N-glycosylation beta

| | CAS9 | Dose | gRNA | Dose |
|---|---|---|---|---|
| 1 | CAS9 | 2 ug | TRAC7 | 1 ug |
| 2 | CAS9 | 4 ug | TRAC7 | 2 ug |
| 3 | CAS9 | 8 ug | TRAC7 | 4 ug |
| 4 | CAS9 | 10 ug | TRAC7 | 5 ug |
| 5 | CAS9 | 20 ug | TRAC7 | 10 ug |

Figure 20A

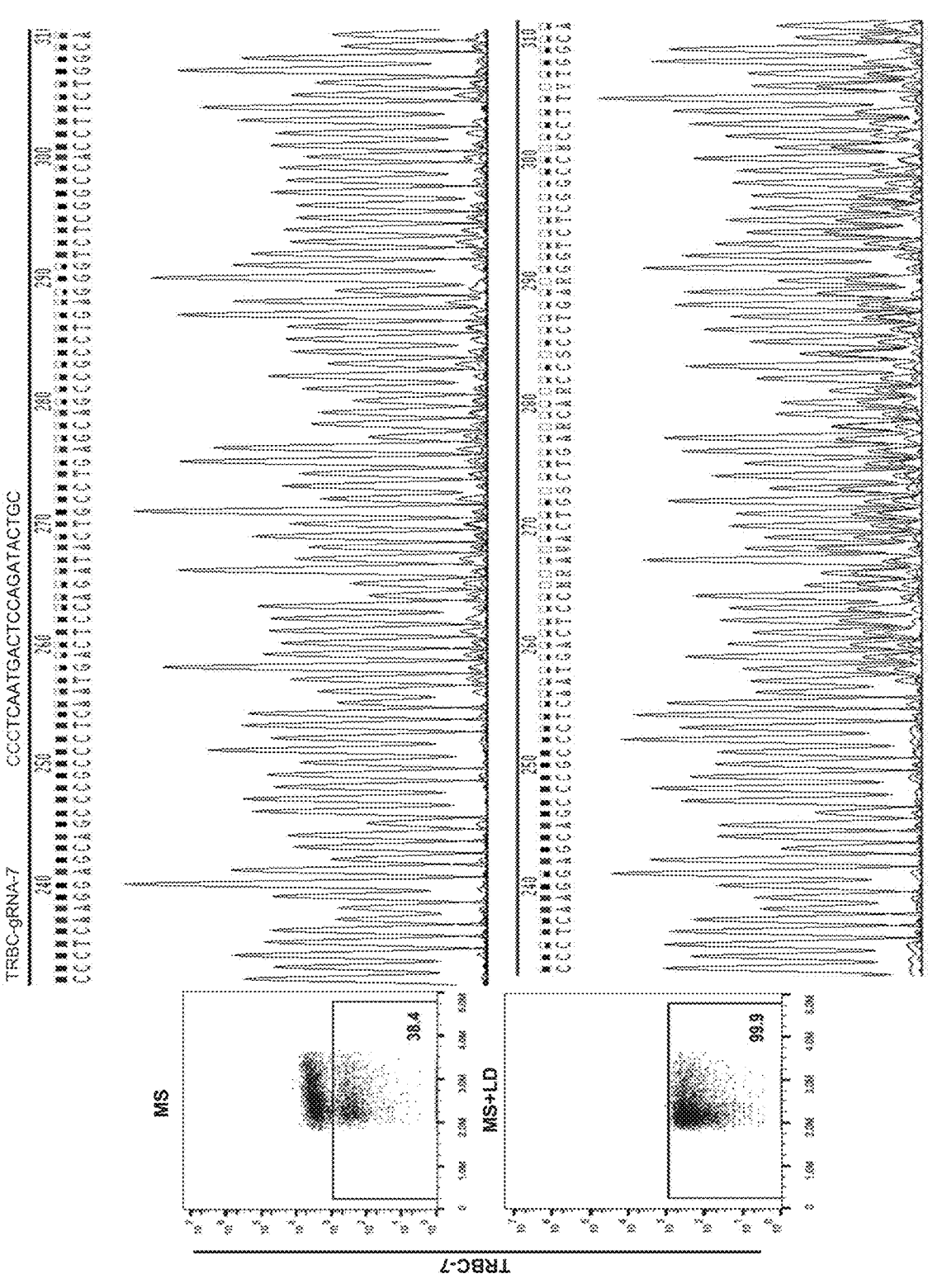
Figure 21, continued

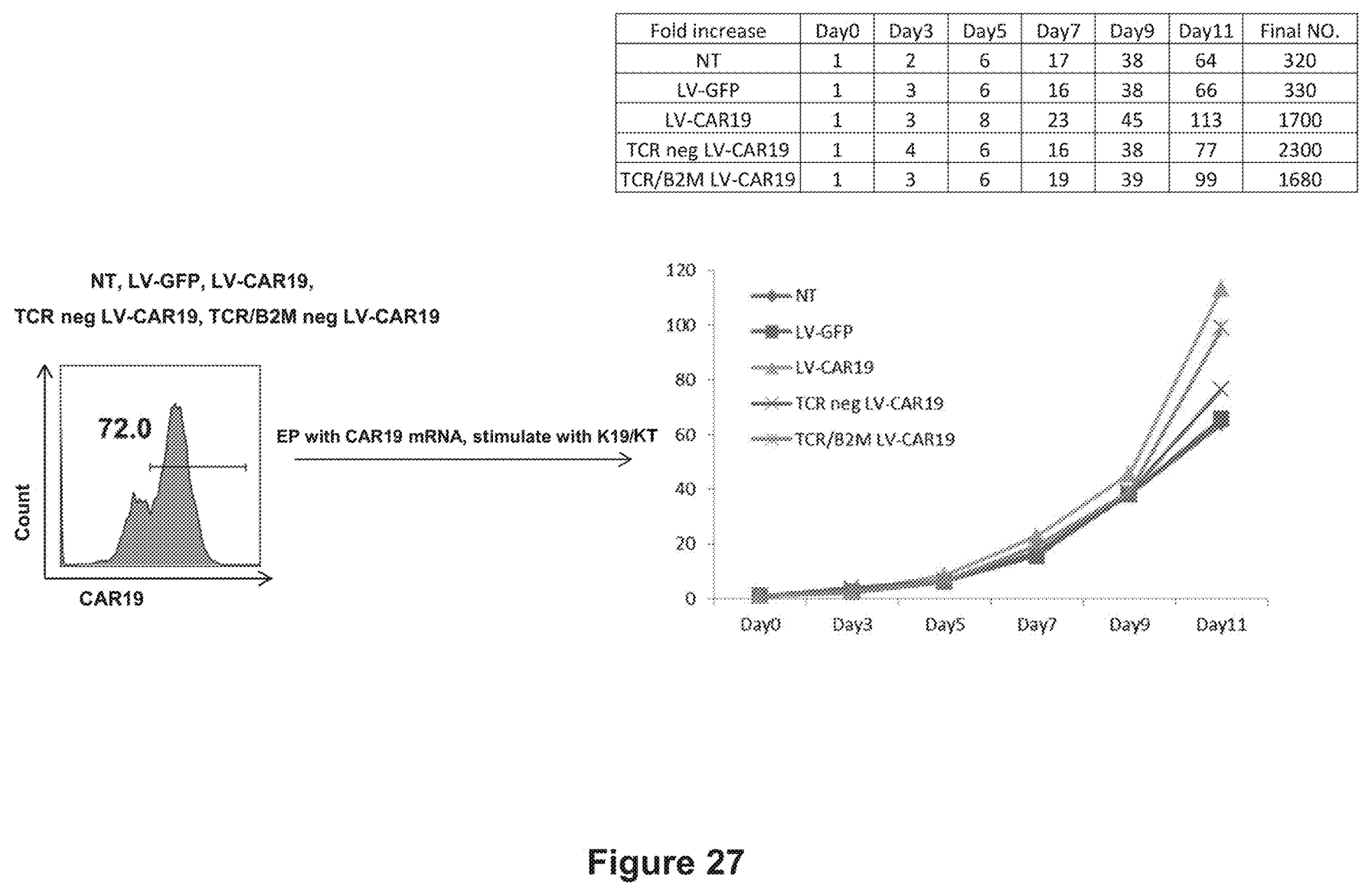

| Fold increase | Day0 | Day3 | Day5 | Day7 | Day9 | Day11 | Final NO. |
|---|---|---|---|---|---|---|---|
| NT | 1 | 2 | 6 | 17 | 38 | 64 | 320 |
| LV-GFP | 1 | 3 | 6 | 16 | 38 | 66 | 330 |
| LV-CAR19 | 1 | 3 | 8 | 23 | 45 | 113 | 1700 |
| TCR neg LV-CAR19 | 1 | 4 | 6 | 16 | 38 | 77 | 2300 |
| TCR/B2M LV-CAR19 | 1 | 3 | 6 | 19 | 39 | 99 | 1680 |

NT, LV-GFP, LV-CAR19,
TCR neg LV-CAR19, TCR/B2M neg LV-CAR19

EP with CAR19 mRNA, stimulate with K19/KT

CAR19

72.0

Count

Figure 27

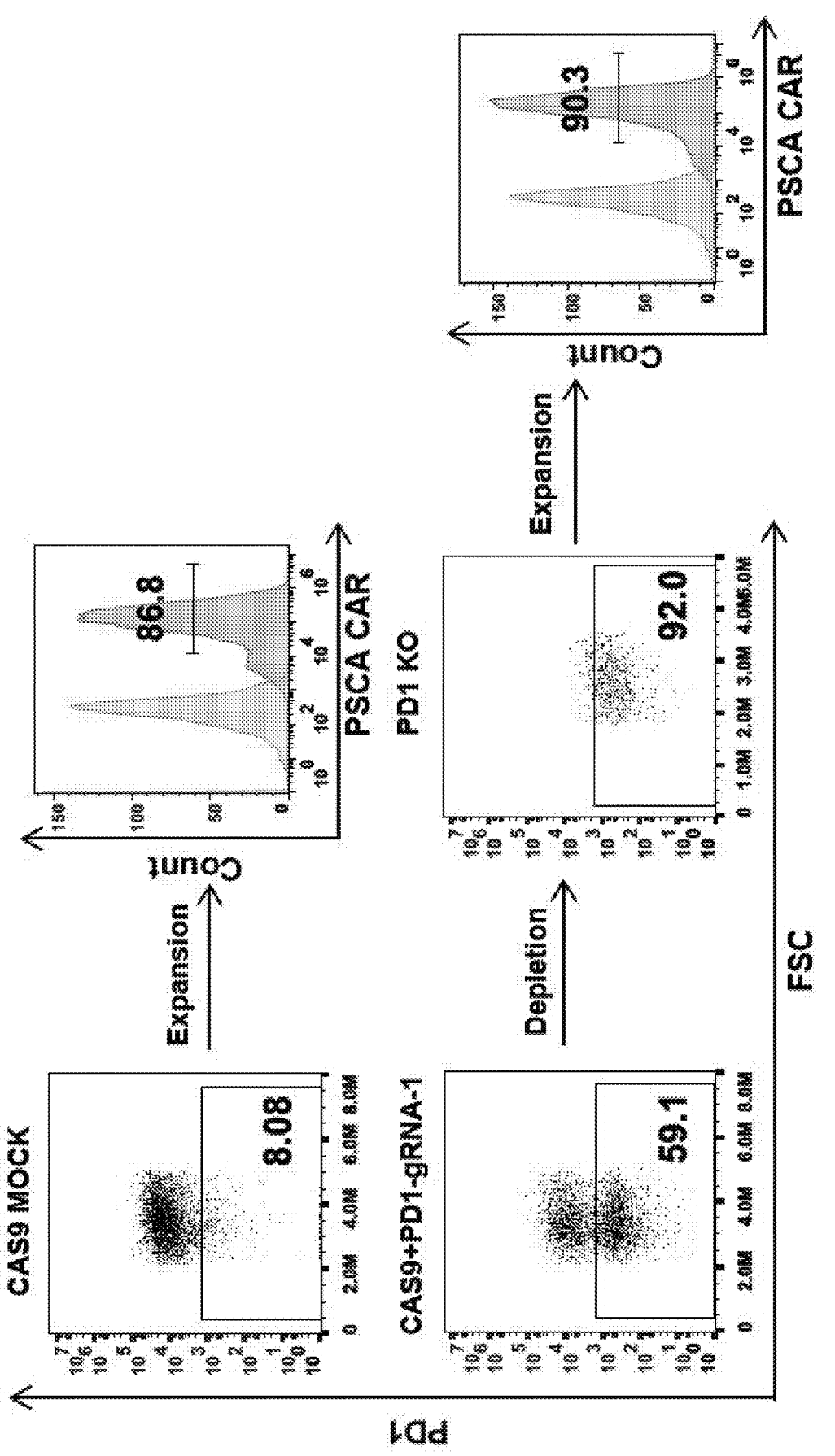
Figure 36, continued

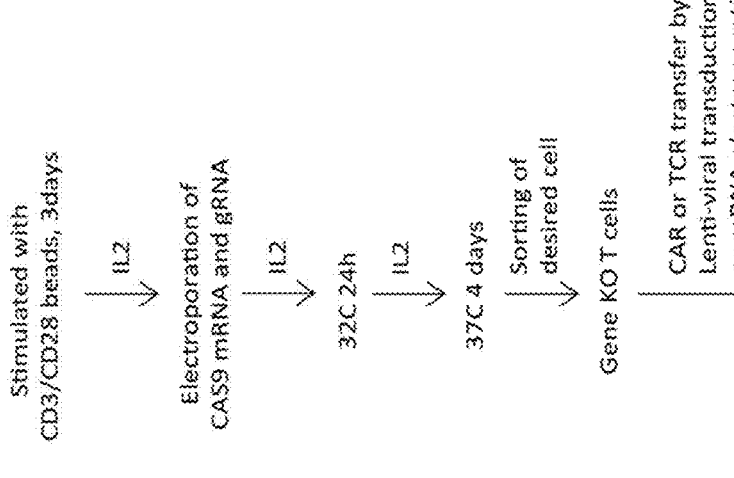
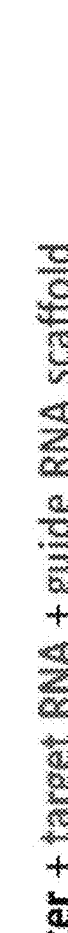
T7 promoter + target RNA + guide RNA scaffold
TAATACGACTCACTATAGNNNNNNNNNNNN
NNNNNNGTTTTAGAGCTAGAAATAGCAAGTTA
AAATAAGGCTAGTCCGTTATCAACTTGAAAAAGT
GGCACCGAGTCGGTGCTTTTTT
Figure 49

| CAS9/<br>times | gRNA/<br>times | Protein<br>% | Genome<br>% |
|---|---|---|---|
| 1 | 0 | 0 | 0 |
| 1 | 1 | 17 | 27.7 (5/18) |
| 1 | 2 | 49 | 60 (12/20) |
| 1 | 3 | 82.4 | 89.4 (17/19) |
| 1 | 4 | 47.8 | 55 (11/20) |

Figure 51B

TRAC WT  TATATCACAGACAAAACTGTGCTAGACATGAGGTCTATGGACTTCAAGAGCAACAGTGCTGTGGCCT
(X4)     TATATCACAGACAAAACTGTGCTAGACATGAG-TCTATGGACTTCAAGAGCAACAGTGCTGTGGCCT
(X3)     TATATCACAGACAAAACTGTGCTAGACATG--GTCTATGGACTTCAAGAGCAACAGTGCTGTGGCCT
(X1)     TATATCACAGACAAAACTGTGCTAGACATGCA-GTCTATGGACTTCAAGAGCAACAGTGCTGTGGCCT
(X1)     TATATCACAGACAAAACTGTGCTAGACATG---TCTATGGACTTCAAGAGCAACAGTGCTGTGGCCT
(X1)     TATATCACAGACAAAACTGTGCTAGAC-TGAGGTCTATGGACTTCAAGAGCAACAGTGCTGTGGCCT
(X1)     TATATCACAGACAAAACTGTGCT-----TGAGGTCTATGGACTTCAAGAGCAACAGTGCTGTGGCCT
(X1)     TATATCACAGACAAAACTGTGCT-----TGAGGTCTATGGACTTCAAGAGCAACAGTGCTGTGGCCT
(X1)     TATATCACAGACAAAACTGTGCTAGACATGAGGTCTATGGACTTCAAGAGCAACAGTGCTGTGGCC
(X1)     TATATCACAGACAAAACTGTGCTAGACATGAGGTCTATGGACTTCAAGAGCAACAGTGCTGTGGCC

TRBC1 WT  AGCAGCCCGCCTCCAATGACTCCAGATACTGCCTGAGCAGCCGCCTGAGGGTCTCGGCCACCTTCTG
(X2)      AGCAGCCCGCCCTC-ATGACTCCAGATACTGCCTGAGCAGCCGCCTGAGGGTCTCGGCCACCTTCTG
(X2)      AGCAGCCCGCCGC-TCAATGACTCCAGATACTGCCTGAGCAGCCGCCTGAGGGTCTCGGCCACCTTCTG
(X1)      AGCAGCCCGCCCTCCAATGACTC-AGATACTGCCTGAGCAGTCGCCTGAGGGTCTCGGCCACCTTCTG
(X1)      AGCAGCCCGCCCTCCAATGACT--AGATACTGCCTGAGCAGCCGCCTGAGGGTCTCGGCCACCTTCTG
(X1)      AGCAGCCCGCCC-----GACTCCAGATACTGCCTGAGCAGCCGCCTGAGGGTCTCGGCCACCTTCT
(X1)      AGCAGCCCGCCCTCCAATGACTCCAGATACTGCCTGAGCAGCCGCCTGAGGGTCTCGGCCACCTTCT
(X1)      AGCAGCCCGCCCTCCAATGACTCCCAGATACTGCCTGAGCAGCCGCCTGAGGGTCTCGGCCACCTTCT

TRBC2 WT  AGCAGCCCGCCCTCCAATGACTCCAGATACTGCCTGAGCAGCCGCCTGAGCGTCTCGGCCACCTTCTG
(X3)      AGCAGCCCGCCCTCCAATGAC---AGATACTGCCTGAGCAGCCGCCTGAGGGTCTCGGCCACCTTCTG
(X2)      AGCAGCCCGCCCTCAATGACTC-AGATACTGCCTGAGCAGCCGCCTGAGGGTCTCGGCCACCTTCTG
(X1)      AGCAGCCCGCCCTCA-------ACTCCCTGAGCAGCCGCCTGAGGGTCTCGGCCACCTTCTG
(X1)      AGCAGCCCCGCC-TCA-TGACT-CAGATACTG-CTGAGCAGCAGCCGCCTGAGGGTCTCGGCCACCTTCT
(X1)      AGCAGGC--------ACTG-----C-G------TGAGCAGCCGCCTGAGCGTCTCGGCCACCTTCT
(X1)      AGCAGCCCGCCCTCCAATGACTCCCGAGATACTGCCTGAGCAGCCGCCTGAGCGTCTCGGCCACCTTCT

Figure 53A

PD1-gRNA: GGCCAGGATGGTTCTTAGGT

WT: TGGGCTGGGCGGCCAGGATGGTTCTTAGGTAGGTGGGGT

1: TGGGCTGGGCGGCCAGGATGGTTCTTAGGTAGGTGGGGT

6: TGGGCTGGGCGGCCAGGATGG---TAGGTAGGTGGGGT

7: TGGGCTGGGCGGCCAGGATGGTT-TTAGGTAGGTGGGGT

8: TGGGCTGGGCGGCCAGGATGG----TAGGTAGGTGGGGT

13: TGGGCTGGGCGGCCAGGATGGTTCTTAGGTAGGTAGGTGG

16: TGGGCTGGGCGGCCAGGATGGTTCTTAGGTAGGTGGGGT

19: TGGGCTGGGCGGCCAGGATGGTTCTTAGGGGTAGGTGGG

Figure 79B

| EP # | EP1 condition | EP2 condition | EP1 RNA (ug) | EP2 RNA (ug) | | Cuvette | volume (ul) | CD3-% | B2M-% | Fold Exp. |
| | | | CAS9 gRNA | gRNA | | | | | | |
|---|---|---|---|---|---|---|---|---|---|---|
| 1 | 360v 1ms | 360v 1ms | 40 | 20 | 10 | 2mm | 200 | 81.8 | 88.6 | 2.7 |
| 2 | 360v 1ms | 360v 1ms | 40 | 10 | 5 | 2mm | 200 | 71.6 | 77.5 | 4.7 |
| 3 | 360v 1ms | 360v 1ms | 40 | 5 | 5 | 2mm | 200 | 66.2 | 59.5 | 7.3 |
| 4 | 360v 1ms | 360v 1ms | 40 | 0 | 10 | 2mm | 200 | 76.9 | 75.4 | 8.5 |
| 5 | 360v 1ms | 360v 1ms | 20 | 10 | 5 | 2mm | 200 | 68.2 | 56.2 | 5.5 |
| 6 | 360v 1ms | 360v 1ms | 40 | 20 | 10 | 4mm | 200 | 35.6 | 17.8 | 16.8 |
| 7 | 360v 1ms | 360v 1ms | 20 | 10 | 5 | 4mm | 200 | 15.8 | 3.8 | 19.1 |
| 8 | 360v 1ms | 360v 1ms | 80 | 40 | 20 | 4mm | 400 | 38 | 13.8 | 9.7 |
| 9 | 500v 500us | 360v 1ms | 40 | 20 | 10 | 4mm | 200 | 37.4 | 17.8 | 17.2 |
| 10 | 500v 1ms | 500v 500us | 20 | 10 | 5 | 4mm | 200 | 22.8 | 9.3 | 18.5 |
| 11 | 500v 700us | 500v 500us | 20 | 10 | 5 | 4mm | 200 | 18.3 | 5 | 16.7 |
| 12 | No EP | Only wash | | | | | 200 | 1.8 | 1.5 | 18.8 |

Figure 80

| EP # | EP1 condition | EP2 condition | CAS9 gRNA | gRNA | Cuvette | EP volume (ul) | CD3- | B2M- | D7 Expansion |
|---|---|---|---|---|---|---|---|---|---|
| 1 | 500v 1ms | 1ms | 80 | 20 | 4mm | 400 | 78.8 | 80.8 | 3.4 |
| 2 | 500v 1ms | | 80 | 20 | 4mm | 400 | 58.4 | 69.9 | 5.6 |
| 3 | 500v 1ms | 1ms | 80 | 10 | 4mm | 400 | 37.6 | 47.6 | 7.0 |
| 4 | 500v 2ms | 2ms | 80 | 20 | 4mm | 400 | 74.2 | 83.7 | 2.9 |
| 5 | 500v 2ms | 2ms | 80 | 10 | 4mm | 400 | 80.5 | 83.4 | 3.0 |
| 6 | 400v 2ms | 2ms | 80 | 10 | 4mm | 400 | 40.5 | 51.0 | 6.7 |
| 7 | 400v 2ms | 2ms | 80 | 10 | 4mm | 400 | 55.7 | 64.1 | 5.7 |
| 8 | 400v 2ms | 2ms | 80 | 20 | 4mm | 400 | 50.0 | 64.0 | 6.5 |
| 9 | 400v 3ms | 1ms | 80 | 20 | 4mm | 400 | 61.8 | 74.1 | 6.1 |
| 10 | 360v 1ms | 360v 1ms | 40 | 10 | 2mm | 200 | 82.8 | 85.5 | 1.1 |
| 11 | 360v 1ms | 360v 1ms | 40 | 10 | 2mm | 200 | 84.8 | 82.4 | 0.8 |
| 12 | 360v 1ms | 360v 1ms | 40 | 10 | 2mm | 200 | 85.9 | 85.3 | 0.8 |
| 13 | 360v 1ms | 360v 1ms | 40 | 10 | 2mm | 200 | 67.8 | 79.9 | 1.0 |
| 14 | 500v 1ms | 80us | 80 | 20 | 4mm | 400 | 51.3 | 62.8 | 6.9 |
| 15 | No EP | | 0 | | | 200 | 4.1 | 6.3 | 13.0 |

Figure 81

| # | EP1 condition | | EP2 condition | | CAS9 | gRNA | CD3- | B2M- | D7 Expansion |
|---|---|---|---|---|---|---|---|---|---|
| 1 | 400v | 3ms | 500v | 1ms | 80 | 20 | 62.2 | 84.4 | 3.2 |
| 2 | 400v | 3ms | 500v | 1ms | 120 | 20 | 59.6 | 76.5 | 3.7 |
| 3 | 400v | 3ms | 500v | 1ms | 120 | 30 | 72.6 | 85.1 | 3.4 |
| 4 | 400v | 2ms | 500v | 1ms | 120 | 20 | 63.5 | 84.8 | 5.2 |
| 5 | 400v | 2ms | 500v | 1ms | 120 | 30 | 67.3 | 86.7 | 3.6 |
| 6 | 400v | 2ms | 500v | 800us | 120 | 20 | 54.8 | 79.3 | 3.9 |
| 7 | 400v | 2ms | 500v | 800us | 120 | 30 | 69.7 | 87.1 | 3.6 |
| 8 | 400v | 2ms | 500v | 800us | 80 | 20 | 63.6 | 85.2 | 3.3 |
| 9 | 500v | 2ms | 500v | 800us | 120 | 20 | 64.2 | 83.0 | 2.9 |
| 10 | 500v | 2ms | 500v | 800us | 120 | 30 | 76.5 | 84.1 | 2.1 |
| 11 | 500v | 2ms | 500v | 800us | 120 | 30 | 75.9 | 87.6 | 2.0 |
| 12 | 500v | 2ms | 500v | 1ms | 120 | 30 | 81.4 | 89.8 | 2.0 |
| 13 | 450v | 2ms | 500v | 1ms | 80 | 20 | 66.3 | 88.1 | 3.1 |
| 14 | 450v | 2ms | 500v | 1ms | 120 | 20 | 71.0 | 88.2 | 2.7 |
| 15 | 450v | 3ms | 500v | 1ms | 120 | 20 | 74.8 | 88.2 | 1.8 |
| 16 | 400v | 3ms | 500v | 1ms | 80 | 20 | 60.6 | 72.0 | 2.2 |
| 17 | NO EP | | | | | | 0.5 | 0.7 | 9.9 |

Figure 82

| EP # | I condition | EP2 condition | CAS9 | gRNA | CD3- | B2m- | Day8 Exp. |
|---|---|---|---|---|---|---|---|
| 1 | 400v 2ms | 500v 1ms | 120 | 20 | 68.8 | 78.9 | 7.8 |
| 2 | 400v 2ms | 500v 1ms | 120 | 10 | 51.5 | 60.3 | 9.7 |
| 3 | 500v 1ms | 500v 1ms | 120 | 20 | 70.6 | 79 | 8.3 |
| 4 | 500v 1ms | 500v 1ms | 120 | 10 | 52.1 | 62.9 | 10.1 |
| 5 | 500v 1ms | 500v 1ms | 120 | 5 | 30.6 | 31.4 | 11.4 |
| 6 | 500v 1ms | 500v 1ms | 120 | 1 | 8.91 | 5.51 | 12.4 |
| 7 | 500v 1ms | 400v 1ms | 120 | 20 | 55.9 | 67 | 10.3 |
| 8 | 400v 2ms | 500v 800us | 120 | 20 | 61.6 | 73.4 | 8.6 |
| 9 | 400v 2ms | 500v 800us | 120 | 10 | 42.9 | 49.9 | 10.4 |
| 10 | 400v 2ms | 500v 800us | 80 | 10 | 41.8 | 49.3 | 10.0 |
| 11 | 400v 2ms | 500v 1ms | 120 | 20 | 59.1 | 68.1 | 6.8 |
| 12 | NO EP | | | | 3.73 | 2.79 | 17.0 |

Figure 83

Figure 6. T cell stimulation/LVV transduction/CRISPR EP procedure

| | |
|---|---|
| Day 0 | CD3/CD28 Beads stimulation |
| | 1. Count/calculate T cell , wash CD3/CD28 Beads mix with T cells at T:Beads=1:3 |
| | 2. adjust to 0.5e6-1e6/ml with MM, 100ml/flask in T150 |
| Day 1 | CD19 CAR lenti-transduction |
| | 1. Thaw hCD19 LVV, add to the T cells at MOI 2 |
| Day 3 | De-Beads |
| | 1. After de-beads, spin and wash the cells with OPTI-MEM 2 times. |
| | 2. Re-suspend the cells in OPTI-MEM at 50e6/ml. |
| | 3. Electroporation with BTX830 at 500V and 1 ms, 120ug Cas9 /400ul T cells |
| | 4. After EP add T cell to original culture volume of half fresh and half condition medium |
| Day 3 | Cas9 RNA EP |
| Day 4 | TRBC&B2m gRNA EP |
| | 1. Spin and wash the cells with OPTI-MEM 2 times. |
| | 2. Re-suspend the cells in OPTI-MEM at 50e6/ml. |
| | 3. Electroporation with BTX830 at 500V and 1 ms, 20ug TRBC4 and B2M gRNA/400ul T cells |
| | 4. After EP add T cell to original culture volume of half fresh and half condition medium |
| Day 8 | CD3 positive T cell depletion |
| | 1. Harvest cells, spin and follow CD3 negative selection using LD column |
| | 2. Resuspend CD3 negative T cells in MM at 0.5-1e6/ml, 100 ml/T150 to further expand the T cells |
| Day 10 | Harvest T cells |
| | 1. Harvest cells, aliquot&frozen T cells |

Figure 84

Cells#

| Group # | Donor | T cells | Day 0 | Day 3 | Day 5 | Day 6 | Day 7 | Day 8 | Day 10 |
|---|---|---|---|---|---|---|---|---|---|
| 1 | ND391 | CART/MOCK EP | 10.0 | 19.8 | 63.4 | 127.9 | 310.2 | 556.8 | 1090.8 |
| 2 | ND391 | CART/CRISPR | 100.0 | 178.2 | 175.4 | 350.4 | 571.6 | 1036.8 | 2985.6 |
| 3 | ND463 | CART/MOCK EP | 10.0 | 17.1 | 57.0 | 115.1 | 301.9 | 648.6 | 1282.5 |
| 4 | ND463 | CART/CRISPR | 90.0 | 153.5 | 150.8 | 309.6 | 522.8 | 861.6 | 2839.2 |
| 5 | ND463 | UNMOD | 30.0 | 43.5 | 173.8 | 305.2 | 733.2 | 1503.2 | 2935.2 |
| 6 | ND469 | CART/MOCK EP | 10.0 | 12.0 | 66.6 | 99.3 | 301.9 | 577.2 | 1017.9 |
| 7 | ND469 | CART/CRISPR | 60.0 | 108.2 | 74.1 | 147.0 | 252.0 | 521.6 | 1190.4 |

FoldExpansion

| Group # | Donor | T cells | Day 0 | Day 3 | Day 5 | Day 6 | Day 7 | Day 8 | Day 10 |
|---|---|---|---|---|---|---|---|---|---|
| 1 | ND391 | ND391 CART/MOCK EP | 1 | 2 | 6 | 13 | 31 | 56 | 109 |
| 2 | ND391 | ND391 CART/CRISPR | 1 | 2 | 2 | 4 | 6 | 10 | 30 |
| 3 | ND463 | ND463 CART/MOCK EP | 1 | 2 | 6 | 12 | 30 | 65 | 128 |
| 4 | ND463 | ND463 CART/CRISPR | 1 | 2 | 2 | 3 | 6 | 10 | 32 |
| 5 | ND463 | ND463 UNMOD | 1 | 1 | 6 | 10 | 24 | 50 | 98 |
| 6 | ND469 | ND469 CART/MOCK EP | 1 | 1 | 7 | 10 | 30 | 58 | 102 |
| 7 | ND469 | ND469 CART/CRISPR | 1 | 2 | 1 | 2 | 4 | 9 | 20 |

Figure 85

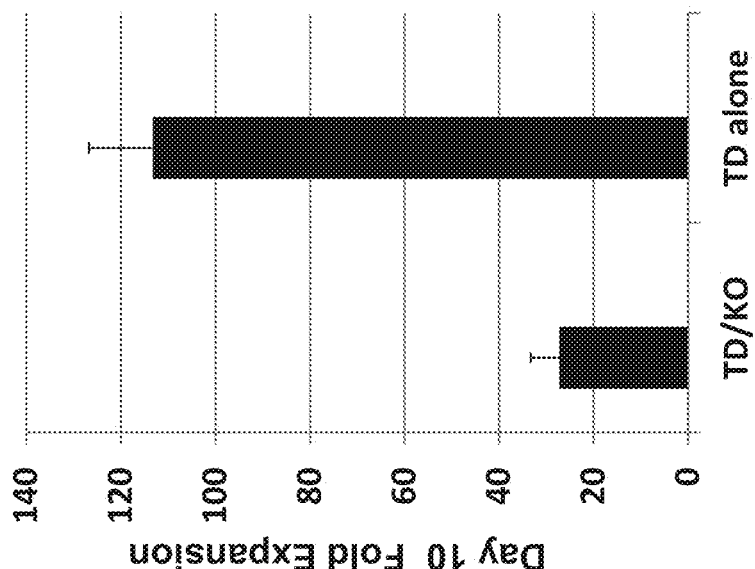
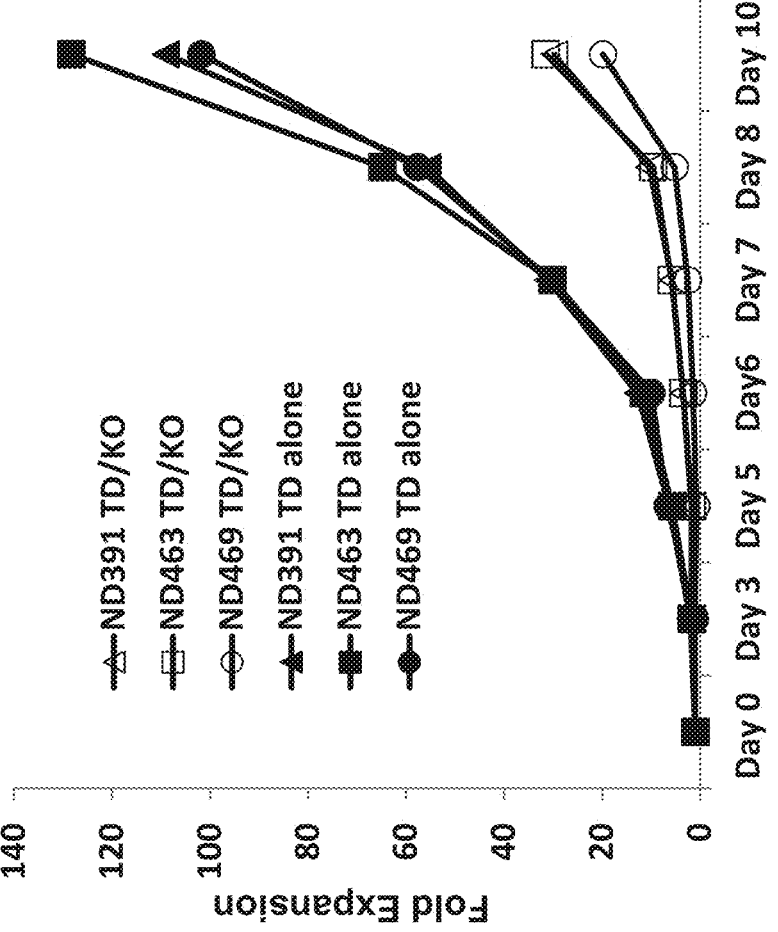
Figure 86

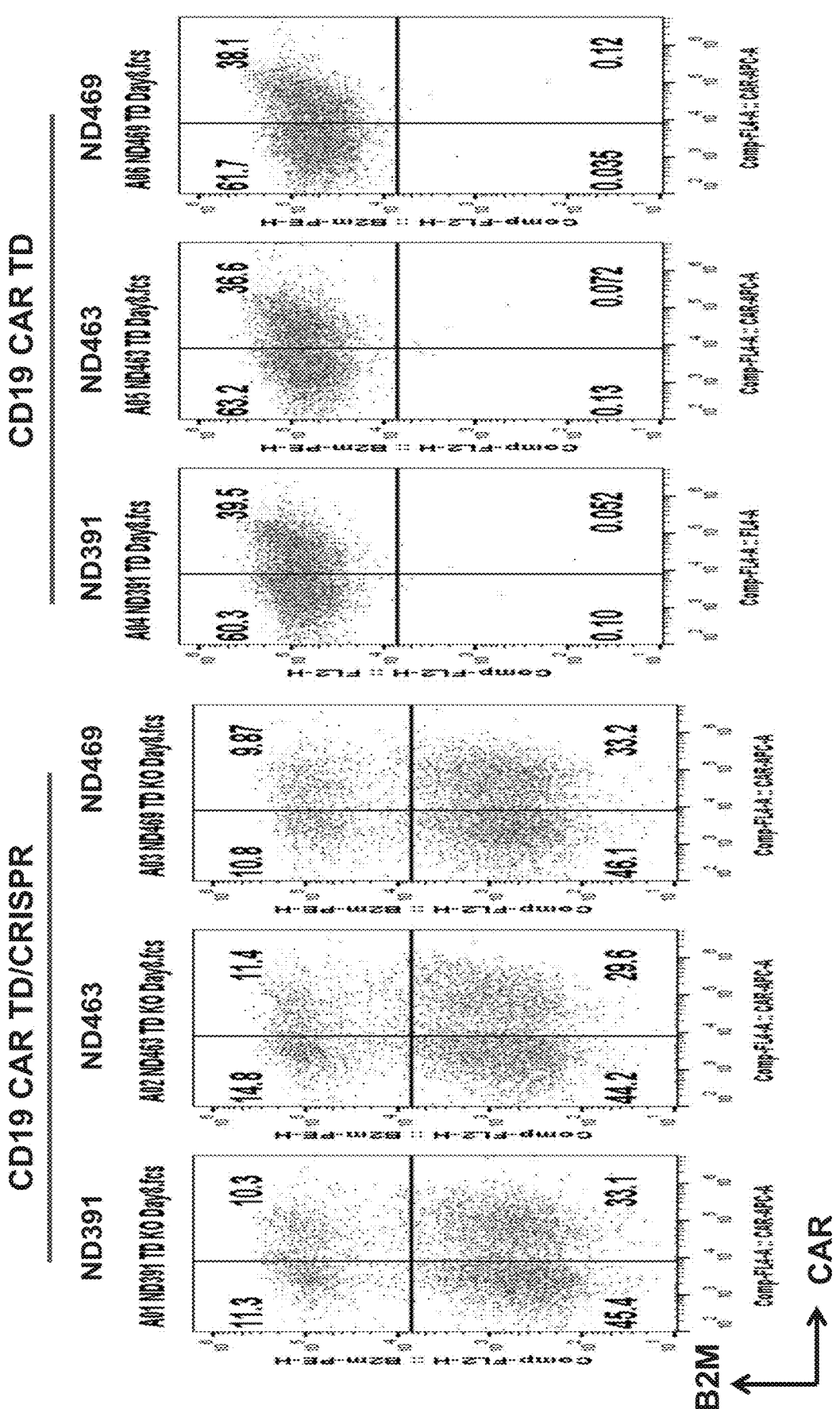
Figure 87, continued

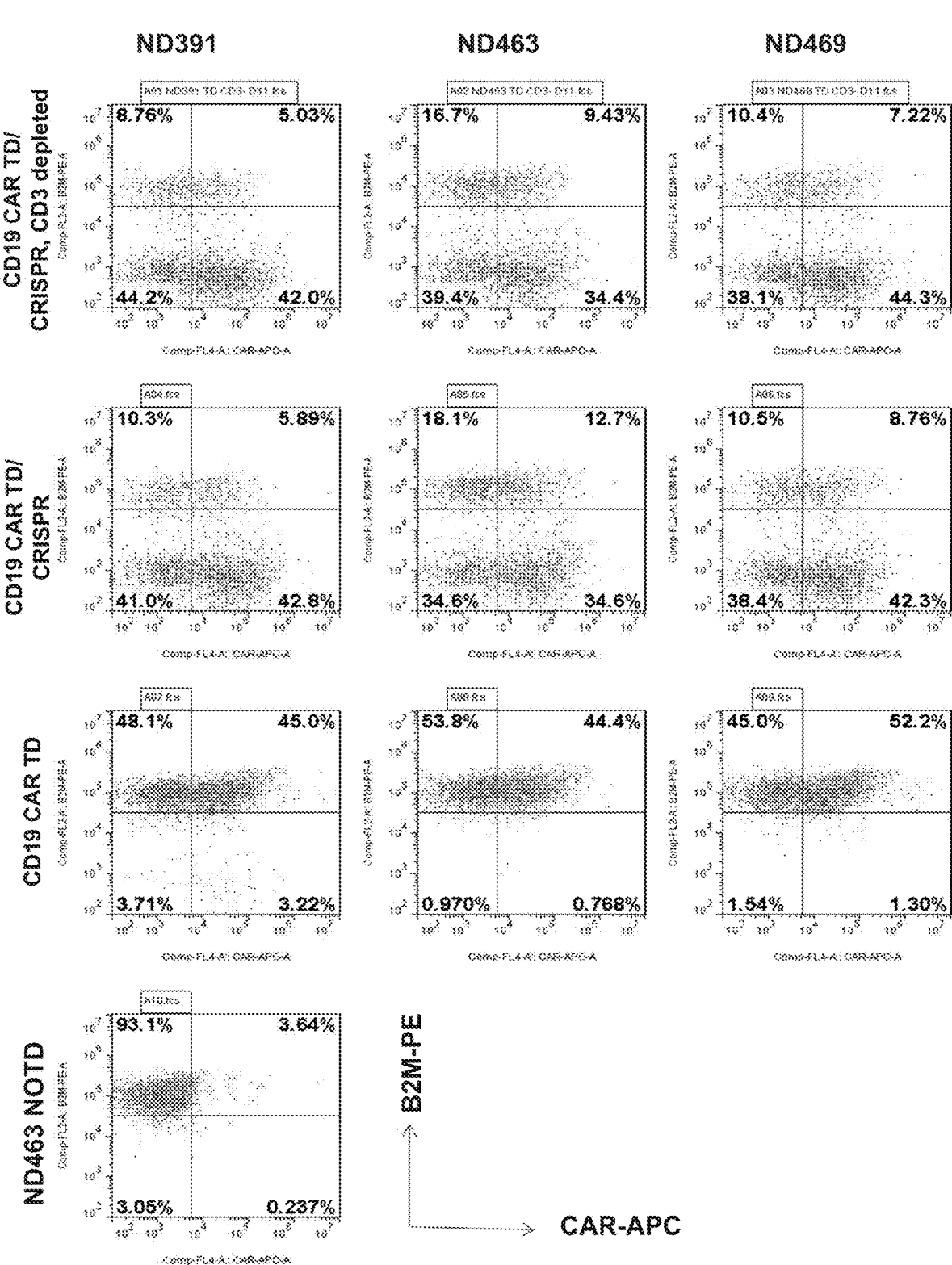
Figure 91, continued

| Donor cell ID | %CAR19+ | %CAR19+ CD3- B2M- | %CAR19+ CD3- B2M+ | %CAR19 +CD3+ B2M- | %CAR19 +CD3+ B2M+ |
|---|---|---|---|---|---|
| ND391 | 51.4 | 85.2 | 12.8 | 1.6 | 0.4 |
| ND463 | 48.5 | 73.4 | 22.9 | 1.8 | 1.9 |
| ND469 | 55.8 | 82.1 | 16.5 | 0.8 | 0.6 |

Figure 92

ALTERING GENE EXPRESSION IN MODIFIED T CELLS AND USES THEREOF

CROSS-REFERENCE TO RELATED APPLICATION

The present application is a divisional of U.S. patent application Ser. No. 15/516,052, filed Mar. 31, 2017, issued as U.S. Pat. No. 11,208,661, which is a 35 U.S.C. § 371 national phase application from, and claims priority to, International Patent Application No. PCT/US2015/055780, filed Oct. 15, 2015, which is entitled to priority under 35 U.S.C. § 119(e) to U.S. Provisional Patent Application No. 62/073,651, filed Oct. 31, 2014, all of which are incorporated by reference herein in their entireties.

STATEMENT REGARDING FEDERALLY SPONSORED RESEARCH OR DEVELOPMENT

This invention was made with government support under CA120409 awarded by the National Institute of Health. The government has certain rights in the invention.

STATEMENT REGARDING SEQUENCE LISTING SUBMITTED ELECTRONICALLY VIA EFS-WEB

The content of the electronically submitted sequence listing in ASCII text file (Name: 046483-7051US3-Se-quence-Listing; Size: 30,644 bytes; and Date of Creation: Nov. 24, 2021) is herein incorporated by reference in its entirety.

BACKGROUND OF THE INVENTION

Adoptive cell transfer (ACT) using chimeric antigen receptor (CAR) modified T cells has been shown to be a promising strategy for the treatment of cancers (Louis et al., 2011, Blood 118:6050-6056; Kochenderfer et al., 2010, Blood 116:3875-3886 and Porter et al., 2011, N Engl J Med 365:725-733).

Integration associated safety concerns using lentiviral or retroviral vectors are a major concern for modification of cells used for ACT. Some advances have been made to avoid on-target or off-target unwanted side effects, such as RNA transfection of T cells with T cell receptor (TCR) or CAR RNA electroporation (Zhao, 2006, *Mol Ther* 13:151-159; Mitchell et al., Smits et al., 2004, *Leukemia* 18:1898-1902). By minimizing dosage of both RNA and T cells, such methods efficiently permit the introduction of multiple genes into cells. However, the major constraint for transient expression of CARs is the suboptimal effector activity and functionality of RNA transfected T cells. Multiple T cell infusions and/or significant use of low dose chemotherapy have been used to improve CAR function (Barrett et al., 2013, Hum Gene Ther 24(8):717-27).

Various attempts have been made to improve effector activity and functionality of CARs while in order to avoid the need for combination therapies and additional treatments. Increasing RNA during the transfection process poses a negative impact on T cell function, especially in vivo anti-tumor activities (Barrett et al., 2011, Hum Gene Ther 22:1575-1586). Alternative constructs fusing an anti-CD3 antigen antibody fragment to an anti-tumor antigen antibody fragment have also been tested in clinical trials for cancer treatments (Bargou et al., 2008, Science 321:974-977; Klinger et al., 2012, Blood 119:6226-6233). Unfortunately, these constructs were severely limited in functionality because of a short half-life, poor accessibility to target cell sites, and a lack of proper long term signaling function.

Clinical TCR studies have been hampered by low expression levels of the transduced TCR, as well as mispairing of a and R chains. Because four TCRs can potentially be expressed at the cell surface when a T cell transcribes the chains of two different TCRs (native alpha/beta, exogenous alpha/beta, and native/exogenous "mispaired" heterodimers), significant obstacles to the use of this approach are evident. In studies performed to date, preclinical studies have clearly demonstrated that TCR miss-pairings have the potential to induce harmful recognition of self-antigens.

Although early TCR and CAR T cell clinical data obtained in treating cancers has shown promising results, the risk to the patient is high, and some patients' T cells are not potent enough for effective treatment even after TCR or CAR redirection, forcing modification of allogeneic donor-derived T cells. However, the endogenous αβ T-cell receptor on infused allogeneic T cells may recognize major and minor histocompatibility antigens in the recipient, leading to graft-versus-host-disease (GVHD). As a result, the majority of current clinical trials using infusion of autologous CAR T cells rely on immune tolerance to prevent TCR-mediated deleterious recognition of normal tissues after adoptive cell transfer. This approach has achieved early clinical successes but is limited by the time and expense to manufacture patient-specific T-cell products. Therefore a need exists for safer methods of modifying T cells, while circumventing the time and expense to manufacture patient-specific T-cell products.

SUMMARY OF THE INVENTION

As described herein, the present invention relates to compositions and methods for generating a modified T cell with a nucleic acid capable of altering gene expression of an endogenous gene selected from the group consisting of TCR α chain, TCR β chain, beta-2 microglobulin, a HLA molecule, CTLA-4, PD1, and FAS and further comprising a nucleic acid encoding a modified T cell receptor (TCR) comprising affinity for a surface antigen on a target cell.

One aspect of the invention includes a modified T cell comprising a nucleic acid capable of downregulating gene expression of an endogenous gene selected from the group consisting of TCR α chain, TCR β chain, beta-2 microglobulin, a HLA molecule, CTLA-4, PD1, and FAS; and a nucleic acid encoding a modified T cell receptor (TCR) comprising affinity for a surface antigen on a target cell.

In another aspect, the invention includes a method for generating a modified T cell comprising introducing a nucleic acid capable of downregulating gene expression of an endogenous gene selected from the group consisting of TCR α chain, TCR β chain, beta-2 microglobulin, a HLA molecule, CTLA-4, PD1, and FAS into a T cell; and introducing a nucleic acid encoding a modified T cell receptor (TCR) comprising affinity for a surface antigen on a target cell into the T cell.

In yet another aspect, the invention includes a method of treating a disease or condition associated with enhanced immunity in a subject comprising administering an effective amount of a pharmaceutical composition comprising the modified T cell described herein to a subject in need thereof.

In still another aspect, the invention includes a method of treating a condition in a subject, comprising administering to the subject a therapeutically effective amount of a pharmaceutical composition comprising the modified T cell described herein.

In another aspect, the invention includes a method for stimulating a T cell-mediated immune response to a target cell or tissue in a subject comprising administering to a subject an effective amount of a pharmaceutical composition comprising the modified T cell described herein.

In yet another aspect, the invention includes a method for adoptive cell transfer therapy comprising administering an effective amount of a pharmaceutical composition comprising the modified T cell described herein to a subject in need thereof to prevent or treat an immune reaction that is adverse to the subject.

In still another aspect, the invention includes use of the modified T cell described herein in the manufacture of a medicament for the treatment of an immune response in a subject in need thereof.

In another aspect, the invention includes a composition comprising the modified T cell generated according to the method described herein.

In yet another aspect, the invention includes a pharmaceutical composition comprising the modified T cell generated according to the method described herein.

In various embodiments of the above aspects or any other aspect of the invention delineated herein, the nucleic acid capable of downregulating gene expression is selected from the group consisting of an antisense RNA, antigomer RNA, siRNA, shRNA, and a CRISPR system, such as an pAd5/F35-CRISPR vector.

In one embodiment, the modified TCR is selected from the group consisting of a wildtype TCR, a high affinity TCR, and a chimeric TCR. In another embodiment, the modified TCR comprises at least one disulfide bond. In yet another embodiment, the modified TCR comprises a TCR alpha chain and TCR beta chain. In still another embodiment, the modified TCR comprises a co-stimulatory signaling domain, such as a 4-1BB co-stimulatory signaling domain, at a C' terminal of at least one of the chains. In another embodiment, the TCR beta chain comprises at least one N-deglycosylation. In yet another embodiment, the TCR alpha chain comprises at least one N-deglycosylation. In still another embodiment, the modified TCR comprises at least one murine constant region.

In another embodiment, the modified TCR has higher affinity for the target cell surface antigen than a for a wildtype TCR. In still another embodiment, the target cell surface antigen is selected from the group consisting of viral antigen, bacterial antigen, parasitic antigen, tumor cell associated antigen (TAA), disease cell associated antigen, and any fragment thereof.

In another embodiment, modified T cell described herein further comprises an exogenous nucleic acid encoding a costimulatory molecule, such as CD3, CD27, CD28, CD83, CD86, CD127, 4-1BB, 4-1BBL, PD1 and PD1L. In one embodiment, the method of generating the modified T cell described herein further comprises electroporating a RNA encoding a co-stimulatory molecule into the T cell. In some embodiments where the costimulatory molecule is CD3, the CD3 comprises at least two different CD3 chains, such as CD3 zeta and CD3 epsilon chains.

In another embodiment, the T cell is obtained from the group consisting of peripheral blood mononuclear cells, cord blood cells, a purified population of T cells, and a T cell line.

In yet another embodiment, the method of generating the modified T cell as described herein further comprises expanding the T cell. In one embodiment, expanding the T cell comprises electroporating the T cell with RNA encoding a chimeric membrane protein and culturing the electroporated T cell. In some embodiments where chimeric membrane protein is electroporated in the T cell, the chimeric membrane protein comprises a single chain variable fragment (scFv) against CD3 and an intracellular domain comprises a portion of an intracellular domain of CD28 and 4-1BB. In another embodiment, expanding the T cell comprises culturing the T cell with a factor selected from the group consisting of flt3-L, IL-1, IL-3 and c-kit ligand.

In still another embodiment, the method of generating the modified T cell as described herein further comprising cryopreserving the T cell. In another embodiment, the method described herein further comprises thawing the cryopreserved T cell prior to introducing the nucleic acid into the T cell.

In one embodiment, introducing the nucleic acid is selected from the group consisting of transducing the expanded T cells, transfecting the expanded T cells, and electroporating the expanded T cells.

In yet another embodiment, the method described herein further comprises expressing Klf4, Oct3/4 and Sox2 in the T cells to induce pluripotency of the T cell.

In various embodiments of the above aspects or any other aspect of the invention delineated herein, the invention includes administering the modified T cell to a subject. In one embodiment, the subject has a condition, such as an autoimmune disease. In some embodiments, the autoimmune disease is selected from the group consisting of Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo, Wegener's granulomatosis, and any combination thereof. In another embodiment, the condition is a cancer, such as a cancer selected from the group consisting of breast cancer, prostate cancer, ovarian cancer, cervical cancer, skin cancer, pancreatic cancer, colorectal cancer, renal cancer, liver cancer, brain cancer, lymphoma, leukemia, lung cancer, and any combination thereof.

In another embodiment, the method described herein further comprises inducing lysis, such as antibody-dependent cell-mediated cytotoxicity (ADCC), of the target cell or tissue.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A shows the CRISPR gRNA targeting sites within the genomic locus of TCR-$\alpha$ and $\beta$ constant region. Each exon is shown by a block. Black blocks represent coding regions. Grey columns represent non-coding regions. Thirteen gRNAs were designed to target exon 1 of the TCR $\alpha$ constant region (TRAC), 10 gRNAs target a conserved sequence on exon 1 of the TCR $\beta$ constant regions 1 (TRBC1) and 2 (TRBC2), and 10 gRNAs target exon1 of the beta-2 microglobin gene. FIG. 1B shows a typical gRNA scaffold sequence (SEQ ID NO: 14). gRNA PCR products were generated by overlap PCR and cloned into MSGV vector with a T7 promoter. FIG. 1C shows Sanger sequencing results (SEQ ID NOs: 69-72) showing that multiple peaks exist in 293T TCR TRAC and TRBC genomic PCR products after transfection of CAS9 mRNA and gRNAs (SEQ ID NOs: 15 and 16) into the cells.

FIG. 2, comprising FIGS. 2A-2E, shows the disruption of the TCR 4-CD3 complex in primary T cells. FIG. 2A is a table showing the parameters used for electroporating CAS9 mRNA and gRNA into primary T cells with BTX830. 360V 1 ms with 2 mm cuvettes yielded the best mean fluorescent intensity (MFI) and efficiency for electroporating day 3 beads stimulated primary T cells. FIG. 2B is a panel of graphs showing T cells incubated at 32° C. 5% $CO_2$ having a much higher MFI than normal 37° C. 5% $CO_2$ condition. FIG. 2C is a schematic illustration of the CRISPR system transferred into primary T cells. CAS9 mRNA and gRNA were electro-transferred into T cells three days after bead stimulation of primary T cells. T cells were then cultured with 100 IU/mL of IL-2 and some cells were incubated at 32° C. 5% $CO_2$ for 1 day and then for another 7 to 9 days. CD3 expression was analyzed on days 7-9 after electroporation by flow cytometry. FIG. 2D is a panel of graphs showing that the targeting efficiency at 37° C. was about 2.5 times higher than at 32° C. FIG. 2E is a panel of graphs showing down regulation of CD3 on day 6 after electro-transfer of varying amounts and ratios of CAS9 and gRNA targeting TCRβ. CD3 expression was analyzed by staining for CD3. The representative flow data at day 6 after electroporation is shown. Quadrant represent the percentage of CD3 negative cells in T-cell populations.

FIG. 3, comprising FIGS. 3A-3D, shows that TCR$^{neg}$ alpha or beta knock out in T cells can be enriched by depletion of TCR$^{pos}$ T cells. FIG. 3A is a panel of graphs showing CD3 expression before and after micro-bead depletion of TCR$^{neg}$ alpha or beta knock out in T cells. Flow cytometry illustrates expression of CD3. Numbers in the lower right quadrant represent the percentage of CD3 negative cells in T-cell populations. FIG. 3B is a panel of sequencing graphs (SEQ ID NOs: 73-76) showing that multiple peaks were observed in CD3$^{neg}$ enriched T cell genomic PCR products. TRAC-gRNA-5 and TRBC-gRNA-7 sequences are also shown (SEQ ID NOs: 15 and 16). FIG. 3C is a panel of graphs showing the CD4 and CD8 T cell repertoire analysis after CD3 micro-bead enrichment in single alpha chain, beta chain, and alpha beta double knock out T cells modified with CRISPR. Data shows the ratio of CD8 T cell population was enriched by CRISPR modification, suggesting CD8 T cell may be more easily modified than CD4 T cells. FIG. 3D shows sequencing results (SEQ ID NOs: 19-43) of deletions and insertions introduced to the TCR alpha and beta locus after CRISPR modification.

FIG. 4, comprising FIGS. 4A-4C, shows that multiple electro-transfers of gRNA greatly improved the targeting efficiency of CRISPR system in primary T cells. FIG. 4A is a panel of graphs showing that multiple electroporations of gRNAs greatly improved the targeting efficiency. Electroporating T cells up to three times within 24 hours gave the highest targeting efficiency, nearly 80%. In the initial experiment, only a 15% percent of TCR targeting efficiency was achieved in T cells. Sustained expression of CAS9 was observed after electro-transfer of CAS9 mRNA into the T cells. A likely reason for low cleavage efficiency may be due to rapid degradation of gRNAs. A higher CD3 negative population was obtained. FIG. 4B is a panel of graphs showing that capping impairs the function of gRNA, while early introduction of gRNAs in a second round yielded higher efficiencies. FIG. 4C is a panel of graphs showing that multiple electro-transfers of gRNA targeting TRAC and TRBC in ND221 gave a cleavage rate of approximately 64.5% and 57.5%, respectively.

FIG. 5, comprising FIG. 5A is a panel of graphs showing that TCR$^{neg}$ T cells restored CD3 expression after re-introduction of TCR alpha and beta chains into TCR$^{neg}$ T cells. CD3 and Vb13.1 were detected after electroporating TCR alpha and beta chain into TCR$^{neg}$ T cells. CD3 expression level was comparable to TCR$^{pos}$ T cells. FIG. 5B is a panel of graphs showing fold of expansion after different conditions used to stimulate TCR$^{neg}$ T cells. PBMC REP yielded approximately 500 fold expansion, while CD3/CD28 beads, or K562 aAPC re-stimulation yielded about 25-58 fold expansion.

FIG. 6, comprising FIG. 6A is a panel of graphs showing TCR$^{neg}$ T cell phenotype characteristics after expansion under different conditions. FIG. 6B is a panel of graphs showing TCR$^{neg}$ T cell phenotype characteristics after expansion under different conditions.

FIG. 7, comprising FIG. 7A is a panel of graphs showing that TCR$^{neg}$ T cells could be re-directed by introduction of an anti NY-ESO 1G4 TCR in the cells. Compared with CAS9 MOCK group, when re-directed by 1G4 TCR, TCR$^{neg}$ T cells showed a higher level of Vb13.1 expression due to less miss-pairing of exo and endogenous TCR alpha and beta chains. FIG. 7B is a panel of graphs showing that TCR$^{neg}$ T cells re-directed with 1G4 TCR had high de-granulation activity when cocultured with a tumor (Nalm6-ESO) cell line. FIG. 7C is a graph showing that TCR$^{neg}$ T cells re-directed with 1G4 TCR had high cytotoxicity against a tumor cell line.

FIG. 9, comprising FIG. 9A shows sequencing data (SEQ ID NOs: 77 and 78) of CRISPRs able to disrupt the beta-2 microglobin locus in HEK293 cells. B2m-gRNA-10 sequence is also shown (SEQ ID NO: 44). FIG. 9B is a panel of graphs showing that bHLA-CLASS I negative T cell population was generated by disruption of beta-2 microglobin. FIG. 9C is a panel of graphs showing that cIFNg improved the targeting efficiency of beta-2 microglobin in primary T cells. FIG. 9D is a panel of graphs showing that HLA-CLASS I$^{neg}$ T cells were enriched by microbead depletion.

FIG. 11, comprising FIG. 11A is a panel of graphs showing that CD4 and CD8 T cells were stimulated with CD3/CD28 dynabeads. Three days after stimulation, expanded T cells were electroporated with CAS9 mRNA, together with TCR alpha, beta constant region (TRAC,TRBC) and beta-2 microglobin targeting gRNAs. Both TCR expression and HLA-CLASS I expression were evaluated using anti-CD3 monoclonal antibody (mAb) and anti-beta-2 microglobin mAb six days after electroporation. Numbers represent the percentage of population in each quadrant. FIG. 11B is a schematic illustrating isolation of HLA-CLASS I and TCR alpha and beta chain triple knock out T cells. FIG. 11C is a panel of graphs showing electroporation efficiency tested by GFP expression. FIG. 11D is a panel of graphs showing re-introduction of TCR alpha and beta chains into TCR$^{neg}$ T cells measured by flow cytometry. About 64% of alpha negative and about 14% beta negative population was observed in total TCR$^{neg}$ T cells.

FIG. 12, comprising FIG. 12A is an image showing Sanger sequencing results (SEQ ID NOs: 79 and 80) of multiple peaks when FAS was knocked out in 293T cells. FAS-gRNA-7 sequence is also shown (SEQ ID NO: 45). FIG. 12B is a panel of graphs showing FACS data revealing surface expression of FAS protein was disrupted by CRIS-PRs. FIG. 12C is a panel of images showing FAS protein was replaced by GFP after homologous recombination with CRISPRs. FIG. 12D is a panel of graphs of FACS data showing the percentage of homologous recombinations with CRISPRs.

FIG. 14, comprising FIG. 14A is an image showing Sanger sequencing results (SEQ ID NOs: 81 and 82) of multiple peaks when PD1 were targeted in 293T cells. PD1-gRNA-2 sequence is also shown (SEQ ID NO:

46). FIG. 14B is a panel of graphs showing FACS data of surface expression of PD1 protein disrupted by CRISPRs.

FIG. 15, comprising FIGS. 15A and 15B, shows knock out of CTLA4 in 293T and primary cells, such as CCD1079-SK. FIG. 15A is an image showing Sanger sequencing results (SEQ ID NOs: 83 and 84) of multiple peaks when CTLA4 were targeted in 293T cells. CTLA-4-gRNA-2 sequence is also shown (SEQ ID NO: 47). FIG. 15B is an image showing sequence data after limiting dilution and single cell expansion. Sanger sequencing results (SEQ ID NOs: 48-60) identified the deletions and insertions at the CTLA4 genomic locus.

FIG. 17, comprising FIG. 17A is a panel of images showing morphological change during the process of reprogramming FAS$^{neg}$ T cells to iPSCs. Typical embryonic stem cell morphology formation indicating FAS-$^{neg}$ T cells can be induced to pluripotent state. FIG. 17B is a graph showing that FAS$^{neg}$ T cells were reprogrammed to iPSCs at an efficiency of about 5 times of the wild type counterparts. p53 deficient cell lines have been reported as easier to reprogram due to the hinderance of the apoptosis pathway. FAS knock out may facilitate the reprogramming process by a similar mechanism.

FIG. 18, comprising FIG. 18A is a panel of images showing ES-like morphology formed by CD3$^{neg}$ TCR alpha or beta chain knock out T cells under defined reprogramming conditions. The morphology remains constant after several passages. FIG. 18B is a series of graphs showing that reprogramming CD3$^{neg}$ T cells was about 5 time more efficient than the wild type counterparts, suggesting that TCR knock-out may play a role in the process of T cell reprogramming or affect the cell viability after Sendai virus infection.

FIG. 20, comprising FIGS. 20A and 20B, shows TCR knockout by CAS9 RNA and gRNA. Six days after elec-troporation, cells were analyzed for TCR expression by assessing CD3.

FIG. 23, comprising FIG. 23A shows TCR expression of T cells electroporated with TCR siRNA (solid open histo-gram), control siRNA (dotted open histogram) and T cells without any siRNA (filled histogram). FIG. 23B shows transgene (TCR vb13.1) expression of wild type NY-ESO-1 TCR (wt) or modified TCR (SD) RNA electroporated T cells with TCR siRNA, control siRNA, or no siRNA. FIG. 23C shows NY-ESO-1 tetramer staining of wild type NY-ESO-1 TCR (wt) or modified TCR (SD) RNA electroporated T cells with TCR siRNA, control siRNA, or no siRNA. FIG. 23D shows specific lysis of a HLA-A2/NY-ESO-1 positive tumor line by TCR siRNA knockdown, wildtype NY-ESO-1 TCR RNA electroporated T cells.

FIG. 27 is a panel of graphs and a table showing fold expansion of CD19 positive cells after stimulation with irradiated CD19 presenting K562 cells.

FIG. 49 is a panel of images showing the strategy of introducing CRISPR/Cas9 into T cells. Schematic represen-tation of gRNAs driven by the T7 promoter is shown on the left. Schematic representation of the generation of gene-edited antigen-specific T cells using the CRISPR system is shown on the right. T cells were electroporated with Cas9 mRNA and gRNAs targeting a specific gene 3 days after CD3/CD28 bead stimulation and then cultured for 24 hours at 32° C. in the presence of 1L2 before being returned to the normal 37° C. culture condition. Specific gene-disrupted T cells were sorted on day 8 and redirected with CAR or TCR by lentiviral transduction or mRNA electroporation gene transfer.

FIG. 51B is a table showing the targeting efficiency calculated by both flow cytometry and clonal sequencing.

FIG. 53A is an image of indels (in gene disruption) observed by clonal sequence analysis of PCR amplicons after CRISPR-mediated recombination of the TCR α and β locus (SEQ ID NOs: 19-43).

FIG. 79B shows the sequences of the targeting events in MDA231 cells after Adenoviral-CRISPR manipulation. PD1 PCR products were cloned into TOPO vector and sequenced (SEQ ID NOs: 17, 18, and 65-68).

FIG. 80 is a chart showing that a decrease in gRNA use improved T cell fold expansion and only slightly decreased knockout efficiency.

FIG. 81 is a chart showing the parameters used for optimizing electroporation conditions to obtain high CD3/B2M knockout efficiency with improved T cell fold expansion. Compared with standard electroporation (EP) conditions in a 2 mm cuvette (EP #10-13) or 4 mm cuvette. High CD3/B2M knockout efficiency was observed with improved T cell fold expansion (EP #1 and 5).

FIG. 82 is a chart showing optimization of EP conditions to achieve maximum fold expansion with tolerable knockout efficiency.

FIG. 83 is a chart showing additional optimization of EP conditions to achieve maximum fold expansion with tolerable knockout efficiency.

FIG. 84 diagrams the T cell stimulation, lentiviral transduction and CRISPR electroporation procedure.

FIG. 85 is a chart showing T cell numbers (upper chart) and fold expansion (lower chart) after the electroporation and culturing procedure.

FIG. 86 is a panel of graphs showing the average expansion of T cells. Fold expansion of the T cells transduced with CD19 CAR alone (TD alone) or transduced with CD19 CAR and edited with CRISPR (TD/KO) (left graph). Fold expansion of the T cells on day 10 is shown in the right graph.

Figure 89:
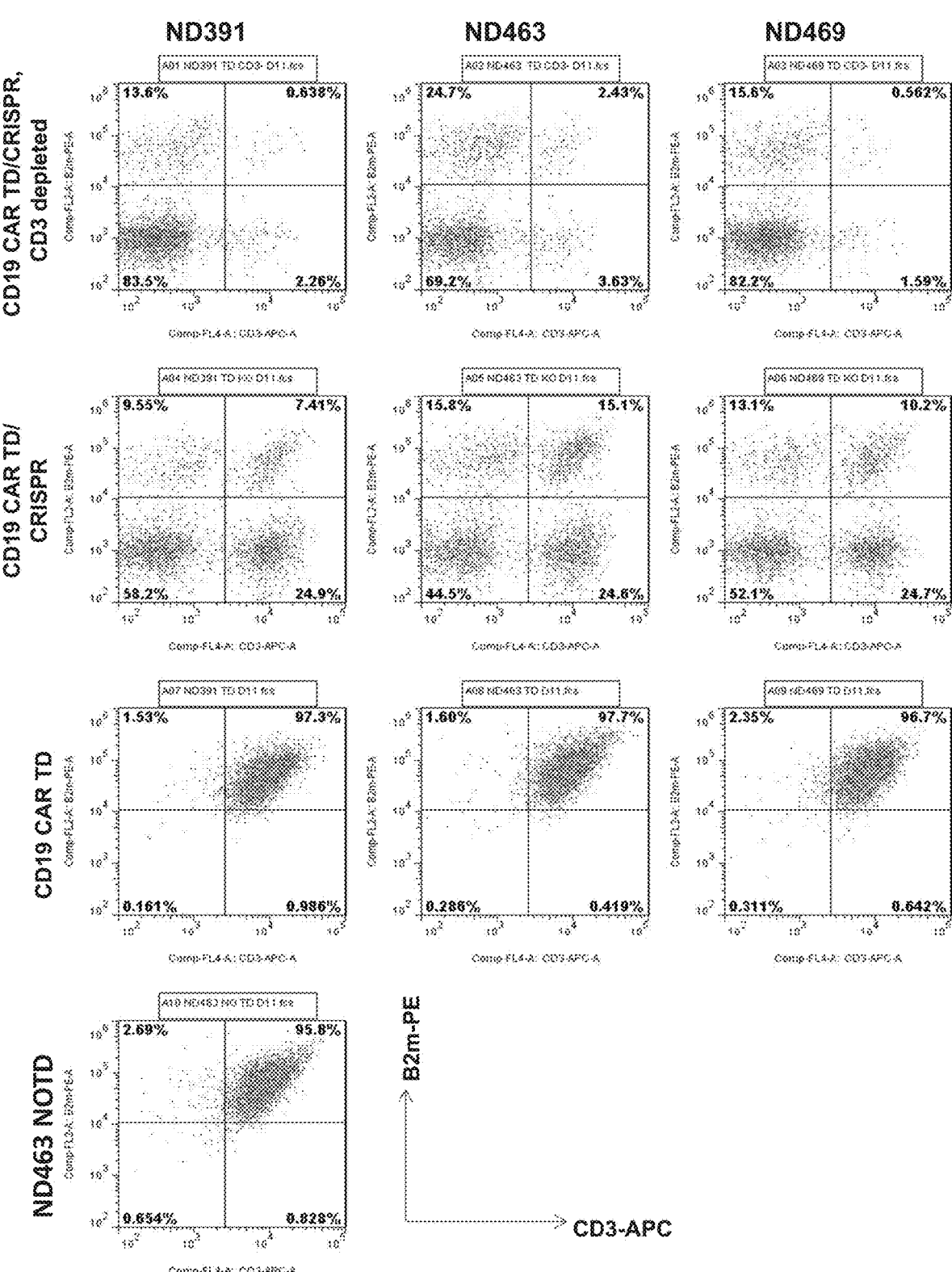

FIG. 89 is a panel of graphs showing CD3/B2M expression on day 11 in CD19 CAR TD (transduced)/CRISPR electroporated, CD3 depleted T cells; CD19 CAR TD/CRISPR electroporated T cells; and CD19 CAR TD T cells. ND463 non-transduced (NOTD) were used as a negative control.

Figure 90:
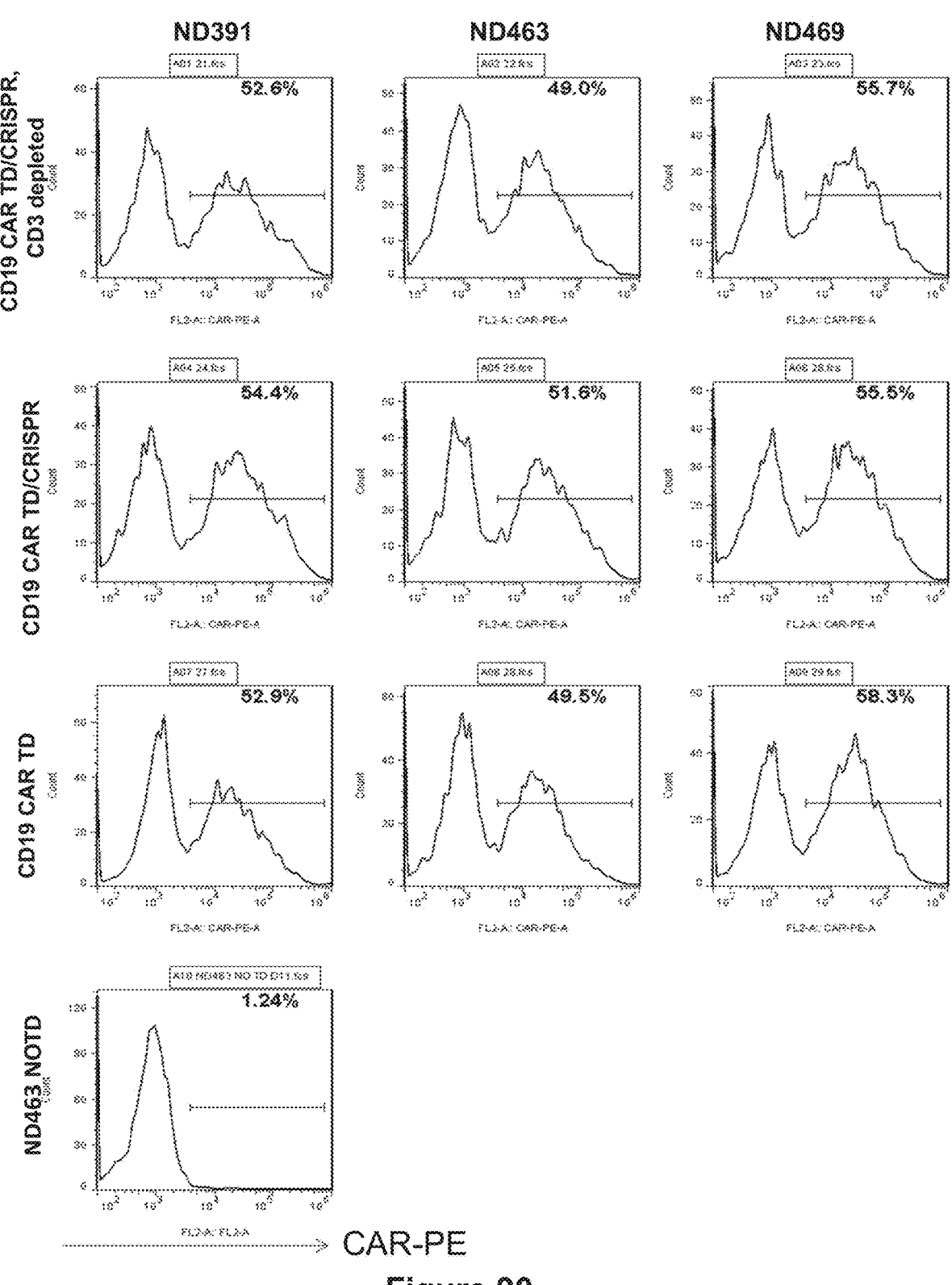

FIG. 90 is a panel of graphs showing CD19 CAR expression on day 11 in CD19 CAR TD (transduced)/CRISPR electroporated, CD3 depleted T cells; CD19 CAR TD/CRISPR electroporated T cells; and CD19 CAR TD T cells. ND463 non-transduced (NOTD) were used as a negative control.

Figure 91:
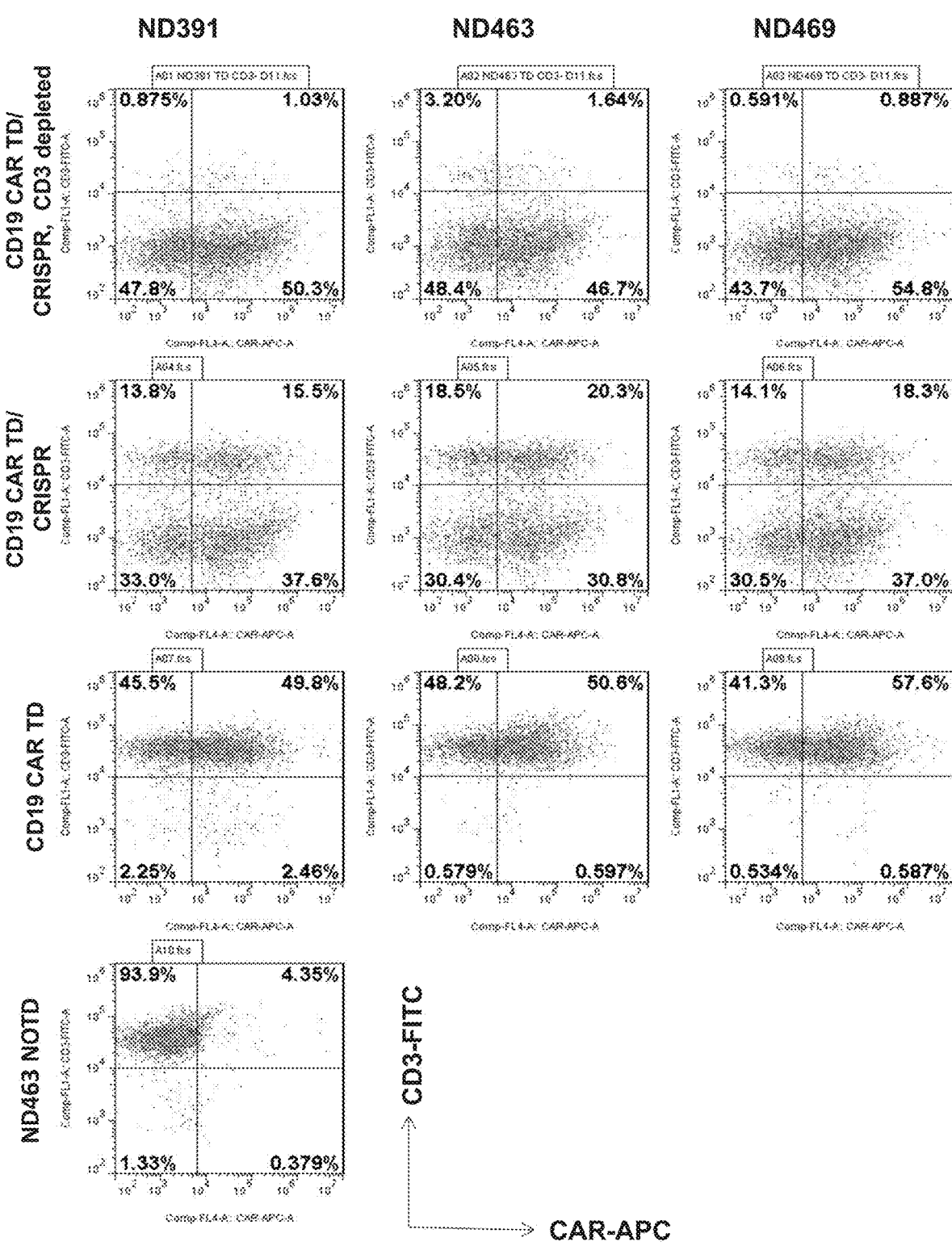

FIG. 91 is a panel of graphs showing CD3/B2M/CAR expression on day 11 in CD19 CAR TD (transduced)/CRISPR electroporated, CD3 depleted T cells; CD19 CAR TD/CRISPR electroporated T cells; and CD19 CAR TD T cells. ND463 non-transduced (NOTD) were used as a negative control.

FIG. 92 is a chart summarizing CD3/B2M/CAR expression in CD19 CAR TD (transduced)/CRISPR electroporated, CD3 depleted T cells; CD19 CAR TD/CRISPR electroporated T cells; and CD19 CAR TD T cells.

Figure 93:
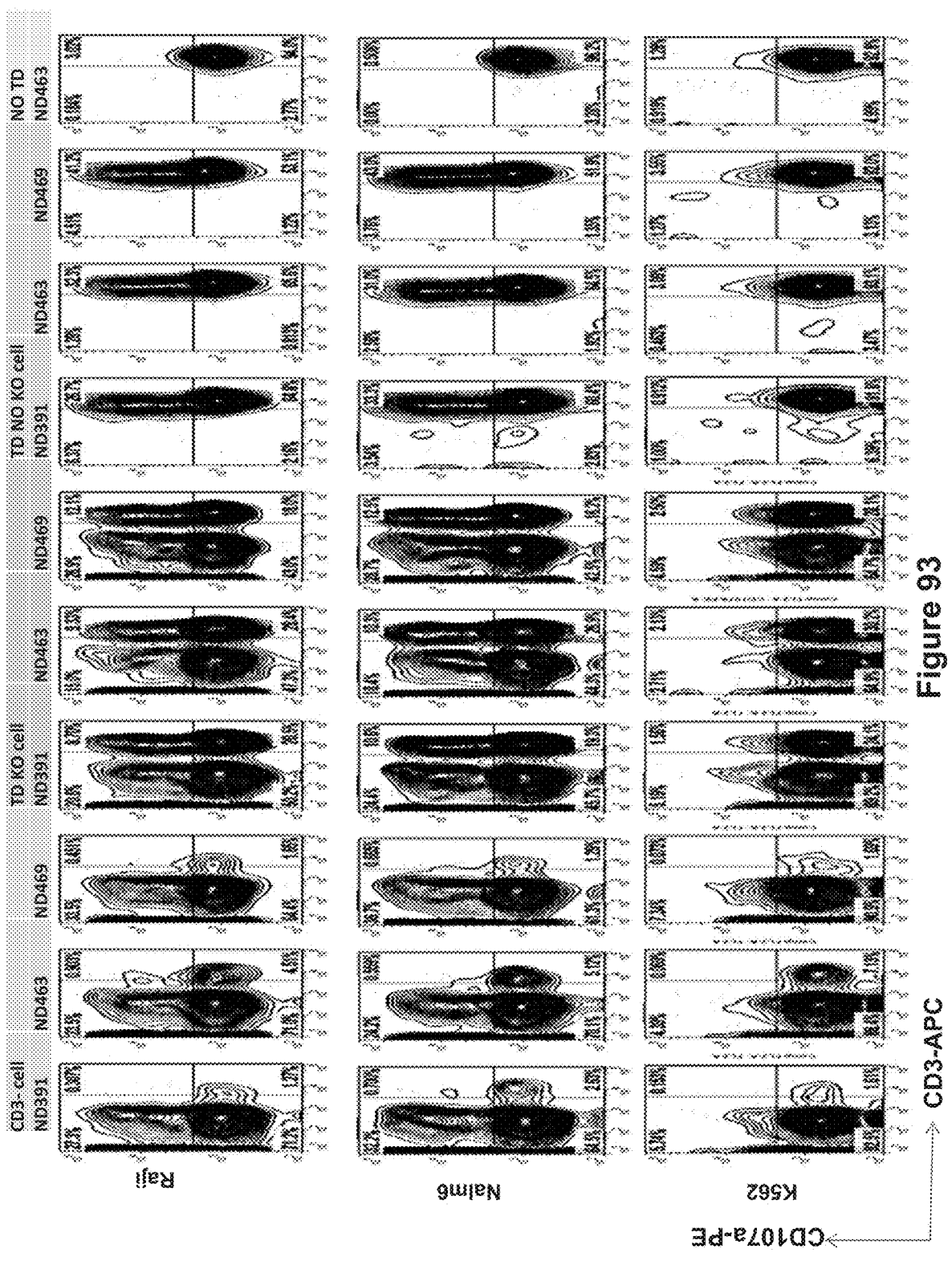

FIG. 93 is a panel of graphs showing CD107a upregulation in CD19 CAR TD (transduced)/CRISPR electroporated, CD3 depleted T cells; CD19 CAR TD/CRISPR electroporated T cells; and CD19 CAR TD T cells.

Figure 94:
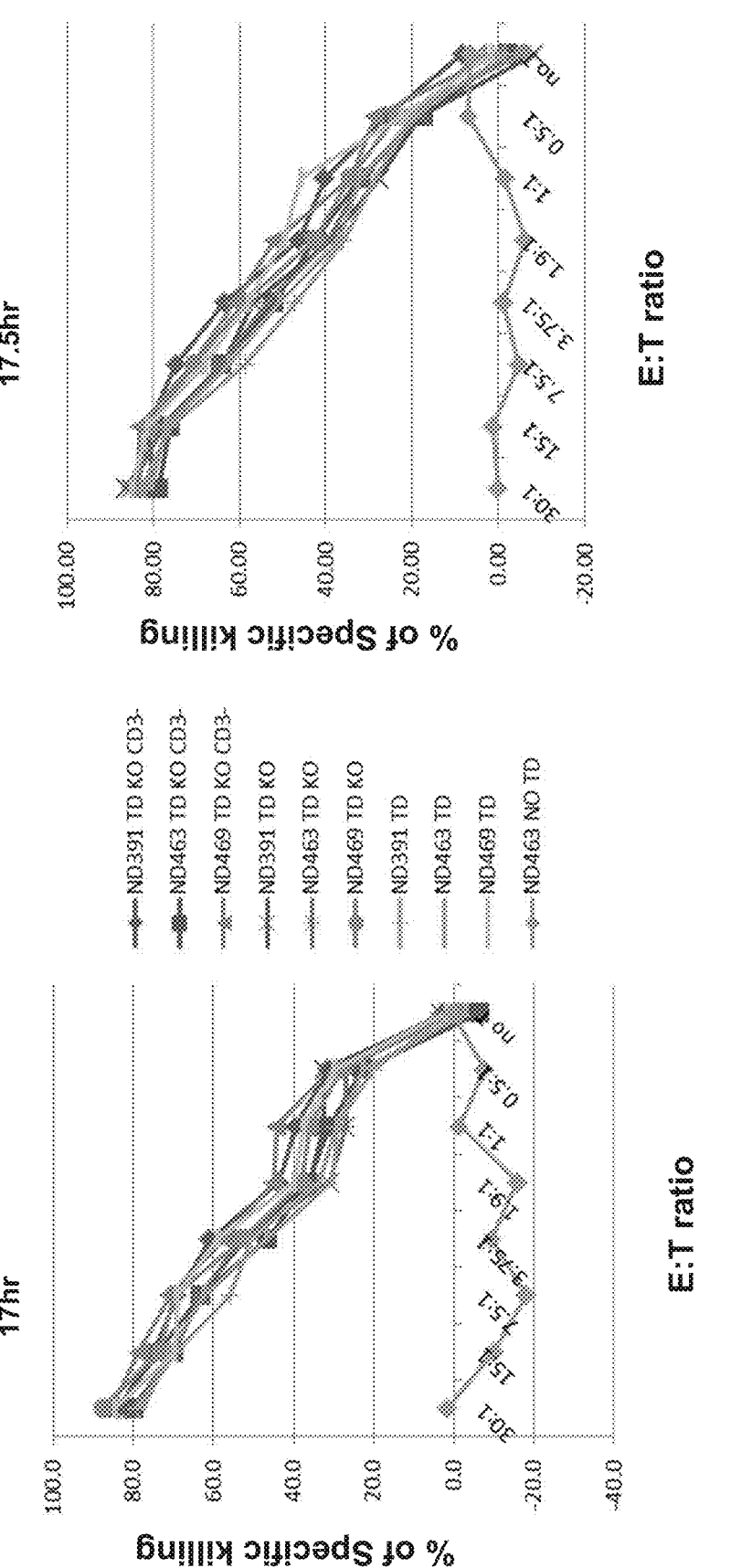

FIG. 94 is a panel of graphs showing lytic activity of the T cells on day 11.

Figure 95:
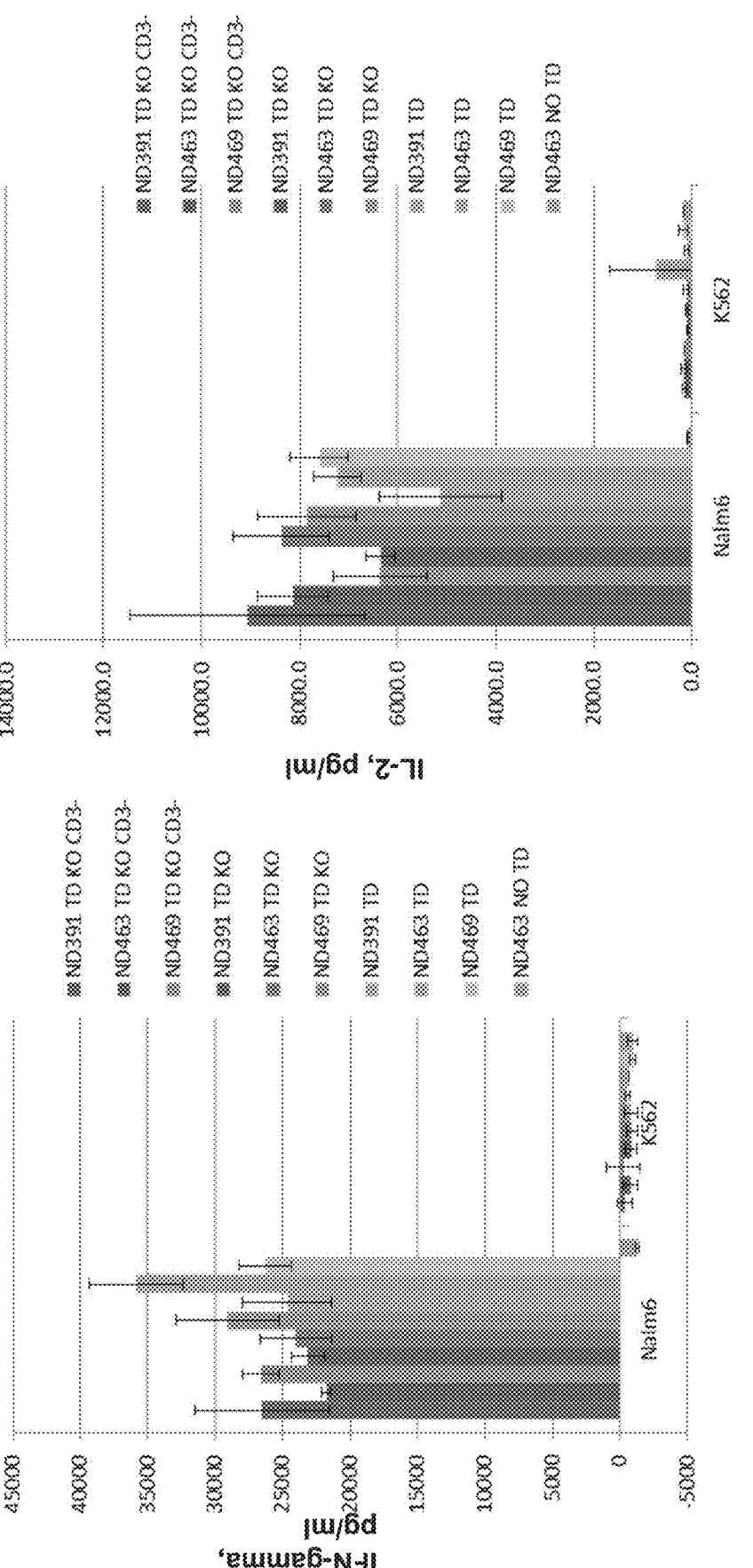

FIG. 95 is a panel of graphs showing cytokine production of the T cells on day 11.

Figure 96:
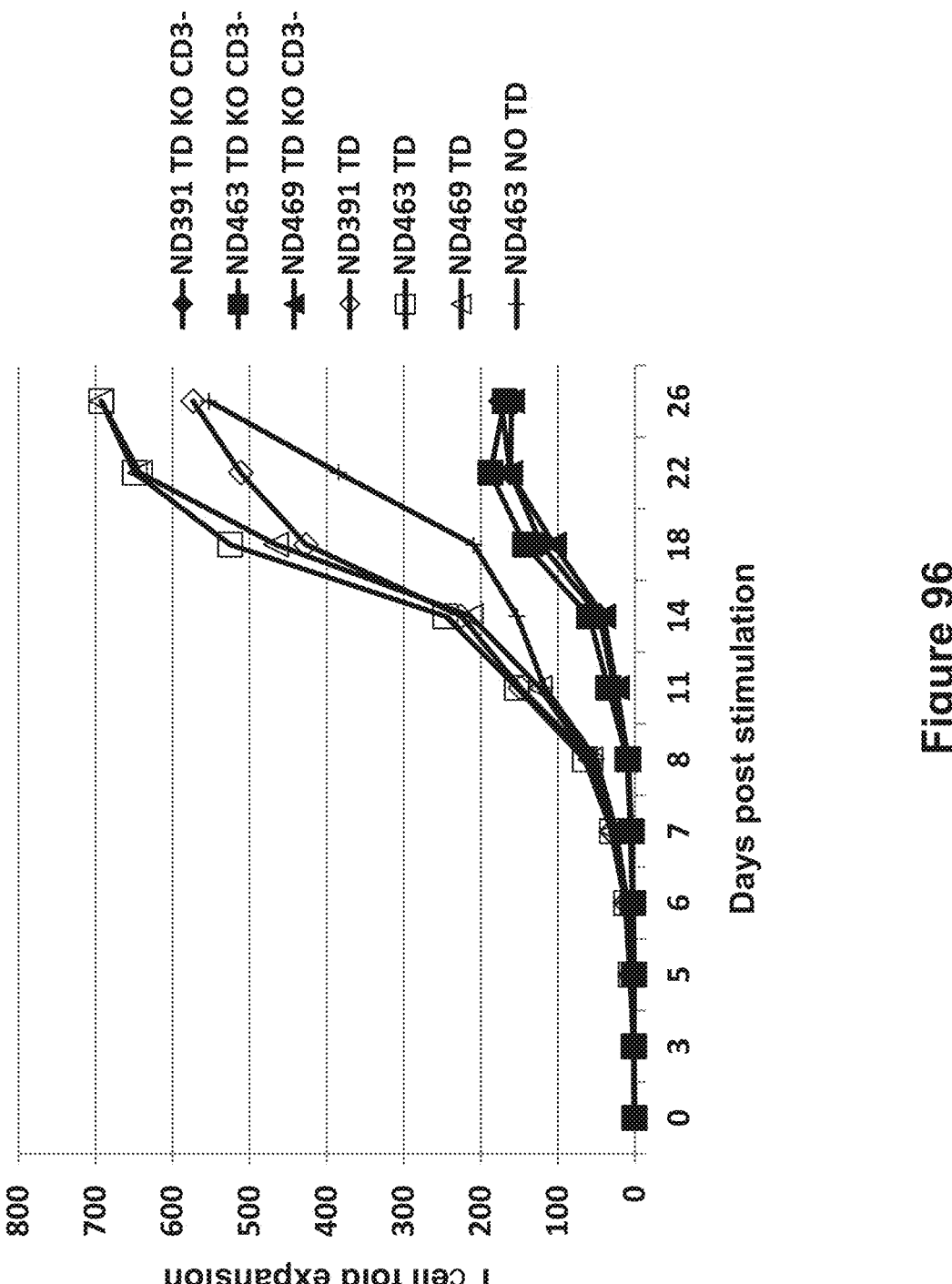

FIG. 96 is a panel of graphs showing T cell expansion. No abnormal T cell growth was observed.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)₂, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')₂, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In some aspects, CARs comprise fusions of single-chain variable fragments (scFv) derived monoclonal antibodies, fused to CD3-zeta transmembrane and intracellular domain. The specificity of CAR designs may be derived from ligands of receptors (e.g., peptides). In some embodiments, a CAR can target cancers by redirecting the specificity of a T cell expressing the CAR specific for tumor associated antigens.

The term "cleavage" refers to the breakage of covalent bonds, such as in the backbone of a nucleic acid molecule. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

The term "CRISPR/CAS," "clustered regularly interspaced short palindromic repeats system," or "CRISPR" refers to DNA loci containing short repetitions of base sequences. Each repetition is followed by short segments of spacer DNA from previous exposures to a virus. Bacteria and archaea have evolved adaptive immune defenses termed CRISPR-CRISPR-associated (Cas) systems that use short RNA to direct degradation of foreign nucleic acids. In bacteria, the CRISPR system provides acquired immunity against invading foreign DNA via RNA-guided DNA cleavage.

In the type II CRISPR/Cas system, short segments of foreign DNA, termed "spacers" are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Recent work has shown that target recognition by the Cas9 protein requires a "seed" sequence within the crRNA and a conserved dinucleotide-containing protospacer adjacent motif (PAM) sequence upstream of the crRNA-binding region.

To direct Cas9 to cleave sequences of interest, crRNA-tracrRNA fusion transcripts, hereafter referred to as "guide RNAs" or "gRNAs" may be designed, from human U6 polymerase III promoter. CRISPR/CAS mediated genome editing and regulation, highlighted its transformative potential for basic science, cellular engineering and therapeutics.

The term "CRISPRi" refers to a CRISPR system for sequence specific gene repression or inhibition of gene expression, such as at the transcriptional level.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies.

Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

As used here, "induced pluripotent stem cell" or "iPS cell" refers to a pluripotent stem cell that is generated from adult cells, such as T cells. The expression of reprogramming factors, such as Klf4, Oct3/4 and Sox2, in adult cells convert the cells into pluripotent cells capable of propagation and differentiation into multiple cell types.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "Sendai virus" refers to a genus of the Paramyxoviridae family. Sendai viruses are negative, single stranded RNA viruses that do not integrate into the host genome or alter the genetic information of the host cell. Sendai viruses have an exceptionally broad host range and are not pathogenic to humans. Used as a recombinant viral vector, Sendai viruses are capable of transient but strong gene expression.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (a) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Universal T cells that avoid graft vs host disease (GVHD) are highly desired in the clinical setting. However, use of allogeneic T cells is a risk because of rejection by the host's immune system through the recognition of HLA-A molecules. Targeting strategies to manipulate multiple genes are complicated and efforts have yielded low efficiency in T cells without preventing GVHD and host vs graft reactions simultaneously.

The FAS receptor/FAS ligand (FAS/FASL) apoptosis signaling pathway negatively regulates T cell function. PD1 and CTLA4 are two major inhibitory signaling pathways in T cells. The enhanced anti-tumor immunity that results from antibody-mediated blockade of CTLA-4, PD-1 or PD-L1 suggests the potential to improve efficiency of immunotherapies by inhibiting these pathways. The invention includes the generation of modified T cells where the TCR α and β chain, beta-2 microglobulin, a HLA molecule, CTLA-4, PD-1, and/or FAS are depleted as a means to generate modified T cells with reduced immunogenicity.

The present invention includes methods and compositions for generating a modified T cell by knocking down endogenous gene expression and expressing either a modified T cell receptor or a chimeric antigen receptor. In some embodiments, the invention includes a method for generating the modified T cell. Such a modified T cell can be included in a therapeutic composition and administered to a patient in need thereof.

Knockdown of Endogenous Gene Expression

The present invention includes downregulation of endogenous gene expression in a T cell, such as downregulating an alpha and/or beta chain of the T cell receptor (TCR), beta-2 microglobulin, CTLA-4, FAS, PD1, or a major histocompatibility complex protein such as a HLA molecule. In one embodiment, the T cell with downregulated gene expression has reduced immunogenicity in an allogeneic environment. In another embodiment, the T cell with reduced immunogenicity expresses a modified TCR or a CAR for targeted effector activity.

In one aspect, the invention includes a method for generating a modified T cell comprising introducing a nucleic acid into a T cell capable of downregulating endogenous gene expression, where the gene is selected from the group consisting of TCR α chain, TCR β chain, beta-2 microglobulin, a HLA molecule, CTLA-4, PD1, and FAS. Downregulating expression of an endogenous gene that is involved in producing an immune response to a cell, such as TCR α chain, TCR β chain, beta-2 microglobulin, or a HLA molecule, reduces immune-mediated rejection of the modified T cell. For example, downregulating expression of endogenous TCR, MHC or beta-2 microglobulin genes removes surface presentation of alloantigens on the T cell that could cause rejection by the host immune system. Also, downregulating an endogenous gene that regulates inhibitory signaling pathways in T cells, such as CTLA-4, PD1, and/or FAS, enhances anti-tumor efficacy of the modified T cell when exposed to an immunosuppressive microenvironment.

In one aspect, a nucleic acid capable of downregulating endogenous gene expression is introduced, such as by electroporation, transfection, or lenti- or other viral transduction, into the T cell. In another aspect, the invention includes a modified T cell comprising an electroporated nucleic acid capable of downregulating endogenous gene expression. In yet another aspect, a modified T cell includes an electroporated nucleic acid capable of downregulating endogenous TCR gene expression. In another aspect, the composition comprising the modified T cell is generated according to a method described herein. In yet another aspect, the invention includes a pharmaceutical composition comprising the modified T cell or a modified T cell generated according to the method described herein and a pharmaceutically acceptable carrier.

The nucleic acid capable of regulating endogenous gene expression may downregulate the endogenous gene expression. In one embodiment, the nucleic acid capable of downregulating endogenous gene expression is selected from the group consisting of an antisense RNA, antigomer RNA, siRNA, shRNA, and a CRISPR system. Endogenous gene expression may be downregulated, knocked-down, decreased, and/or inhibited by, for example, an antisense RNA, antigomer RNA, siRNA, shRNA, a CRISPR system, etc.

CRISPR/Cas

The CRISPR/Cas system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The CRISPR/CAS system can thereby be engineered to cleave virtually any DNA sequence by redesigning the gRNA in cell lines (such as 293T cells), primary cells, and CAR T cells. The CRISPR/CAS system can simultaneously target multiple genomic loci by co-expressing a single CAS9 protein with two or more gRNAs, making this system uniquely suited for multiple gene editing or synergistic activation of target genes.

One example of a CRISPR/Cas system used to inhibit gene expression, CRISPRi, is described in U.S. Publication No.: 2014/0068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In one embodiment, the CRISPR system comprises an expression vector, such as, but not limited to, an pAd5F35-CRISPR vector. In one embodiment, a modified T cell is generated by introducing a Cas expression vector and a guide nucleic acid sequence specific for a gene into a T cell. In another embodiment, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combination thereof.

In one embodiment, inducing the Cas expression vector comprises exposing the T cell to an agent that activates an inducible promoter in the Cas expression vector. In such an embodiment, the Cas expression vector includes an inducible promoter, such as one that is inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

The guide nucleic acid sequence is specific for a gene and targets that gene for Cas endonuclease-induced double strand breaks. The sequence of the guide nucleic acid sequence may be within a loci of the gene. In one embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

The guide nucleic acid sequence may be specific for any gene, such as a gene that would reduce immunogenicity or reduce sensitivity to an immunosuppressive microenvironment. In one embodiment, the gene may include a sequence specific for a T cell receptor (TCR) chain (such as an alpha, beta, gamma and/or delta chain), beta-2 microglobulin, FAS, PD1, a major histocompatibility complex protein (such as a HLA class I molecule and/or HLA class II molecule), CTLA-4, or any combination thereof.

The guide nucleic acid sequence includes a RNA sequence, a DNA sequence, a combination thereof (a RNA-DNA combination sequence), or a sequence with synthetic nucleotides. The guide nucleic acid sequence can be a single molecule or a double molecule. In one embodiment, the guide nucleic acid sequence comprises a single guide RNA.

T Cell Receptor

Adoptive immunotherapy with T cells harboring antigen-specific TCRs have therapeutic potential in the treatment of cancer and certain chronic viral infections. Gene-engineering of T cells with a specific TCR has the advantage of redirecting the T cell to an intracellular antigen. Given that most oncogenic proteins are intracellular, development of a panel of TCRs specific to an oncogenic driver protein has great appeal.

The present invention also includes a modified T cell with downregulated gene expression as described herein and an exogenous T cell receptor (TCR). In one aspect, the invention includes a method for generating a modified T cell comprising introducing a nucleic acid encoding a modified T cell receptor (TCR) comprising affinity for a surface antigen on a target cell into the T cell and a nucleic acid capable of regulating endogenous gene expression selected from the group consisting of TCR α chain, TCR β chain, beta-2 microglobulin, PD1, and FAS, wherein the T cells are capable of expressing the modified TCR.

In another aspect, the invention includes a modified T cell comprising an exogenous nucleic acid encoding a modified T cell receptor (TCR) comprising affinity for a surface antigen on a target cell and a nucleic acid capable of downregulating endogenous gene expression selected from the group consisting of TCR α chain, TCR β chain, beta-2 microglobulin, PD1, and FAS, wherein the T cell expresses the modified TCR and wherein the endogenous gene expression is downregulated in the T cell. The invention also includes a population of cells comprising the modified T cell described herein.

A T cell receptor is a complex of membrane proteins that participate in the activation of T cells in response to the presentation of antigen. Stimulation of the TCR is triggered by major histocompatibility complex molecules (MHC) on antigen presenting cells that present antigen peptides to the T cells and bind to the TCR complexes to induce a series of intracellular signaling cascades.

The TCR is generally composed of six different membrane bound chains that form the TCR heterodimer responsible for ligand recognition. TCRs exist in alpha/beta and gamma/delta forms, which are structurally similar but have distinct anatomical locations and functions. In one embodiment, the TCR comprises a TCR alpha and TCR beta chain, such as the nucleic acid encoding the TCR comprises a nucleic acid encoding a TCR alpha and a TCR beta chain. In another embodiment, a TCR alpha chain or a TCR beta chain or both chains comprise at least one N-deglycosylation.

Each chain is composed of two extracellular domains, a variable and constant domain. In one embodiment, the TCR comprises at least one murine constant region. The constant domain is proximal to the cell membrane, followed by a transmembrane domain and a short cytoplasmic tail. In one embodiment, the modified TCR comprises a cytoplasmic domain including a co-stimulatory signaling domain, such as a 4-1BB co-stimulatory signaling domain. The variable domain contributes to the determination of the particular antigen and MHC molecule to which the TCR has binding specificity. In turn, the specificity of a T cell for a unique antigen-MHC complex resides in the particular TCR expressed by the T cell.

Each of the constant and variable domains may include an intra-chain disulfide bond. In one embodiment, TCR comprises at least one disulfide bond. The variable domains include the highly polymorphic loops analogous to the complementarity determining regions (CDRs) of antibodies. The diversity of TCR sequences is generated via somatic rearrangement of linked variable (V), diversity (D), joining (J), and constant genes.

Functional alpha and gamma chain polypeptides are formed by rearranged V-J-C regions, whereas beta and delta chains consist of V-D-J-C regions. The extracellular constant domain includes a membrane proximal region and an immunoglobulin region.

In one embodiment, the TCR includes a wildtype TCR, a high affinity TCR, and a chimeric TCR. When the TCR is modified, it may have higher affinity for the target cell surface antigen than a wildtype TCR. In embodiments where the TCR is a chimeric TCR, the TCR may include chimeric domains, such as the TCR comprises a co-stimulatory signaling domain at a C' terminal of at least one of the chains. In other embodiment, the TCR may include a modified chain, such as a modified alpha or beta chain. Such modifications may include, but are not limited to, N-deglycosylation, altered domain (such as an engineered variable region to target a specific antigen or increase affinity), addition of one or more disulfide bonds, entire or fragment of a chain derived from a different species, and any combination thereof.

In one embodiment, the TCR comprises specificity to a target cell antigen. The target cell surface antigen may include any type of ligand that defines the surface of a target cell. For example, the target cell surface antigen may be chosen to recognize a ligand that acts as a cell surface marker on target cells associated with a particular disease state. Thus examples of cell surface markers that may act as ligands for the antigen binding domain of the TCR including those associated with viral, bacterial and parasitic infections, autoimmune disease and cancer cells. In one embodiment, the target cell surface antigen includes any tumor associated antigen (TAA) and viral antigen, disease cell associated antigen, or any fragment thereof.

The target cell antigen may include any protein that can be processed and presented by major histocompability complexes. For example, the target antigen may be associated with a particular disease state. Thus examples of cell markers that may act as targets of the TCR include those associated with viral, bacterial and parasitic infections, autoimmune disease and cancer cells. In one embodiment, the target antigen includes any of tumor associated antigens (TAA) and viral antigens, or any fragment thereof.

In one aspect, the invention includes a population of modified T cells comprising a nucleic acid encoding a modified T cell receptor (TCR) comprising affinity for a surface antigen on a target cell and a nucleic acid capable of downregulating endogenous gene expression selected from the group consisting of TCR α chain, TCR β chain, beta-2 microglobulin, a HLA molecule, CTLA-4, PD1, and FAS, wherein the T cells are capable of expressing the modified TCR.

Techniques for engineering and expressing T cell receptors include, but are not limited to, the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

Chimeric Antigen Receptor (CAR)

The present invention also includes a modified T cell with downregulated gene expression as described herein and a CAR. Thus, the present invention encompasses the modified T cell comprising a CAR or a nucleic acid encoding a CAR, wherein the CAR includes an antigen binding domain, a transmembrane domain and an intracellular domain.

In one aspect, the invention includes a method of generating a modified T cell comprising introducing a nucleic acid capable of downregulating endogenous gene expression selected from the group consisting of TCR α chain, TCR β chain, beta-2 microglobulin, a HLA molecule, CTLA-4, PD1, and FAS into a T cell and a nucleic acid encoding a chimeric antigen receptor (CAR) into the T cell, wherein the CAR comprises an antigen binding domain, a transmembrane domain and an intracellular domain of a co-stimulatory molecule.

In another aspect, the invention includes a modified T cell comprising a nucleic acid capable of downregulating endogenous gene expression and a nucleic acid encoding a chimeric antigen receptor (CAR), wherein the downregulated gene expression is selected from the group consisting of TCR α chain, TCR β chain, beta-2 microglobulin, a HLA molecule, CTLA-4, PD1, and FAS, and wherein the CAR comprises an antigen binding domain, a transmembrane domain and an intracellular domain of a co-stimulatory molecule. In one embodiment, the modified T cell further comprises an exogenous nucleic acid encoding a modified TCR comprising affinity for a surface antigen on a target cell as described elsewhere herein. The invention also includes a population of cells comprising the modified T cell described herein.

One or more domains or a fragment of a domain of the CAR may be human. In one embodiment, the present invention includes a fully human CAR. The nucleic acid sequences coding for the desired domains can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than as a cloned molecule.

Example of CARs are described in U.S. Pat. Nos. 8,911,993, 8,906,682, 8,975,071, 8,916,381, 9,102,760, 9,101,584, and 9,102,761, all of which are incorporated herein by reference in their entireties.

Antigen Binding Domain

In one embodiment, the CAR comprises an antigen binding domain that binds to an antigen on a target cell. Examples of cell surface markers that may act as an antigen that binds to the antigen binding domain of the CAR include those associated with viral, bacterial and parasitic infections, autoimmune disease, and cancer cells.

The choice of antigen binding domain depends upon the type and number of antigens that are present on the surface of a target cell. For example, the antigen binding domain may be chosen to recognize an antigen that acts as a cell surface marker on a target cell associated with a particular disease state.

In one embodiment, the antigen binding domain binds to a tumor antigen, such as an antigen that is specific for a tumor or cancer of interest. In one embodiment, the tumor antigen of the present invention comprises one or more antigenic cancer epitopes.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof.

The antigen binding domain may bind one or more antigens, such as but not limited to CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bD-Galp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D);

chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WTi); Cancer/testis antigen 1 (NY-ESO-1); Cancer/testis antigen 2 (LAGE-la); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYPiB1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLECl12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some instances, it is beneficial for the antigen binding domain to be derived from the same species in which the CAR will ultimately be used in. For example, for use in humans, it may be beneficial for the antigen binding domain of the CAR to comprise a human antibody, humanized antibody as described elsewhere herein, or a fragment thereof.

It is also beneficial that the antigen binding domain is operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

Transmembrane Domain

With respect to the transmembrane domain, the CAR can be designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Intracellular Domain

The intracellular domain or otherwise the cytoplasmic domain of the CAR is responsible for activation of the cell in which the CAR is expressed. The term "intracellular domain" is thus meant to include any portion of the intracellular domain sufficient to transduce the activation signal. In one embodiment, the intracellular domain includes a domain responsible for an effector function. The term "effector function" refers to a specialized function of a cell. Effector function of a T cell, for example, may be cytolytic activity or helper activity including the secretion of cytokines.

In one embodiment, the intracellular domain of the CAR includes a domain responsible for signal activation and/or transduction. The intracellular domain may transmit signal activation via protein-protein interactions, biochemical changes or other response to alter the cell's metabolism, shape, gene expression, or other cellular response to activation of the chimeric intracellular signaling molecule.

Examples of an intracellular domain for use in the invention include, but are not limited to, the cytoplasmic portion of the T cell receptor (TCR) and any co-stimulatory molecule that acts in concert to initiate signal transduction following antigen receptor engagement, as well as any derivative or variant of these elements and any synthetic sequence that has the same functional capability. In one embodiment, the intracellular domain of the CAR comprises dual signaling domains. The dual signaling domains may include a fragment or domain from any of the molecules described herein.

Examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

In one embodiment, the intracellular domain of the CAR includes any portion of a co-stimulatory molecule, such as at least one signaling domain from CD3, CD27, CD28, ICOS, 4-1BB, PD-1, T cell receptor (TCR), any derivative or variant thereof, any synthetic sequence thereof that has the same functional capability, and any combination thereof.

Between the antigen binding domain and the transmembrane domain of the CAR, or between the intracellular domain and the transmembrane domain of the CAR, a spacer domain may be incorporated. As used herein, the term "spacer domain" generally means any oligo- or polypeptide that functions to link the transmembrane domain to, either the antigen binding domain or, the intracellular domain in the polypeptide chain. In one embodiment, the spacer domain may comprise up to 300 amino acids, preferably 10 to 100 amino acids and most preferably 25 to 50 amino acids. In another embodiment, a short oligo- or polypeptide linker, preferably between 2 and 10 amino acids in length may form the linkage between the transmembrane domain and the intracellular domain of the CAR. An example of a linker includes a glycine-serine doublet.

Human Antibodies

It may be preferable to use human antibodies or fragments thereof when using bispecific antibodies or the antigen binding domains of a CAR. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The bispecific antibody can also include an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially follow- ing the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229, 275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human anti- body can be humanized, where specific sequences or regions of the antibody are modified to increase similarity to an antibody naturally produced in a human. For instance, in the present invention, the antibody or fragment thereof may comprise a non-human mammalian scFv. In one embodi- ment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/ 5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565, 332, which is incorporated herein in its entirety by refer- ence), and techniques disclosed in, e.g., U.S. Patent Appli- cation Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identi- fied by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhu- man. These nonhuman amino acid residues are often referred to as "import" residues, which are typically taken from an "import" variable domain. Thus, humanized anti- bodies comprise one or more CDRs from nonhuman immu- noglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chi- meric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorpo- rated herein by reference herein in their entirety). Another method uses a particular framework derived from the con- sensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, human- ized antibodies are prepared by a process of analysis of the parental sequences and various conceptual humanized prod- ucts using three-dimensional models of the parental and humanized sequences. Three-dimensional immunoglobulin models are commonly available and are familiar to those skilled in the art. Computer programs are available which illustrate and display probable three-dimensional conforma- tional structures of selected candidate immunoglobulin sequences. Inspection of these displays permits analysis of the likely role of the residues in the functioning of the candidate immunoglobulin sequence, i.e., the analysis of residues that influence the ability of the candidate immuno- globulin to bind the target antigen. In this way, FR residues can be selected and combined from the recipient and import sequences so that the desired antibody characteristic, such as increased affinity for the target antigen, is achieved. In general, the CDR residues are directly and most substan- tially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

Other Molecules

The present invention also includes the modified T cell described herein further comprising a co-stimulatory molecule or a nucleic acid encoding the co-stimulatory molecule. In one embodiment, the modified T cell of the invention further includes an exogenous nucleic acid encoding a co-stimulatory molecule, such that the modified T cell expresses the co-stimulatory molecule. The nucleic acid may be introduced into the T cell by transducing the T cell, transfecting the T cell, or electroporating the T cell. In another embodiment, the co-stimulatory molecule is selected from CD3, CD27, CD28, CD83, CD86, CD127, 4-1BB, 4-1BBL, PD1 and PD1L. In another embodiment, the so-stimulatory molecule includes CD3 and comprises at least two different CD3 chains, such as CD3 zeta and CD3 epsilon chains.

In another embodiment, the modified T cell further comprises KIf4, Oct3/4, and/or Sox2 or a nucleic acid encoding Klf4, Oct3/4, and/or Sox2 to induce pluripotency of the T cell. The T cell can be induced to pluripotency by expressing KIf4, Oct3/4 and Sox2. Klf4, Oct3/4 and Sox2 may be expressed from a nucleic acid, viral vector(s) or RNA molecule(s). In one embodiment, a viral vector encoding for Klf4, Oct3/4 and Sox2 is introduced into the T cell to induce pluripotency. In another embodiment, a Sendai viral vector is introduced into the T cells to induce pluripotency, wherein the Sendai viral vector encodes Klf4, Oct3/4 and Sox2.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, a nucleic acid encoding a T cell receptor (TCR) comprising affinity for a surface antigen on a target cell is introduced into the expanded T cells. The nucleic acid encoding the TCR may be the same or separate nucleic acid that is capable of downregulating endogenous TCR gene expression. The nucleic acid encoding the TCR may be introduced into the T cell at the same time or sequentially with the nucleic acid capable of downregulating endogenous TCR gene expression. In one embodiment, the nucleic acid encoding the TCR is introduced prior to the nucleic acid capable of downregulating endogenous TCR gene expression.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the T cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA Transfection

In some embodiments, the RNA encoding a TCR is electroporated into the cells. In one embodiment, the RNA encoding the TCR is in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993, 434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In one embodiment, the method includes electroporating a RNA encoding a TCR alpha and beta chain. The TCR alpha and beta chain can be encoded on the same or separate RNAs. When the alpha and beta are encoded by separate RNAs, the RNA may be co-electroporated.

In another embodiment, the method may further include electroporating a nucleic acid encoding a costimulatory molecule. The costimulatory molecule nucleic acid may be co-electroporated with the TCR RNA.

Sources of T Cells

Prior to expansion, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Chimeric Membrane Protein

Generally, T cells are expanded by contact with a surface having attached thereto an agent that stimulates a CD3/TCR complex associated signal and a ligand that stimulates a co-stimulatory molecule on the surface of the T cells. The present invention comprises a novel method of expanding a population of T cells comprising electroporating the T cells with RNA encoding a chimeric membrane protein and culturing the electroporated T cells, wherein the electroporated T cells within the population expand at least 10 fold. The chimeric membrane protein of the invention comprises an extracellular and intracellular domain. The extracellular domain comprises a target-specific binding element, such as an antibody. In one embodiment, the chimeric membrane protein comprises a single chain variable fragment (scFv) against CD3 and an intracellular domain derived from a portion of an intracellular domain of CD28 and 4-1BB.

Expression of the chimeric membrane protein allows interaction with other cells in the population, such as cells that express CD3, to stimulate and activate expansion of the electroporated T cells. Not wishing to be held to any particular theory, the cells that express CD3 may come into contact and bind with the chimeric membrane protein that is expressed on the surface of the electroporated T cells. At least one T cell expressing the chimeric membrane protein interacts with another cell expressing CD3. This interaction stimulates expansion of the electroporated T cells.

In one embodiment, the T cells are expanded prior to downregulation of an endogenous gene. In another embodiment, the modified T cells are expanded.

Extracellular Domain

The present invention includes an extracellular domain comprising an antigen binding domain derived from an antibody directed against a co-stimulatory molecule. The co-stimulatory molecule can include any molecule that co-stimulates T cells, such as, but not limited to, CD3, CD28, or a combination thereof. In one embodiment, the extracellular domain can include an antigen binding domain derived from anti-CD3, anti-CD28, or a combination thereof. In another embodiment, the extracellular domain comprises a single chain variable fragment (scFv) against CD3.

In another embodiment, the extracellular domain can include any portion of an antibody that binds to antigen including, but not limited to, the antigen binding domain of a synthetic antibody, human antibody, humanized antibody, single domain antibody, single chain variable fragments, and fragments thereof. In some instances, it is beneficial for the extracellular domain to be derived from the same species in which the chimeric membrane protein will ultimately be used in. For example, for use in humans, it may be beneficial for the extracellular domain of the chimeric membrane protein to comprise a human antibody or fragment thereof. Thus, in one embodiment, the extracellular domain portion comprises a human antibody or a fragment thereof as described elsewhere herein. Alternatively, in some embodiments, the extracellular domain portion comprises a non-human antibody that is humanized as described elsewhere herein.

Intracellular Domain

The intracellular domain or cytoplasmic domain comprises a costimulatory signaling region. The costimulatory signaling region refers to an intracellular domain of a costimulatory molecule. Costimulatory molecules are cell surface molecules other than antigen receptors or their ligands that are required for an efficient response of lymphocytes to antigen.

The cytoplasmic domain or the intracellular signaling domain of the chimeric membrane protein is responsible for activation of at least one of effector functions of the T cell. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

Nonlimiting examples of intracellular signaling domains for use in the chimeric membrane protein include any portion of the intracellular domain of CD28, 4-1BB, T cell receptor (TCR), co-stimulatory molecules, any derivative or variant of these sequences, any synthetic sequence that has the same functional capability, and any combination thereof. In one embodiment, the intracellular domain comprises a portion of an intracellular domain of CD28 and 4-1BB.

Other Domains of the Chimeric Membrane Protein

Between the extracellular domain and the transmembrane domain of the chimeric membrane protein, or between the cytoplasmic domain and the transmembrane domain of the chimeric membrane protein, there may be incorporated a spacer domain, such as an oligo- or polypeptide that functions to link the transmembrane domain to, either the extracellular domain or, the cytoplasmic domain in the polypeptide chain. The spacer domain may comprise up to 300 amino acids, preferably 10 to 100 amino acids and most preferably 25 to 50 amino acids.

In some embodiments, the chimeric membrane protein further comprises a transmembrane domain. In some embodiment, the chimeric membrane protein further comprises a hinge domain. In one embodiment, the RNA encoding the chimeric membrane protein further comprises a transmembrane and hinge domain, such as a CD28 transmembrane domain and a CD8-alpha hinge domain.

Expansion of T Cells

As demonstrated by the data disclosed herein, expanding the T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), inter-leukin-2 (IL-2), insulin, IFN-gamma, IL-4, IL-7, GM-CSF, IL-10, IL-12, IL-15, TGF-beta, and TNF-$\alpha$. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In one embodiment, the method includes introducing a nucleic acid encoding a T cell receptor (TCR) comprising affinity for a surface antigen on a target cell into the expanded T cells, and electroporating a RNA encoding a co-stimulatory molecule into the T cells, wherein the elec-troporated T cells are capable of expressing the TCR and the co-stimulatory molecule.

In another embodiment, the method further comprises stimulating the expanded T cells with at least one co-stimulatory molecule selected from the group consisting of CD3, CD27, CD28, CD83, CD86, CD127, 4-1BB, 4-1BBL, PD1 and PD1L. The stimulation may include co-electropo-ration with RNA encoding the co-stimulatory molecule. In such an embodiment, the expanded T cells are further electroporated or co-electroporated with a RNA encoding CD3. The CD3 includes comprises at least two different CD3 chains, such as CD3 zeta and CD3 epsilon chains.

In another embodiment, the method of expanding the T cells can further comprise isolating the expanded T cells for further applications. In yet another embodiment, the method of expanding can further comprise a subsequent electropo-ration of the expanded T cells followed by culturing. The subsequent electroporation may include introducing a nucleic acid encoding an agent, such as a transducing the expanded T cells, transfecting the expanded T cells, or electroporating the expanded T cells with a nucleic acid encoding a TCR, into the expanded population of T cells, wherein the agent further stimulates the T cell. The agent may stimulate the T cells, such as by stimulating further expansion, effector function, or another T cell function. In one embodiment, the agent nucleic acid is co-electroporated with the chimeric membrane protein RNA. In another embodiment, the agent nucleic acid, such as a TCR RNA, is electroporated after culturing the electroporated population. In a further embodiment, the agent nucleic acid, such as a TCR RNA, is electroporated into expanded T cells that were cryopreserved.

Therapy

The modified T cells described herein may be included in a composition for therapy. The composition may include a pharmaceutical composition and further include a pharma-ceutically acceptable carrier. A therapeutically effective amount of the pharmaceutical composition comprising the modified T cells may be administered.

In one aspect, the invention includes a method for stimu-lating a T cell-mediated immune response to a target cell or tissue in a subject comprising administering to a subject an effective amount of a modified T cell. In this embodiment, the T cell is modified as described elsewhere herein. The modified T cells may be administered to induce lysis of the target cell or tissue, such as where the induced lysis is antibody-dependent cell-mediated cytotoxicity (ADCC).

In another aspect, the invention includes a method for adoptive cell transfer therapy comprising administering an effective amount of pharmaceutical composition comprising the modified T cell described herein to a subject in need thereof to prevent or treat an immune reaction that is adverse to the subject.

In yet another embodiment, a method of treating a disease or condition associated with enhanced immunity in a subject comprising administering an effective amount of a pharma-ceutical composition comprising the modified T cell described herein to a subject in need thereof.

The modified T cells generated as described herein can be uniform and possess T cell function. Further, the modified T cells can be administered to an animal, preferably a mam-mal, even more preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease. In one aspect, the invention includes treating a condition, such as an autoimmune disease, in a subject, comprising adminis-tering to the subject a therapeutically effective amount of a pharmaceutical composition comprising the modified T cell described herein.

Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The T cells generated as described herein can also be modified and used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In another embodiment, the modified T cell described herein may be used for the manufacture of a medicament for the treatment of an immune response in a subject in need thereof.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeneic or xenogeneic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

The cells described herein can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Pharmaceutical Compositions

Pharmaceutical compositions of the present invention may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-immune response effective amount", "an immune response-inhibiting effective amount", or "therapeutic amount" is indicated, the precise amount of the compositions of the present invention to be administered can be determined by a physician with consideration of individual differences in age, weight, immune response, and condition of the patient (subject). It can generally be stated that a pharmaceutical composition comprising the modified T cells described herein may be administered at a dosage of $10^4$ to $10^9$ cells/kg body weight, preferably $10^1$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 ml to 400 ml. In certain embodiments, T cells are activated from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present invention, cells expanded and modified using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Primary human lymphocytes. Primary lymphocytes were stimulated with microbeads coated with CD3 and CD28 stimulatory antibodies (Life Technologies, Grand Island, NY, Catalog) as described (*Human gene therapy* 2011, 22(12):1575-1586). T cells were cryopreserved at day 10 in a solution of 90% fetal calf serum and 10% dimethylsulfoxide (DMSO) at $1 \times 10^8$ cells/vial.

NALM-6 was purchased from the German DSMZ Cell Collection (DSMZ catalog code: ACC 128). K562 and PC3 were purchased from American Type Culture Collection. 624mel melanoma line was obtained from the Surgery Branch (NCI/NIH). All the cell lines were cultured as instructed and routinely tested for mycoplasma contamination and confirmed as being negative.

Generation of TCR constructs for mRNA electroporation and lentiviral transduction. 1G4 NY-ESO-1 TCR with different mutations (1G4 and 8F) and CARs (PSCA or CD19) were synthesized and/or amplified by PCR, based on sequencing information provided by the relevant publications (*The Journal of experimental medicine* 2005, 201(8): 1243-1255; *J Immunol* 2008, 180(9):6116-6131), and sub-cloned into pGEM.64A RNA based vector or pTRPE lentiviral vectors.

Human primary T cell preparation. Primary human CD4 and CD8 T cells were isolated from healthy volunteer donors following leukapheresis by negative selection using Roset-teSep kits (Stem Cell Technologies, Vancouver BC, Canada). All specimens were collected under a University Institutional Review Board-approved protocol, and written informed consent was obtained from each donor.

Figures 1A, 1B:
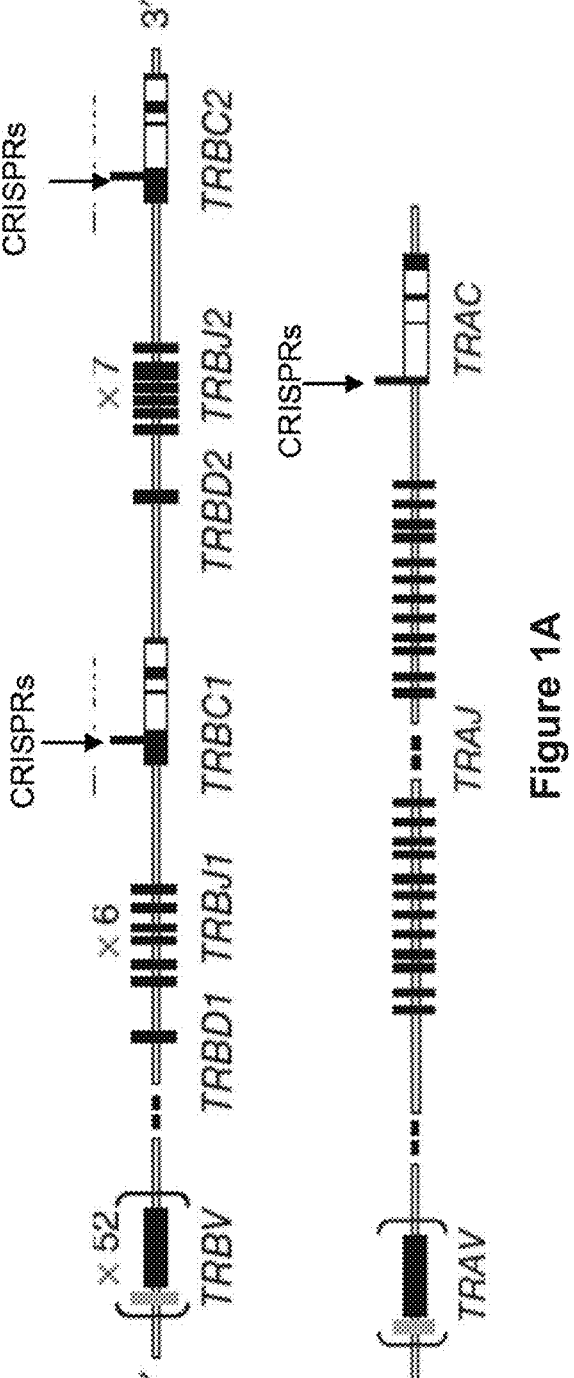
FIGS. 1A-1C, is an illustration of the CRISPR design and targeting of the TCR $\alpha\beta$-CD3 complex in 293T cells.

Design and construction of CRISPRs. Cas9 DNA was synthesized by PCR then inserted to PGEM vector. gRNAs were selected by GN19 with a NGG PAM site, with some selected from N20 with a NGG PAM site. All gRNAs contained complementary sequences comprised of more than 13 base pair mispairs, with potential off-target mRNA sites excluded (Table 1). GRNAs were designed, as shown in FIG. 1A, and synthesized by overlap PCR. All gRNA PCR products were ligated into the MSGV vector. In vitro transcribed CAS9 and gRNA targeted constant regions of TCR α, β chains and beta-2 microglobin. gRNAs were designed to target either a sequence within exon 1 of the TCR α constant region, a consensus sequence common to exon 1 of both TCR β constant regions 1 and 2, beta-2 microglobulin or PD1. Sequences encoding the gRNAs were assembled using overlap PCR and cloned into the MSGV vector containing a T7 promoter. These plasmids were linearized with EcoRI. gRNA was in vitro transcribed. Cas9 mRNA was in vitro transcribed using mMESSAGE mMA-CHINE T7 ULTRA kit (Life Technologies, Carlsbad, CA). The mRNA was stored at −80° C. in nuclease-free vials for single use. The gRNA targeting sequences used for the animal study were as follows:

```
TRAC-gRNA:
                         SEQ ID NO: 1
TGTGCTAGACATGAGGTCTA,

TRBC-gRNA:
                         SEQ ID NO: 2
GCAGTATCTGGAGTCATTGA,

B2M-gRNA:
                         SEQ ID NO: 3
CGCGAGCACAGCTAAGGCCA,

PD1-gRNA:
                         SEQ ID NO: 4
GGCGCCCTGGCCAGTCGTCT,

FAS-gRNA:
                         SEQ ID NO: 5
GAGGGTCCAGATGCCCAGCA,
```

Flow cytometry. The following monoclonal antibodies and reagents were used with indicated specificity and the appropriate isotype controls. From BD Biosciences (San Jose, CA): APC-conjugated anti-CD3 (555335), FITC-anti-CD8(555366), PE-anti-CD8(555635), FITC-anti-CD27 (555440), PE-anti-CD107(555801), PE-anti-beta-2 micro-globin (551337), FITC-anti-HLA (555552); Biolegend (San Diego, CA). FITC-anti-CD45RO (304204), APC-anti-CD62L (304814), APC-anti-CCR7(353214); and Beckman Coulter (Pasadena, CA): PE-anti-Vb13.1 (IM2021U). Data was acquired on a FACS Accuri (BD Biosciences, San Jose, CA) using CellQuest version 3.3 (BD Biosciences, San Jose, CA) and analyzed by FCS Express version 3.00 (De Novo Software, Los Angeles, CA) or FlowJo version 7.6.1 (Tree Star, Inc. Ashland, OR).

Propagation of primary T cells. Primary human T cells were cultured in RPMI 1640 supplemented with 10% FCS, 100-U/ml penicillin, 100-g/ml streptomycin sulfate, 10-mM Hepes, and stimulated with magnetic beads coated with anti-CD3/anti-CD28 at a 1:3 cell to bead ratio. Cells were counted and fed every 2 days and once T cells appeared to rest down, as determined by both decreased growth kinetics and cell size, the T cells were either used for functional assays or cryopreserved.

Generation of $CD3^{neg}$ T cells. DNA supercoiled plasmids were linearized by SpeI and EcoRI, respectively. gRNA was in vitro transcribed by T7 mScript™ Standard mRNA Production System (Cambio, C-MSC100625, Cambridge, England). All mRNA (Cas9, TCR α, TCR β and CARs) was in vitro transcribed using mMESSAGE mMACHINE T7 ULTRA kit (Life Technologies, AM1345, Carlsbad, CA). T cells were stimulated by CD3/CD28 dynabeads for three days prior to electroporation. Ten million primary T cells were de-beaded prior to electro-transfer of 20 μg Cas9, 10 μg gRNA species into the cells with a 360V, 1 ms parameter by BTX830, following a second and/or a third electro-transfer of 10 μg gRNA. Also, T cells were washed three times with OPTI-MEM and re-suspended in OPTI-MEM (Invitrogen) at a final concentration of $1-3 \times 10^8$ cells/ml. Subsequently, 0.1 ml of the cells was mixed with 10 μg of IVT RNA (or as indicated) and electroporated in a 2 mm cuvette. Ten million primary T cells were de-beaded prior to the elec-trotransfer of 20 μg of Cas9 and 10 μg of gRNA species into the cells using a BTX830 (Harvard Apparatus BTX) at 360 V and 1 ms; this process was followed by a second and a third electrotransfer of 5 μg of gRNA 12 to 24 hours later.

Following electroporation, cells were immediately placed in 2 mL of pre-warmed culture media and cultured at 37° C., 5% $CO_2$, or 32° C., 5% $CO_2$ for 1 day then returned to 37° C., 5% $CO_2$.

TCR α and β double disruption or TRAC, TRBC and B2M triple disruption. To generate TCR α and β double-knockout T cells, Cas9 mRNA was co-electroporated with two different gRNAs targeting TCR α chain (TRAC), and TCR β chain (TRBC). The TCR α and β double-knockout T cells could be purified in 2 steps: 1) depletion of TCR-positive and a chain single-knockout cells with anti-CD3 microbeads after the electroporation of the 1G4 TCR α chain RNA, and 2) depletion of TCR β chain single-knockout cells with anti-CD3 microbeads after the elec-troporation of the TCR β chain RNA. For TRAC, TRBC and B2M triple disruption, T cells were electroporated with Cas9 mRNA and gRNAs targeting the TCR α and β chains and beta-2 microglobulin 3 days after anti-CD3/CD28 bead stimulation. The HLA-I-negative cell population was enriched on day 9 and electroporated with TCR α chain RNA. The TCR-negative population was enriched on day 10. Five days later, these cells were electroporated with TCR β chain RNA, and the TCR-negative cell population was sorted the next day to obtain universal T cells. On day 18, TCR or CAR RNA was electroporated into the universal T cells to generate universal effector cells. TCR and HLA-I molecule expression was confirmed at each step.

Generation of universal CART cells. Universal CART cells were generated by combing the lentiviral transduction of CD19 or PSCA CAR with the RNA electroporation of CRISPR/gRNAs. 1 day after anti-CD3/CD28 beads stimulation, T cells were transduced with lentiviral-CD19 or PSCA CAR. 2 days later, Cas9 and gRNAs targeting TCR α, β chain, B2M, PD1 were transferred into T cells by electroporation. 6 days after CRISPRs delivery, T cells negative for CD3, HLA-I, PD1 were sorted by microbeads depletion.

Enrichment of CD3$^{neg}$ T cells. Cells washed with Auto MACS buffer were incubated for 30 minutes with CD3 microbeads (Miltenyi Biotec, 130-050-101, Auburn, CA) at 4° C. After washing twice, cells were passed through a LD column (MiltenyiBiotec, 130-042-901, Auburn, CA), and the flow-through fraction was collected for further use. The CD3 expression of CD3$^{neg}$ T cells was restored by co-electroporation of 1G4TCR α and □ mRNA, and the cells were expanded using a single Rapid Expansion Protocol (REP), CD3/CD28 Dynabeads or K562-based aAPC.

Generation and propagation of CD3$^{neg}$ T cells. CD3$^{neg}$ T cells had CD3 expression restored by electro-transfer of exogenous 1G4TCR alpha chain and TCR beta chain in vitro transcribed mRNA (5 μg for each chain). These cells were expanded using a single Rapid Expansion Protocol (REP). PBMCs from three different donors: ND052 $105 \times 10^6$, ND405 $83 \times 10^6$, ND410 $136 \times 10^6$, were irradiated, then mixed together, to obtain a total of $324 \times 10^6$ PBMCs. The PBMCs were re-suspended in a final volume of 90 ml then R10 were added to 300 ml, mixed, and divided into two T150 ml flasks. OKT were added to a final concentration of 30 ng/ml. On day 2, IL-2 was added to 50 CU/ml. From day 5, cells were counted and fed every 2 days and once T cells appeared to rest down, as determined by both decreased growth kinetics and cell size, they were either used for functional assays or cryopreserved.

Sanger sequencing. The level of genomic disruption of TCR α chain (TRAC), TCR β chain 1 (TRBC1), and TCR β chain 2 (TRBC2) in T cells was determined by Surveyor Nuclease assay (Transgenomics, Omaha, NE). The percent target disruption was quantified by densitometry. The PCR primers used for the amplification of target locus were:

```
TRAC forward,
                        SEQ ID NO: 6
5'-TCATGTCCTAACCCTGATCCTCTT-3'

TRAC reverse,
                        SEQ ID NO: 7
5'-TTGGACTTTTCCCAGCTGACAGA-3'

TRBC total forward,
                        SEQ ID NO: 8
5'-TACCAGGACCAGACAGCTCTTAGA-3'

TRBC total reverse,
                        SEQ ID NO: 9
5'-TCTCACCTAATCTCCTCCAGGCAT-3'
```

PCR products were purified and ligated to TOPO cloning vector (Invitrogen) then transformed in *E. coli*. Single clone was picked and sequenced to calculate the indels.

Generation of siRNA and CRISPRi for electroporation. RNA duplex targeting TCR constant regions for either alpha (5'-rArGrGrArGrGrArUrUrCrGrGrArArCrCrCrArArUr-CrArCrUrGrArC-3' SEQ ID NO:10 and 5'-rCrArGrUr-GrArUrUrGrGrGrUrUrCrCrGrArArUrCrCrUrCCT-3' SEQ ID NO:11) or beta (5'-rArCrCrUrCrCrUrUrCrCrCrArUrU-rCrArCrCrCrArCrCrArGrCrUrC-3' SEQ ID NO:12 and 5'-rGrCrUrGrGrUrGrGrGrUrGrArArUrGrGrGrArArGr-GrArGGT-3' SEQ ID NO:13) were designed using Custom RNAi Design Tool (Integrated DNA Technologies, Coralville, IA) and the siRNA was synthesized (Integrated DNA Technologies, Coralville, IA). siRNA for both TCR alpha and beta was mixed and electroporated into stimulated T cells for endogenous TCR knockdown.

mRNA in vitro transcription and T cell electroporation. T7 mscript systems kit (CellScript) was used to generate in vitro transcribed (IVT) RNA. CD3/CD28 bead stimulated T cells were electroporated with IVT RNA using BTX EM830 (Harvard Apparatus BTX) as previously described (*Cancer research* 2010, 70(22):9053-9061). Briefly, T cells were washed three times and resuspended in OPTI-MEM (Invitrogen) at a final concentration of $1-3 \times 10^8$ cells/ml. Subsequently, 0.1 ml of cells were mixed with 10 ug IVT RNA (or as indicated) and electroporated in a 2 mm cuvette.

ELISA assays. Target cells, different tumor cell lines expressing CD19, were washed and suspended at $1 \times 10^6$ cells/ml in R10 medium (RPMI 1640 supplemented with 10% fetal calf serum; Invitrogen). 100 ul of each target cell type was added in duplicate to a 96 well round bottom plate (Corning). Effector T cells were washed, and re-suspended at $1 \times 10^6$ cells/ml in R10 medium and then 100 ul of T cells were combined with the target cells in the indicated wells. In addition, wells containing T cells alone were prepared as a control. The plates were incubated at 37° C. for 18 to 20 hours. After the incubation, supernatant was harvested and subjected to an ELISA assay (eBioscience).

CD107a staining Cells were plated at an Effector cell:T cell ratio of 1:1 ($1 \times 10^5$ effectors to $1 \times 10^5$ targets) in 160 μl of complete RPMI medium in a 96 well plate. 20 μl of phycoerythrin-labeled anti-CD107a antibody (BD Biosciences, 555801) was added and the plate was incubated at 37° C. for 1 hour before adding Golgi Stop (2 ul Golgi Stop in 3 ml RPMI medium, 20 ul/well; BD Biosciences, 51-2092KZ) and incubating the plate for another 2.5 hours. Then 5 μl FITC-anti-CD8 and 5 ul APC-anti-CD3 were added and incubated at 37° C. for 30 min. After incubation, the samples were washed with FACS buffer and analyzed by flow cytometry.

Luciferase based CTL assay. Nam16-CBG tumor cells were generated and employed in a modified version of a luciferase based cytotoxic T lymphocyte assay. Briefly, click beetle green luciferase (CBG) was cloned into the pELNS vector, packaged into lentivirus, transduced into Nam16 tumor cells and sorted for CBG expression. The resulting Nam16-CBG cells were washed and resuspended at $1 \times 10^5$ cells/ml in R10 medium, and 100 ul of CBG-labeled cells were incubated with different ratios of T cells (e.g. 30:1, 15:1, etc) overnight at 37° C. 100 ul of the mixture was transferred to a 96 well white luminometerplate. 100 ul of substrate was added to the cells and luminescence was immediately determined. The results are reported as percent killing based on the luciferase activity in the wells with tumor cells but no T cells (% killing=100−((RLU from well with effector and target cell coculture)/(RLU from well with target cells)×100)).

Mouse xenograft studies. Studies were performed as previously described with certain modifications (*Human gene therapy* 2011, 22(12):1575-1586; *Proceedings of the National Academy of Sciences of the United States of*

*America* 2009, 106(9):3360-3365). Briefly, 6-10 week old NOD/SCID gamma (NSG) mice were injected subcutaneously with $1\times10^6$ PC3-CBG tumors cells on the right flank at day 0 and the same mice were given SK-OV3-CBG tumor cells ($5\times10^6$ cells/mouse, subcutaneously.) on the left flank at day 5. The mice were treated with T cells via the tail vein at day 23 post PC3-CBG tumor inoculation, such that both tumors were approximately 200 mm³ in volume. Lentivirally transduced T cells were given at $1\times10^7$ cells/mouse (10M), or $3\times10^6$ cells/mouse (3M). Briefly, for the Nalm6 tumor model, 6- to 10-week-old NOD/SCID gamma (NSG) mice were injected with $1\times10^6$ click beetle green (CBG) transduced Nalm6 (Nalm6-CBG) cells through the tail vein on day 0. The T cell treatment began on day 7 after the tumor inoculation. For the PC3-PDL1 solid tumor model, 6- to 10-week-old NOD/SCID gamma (NSG) mice were injected subcutaneously with $1\times10^6$ PSCA, PD-L1 and CBG transduced PC3 (PC3-PSCA-PDL1-CBG) tumors cells in the right flank on day 0. The mice were treated with T cells via the tail vein at day 22 post PC3-PDL1-CBG tumor inoculation, such that the tumors were approximately 200 mm³ in volume. T cells were given at $2\times10^6$ cells/mouse (2M). Animals were randomized and grouped based on baseline tumor size. All animals were included in the experiments and blinded tumor assessment was done for all the animal experiments conducted.

T cell stimulation, lentiviral transduction and CRISPR electroporation procedure. FIG. 84 shows the procedure used to stimulate, lentiviral transduce and CRISPR electroporate T cells. On day 0, T cells were obtained from 3 donors ($100\times10^6$ cells/donor). The cells were stimulated with anti-CD3/anti-CD28 beads at a T cell:bead ratio of 1:3. The concentration of cells was adjusted to $0.5\times10^6$/ml with 100 mL/flask. On day 1, stimulated T cells were transduced with CD19 CAR lentivirus at multiplicity of infection (MOI) of 2. 50 mL ($25\times10^6$ cells) of T cells were reserved as unmodified T cells (Group 9). On Day 3, the beads were removed, the cells washed 2× in Opti-MEM media, and the transduced T cells from each donor were separated into two groups, CART/mock EP (10 mL, $50\times10^6$/mL) and CART/CRISPR (10 mL, $50\times10^6$/mL). The cells were then electroporated with CAS9 RNA (1st EP) at 500V/1 ms with 120 μg of CAS9 RNA/400 μL of T cells. After electroporation, Groups 1, 3, 5 and 7 cells were then split by culturing T cells in half new medium and half cultured medium. On day 4, the cells were washed twice and resuspended in Opti-MEM at $50\times10^6$/mL. 20 μg TRBC4 and B2M gRNA was electroporated into the 400 μL of T cells. After electroporation, the cells were cultured at $1\times10^6$ cells/mL in half fresh medium and half cultured medium. On days 5 and 7, the cells were split and resuspended in half fresh medium and half cultured medium. On day 8, CD3+ cells were removed from Groups 2, 4 and 6 via a low-density column. The CD3-T cells were resuspended at $0.5$-$1\times10^6$ cells/mL in half fresh medium and half cultured medium and cultured to expand the cells. On day 11, the T cells were harvested and $25\times10^5$ cells from the three donors were sent for karyotyping. The remaining cells were aliquoted and frozen.

The results of the experiments are now described.

Example 1: Disruption of the TCR-CD3 Complex on T Cells Using CRISPR

Figure 1C:
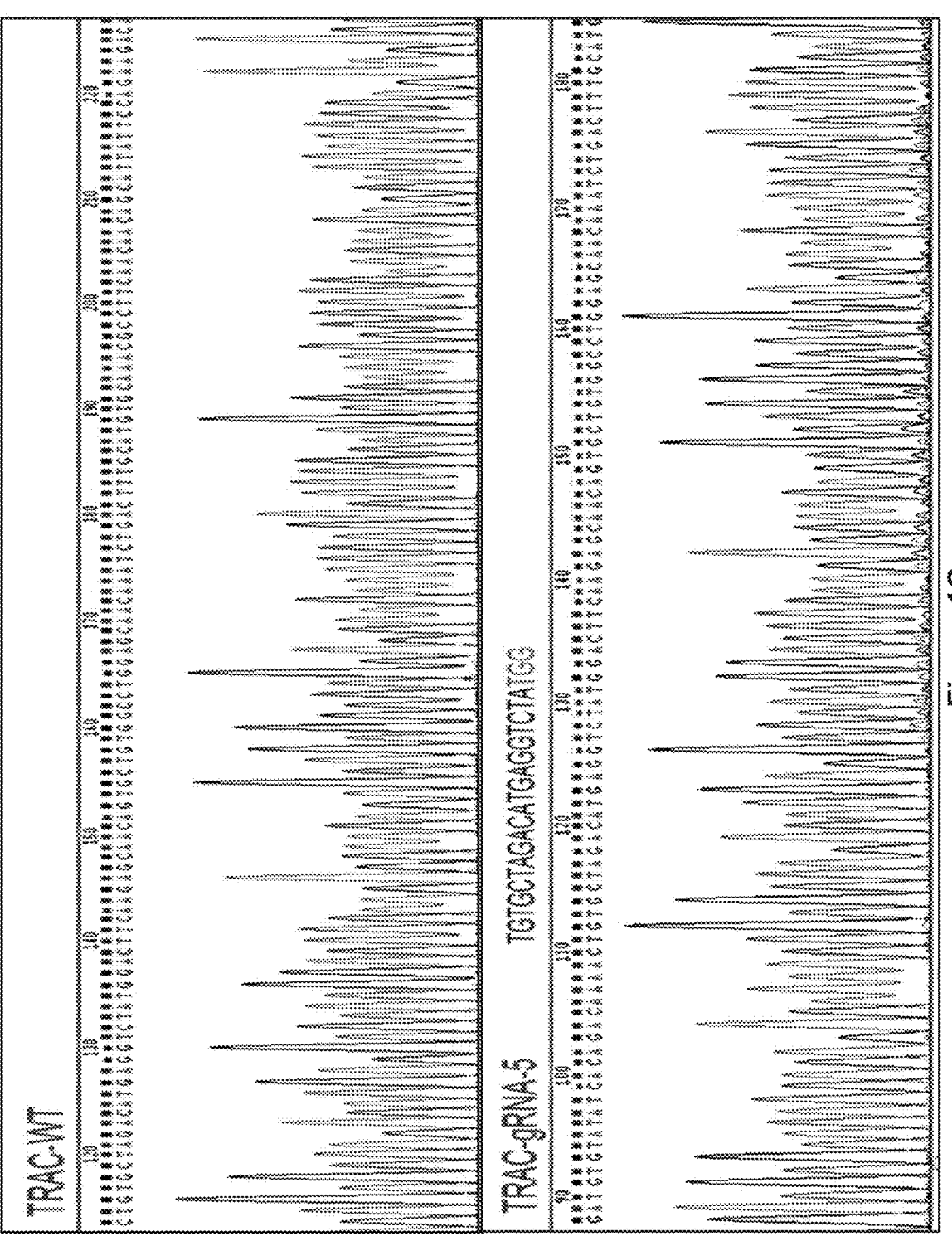
Figure 2B:
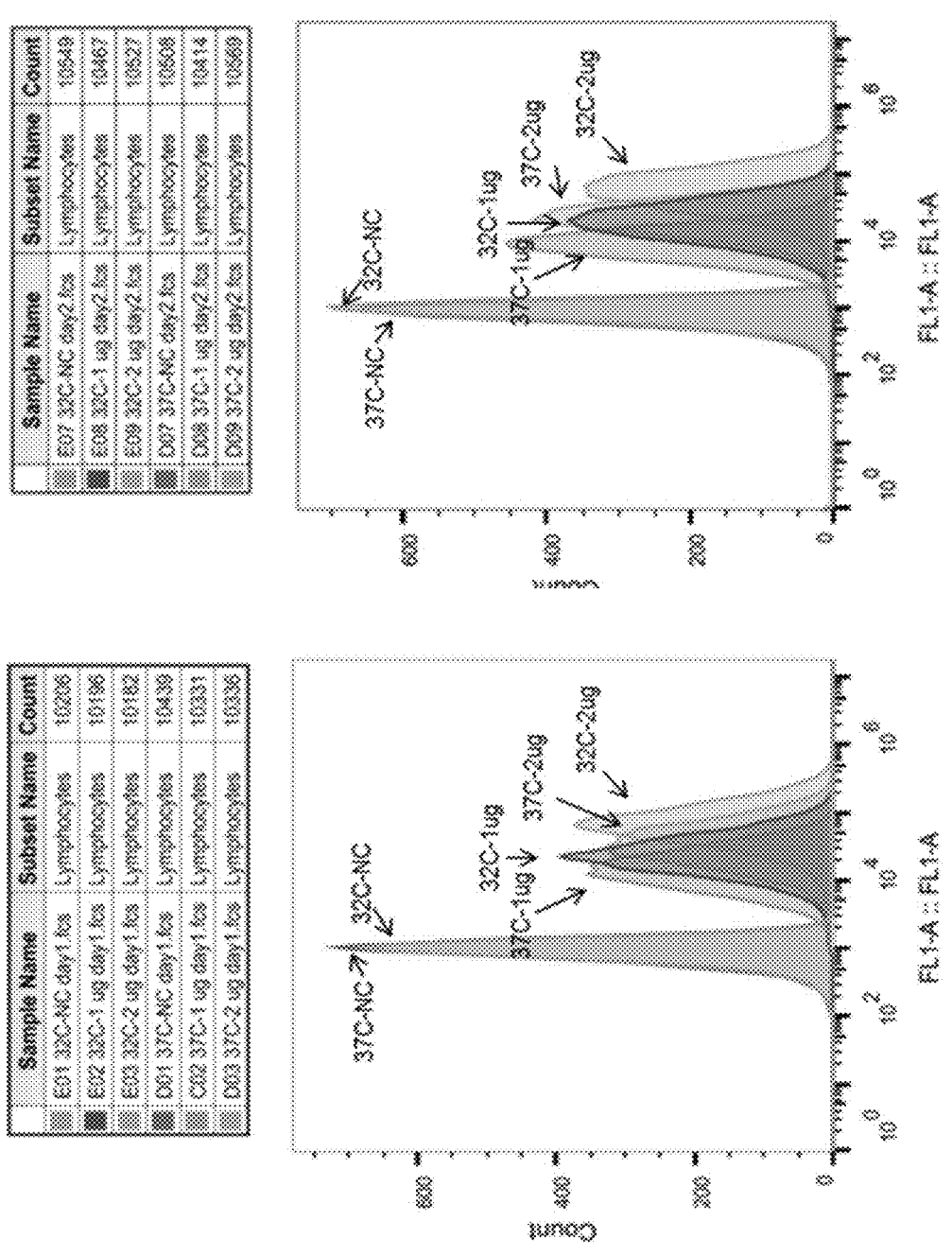
Figure 2C:
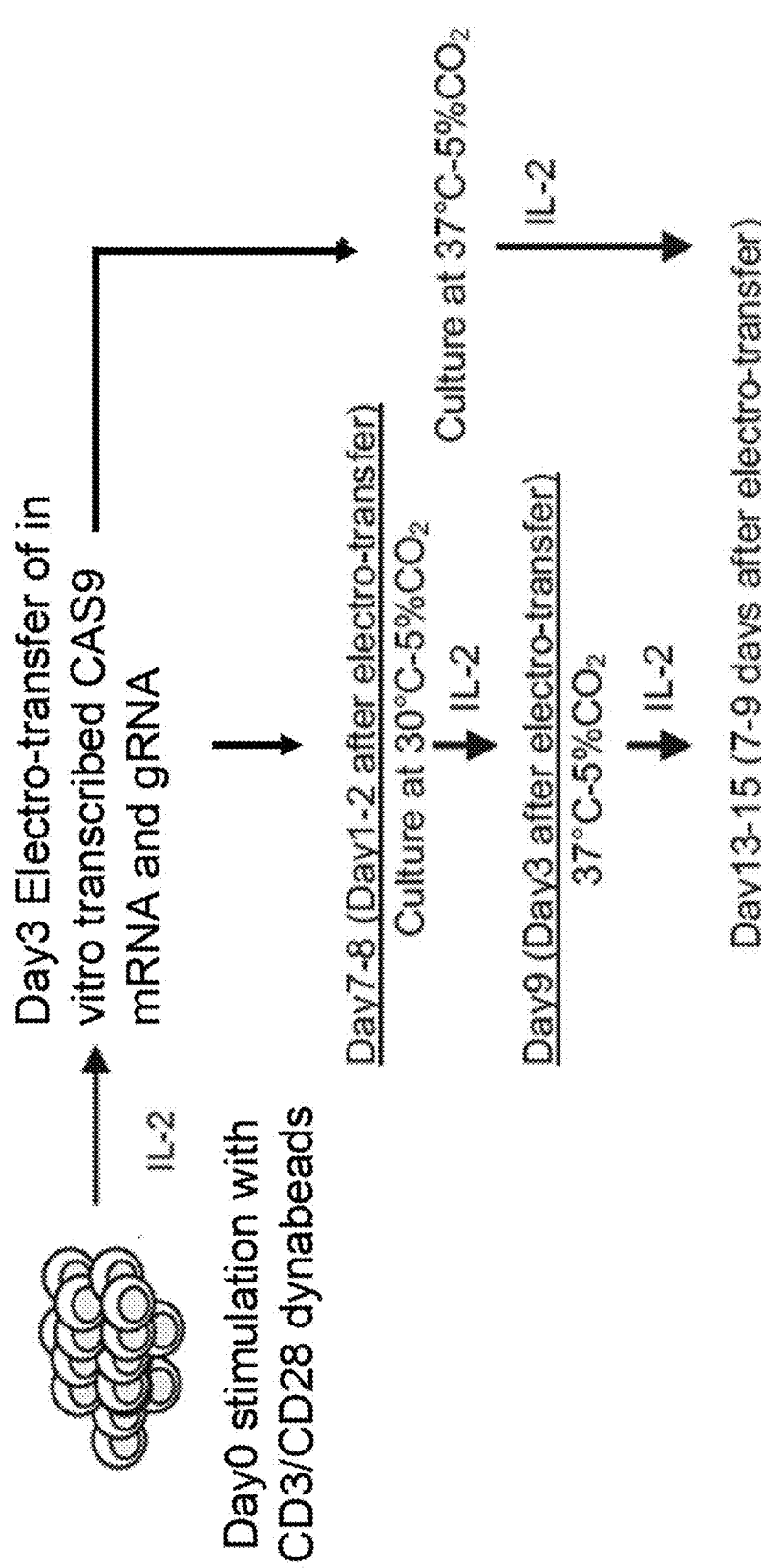

Thirteen gRNAs targeting the constant regions of TCR α chain, 10 gRNAs targeting the constant regions TCR β chain, and 10 RNAs targeting the beta-2 microglobin gene. (FIGS. 1A-1C and FIGS. 9A-9D) were developed and tested in 293T cells. Primary human T cells were propagated ex vivo for three days with anti-CD3/anti-CD28 dynabeads for three days. Since transient expression of CRISPR is sufficient to mediate gene knockout, a "hit-and-run" delivery strategy was developed to transiently express the CRISPRs by utilizing electro-transfer of in vitro transcribed RNA encoding CAS9 and gRNAs (FIG. 2C).

Figure 2D:
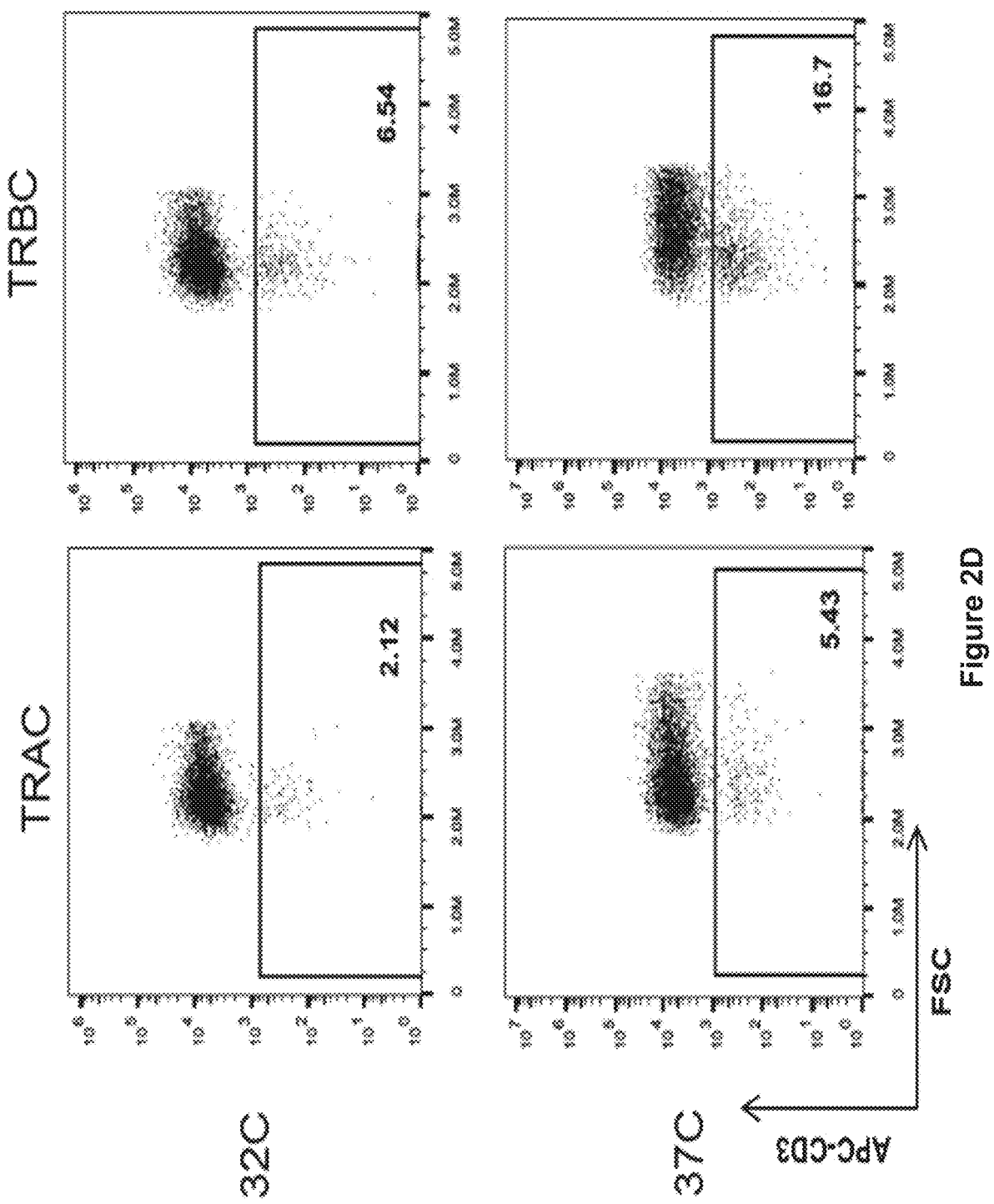
Figure 2E:
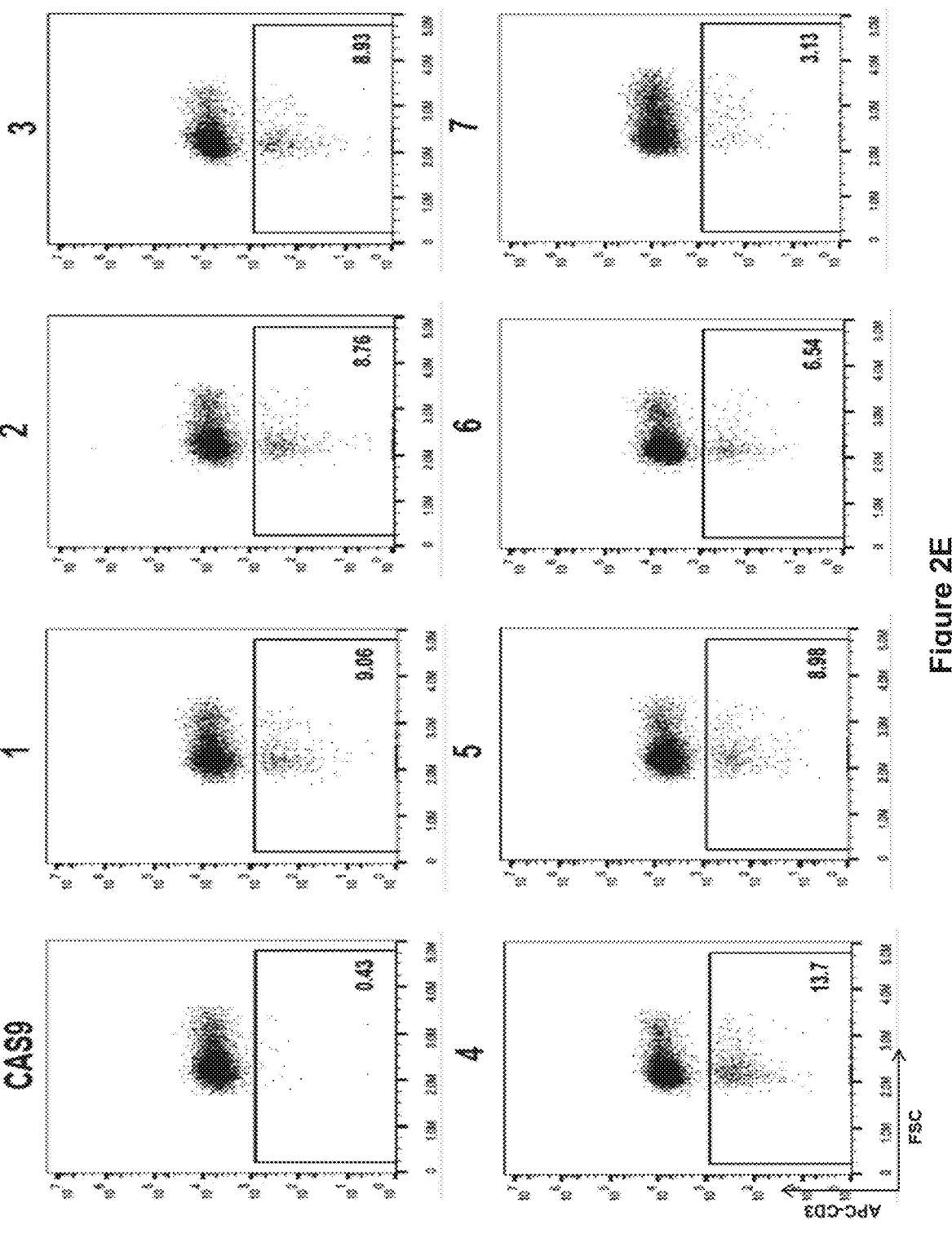

To measure TCR expression, a mAb specific for CD3 was used, which is only present on the cell surface when TCR antibody is expressed. Six days after electro-transfer, flow cytometric analysis revealed that CRISPRs targeting TRBC eliminated CD3 expression on primary T cells at levels of 13.7 (FIG. 2D) in donor ND147. The efficiency of TCR knockout correlated with the amount of electro-transferred mRNA (FIG. 2D). Although the electro-transfer of RNA in primary T cells was well-tolerated, a slight reduction in cell viability was observed that correlated with increasing amounts of introduced RNA. ZFN and TALEN mediated gene disruption has been reported to be more efficient when cells were transiently exposed to mild hypothermia. The same phenomenon was observed with this CRISPR system.

The T cells were cultured for 1 day at 32° C. after electro-transfer. CRISPR-mediated disruption of CD3 was up to 2.5-fold better when electroporated T cells were cultured at 32° C. versus 37° C. Using this approach, 5.43% and 16.7% of electroporated T-cells lost expression of CD3 using the CRISPRs targeting TRAC and TRBC, respectively, (FIG. 2D, lower panel). No change in the levels of CD3 negative cells in the CAS9 MOCK samples and no appreciable decrease in viability (measured by Trypan blue) were observed.

When gRNAs were electro-transferred for a second and a third time, the efficiency of eliminating CD3 expression on primary T cells at levels was greatly improved.

Figure 4C:
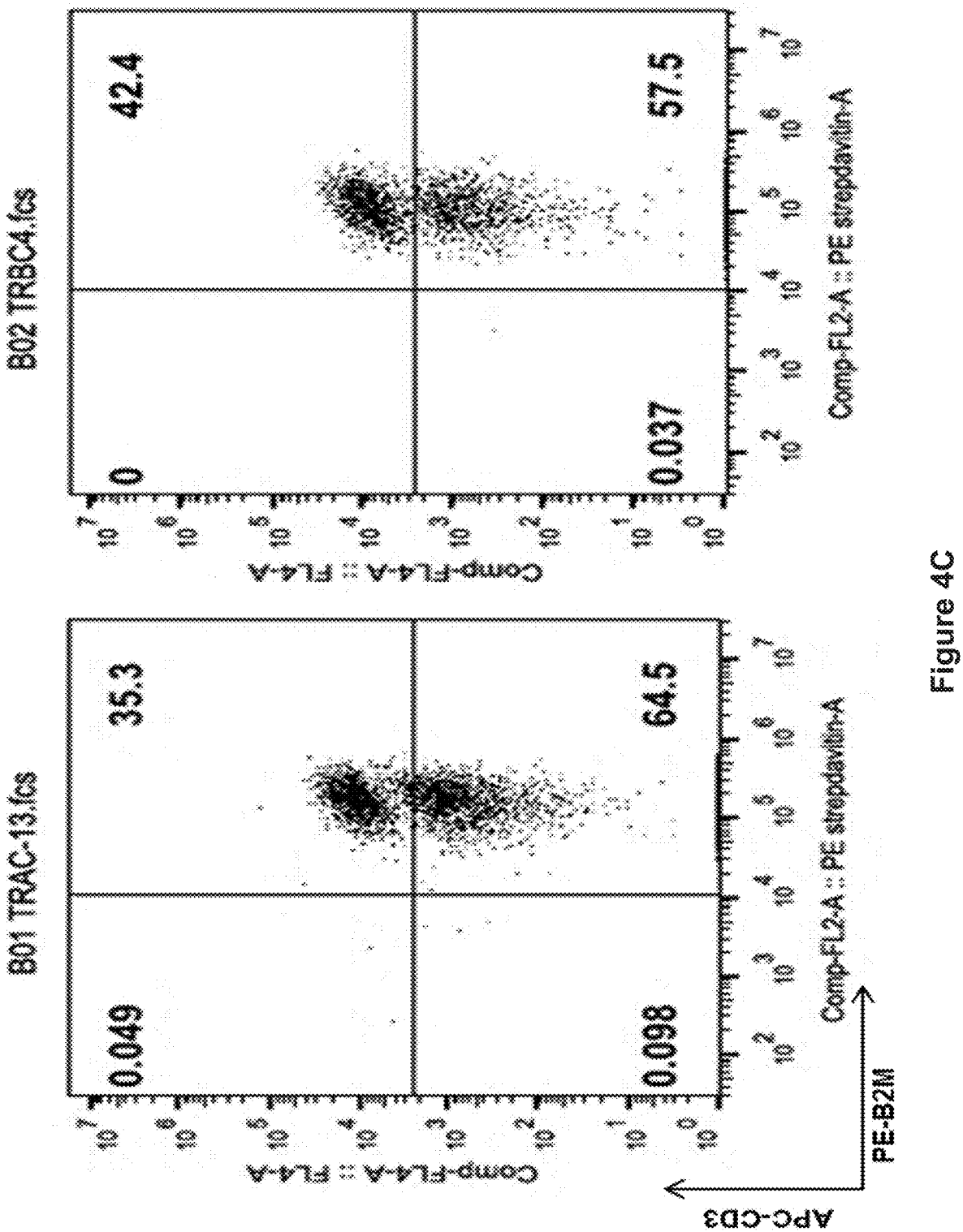
Figure 5A:
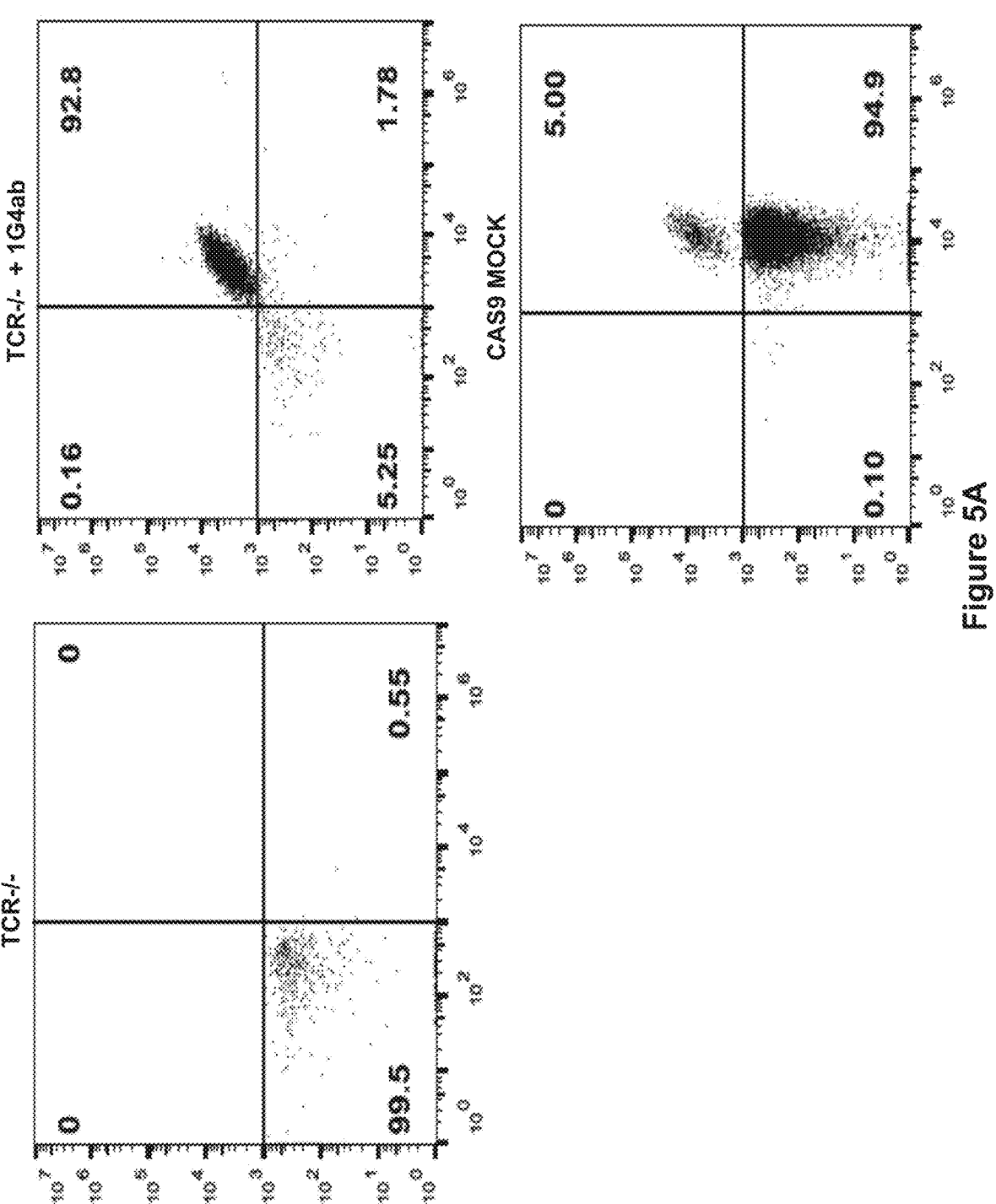
FIGS. 5A and 5B, shows TCR$^{neg}$ T cells could be expanded under different stimulating conditions.
Figure 5B:
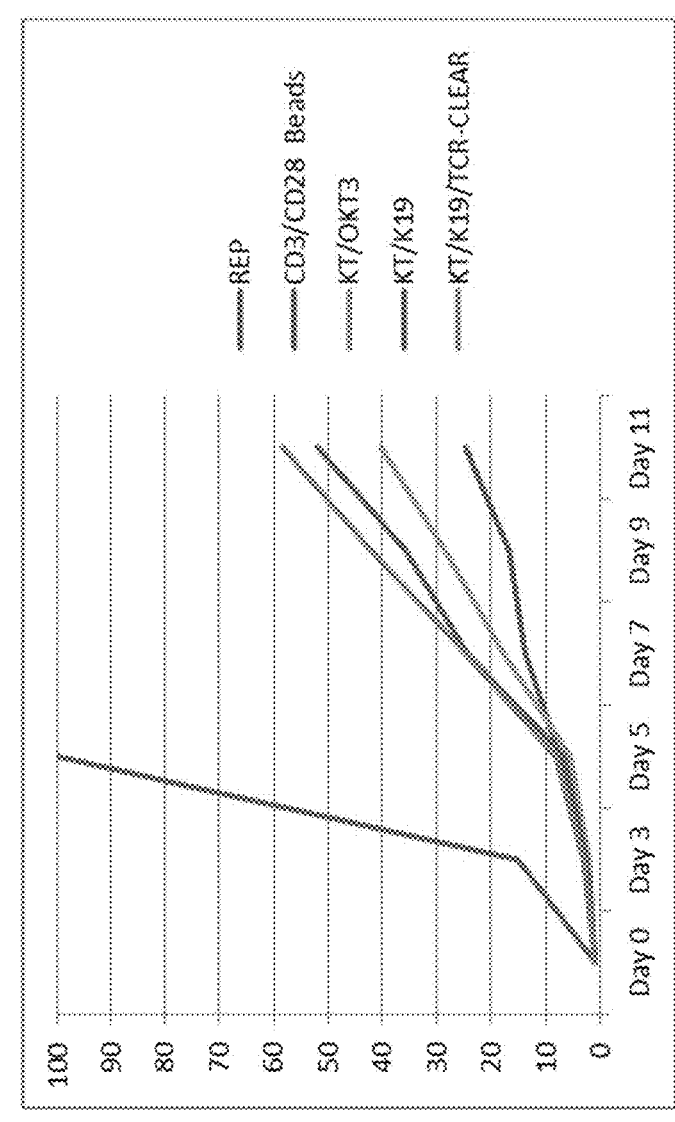

Targeting TRAC: at levels reaching 77% after three times electro-transfer of gRNA (FIG. 4A), Targeting TRAC or TRBC at levels reaching 64.5% or 57.5%, respectively, after a second electro-transfer of gRNAs with a slight decreased viability (FIG. 4C).

Figure 3A:
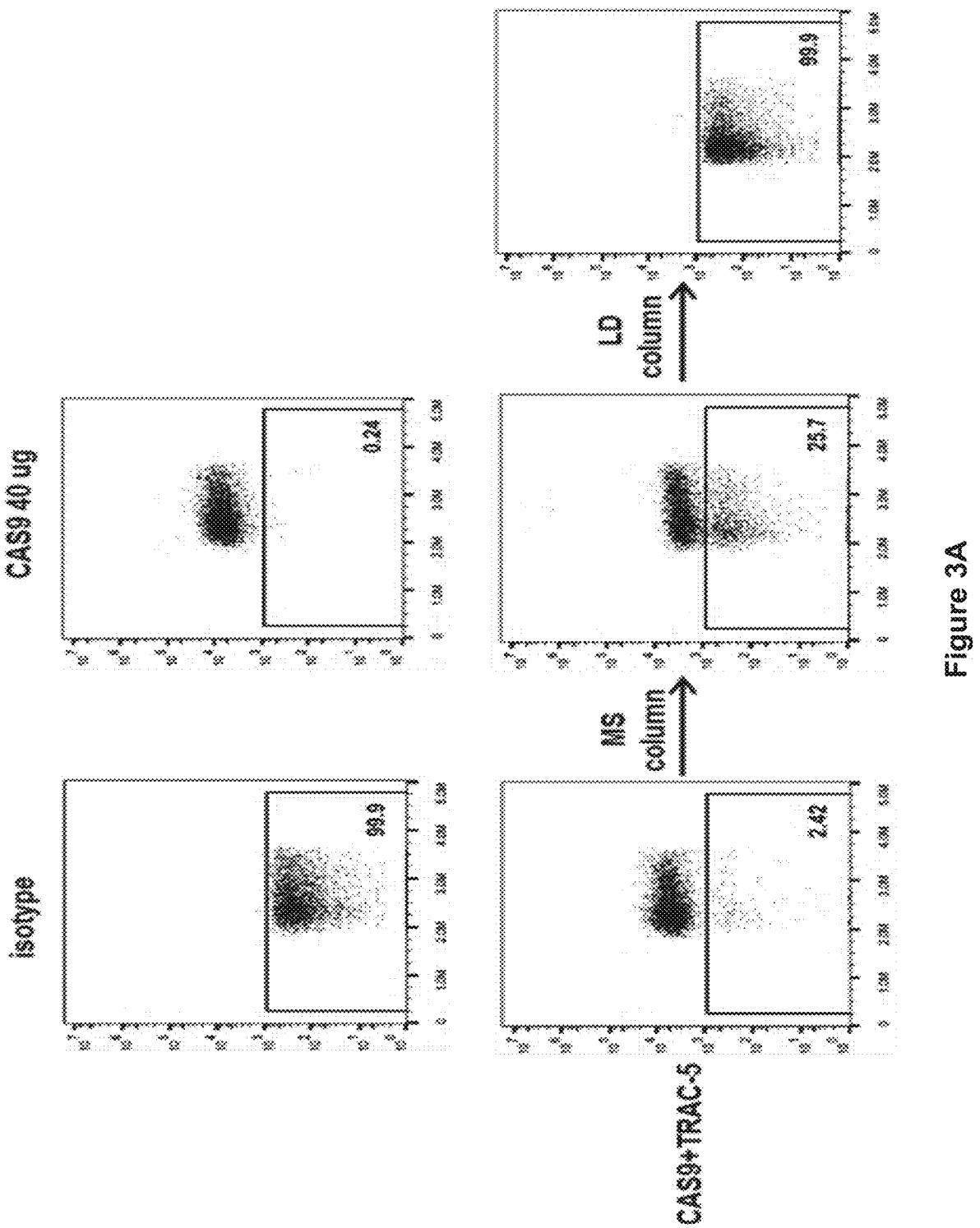
Figure 3B:
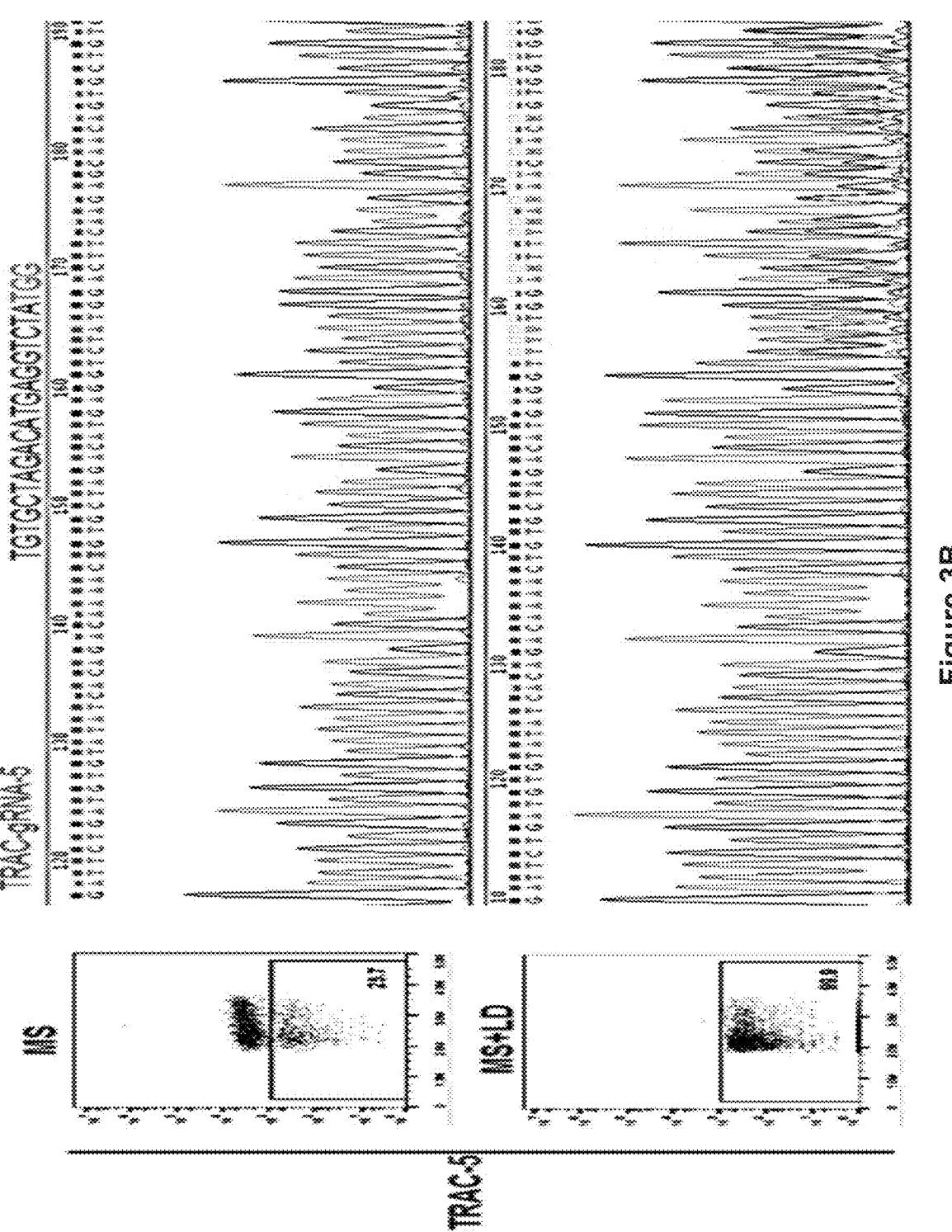

To confirm that electroporated T cells had been genetically modified at the intended gRNA target sites (TCR α or β loci), Sanger sequencing was performed using specific oligonucleotide primers flanking target sites within TRAC, TRBC1, or TRBC2. Multiple peaks at the indicated PCR products starting from the target sites were present only after electro-transfer of CRISPRs and the percent disruption correlated with loss of cell surface CD3 expression (FIGS. 1C and 3B). These experiments in primary T cells confirmed that CRISPRs designed to target TRAC or TRBC led to permanent disruption of αβ TCR expression, as assessed by Sanger sequencing and confirmed by flow cytometric analysis of CD3.

Example 2: Enrichment of TCR αβ Negative T Cells

Figure 3C:
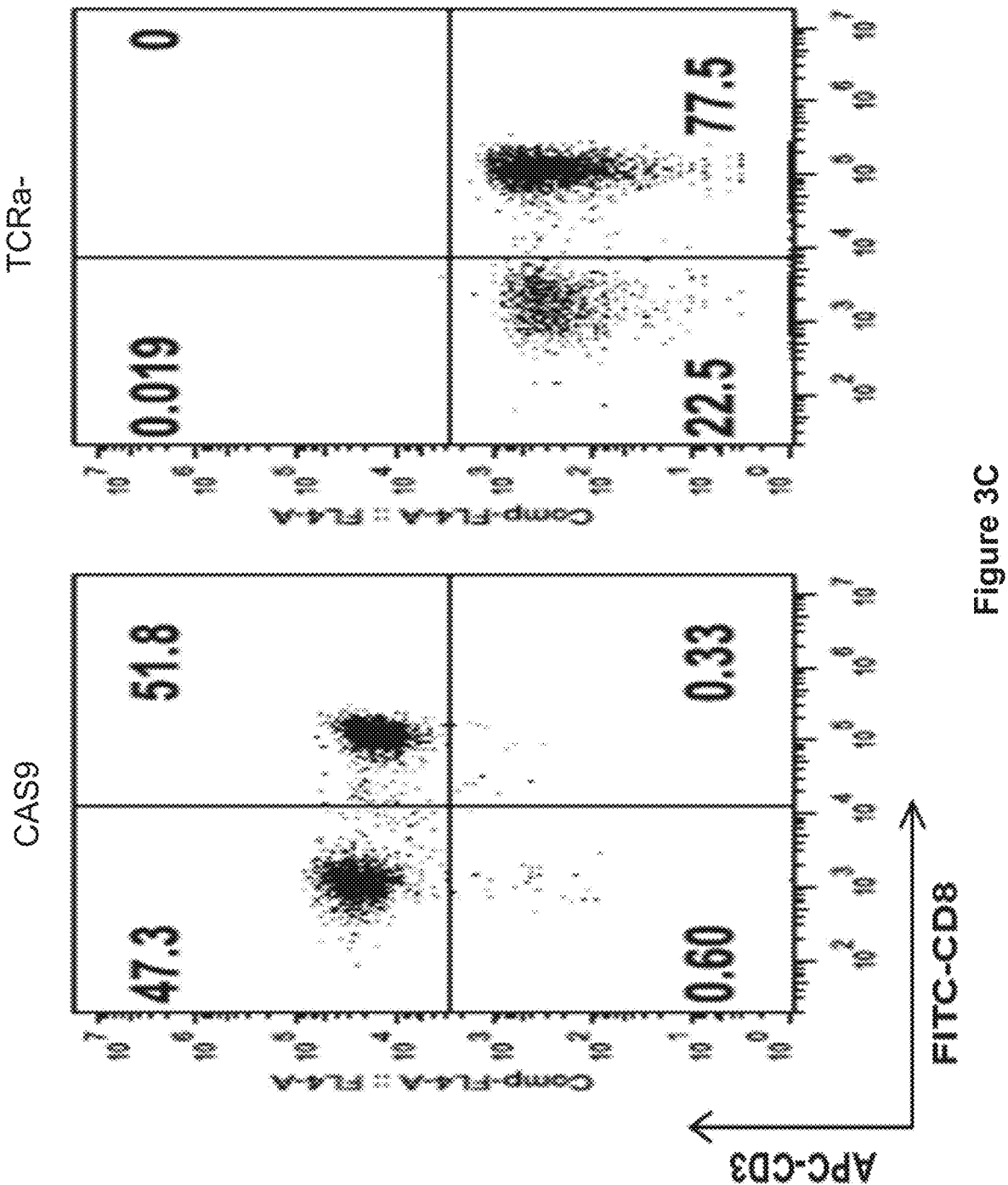

For future clinical applications, rapid and robust methods for isolating sources of TCR disrupted populations may be utilized. To begin to address this issue, the TCR/CD3$^{neg}$ population was enriched by negative selection using clinically-approved paramagnetic beads and a depletion column. With a single depletion step, the CD3$^{neg}$, population was enhanced to over 99% (FIG. 3A). A CD3$^{neg}$ population could not be enriched from untransfected control cells. Back-to-back depletion steps resulted in >99% enrichment, without skewing the CD4 or CD8 T cell subsets (FIG. 3C).

Sequencing results also showed deletions and insertions were introduced to TCR alpha and beta locus after CRISPR modification (FIG. 3D).

Example 3: Generation of HLA-CLASS I$^{neg}$ T Cells by CRISPR

Figure 9A:
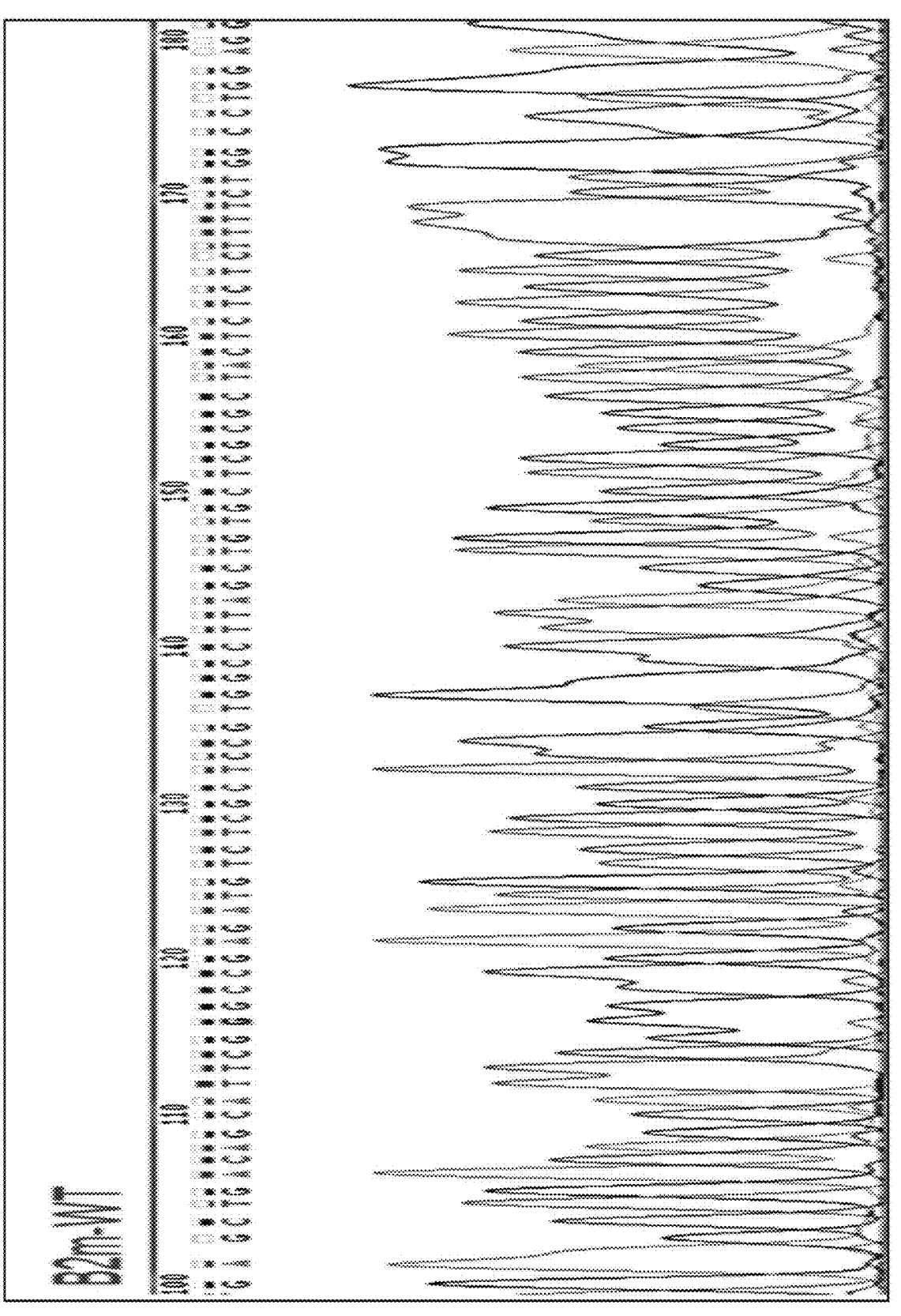
FIG. 9A-9D, shows that HLA-CLASS I elimination was obtained by disruption of beta-2 micro-globin.
Figure 9B:
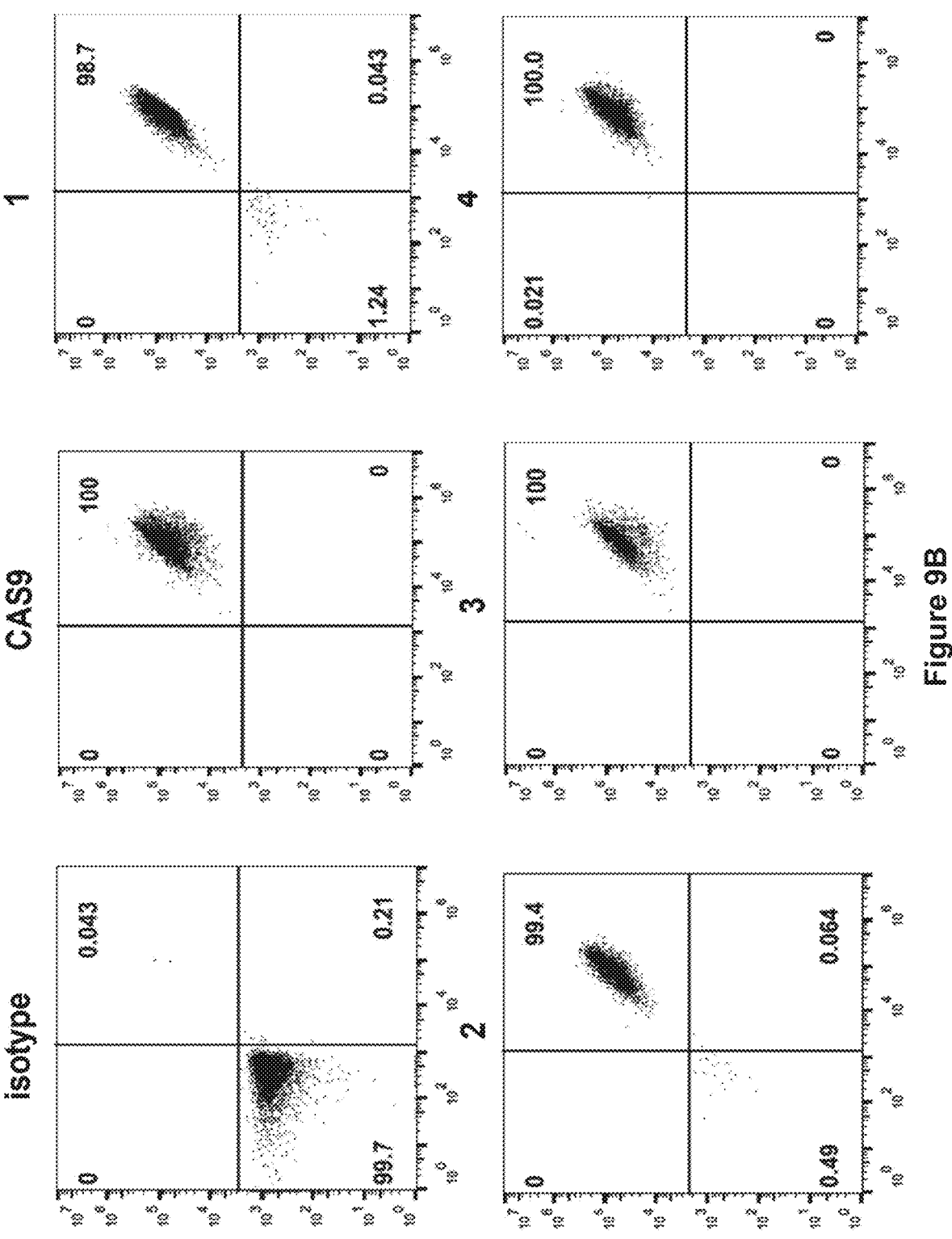

To test the ability of CRISPR to knock out HLA-CLASS I expression from allogeneic T cells, gRNAs targeting beta-2 microglobin were designed. The beta-2 microglobin locus could be manipulated by CRISPR in 293 T cells (FIG. 9A). Evidence showed disruption of beta-2 microglobin abolished T cell surface HLA-CLASS I expression (FIG. 9B).

Figure 9C:
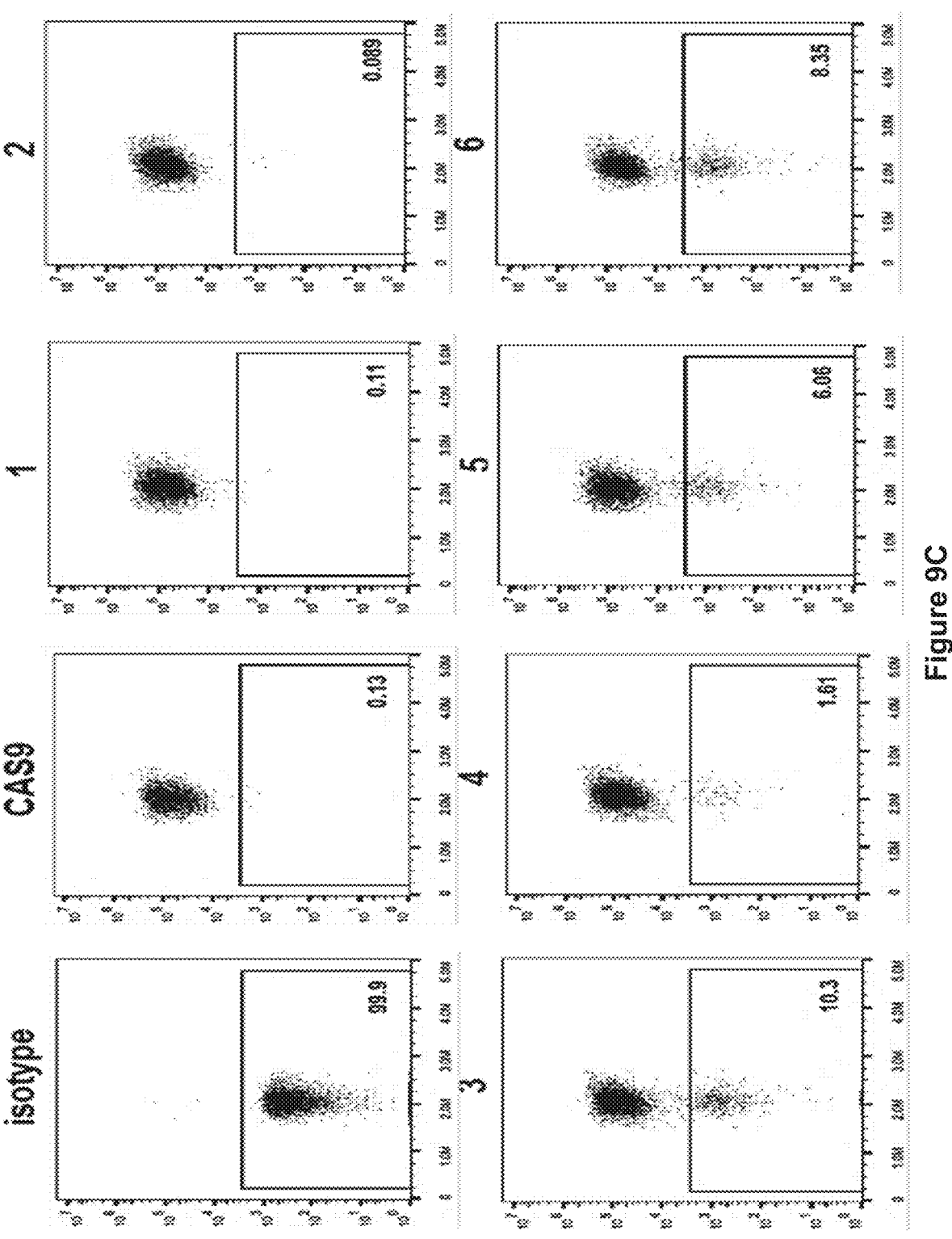
Figure 11A:
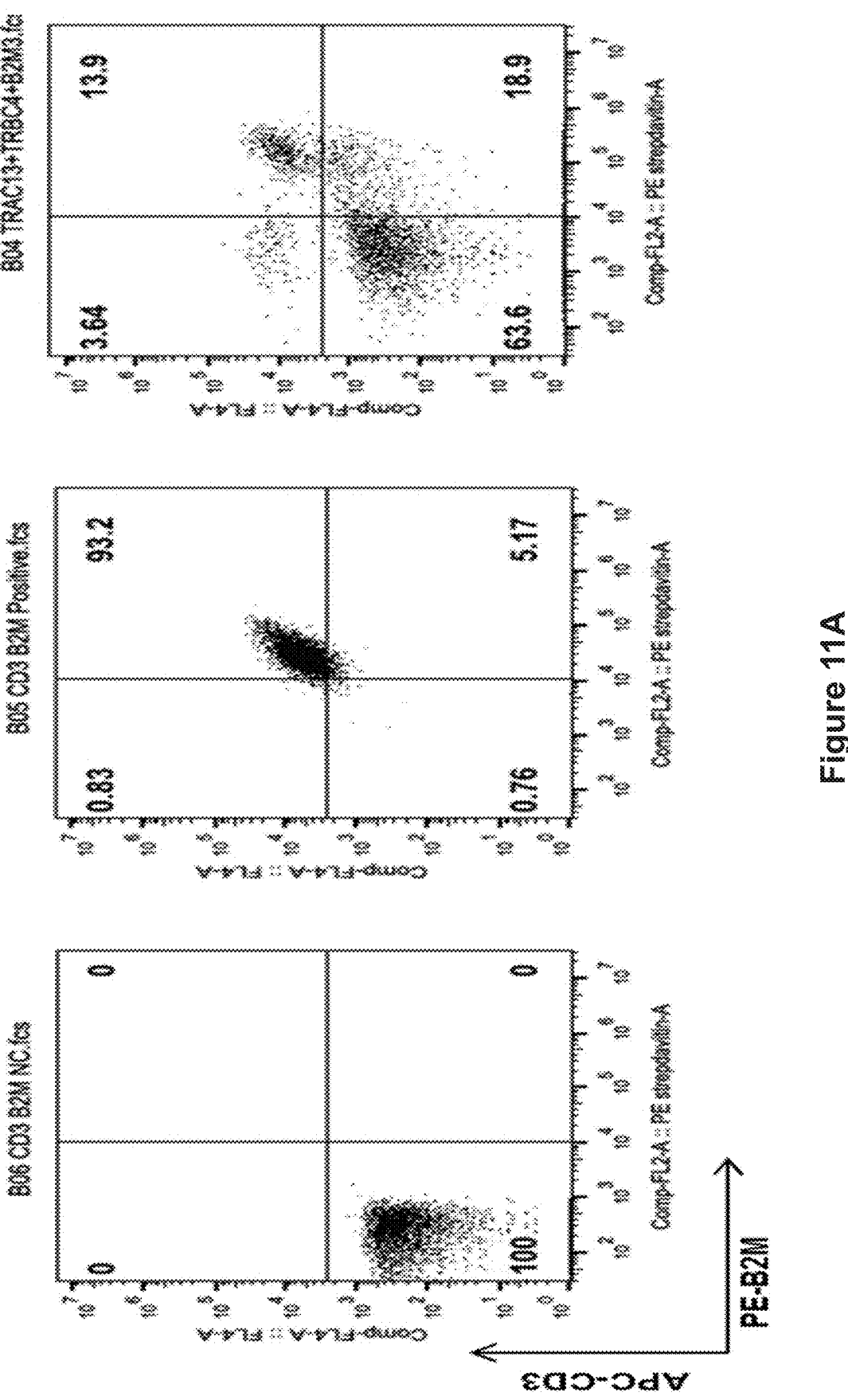
FIGS. 11A-11D, shows triple knock out of HLA-CLASS I and TCR alpha and beta chain in primary T cells.
Figure 11B:
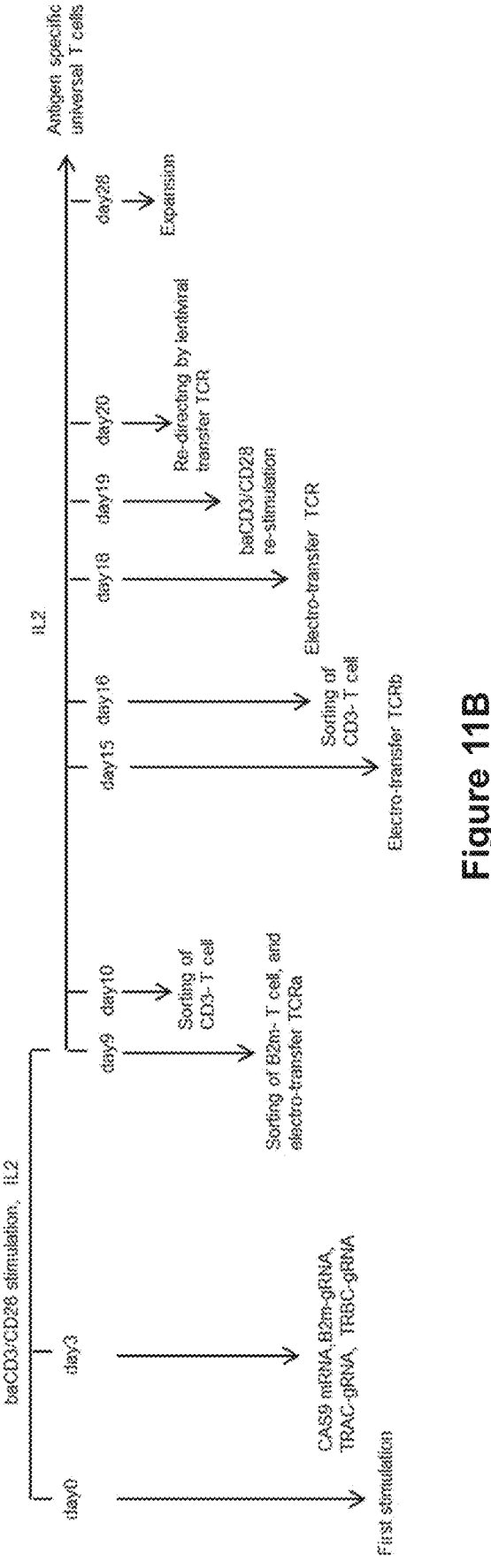
Figure 11C:
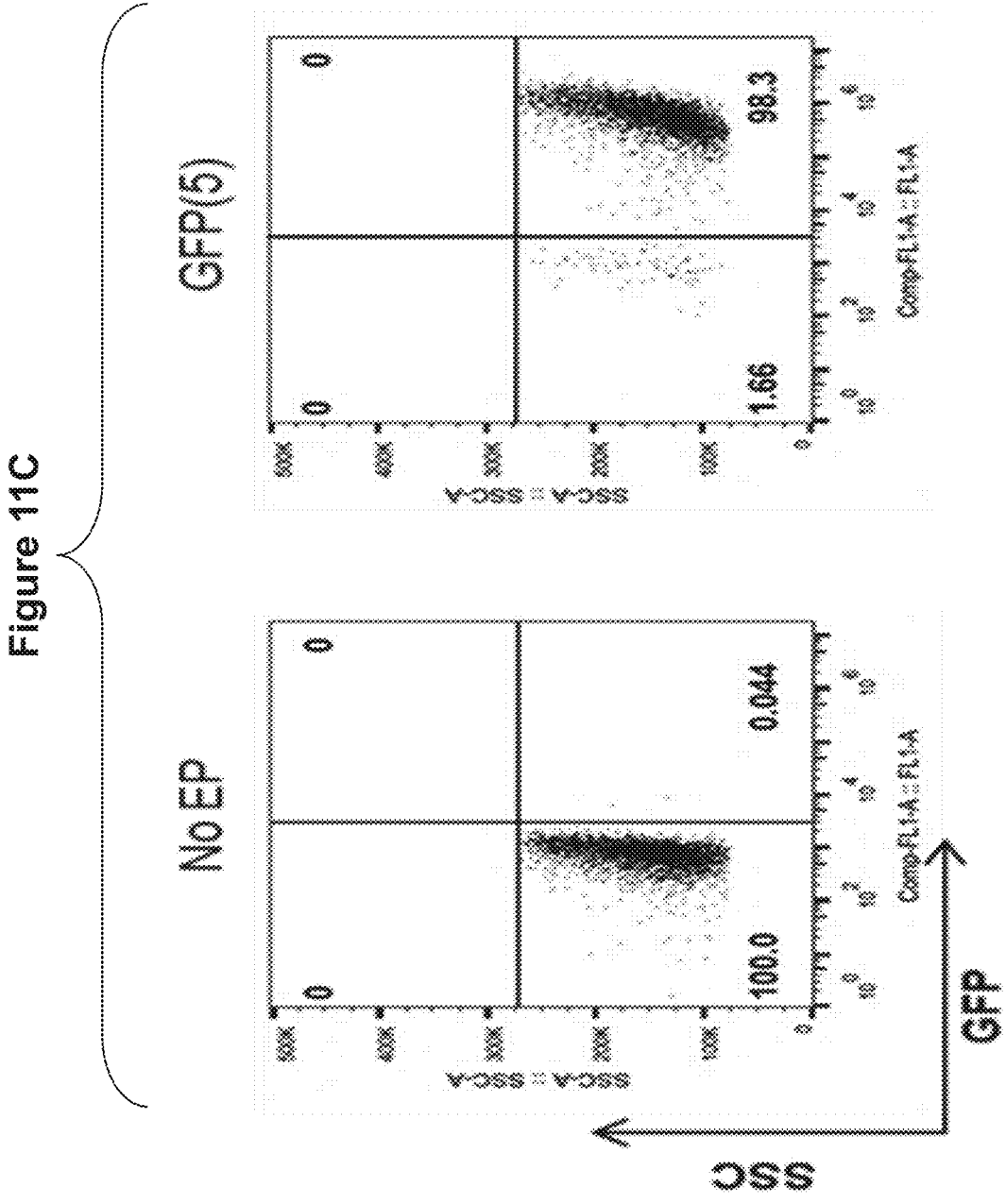
Figure 11D:
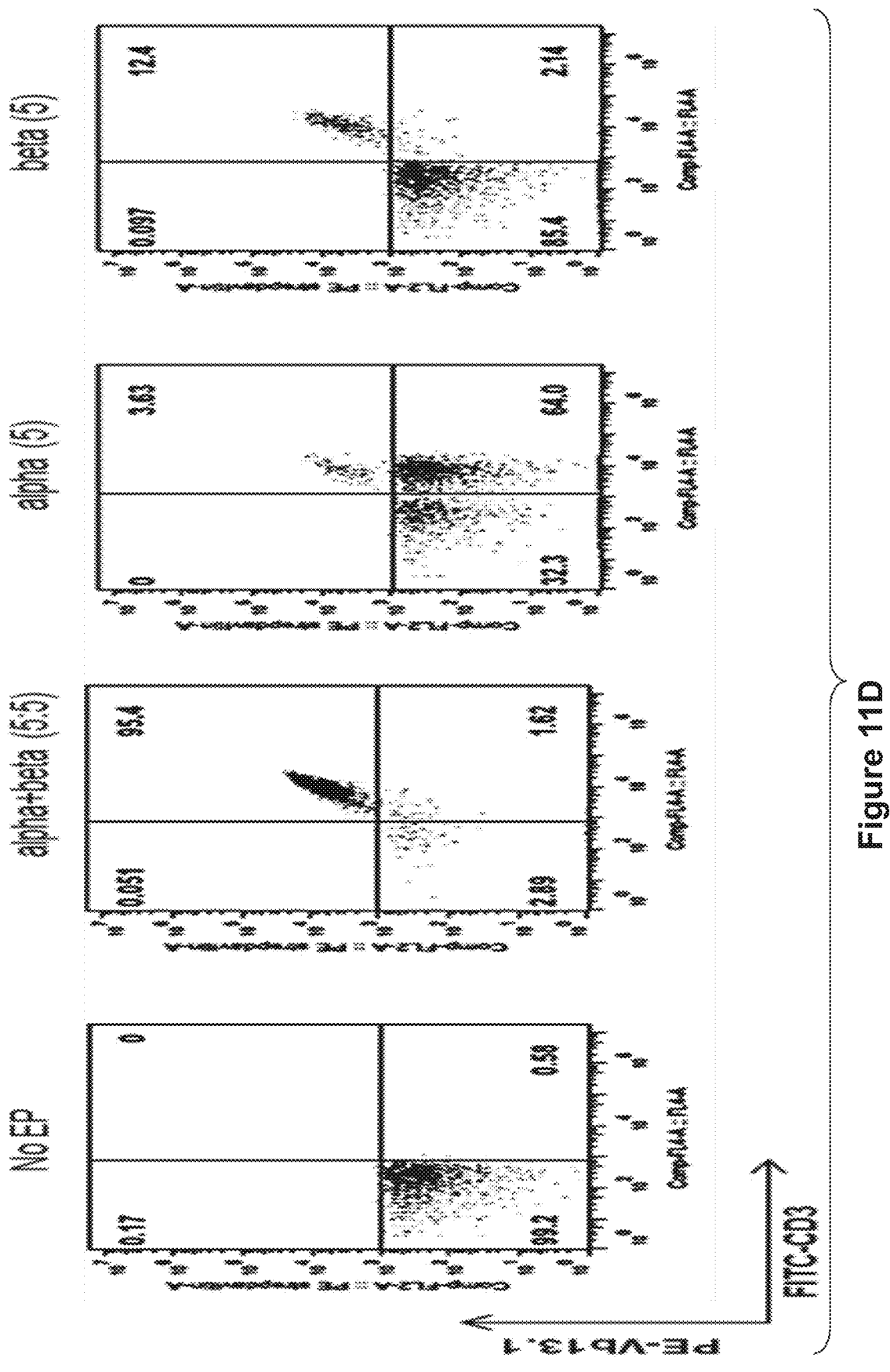
Figure 12A:
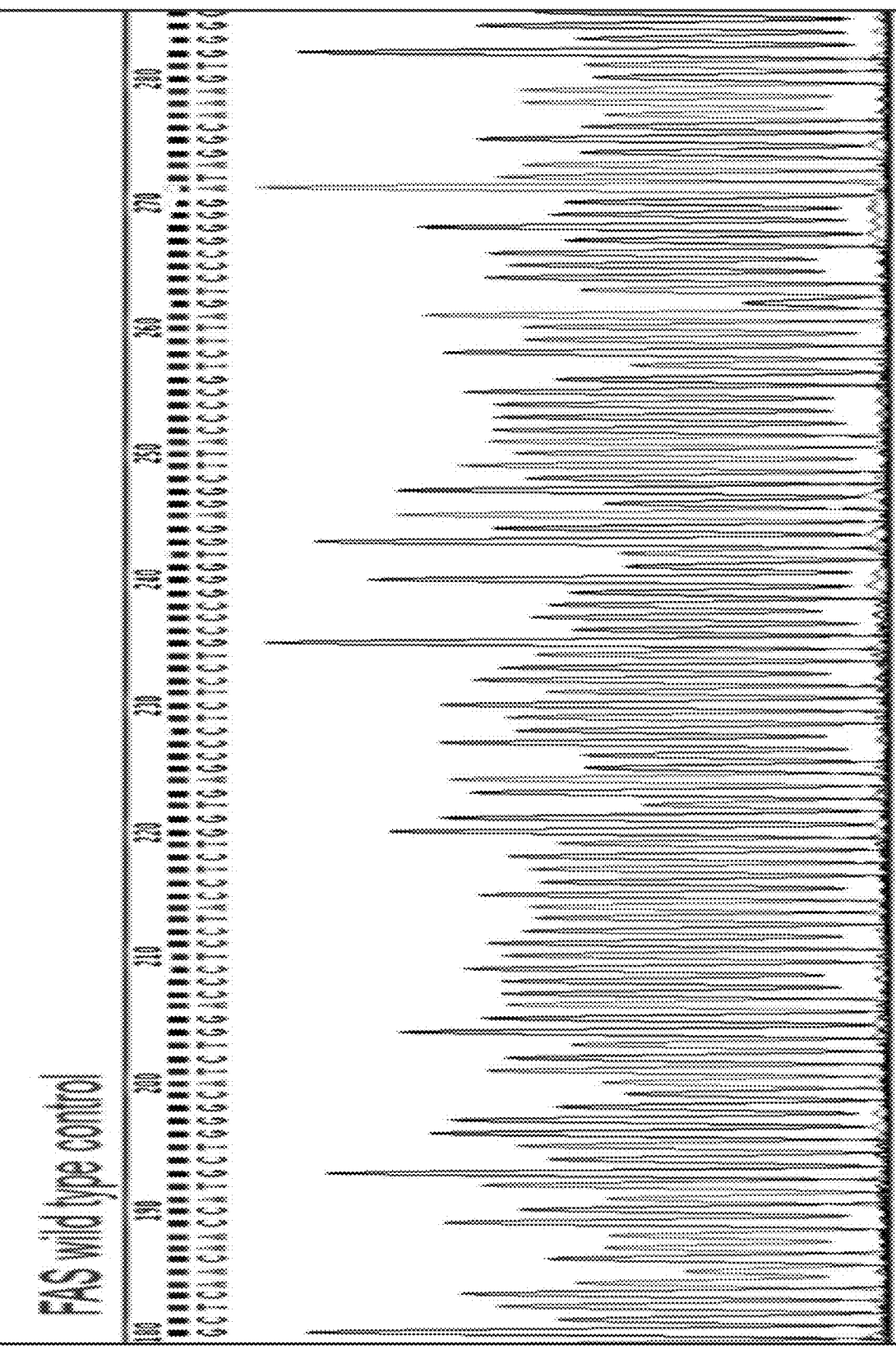
FIGS. 12A-12D, shows knock out of FAS in 293T cells.
Figure 12B:
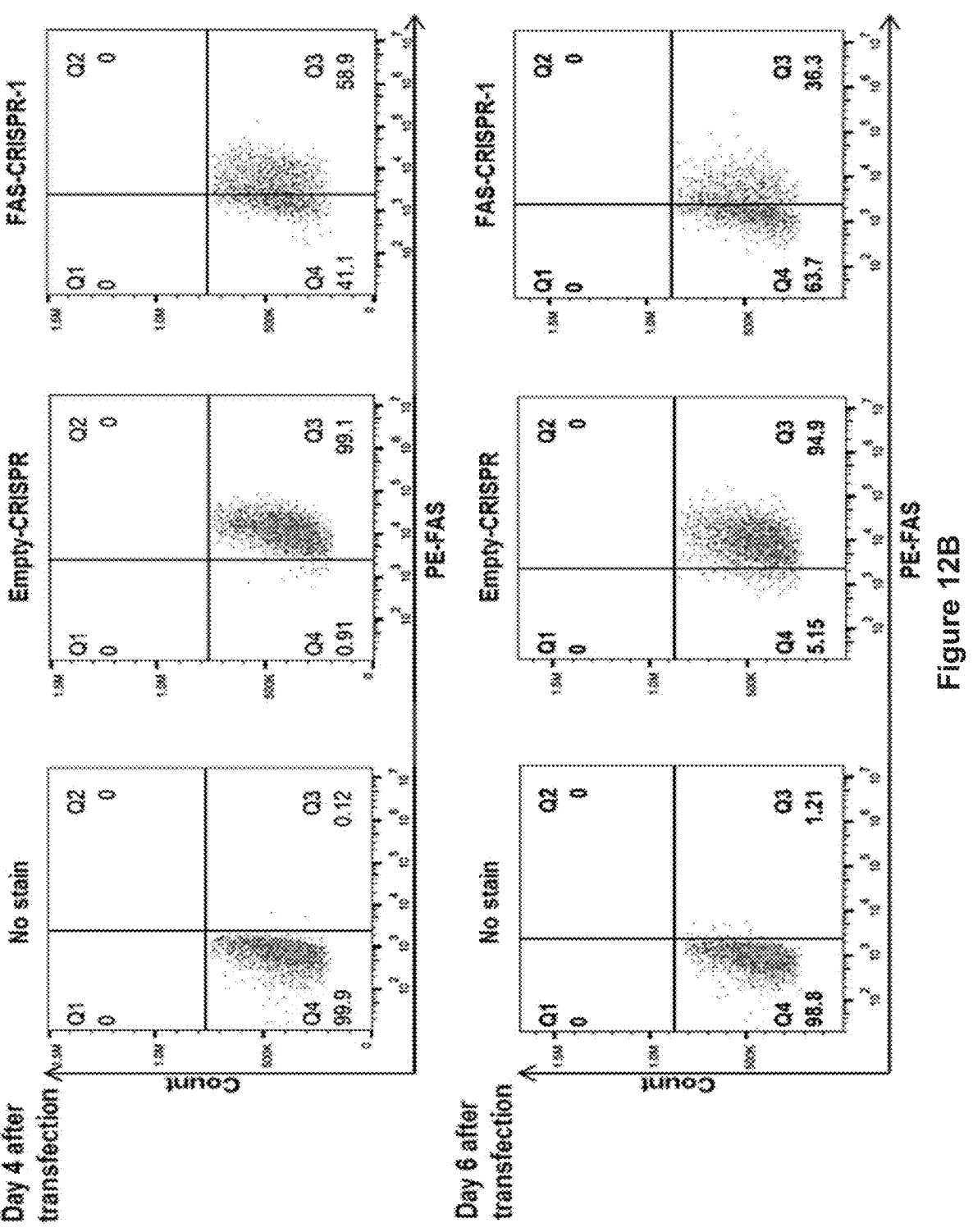
Figure 12C:
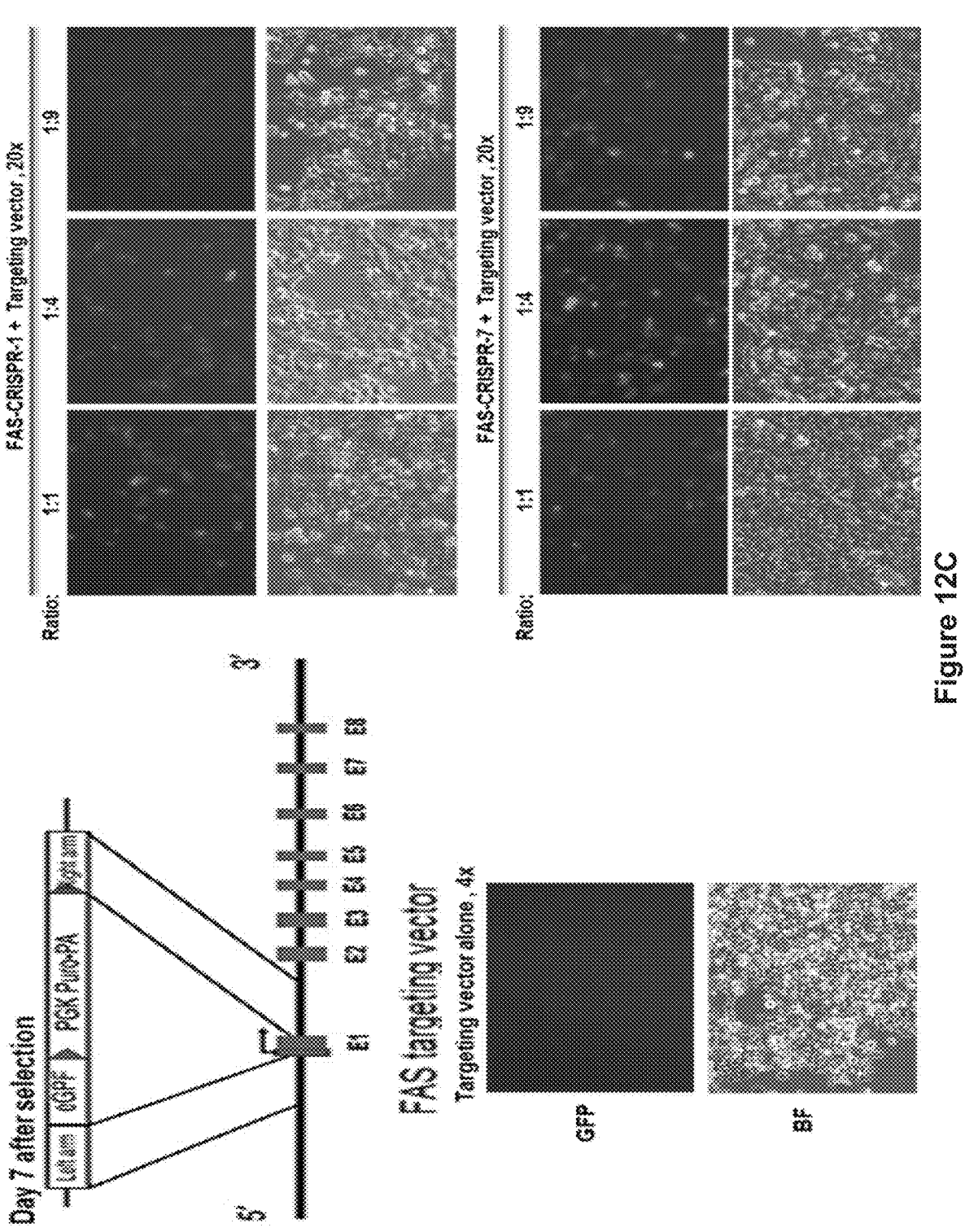
Figure 12D:
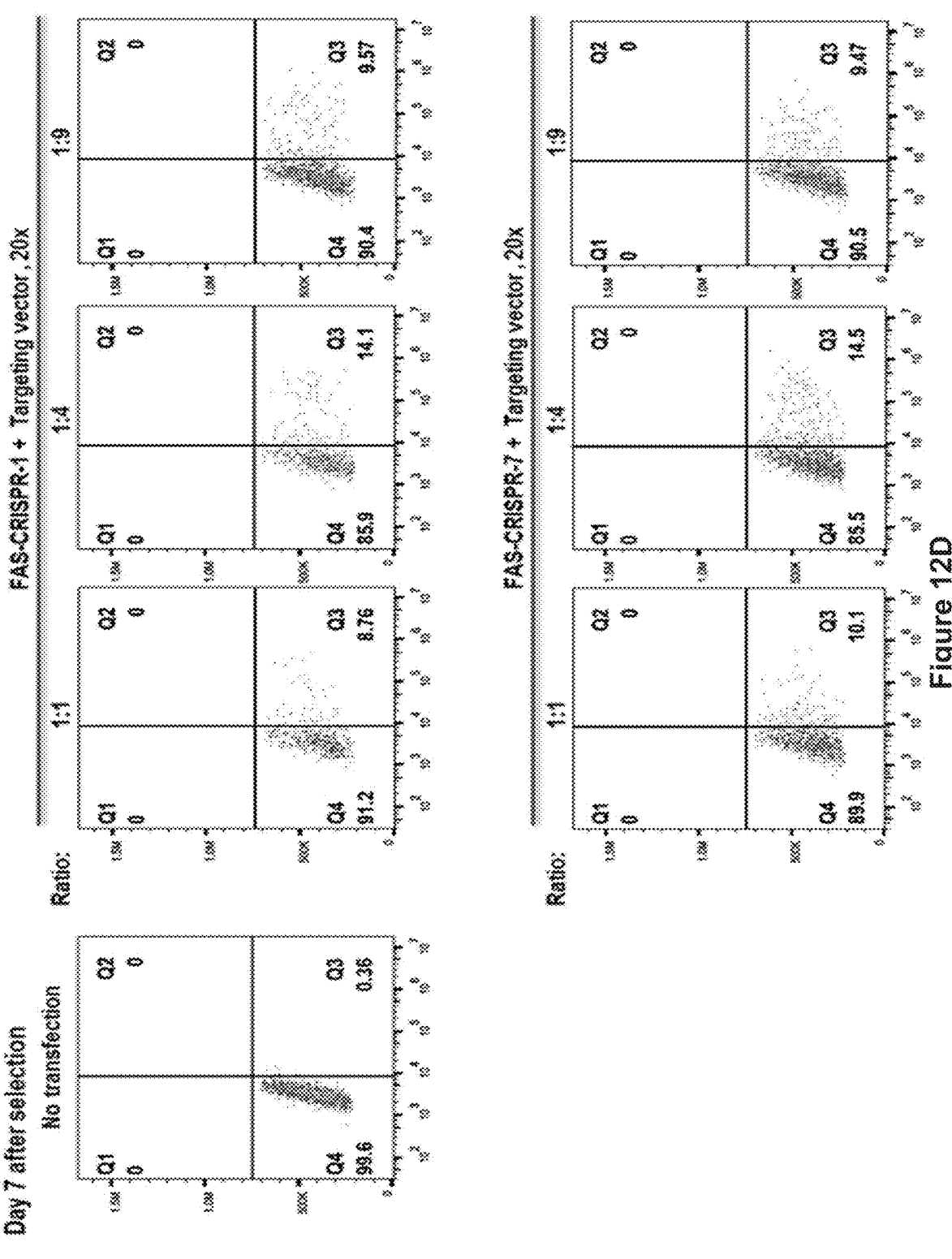
Figure 13:
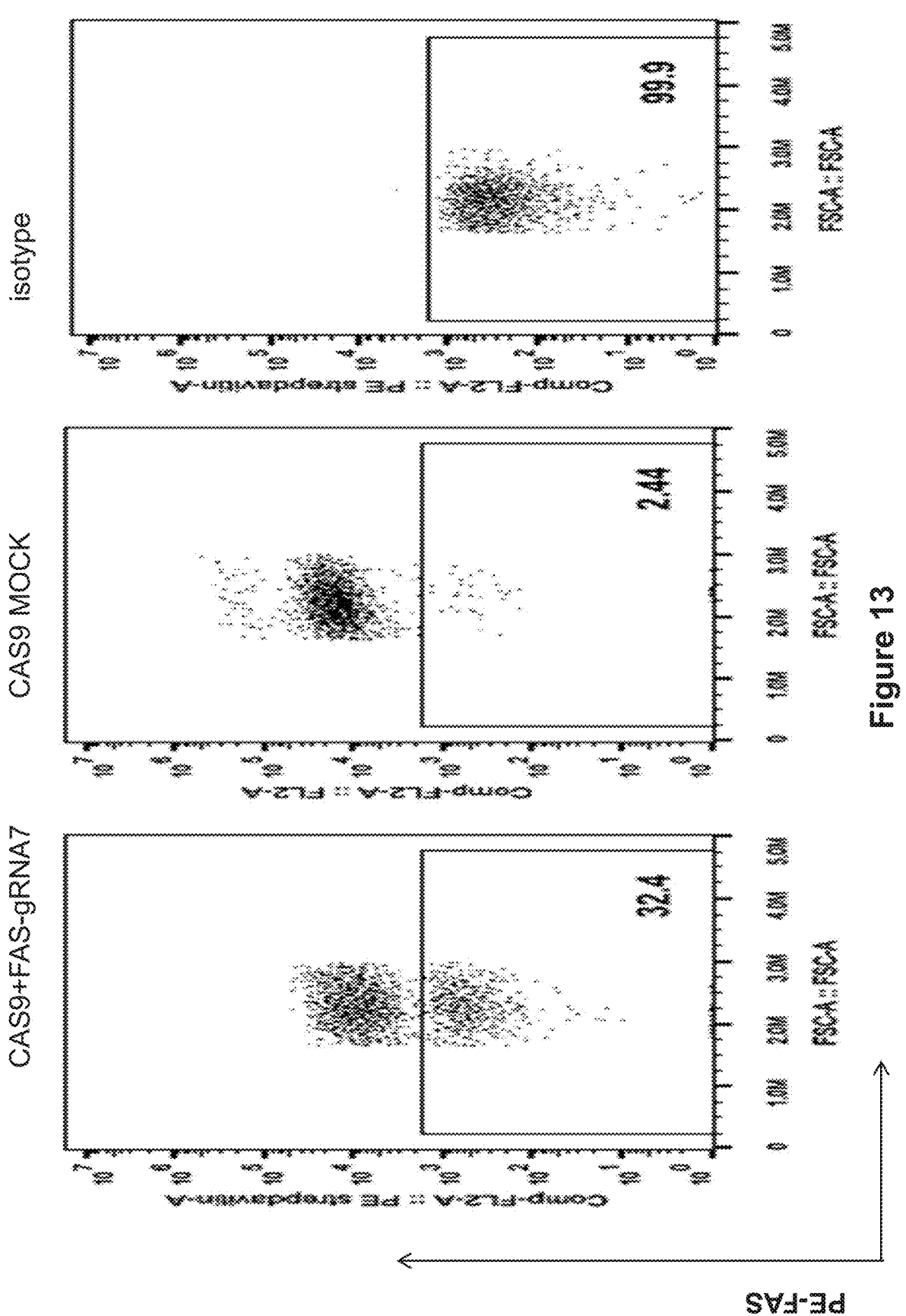
FIG. 13 shows knock out of FAS in primary T cells. FACS data illustrated that surface FAS protein expression was abolished by CRISPRs.
Figure 14A:
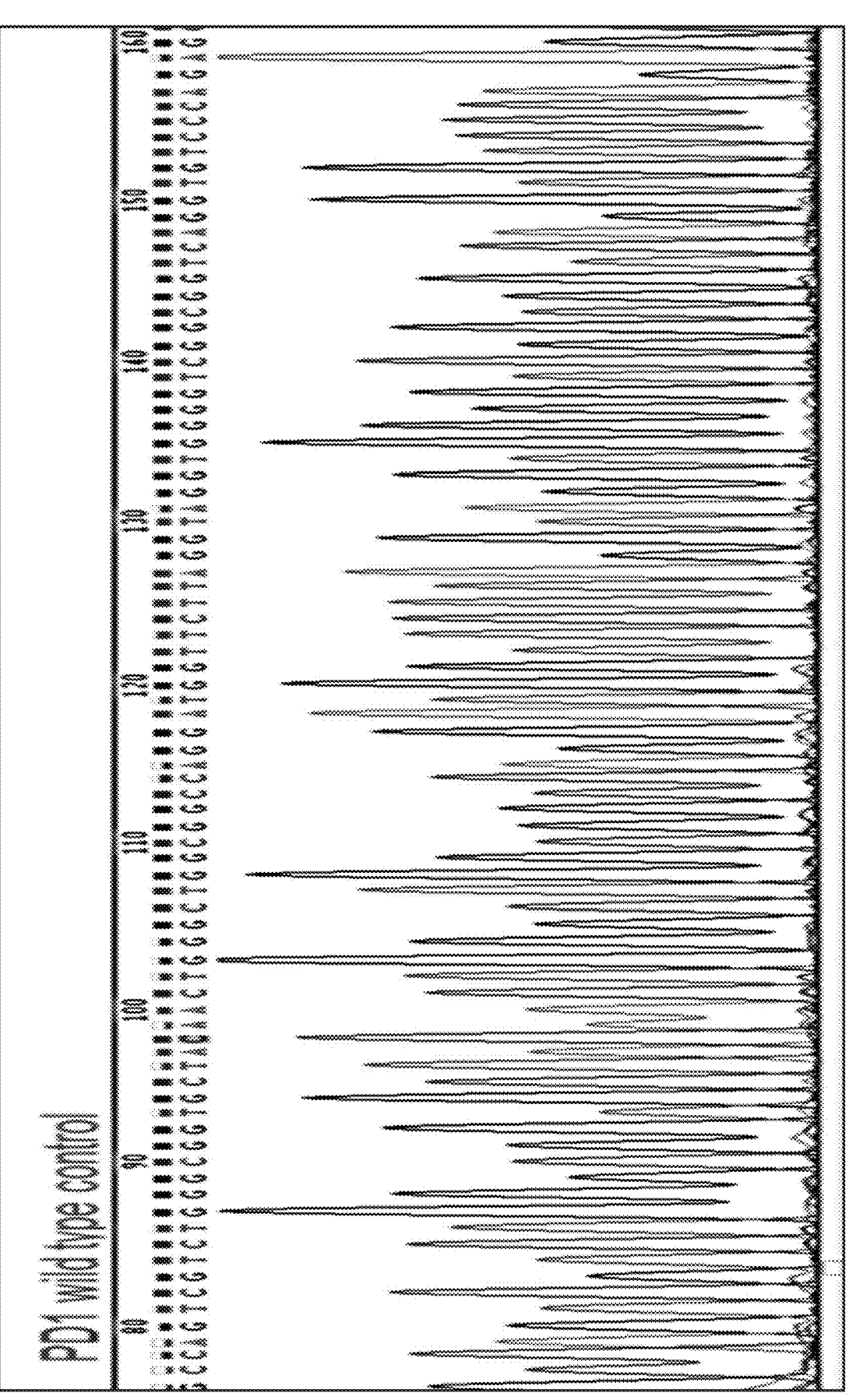
FIGS. 14A and 14B, shows knock out of PD1 in 293T and primary T cells.
Figure 14A:
Figure 14B:
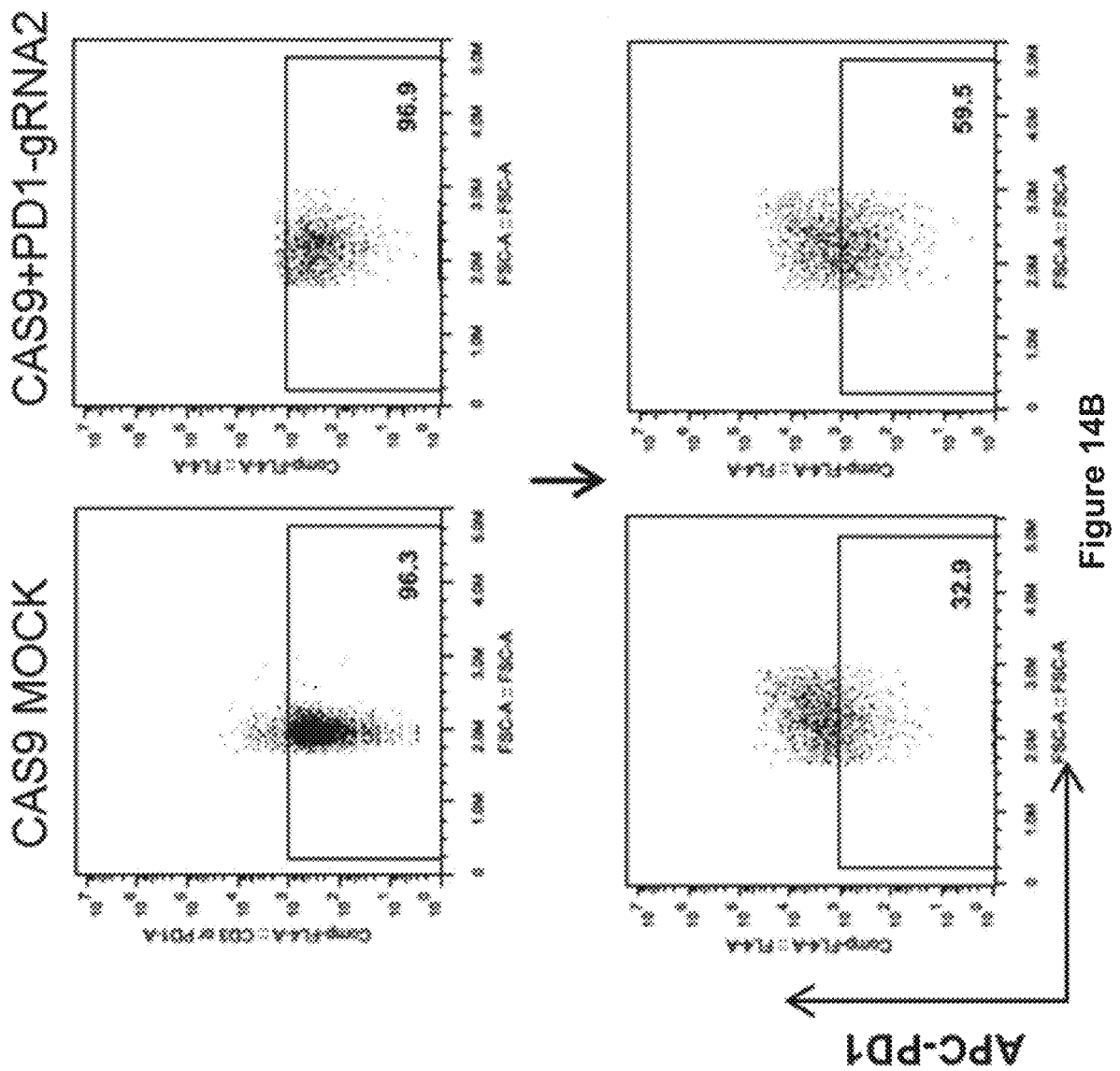
Figure 15A:
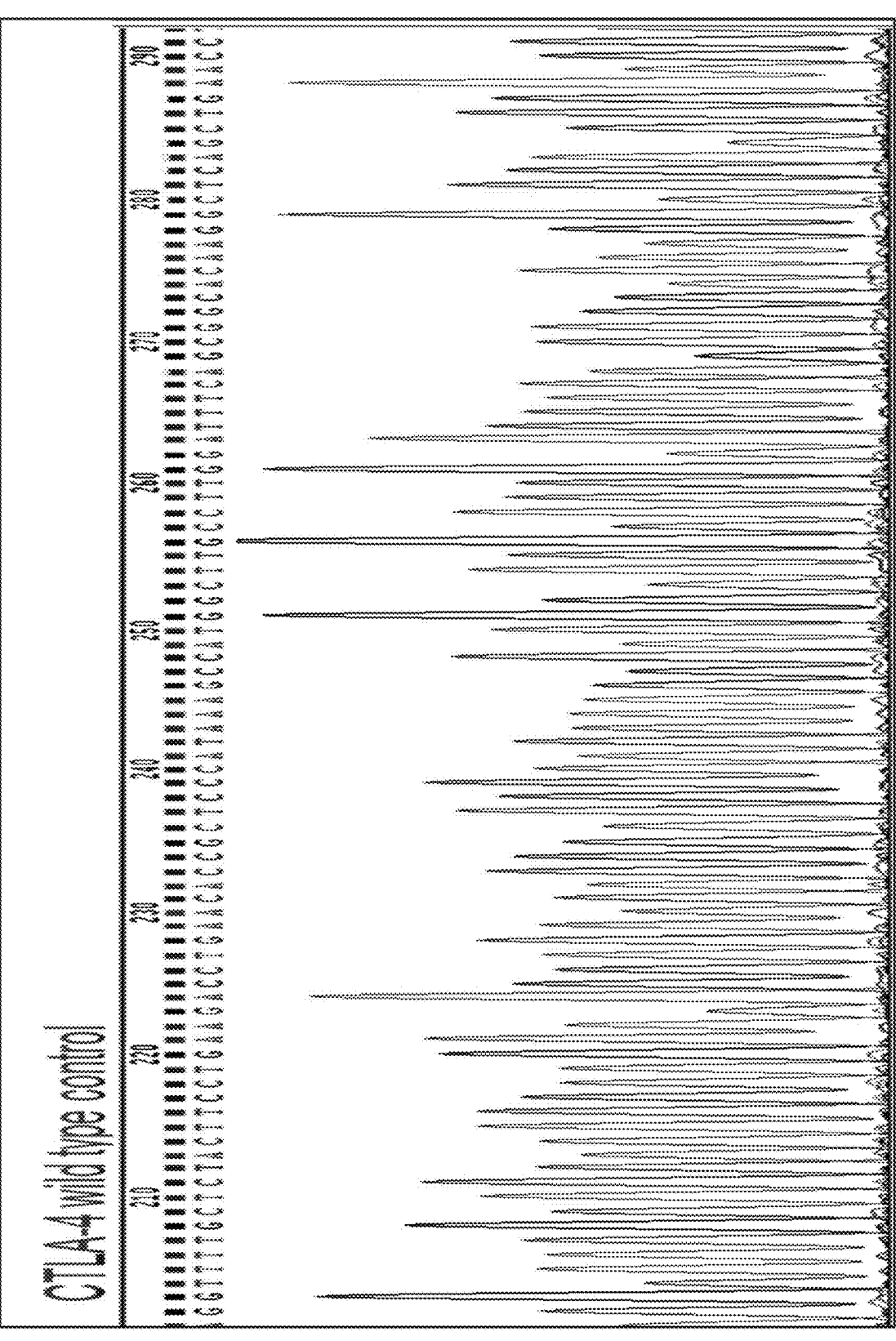
Figure 16:
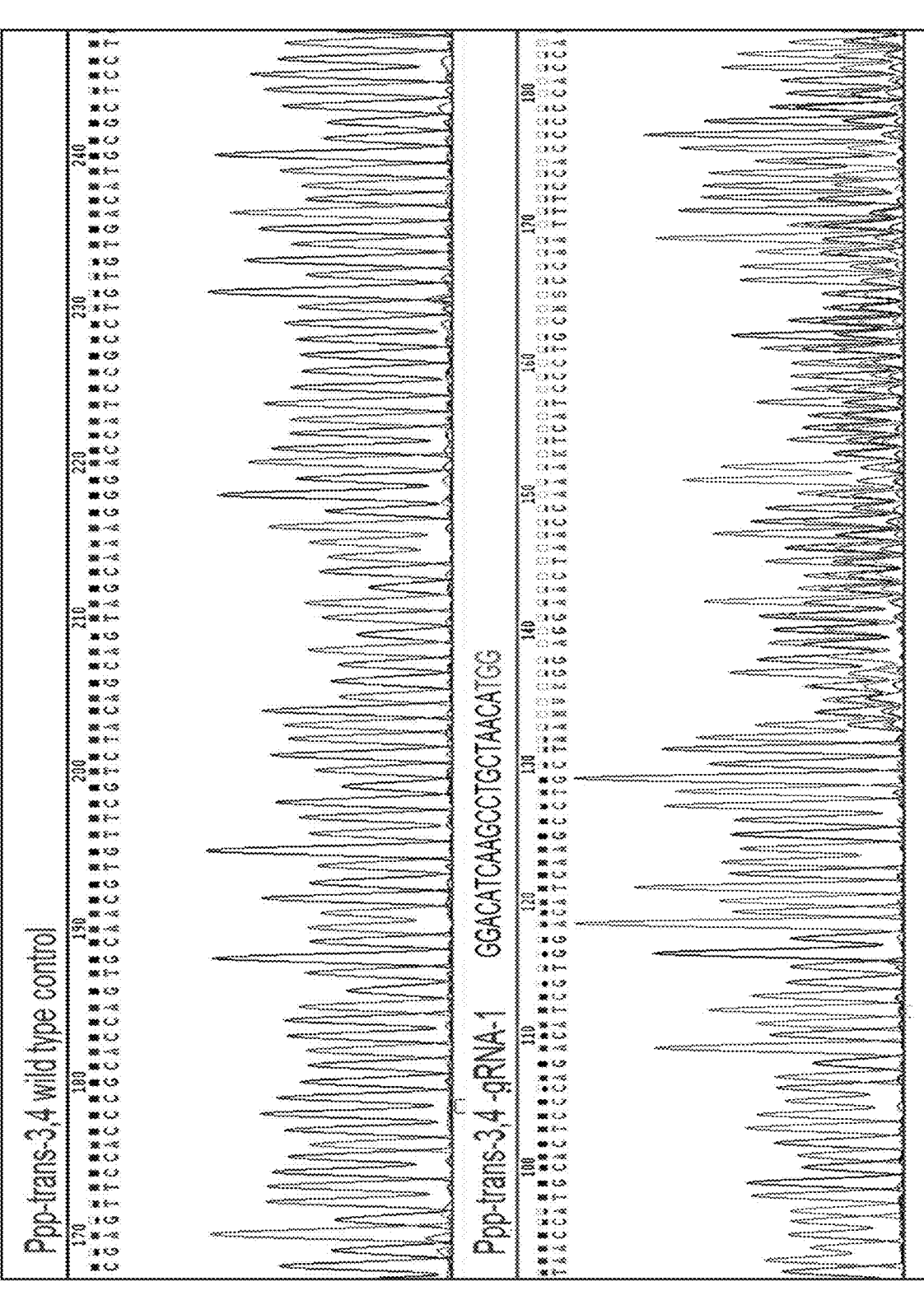
FIG. 16 shows knock out of PPP2r2d in 293T. Sanger sequencing data (SEQ ID NOs: 85-87) indicated PPP2r2d was targeted in 293T cells by CRISPRs. Ppp-trans-3,4-gRNA-1 and Ppp-trans-3,4-gRNA-2 sequences are also shown (SEQ ID NOs: 61 and 62).

IFN-gamma greatly improved, approximately 10 fold, targeting efficiency of beta-2 microglobin in T cells (FIG. 9C). Multiple electro-transfers of beta-2 microglobin gRNAs gave a 66% beta-2 microglobin negative population (FIG. 11A).

Figure 9D:
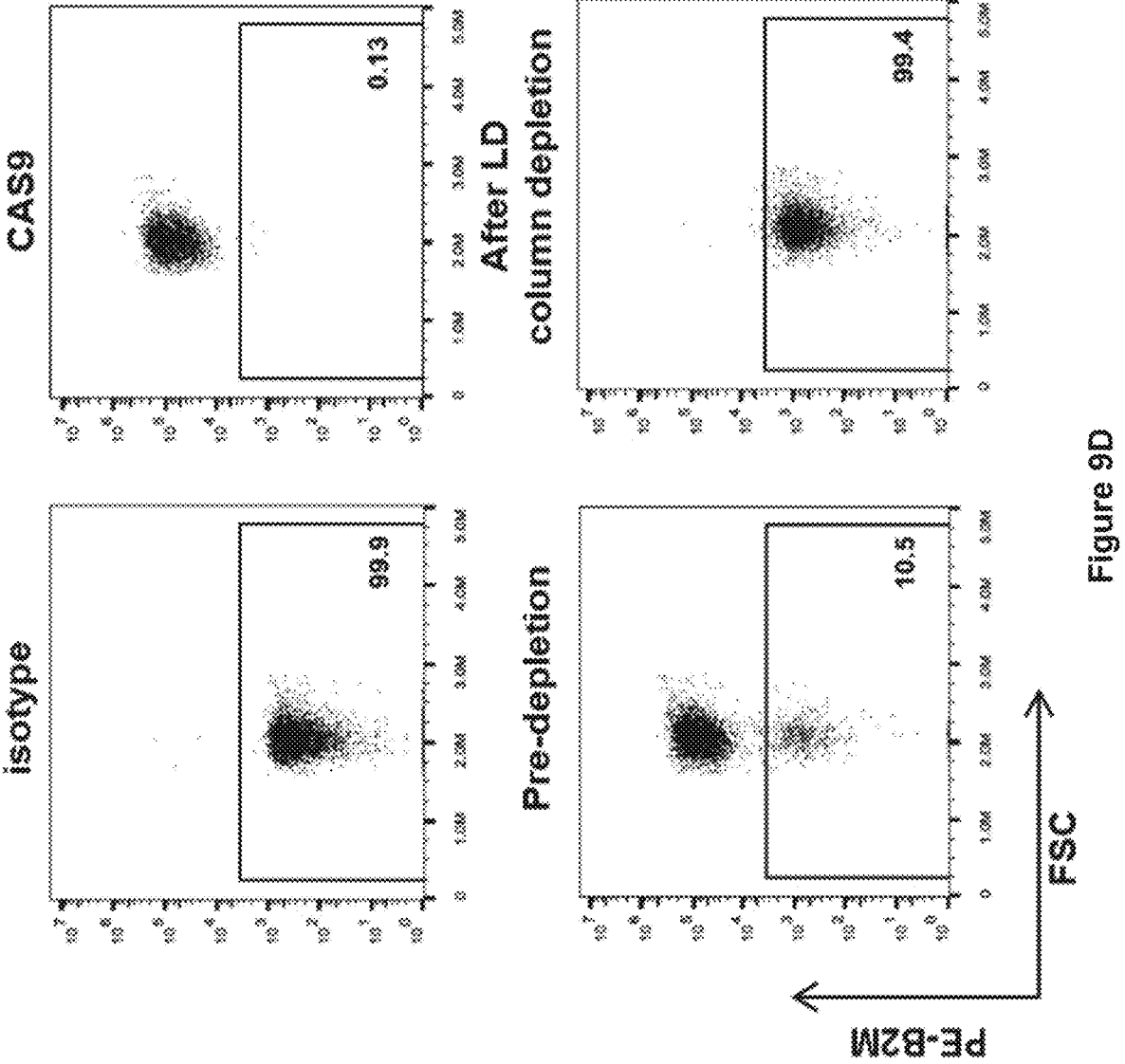
Figure 10:
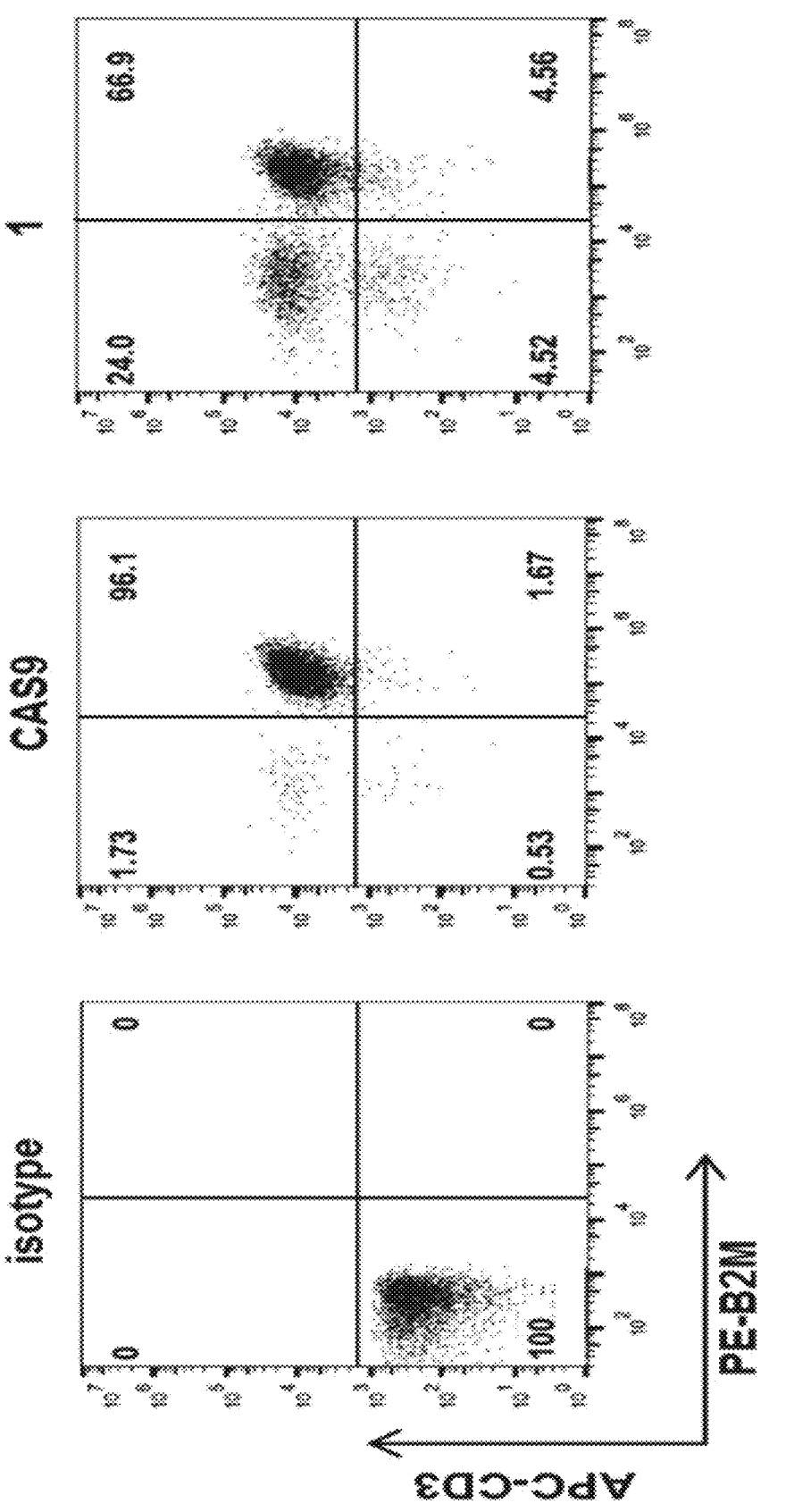
FIG. 10 is a panel of graphs showing simultaneous knock out of HLA-CLASS I and TCR in primary T cells. CD4 and CD8 T cells were stimulated with CD3/CD28 dynabeads. Three days after stimulation, expanded T cells were elec-troporated with CAS9 mRNA together with TCR β constant region (TRBC) and beta-2 microglobin targeting gRNAs. Both TCR expression and beta-2 microglobin expression were evaluated using anti-CD3 monoclonal antibody (mAb) and anti-beta-2 microglobin mAb six days after electropo-ration. Numbers represent the percentage of population in each quadrant.

For future allograft transplantation clinical applications, rapid and robust methods for isolating sources of HLA-CLASS I null populations will be needed. To begin to address this issue, the cells were labeled with PE-anti-beta-2 microglobin antibody, and enriched for a HLA-CLASS I$^{neg}$, population by negative selection using clinically-approved paramagnetic anti-PE microbeads and a depletion column. With a single depletion step, the HLA-CLASS I$^{neg}$ population was enhanced to over 99%. A HLA-CLASS I$^{neg}$ population could not be enriched from untransfected control cells. An analysis of HLA-CLASS I repertoire in enriched HLA-CLASS I$^{neg}$ T cells via flow cytometry validated the elimination of HLA-CLASS I expression from the cell surface (FIG. 9D).

Example 4: CD3$^{neg}$ T Cells can be Propagated by Different Methods

CD3$^{neg}$ T cells restored CD3 expression after electro-transfer of exogenous 1G4-TCR alpha and beta chain in vitro transcribed mRNA (5 µg each). These cells were expanded by: (1) a single Rapid Expansion Protocol (REP), then tested for activity and specificity. PBMCs were obtained from three different donors: ND052 $105 \times 10^6$, ND405 $83 \times 10^6$, ND410 $136 \times 10^6$. Cell were after irradiated, then mixed together, and a total $324 \times 10^6$ PBMCs were obtained. $2 \times 10^6$ cells were electro-transferred with RNA. CD3$^{neg}$ T were re-suspended in a final volume of 90 ml and R10 media was added for a total volume of 300 ml. The cells were divided into 2 T150 ml flasks. OKT was added to a final concentration of 30 ng/ml. On day 2, IL-2 was added to 50 CU/ml. From day 5, cells were counted and fed every 2 days and once T cells appeared to rest down, as determined by both decreased growth kinetics and cell size, they were either used for functional assays or cryopreserved.

After a single REP, CD3$^{neg}$ T cells were expanded for a 500 fold increase in number. These cells were expanded by: (2) stimulated with magnetic beads coated with anti-CD3/anti-CD28 at a 1:3 cell to bead ratio.

After a single REP, CD3$^{neg}$ T cells were expanded for a 500 fold increase in number. These cells were expanded by: (3) co-cultured with irradiated K562-CD19 and K562/86/64/A2(2D11) in equal mixture at a concentration of $1 \times 10^6$/ml.

After a single REP, CD3$^{neg}$ T cells were expanded for a 500 fold increase in number. These cells were expanded by: (4) co-cultured with irradiated K562-CD19 and K562/86/64/A2(2D11) in equal mixture at a concentration of $1 \times 10^6$/ml with 30 ng/ml OKT After a single REP, CD3$^{neg}$ T cells were expanded for a 500 fold increase in number. These cells were expanded by: (5) co-cultured with irradiated K562-CD19 and K562/86/64/A2(2D11) in equal mixture at a concentration of $1 \times 10^6$/ml with 1 mg/ml NY-ESO peptide.

Example 5: Re-Direction of TCR$^{neg}$ T Cells by Electro-Transfer of TCR

Figure 7A:
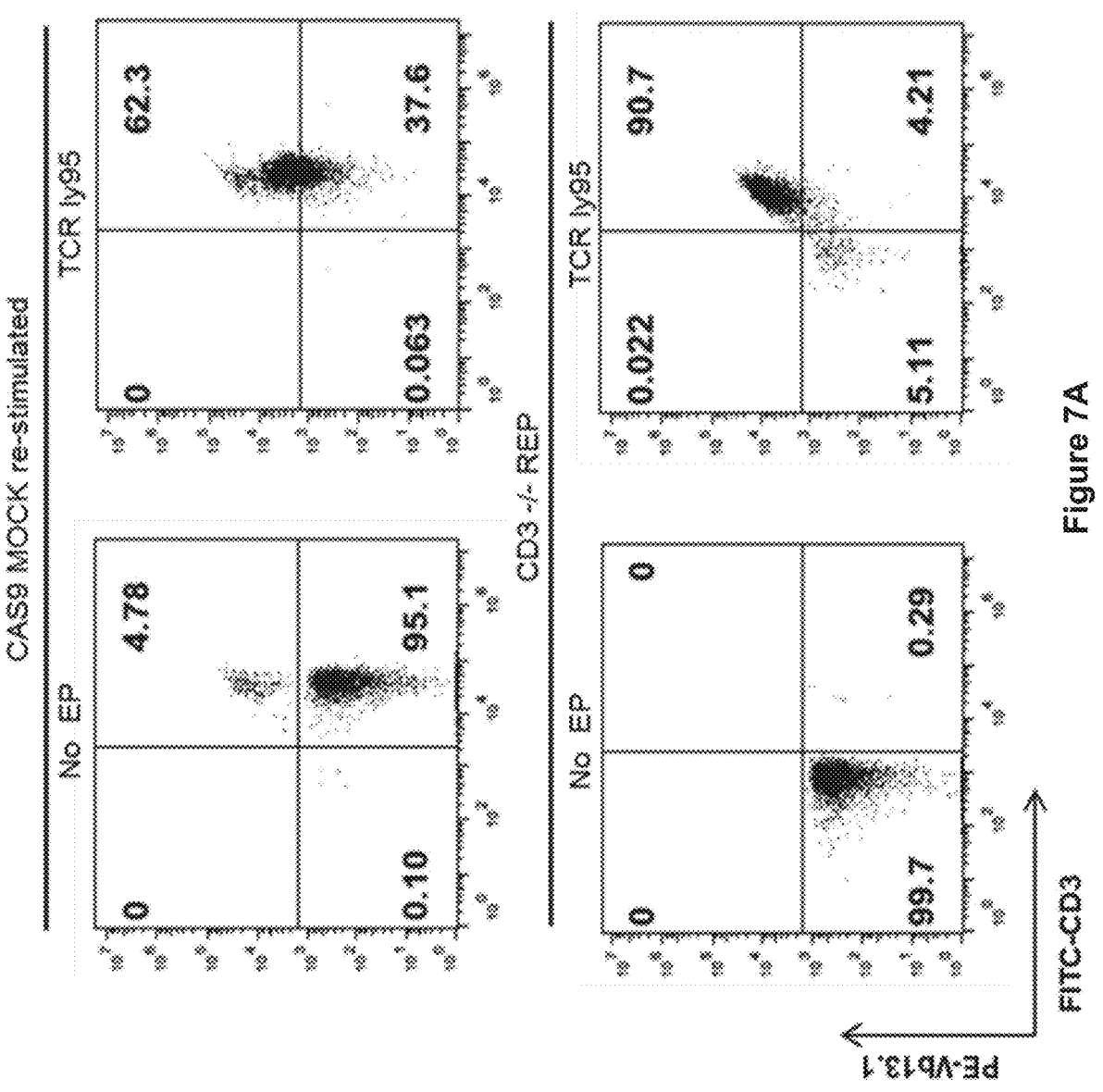
FIGS. 7A-7C, shows expanded TCR$^{neg}$ T cells with potent anti-tumor activity after re-direction in vitro.
Figure 7B:
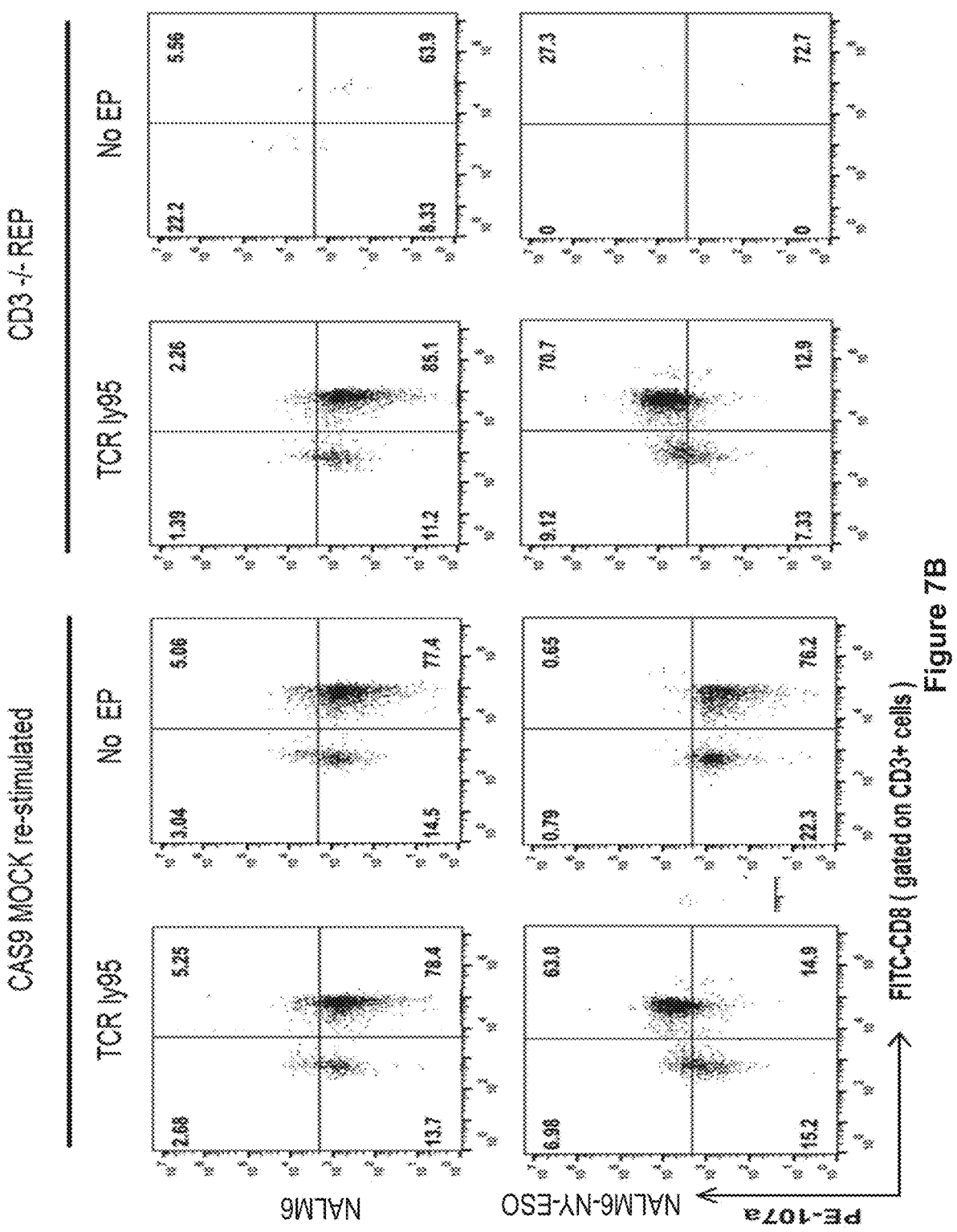
Figure 7C:
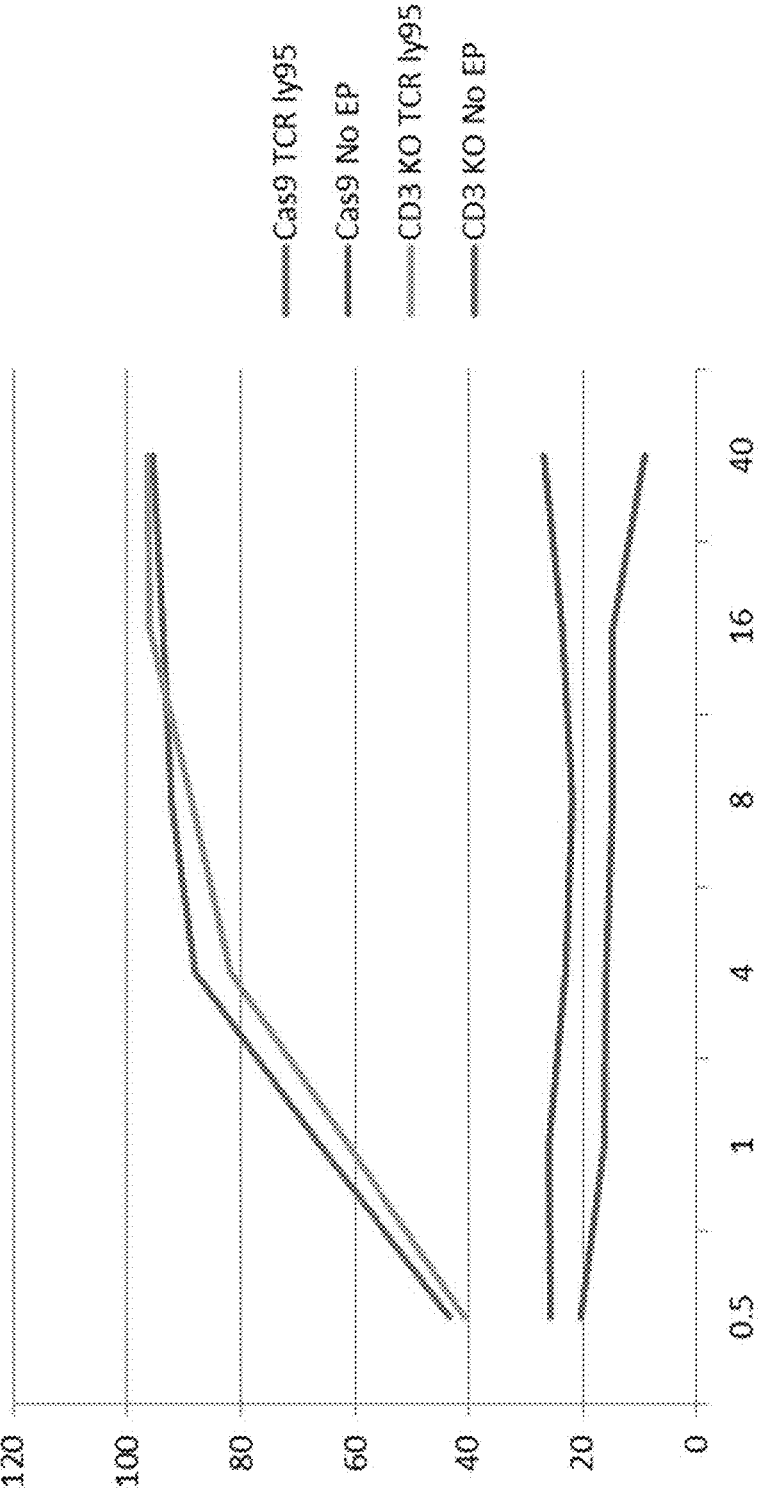
Figure 8:
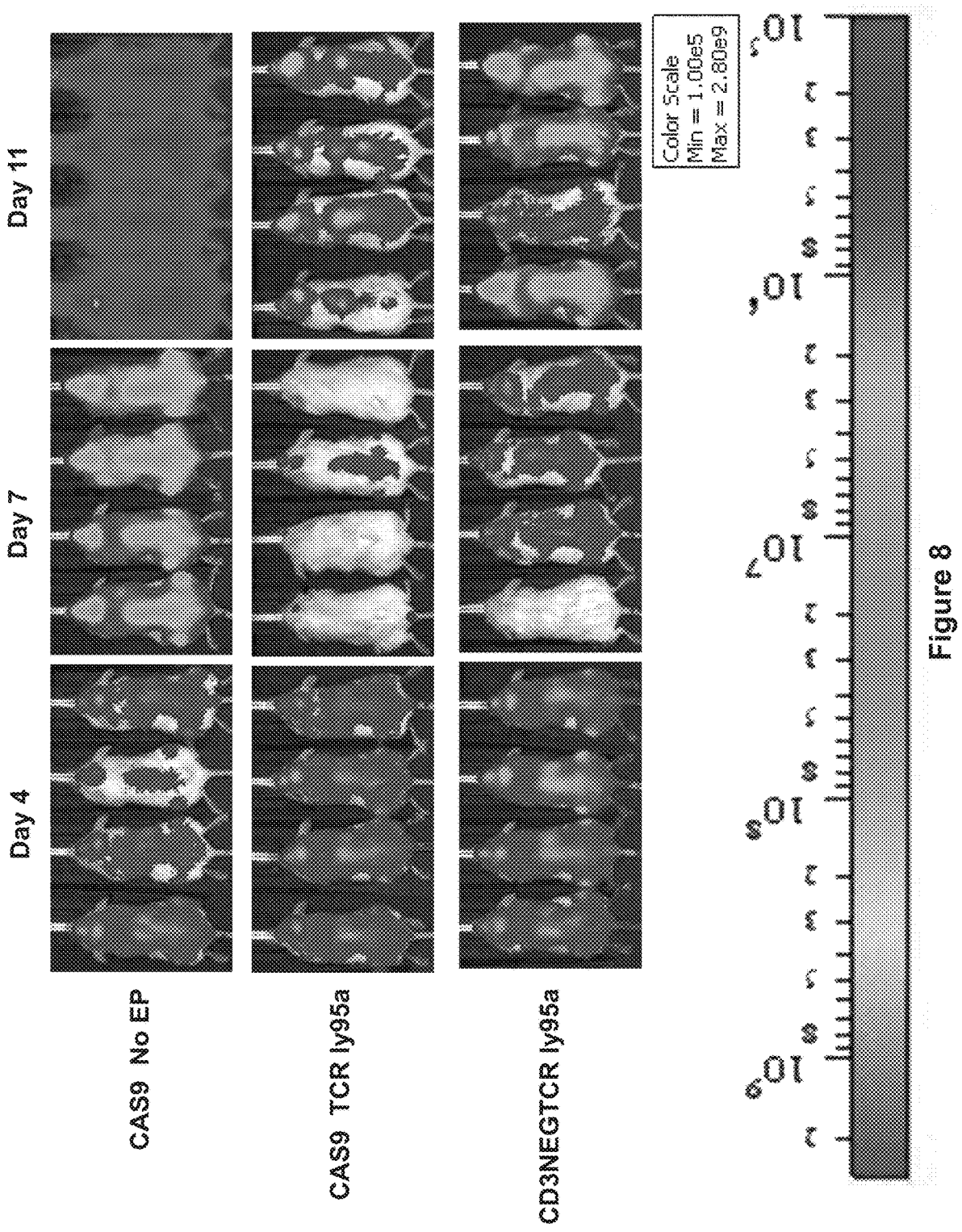
FIG. 8 is a panel of illustrations showing that directed TCR$^{neg}$ T cells control the growth of tumor in NSG mice after re-direction.

To test the function of TCR$^{neg}$ T cells, these cells were re-directed by electro-transfer of TCR. By introducing TCR alpha chain and TCR beta chain, these cells expressed high levels of TCR. The expression of Vb13.1 was much higher in electro-transferred TCR$^{neg}$ T cells compared to CAS9 MOCK control (FIG. 7A). When the cells were co-cultured with the Nalm-6 NY-ESO leukemia cell line, positive for both HLA-A2 and NY-ESO, the cells showed high levels of 107a, indicating elevated de-granulation activity (FIG. 7B). The killing assay also showed potent toxicity towards this cell line (FIG. 7C). This indicated that these cells are potentially safer than traditional clinical trials with T cell expressing CARs and TCRs, as these cells would not trigger GVHD and have less miss-pair toxicity than normal T cells with TCR treatment.

Some reports have shown that T cells can be genetically edited by ZFNs or TALEN to eliminate expression of the endogenous αβ TCR. The methods and compositions described herein to selectively deplete T cells expressing undesired αβ TCR also include incomplete knockout of the endogenous TCR to treat GVHD and inhibit endogenous TCR from adversely affecting CAR function (e.g., through competition for transcription factors). Therefore, a genetic approach was designed using designer ZFNs to permanently disrupt the α and β constant region sequences in T cells, thereby eliminating TCR expression.

ZFNs and TALENs are artificial restriction enzymes generated by fusing a DNA binding domain to a DNA cleavage domain. When ZFNs and TALENs do not work efficiently, it is often difficult to determine the cause. Failure could reflect a problem with the design, with accessibility of the target sequence, or a delivery issue. At the same time, ZFN targeting efficiency is usually low in T cells, making it difficult to manipulate multiple genes at one time.

Distinct ZFNs and TALENs, the CRISPR/Cas system has recently emerged as a potentially facile and efficient alternative to ZFNs and TALENs for inducing targeted genetic alterations. Recent work has shown that target recognition by the Cas9 protein requires a 'seed' sequence within the crRNA and a conserved di-nucleotide-containing proto-spacer adjacent motif (PAM) sequence upstream of the crRNA-binding region. The CRISPR/CAS system can thereby be retargeted to cleave virtually any DNA sequence by redesigning the crRNA. The data disclosed herein shows the potential for gene editing by CRISPR/CAS in 293T cells and primary T cells. The CRISPR/CAS system can simultaneously target multiple genomic loci by co-expressing a single CAS9 protein with two or more gRNAs, making this system uniquely suited for multiplex gene editing or synergistic activation of target genes. By administering different gRNAs together with CAS9, multiple genes can be simultaneously disrupted in T cells.

Example 6: HLA CLASS I and TCR α, β Chain Triple Knockout by CRISPR

To work toward "off-the-shelf" allogeneic t-cell therapies for malignancies and infectious diseases, cell therapy by infusion of T cells was designed to reconstitute immunity against pathogens and malignancies. The amount of time required to manufacture T cells with the desired properties and in sufficient numbers ex vivo is often incompatible with the treatment window for patients. Furthermore, autologous T cells from patients with advanced disease may have compromised function and be tolerant to desired antigens.

To address this, patients can be infused with allogeneic T cells to avoid immune-mediated rejection caused by host T cells recognizing disparate major or minor histocompatibility antigens on the infused cells. To broaden the application of T cell therapy, and for future allograft transplantation, rapid and robust methods for isolating sources of TCR and HLA-CLASS I disrupted populations can be generated.

ZFN and TALEN comprise a zinc finger DNA-binding domain designed to bind a specific DNA sequence fused to the cleavage domain of FokI endonuclease. The design and construction of ZFN and TALEN is very complicated and time consuming if there is more than one gene to be manipulated, because the genes must be targeted individually. With the CRISPR system described herein, the efficiency and shortened the time course of gene disruption can be obtained.

To address this issue, CAS9 was electro-transferred with three different gRNAs targeting TRAC, TRBC and beta-2 microglobin. Cells were labeled with PE-anti-beta-2 microglobin antibody and enriched for a HLA-CLASS I$^{neg}$ population by negative selection using clinically-approved paramagnetic anti-PE microbeads and a depletion column. With a single depletion step, the HLA-CLASS I$^{neg}$ population was enhanced to over 99% (FIG. 9D). Then the cells were re-introduced with TCR alpha chain, and HLA-CLASS I$^{neg}$ CD3$^{neg}$ population was enriched by microbeads (FIG. 11). Five days later, the TCR beta chain was re-introduced into the cells, and a HLA-CLASS I$^{neg}$ CD3$^{neg}$ population was enriched by microbeads again. Two days later, TCR was electro-transferred into these triple knock out cells. On the day after electro-transformation, the cells were stimulated with CD3/CD28 dynabeads. Then, the cells underwent lentiviral delivery of antigen specific TCR the next day and culture expansion.

Example 7: FAS, PD1, CTLA4, PPP2R2D Knockout by CRISPR

The FAS receptor/FAS ligand (FAS/FASL) apoptosis signaling pathway has been widely studied and is well characterized in T cells. PD1 and CTLA4 are two major inhibitory signaling pathway in T cells that have also been extensively studied. Direct evidence for the potential therapeutic impact of targeting these pathways came from studies in preclinical murine tumor models demonstrating enhanced anti-tumor immunity after antibody-mediated blockade of CTLA-4, PD-1 or PD-L1. Similar antibodies for use in humans have been developed, and early clinical data showed promising results. Ppp2r2d knockdown may also inhibit T-cell apoptosis and enhance T-cell proliferation, as well as cytokine production. Ppp2r2d has potential as a target to improve the function of human T cells.

To address this issue, CAS9 and three different gRNAs targeting FAS, PD1, CTLA4, PPP2r2d were electro-transferred into T cells. Sanger sequencing data showed that the indicated locus of FAS, PD1, CTLA4, PPP2r2d had been modified by the CRISPRs. FAS was also replaced by GFP with homologous recombination triggered by CRISPR. FACS data showed the surface expression of FAS and PD1 was abolished.

Example 8: Generation of IPS Cells with Gene Modified Primary and T Cells

Progress in adoptive T-cell therapy for cancer and infectious diseases is hampered by the lack of readily available and antigen-specific human T lymphocytes. Pluripotent stem cells could provide an unlimited source of T lymphocytes. To address this issue, the expression of FAS, PD1, CTLA4, PPP2r2d were disrupted in primary cells and T cells.

Sendai virus was used to reprogram primary cells and T cells. There are multiple methods to generate iPSCs, including virus-mediated gene transduction and chemical induction. While lentiviral and retroviral vectors require integration into host chromosomes to express reprogramming genes, DNA-based vectors, such as adenovirus, adeno-associated virus, and plasmid vectors, exist episomally and do not require integration. However, they may still be integrated into host chromosomes at certain frequencies, and the reprogramming efficiency is relatively low. Likewise, mRNA based reprogramming is complicated and shown to be extremely inefficient.

Unlike these methods, Sendai virus does not integrate into the host genome or alter the genetic information of the host cell. Sendai virus also has reprogramming potential comparable to lentiviral- and retroviral-based gene transduction.

Each well in a 24 well plate was seeded with 0.1 million wild type, FAS$^{neg}$, CD3$^{neg}$ TCR alpha chain and TCR beta chain knock-out T cells. The cells were stimulated with CD3/CD28 beads. At day 3 post stimulation, the beads were removed, the cells resuspended in 1 mL of pre-warmed T cell complete medium, and then incubated with a calculated volume of CytoTune Sendai virus comprising a polycistronic vector for expression of hKlf4, hOct3/4 and hSox2 in the cells (Lifetechnologies, Carlsbad, CA). Treated T cells were seeded in 24 well plates, and centrifuged at 2250 rpm for 90 minutes at room temperature. An additional 1 mL of complete T cell medium was added to each well and the plate was incubated overnight at 37° C. in a humidified atmosphere of 5% CO2.

On the day after transduction, Sendai virus was removed by washing the T cells with fresh complete medium and culturing the cells for 2 days. Media was half changed every day. On day 3 after infection, cells were transferred to MEF feeder plates and cultured in T cell medium without any cytokines. Four days after infection, the cells were cultured in standard hES medium. Media was changed every day. ES-like colonies were observed around day 7. The cells were cultured in conditioned hES medium from day 15 and cultures continued for an additional 10 days. Colonies were picked at around 25 to 30 days after transduction.

Figures 17A, 17B:
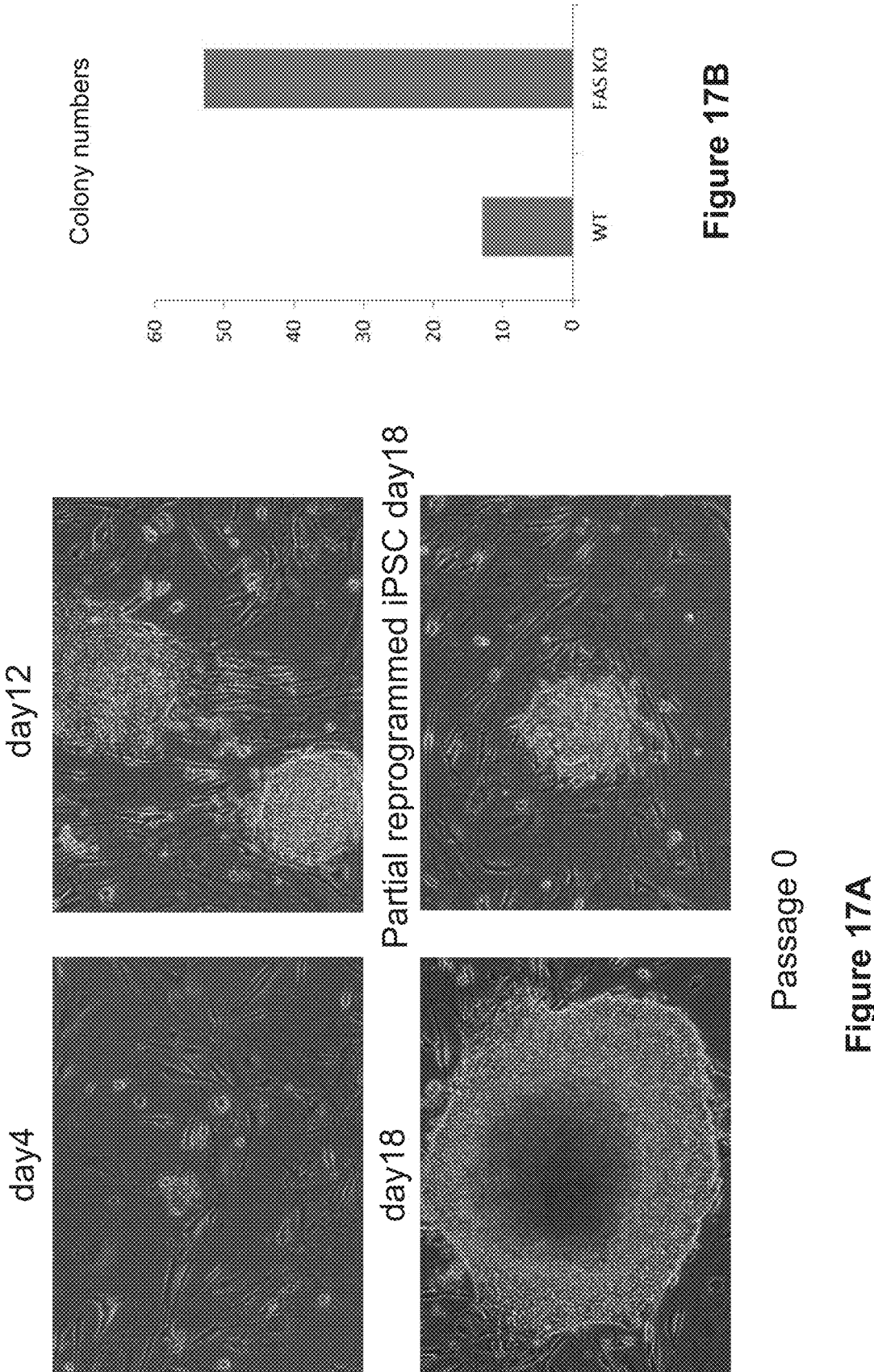
FIGS. 17A and 17B, shows genera-tion of iPSCs from FAS knock out T cells.
Figures 18A, 18B:
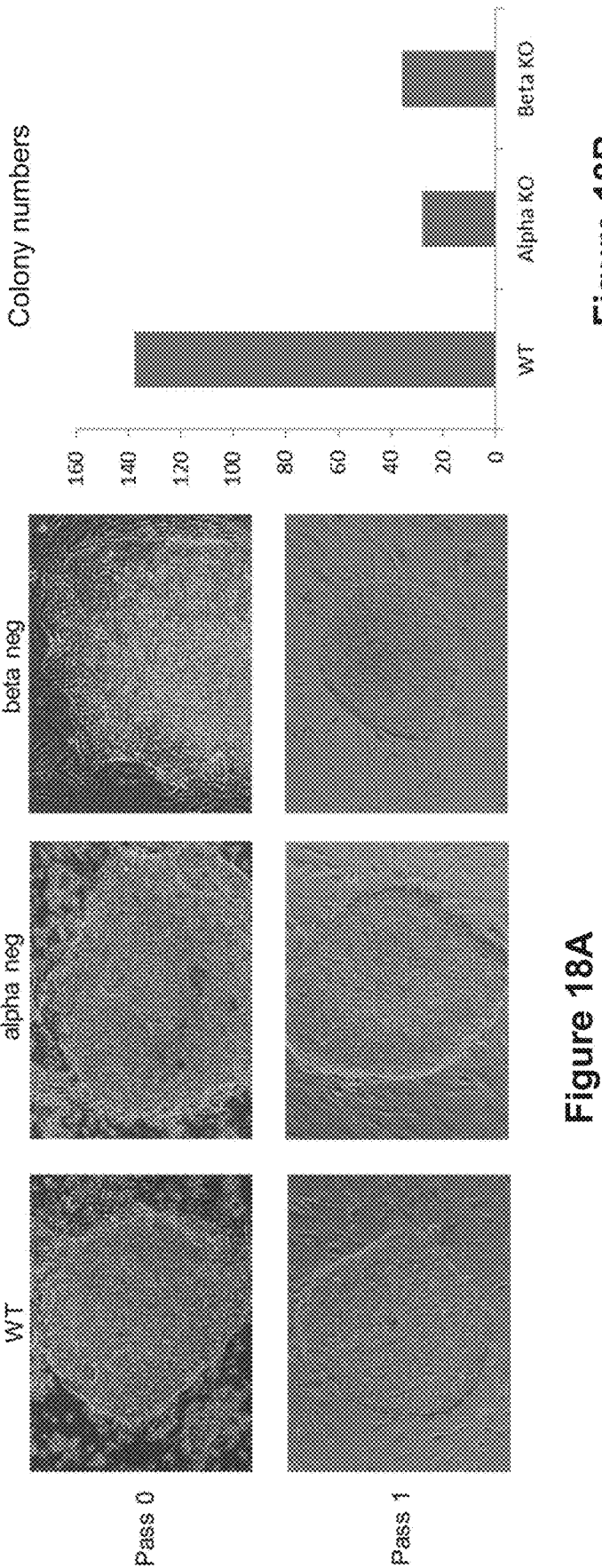
FIGS. 18A and 18B, show the generation of iPSCs from CD3$^{neg}$ T cells.

At around day 4, cell clumps were formed on feeder cells, indicating that the initiation of the reprogramming process. T cells went through dramatic morphological changes during the process of reprogramming to iPSCs. At around day 12, large cell clumps with loose edges began to emerge. At around day 18, T cells were transformed to typical ES-like colonies with well defined edges. Typical embryonic stem cell morphology was observed indicating that the FAS$^{neg}$, CD3$^{neg}$ TCR alpha chain and TCR beta chain knock-out T cells were induced to a pluripotent state under defined reprogramming conditions (FIGS. 17A and 18A).

FAS$^{neg}$ T cells were easier to reprogram to iPSCs, at an efficiency of about 5 times of its wild type counterparts (FIG. 17B). Likewise, reprogramming CD3$^{neg}$ T cell was about 5 times more efficient than the wild type counterparts (FIG. 18B). p53 deficient cell lines have been reported be easier to reprogram since the apoptosis pathway is hindered. FAS knock-out further induces apoptosis resistance. While loss of TCR expression makes T cells less healthy, an indication that apoptosis plays an important role in the process of reprogramming.

Example 9: Knockdown of TCR in T Cells with siRNA

Figure 19:
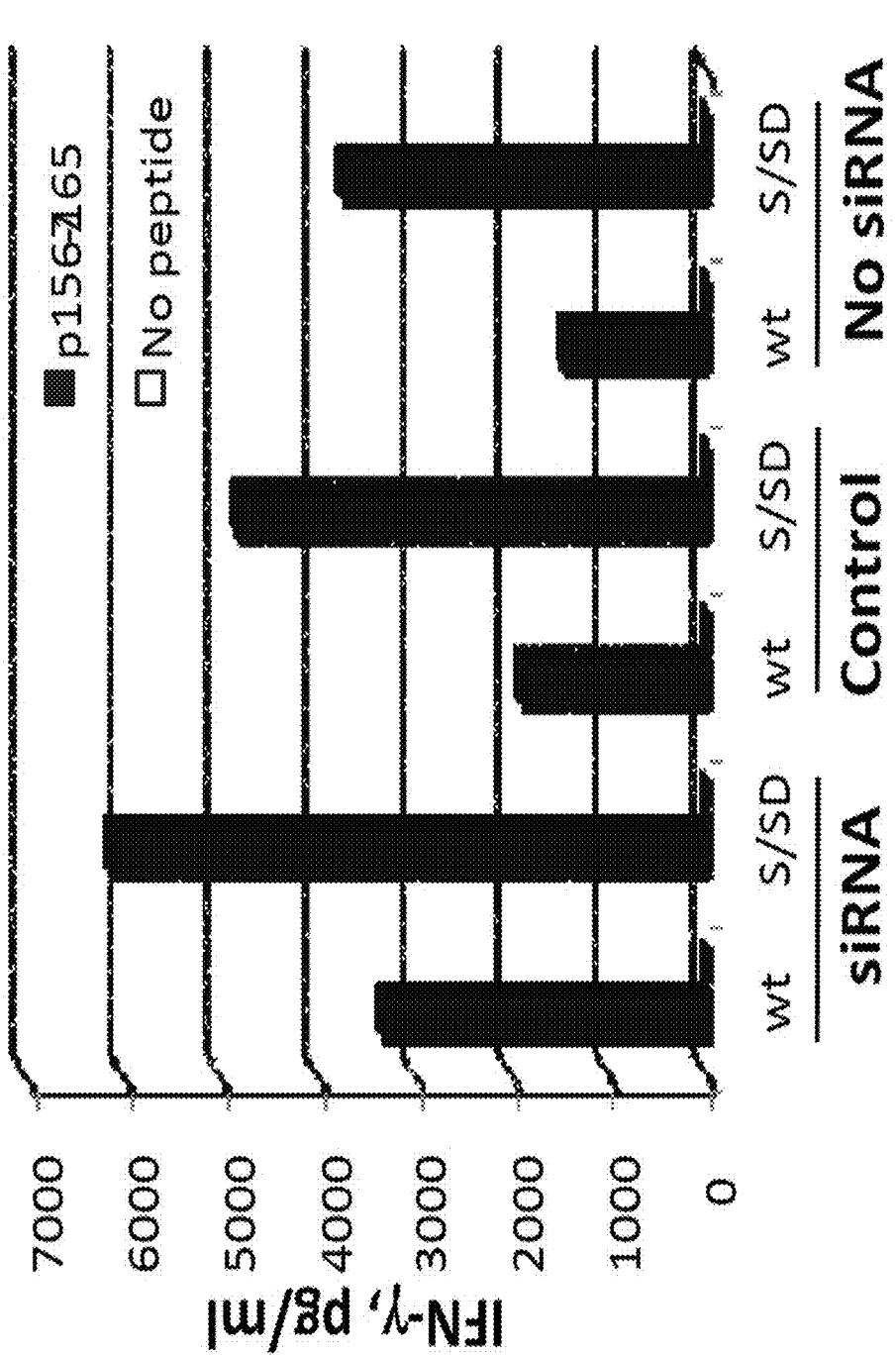
FIG. 19 is a graph showing knockdown of endogenous T cell receptors (TCRs) with siRNA and adding a second disulfide bond and de-N-glycosylation to the beta chain.

FIG. 19 is a graph showing IFN-gamma production of wild type NY-ESO-1 TCR (wt) or modified NY-ESO-1 TCR with a second disulfide bond and de-N-glycosylation to the beta chain (S/SD). RNA was electroporated into T cells with endogenous T cell receptors (TCRs) knocked down with siRNA. IFN-gamma was detected by ELISA after the T cells were stimulated with a HLA-A2 positive cell line pulsed with NY-ESO-1 specific peptide, p156-165, for 18 h.

Figure 20B:
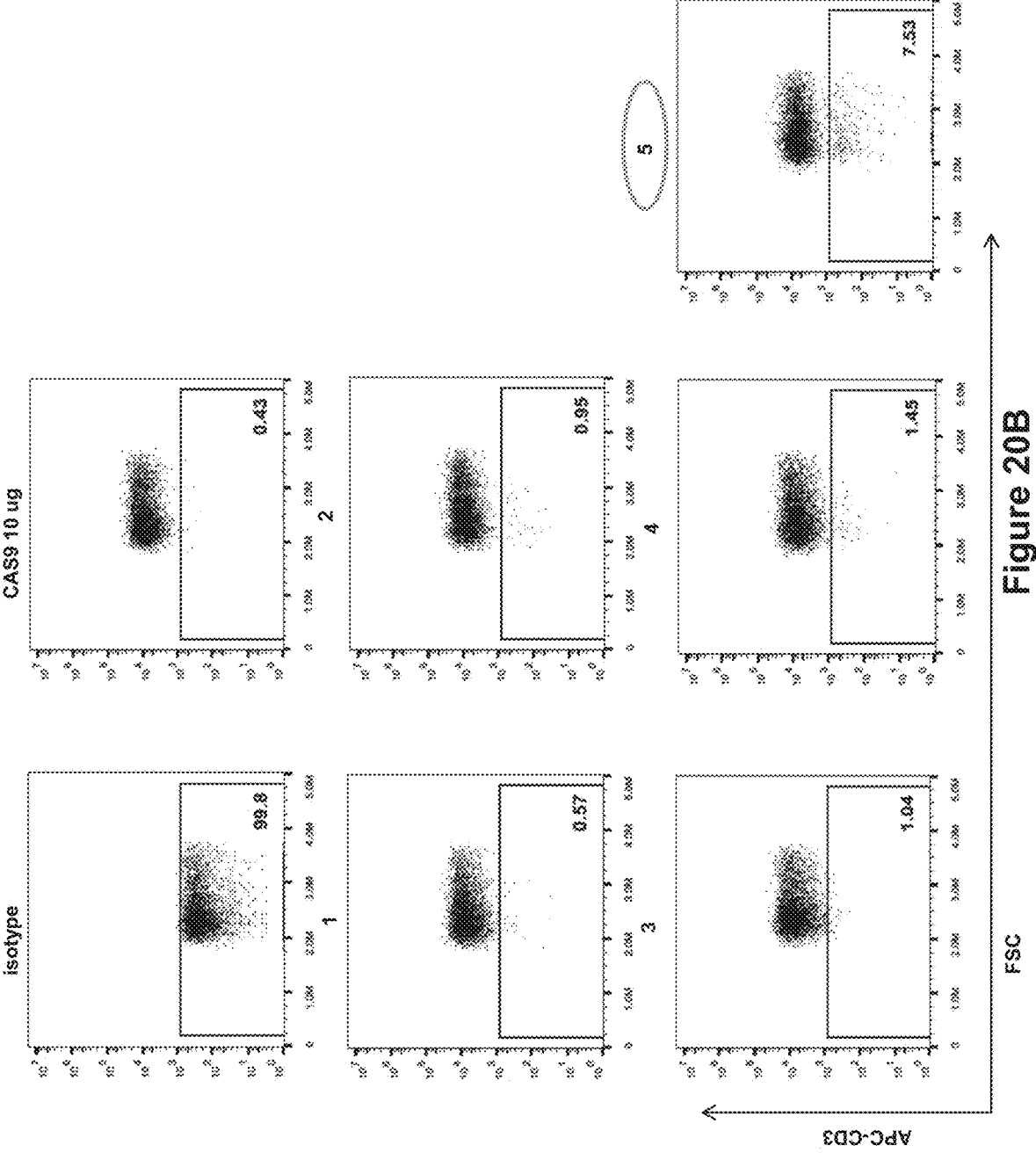

FIG. 20, comprising FIGS. 20A and 20B, shows TCR alpha knockdown by CAS9 RNA and gRNA co-electroporation. Six days after electroporation, cells were analyzed for TCR expression by assessing CD3.

Figure 21:
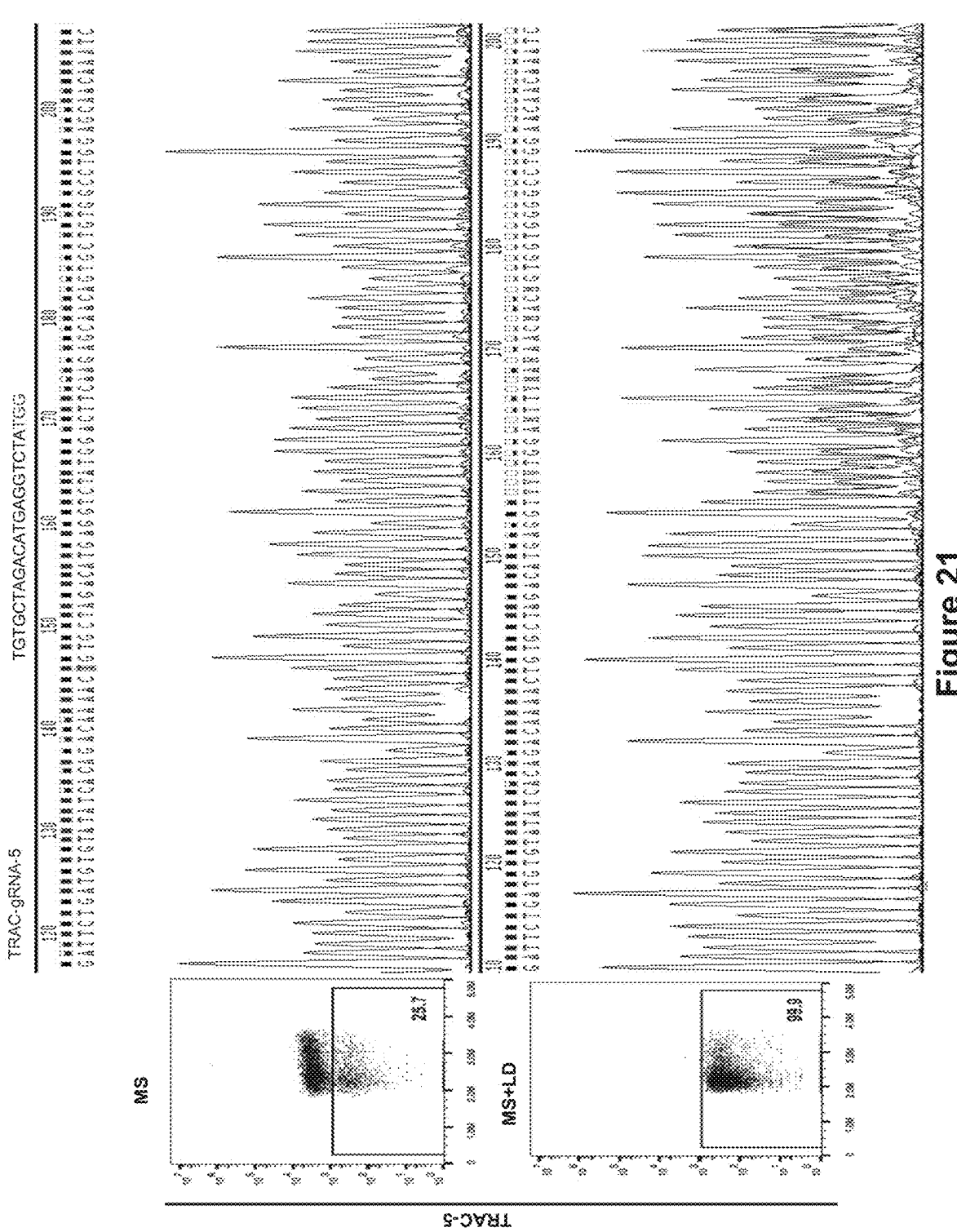
FIG. 21 is an illustration showing PCR sequencing results (SEQ ID NOs: 88-91) after CD3 micro-bead depletion. TRAC-gRNA-5 and TRBC-gRNA-7 sequences are also shown (SEQ ID NOs: 15 and 16).

FIG. 21 shows Sanger sequencing. Results show multiple peaks in CD3 negative enriched T cells, with either CAS9 mRNA and gRNAs electroporated to knockdown TCR alpha (TRAC-5) or TCR beta (TRBC-7).

Figure 22:
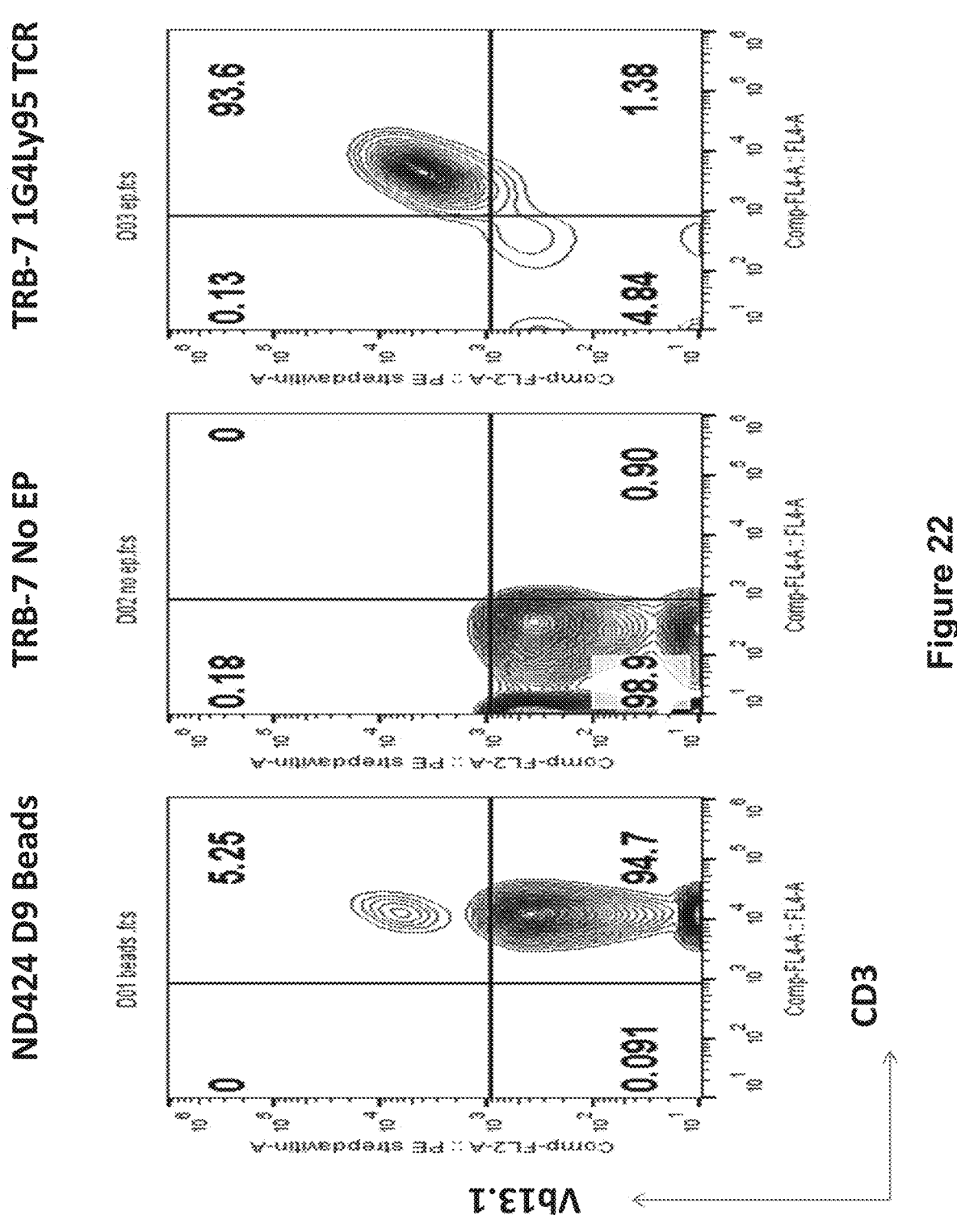
FIG. 22 is a panel of graphs showing re-expression of CD3 four hours after NY-ESO-1 TCR RNA electroporation.

FIG. 22 is a panel of graphs showing CD3 negative T cells with endogenous TCR beta (TRB-7) knockdown re-expressed CD3 four hours after NY-ESO-1 TCR alpha and beta (1G4LY95 TCR) RNA electroporation. Normal T cells (ND424 Beads) were used as control, which showed nearly 100% CD3 positive with 5.25% endogenous TCR vb13.1 expression.

Figure 23A:
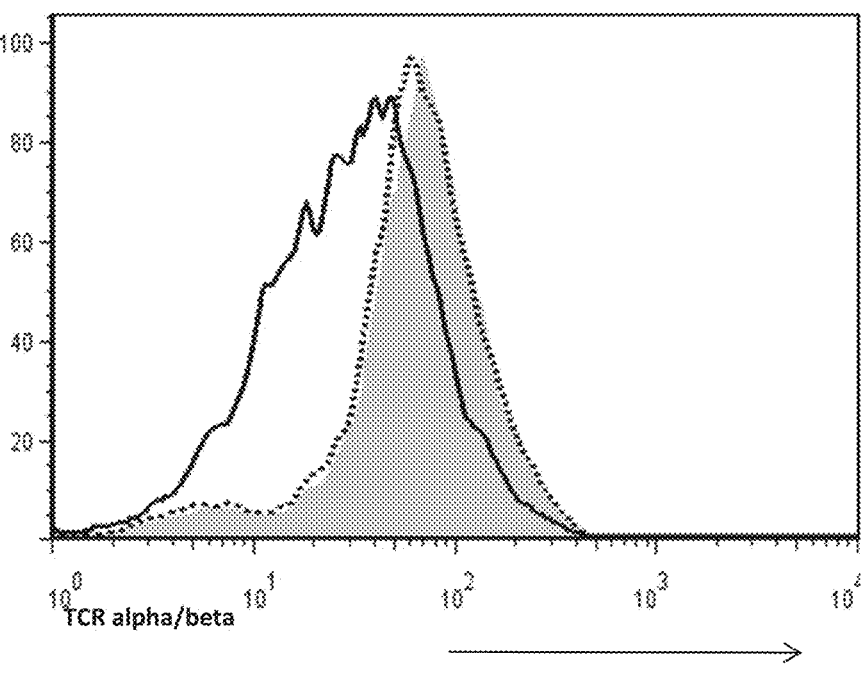
FIGS. 23A-23D, is a panel of graphs showing that knocking down endogenous TCR enhanced both transgene expression and function of TCR RNA elec-troporated T cells.
Figure 23B:
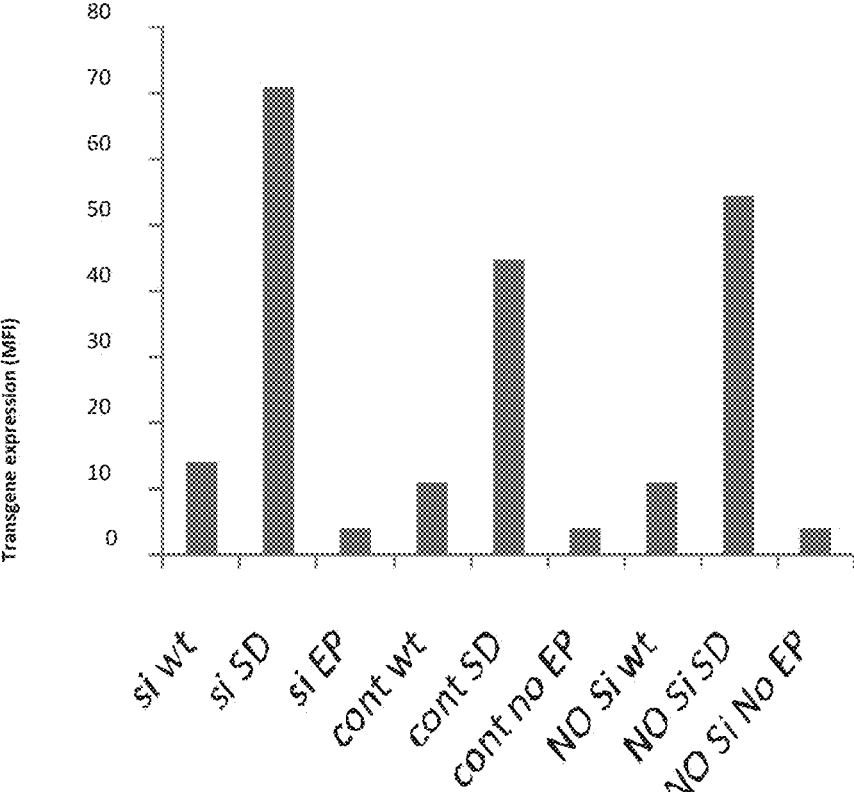
Figure 23C:
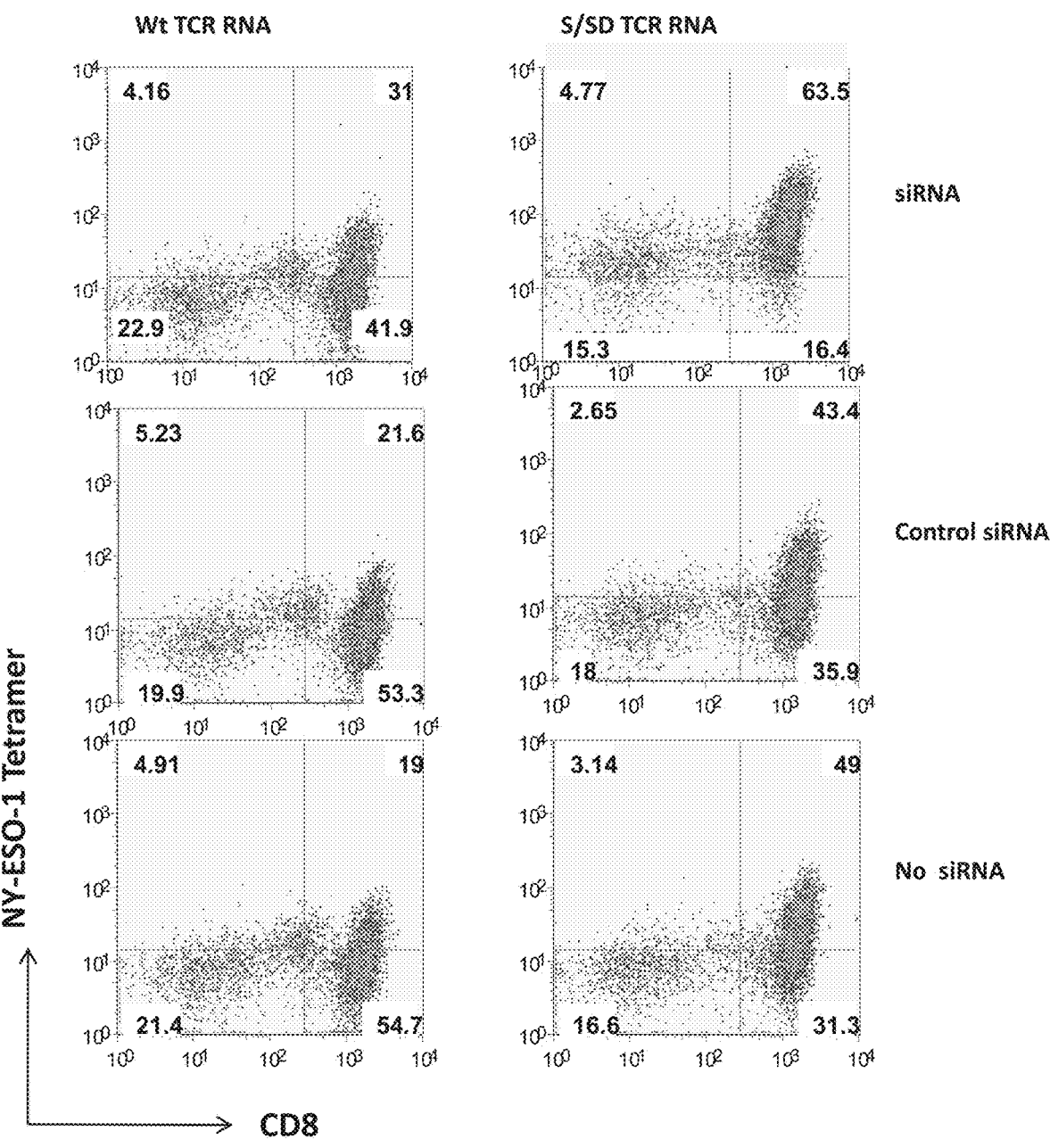
Figure 23D:
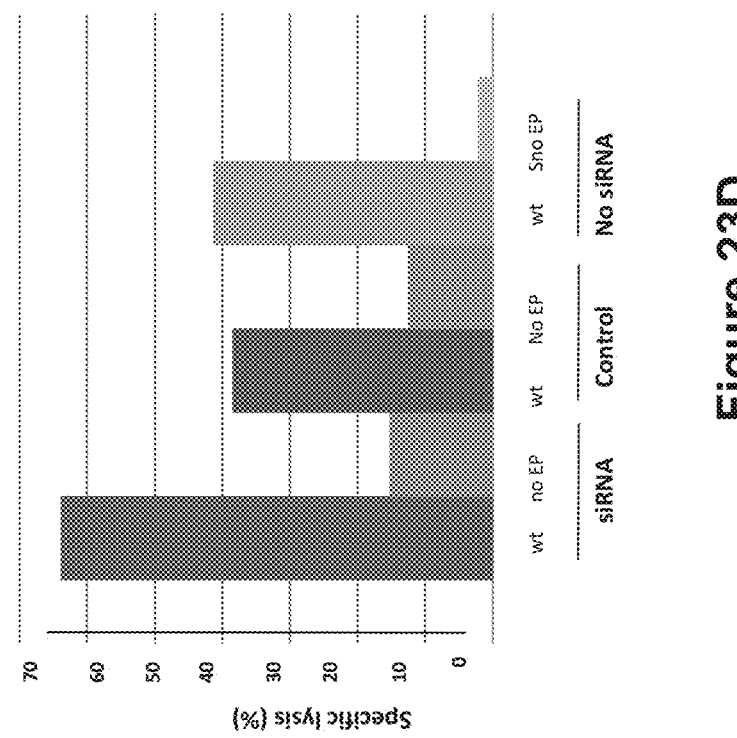

FIG. 23, comprising FIGS. 23A-23D, is a panel of graphs showing knock down of endogenous TCR enhanced with both transgene expression and function of TCR RNA electroporated T cells. FIG. 23A shows TCR expression of T cells electroporated with TCR siRNA (solid open histogram), control siRNA (dotted open histogram) and T cells without any siRNA (filled histogram). FIG. 23B shows transgene (TCR vb13.1) expression of wild type NY-ESO-1 TCR (wt) or modified TCR (SD) RNA electroporated T cells with TCR siRNA, control siRNA, or no siRNA. FIG. 23C shows NY-ESO-1 tetramer staining of wild type NY-ESO-1 TCR (wt) or modified TCR (SD) RNA electroporated T cells with TCR siRNA, control siRNA, or no siRNA. FIG. 23D shows specific lysis of a HLA-A2/NY-ESO-1 positive tumor line by TCR siRNA knockdown, wildtype NY-ESO-1 TCR RNA electroporated T cells.

Figure 24:
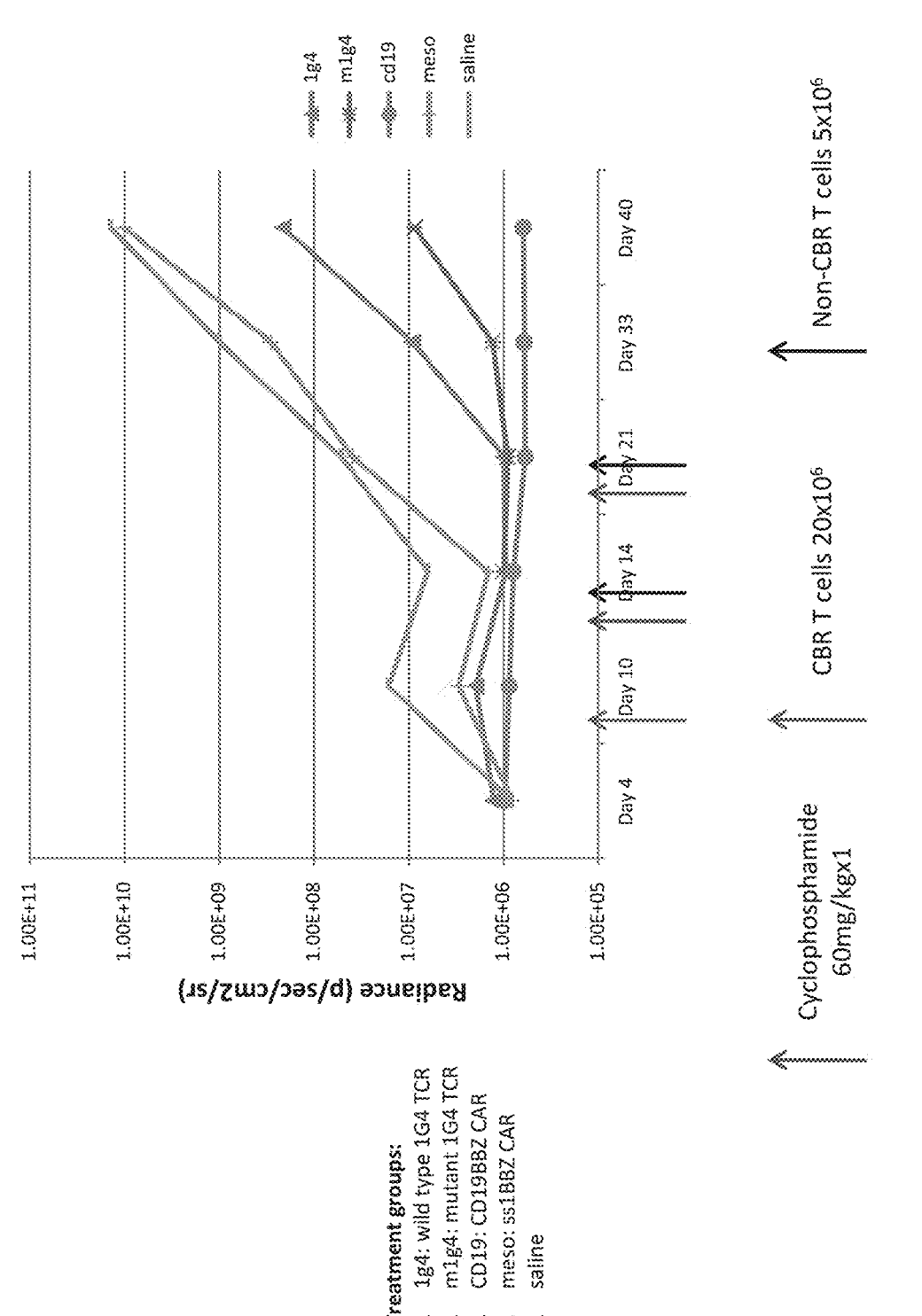
FIG. 24 is a graph showing fluorescence of tumor cells after injection of T cells into a mouse model. Ten million Nalm6-CBG-ESO-GFP (click beetle green) tumor cells that expressed both NY-ESO-1 and GFP were intravenously injected into NOD/SCID mice. Five days after tumor inoculation, CBR transduced and RNA electroporated T cells were injected as indicated in the different groups and tumor cells were detected by fluorescence.

FIG. 24 is a graph showing fluorescence of tumor cells after injection of T cells into a mouse model. Ten million Nalm6-CBG-ESO-GFP (click beetle green) tumor cells that expressed both NY-ESO-1 and GFP were intravenously injected into NOD/SCID mice. Five days after tumor inoculation, CBR (click beetle red) transduced and RNA electroporated T cells were injected as indicated in the different groups and tumor growth was monitored by bioluminescent image (BLI).

Figure 25:
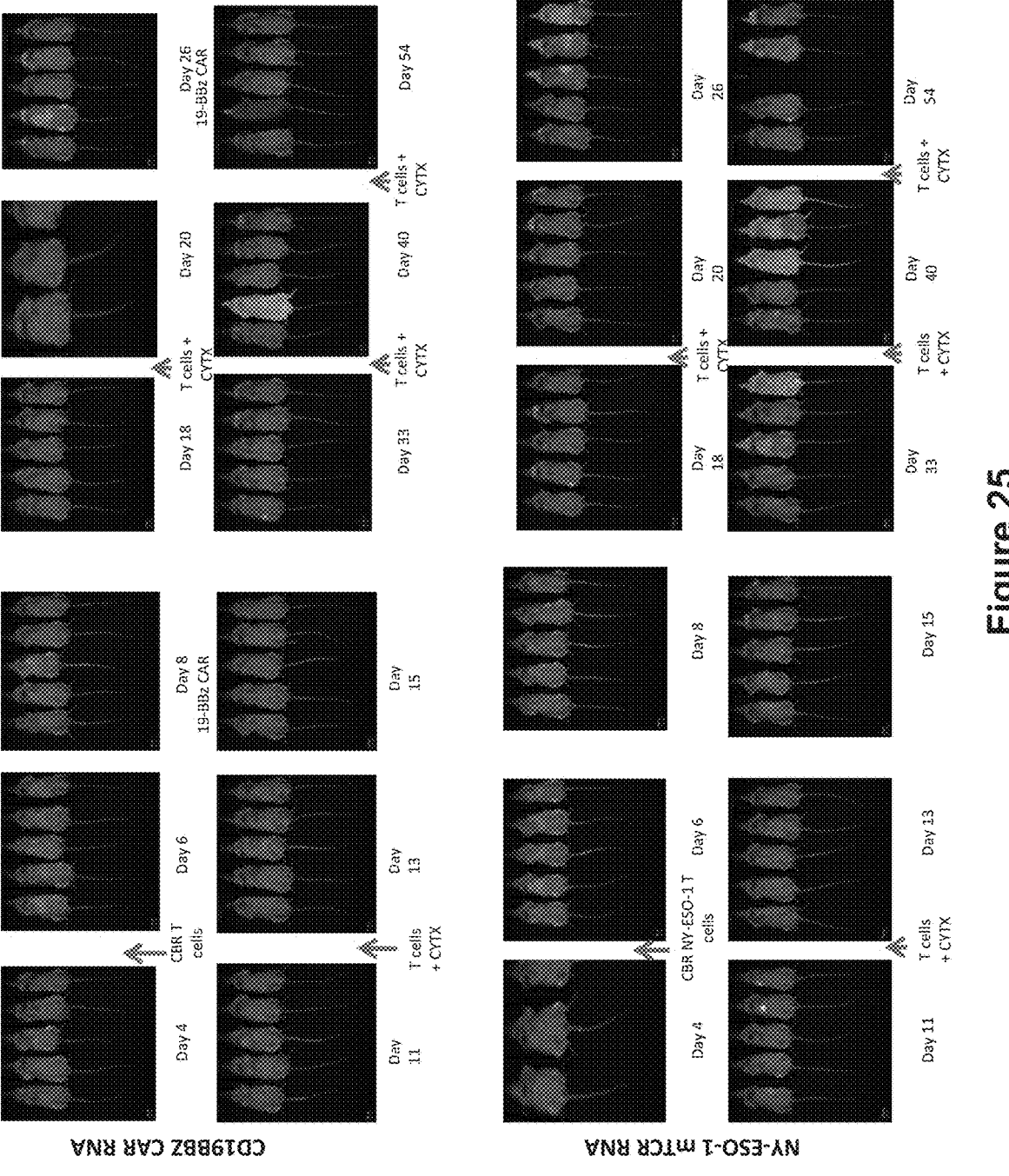
FIG. 25 is a panel of images showing fluorescence of injected tumor and hybrid TCR T cells in mouse models over time.

FIG. 25 show bioluminescent images of the mice from two groups that had been treated by CD19BBZ CAR RNA T cells or modified NY-ESO-1 TCR RNA at different time points.

66

Figure 26:
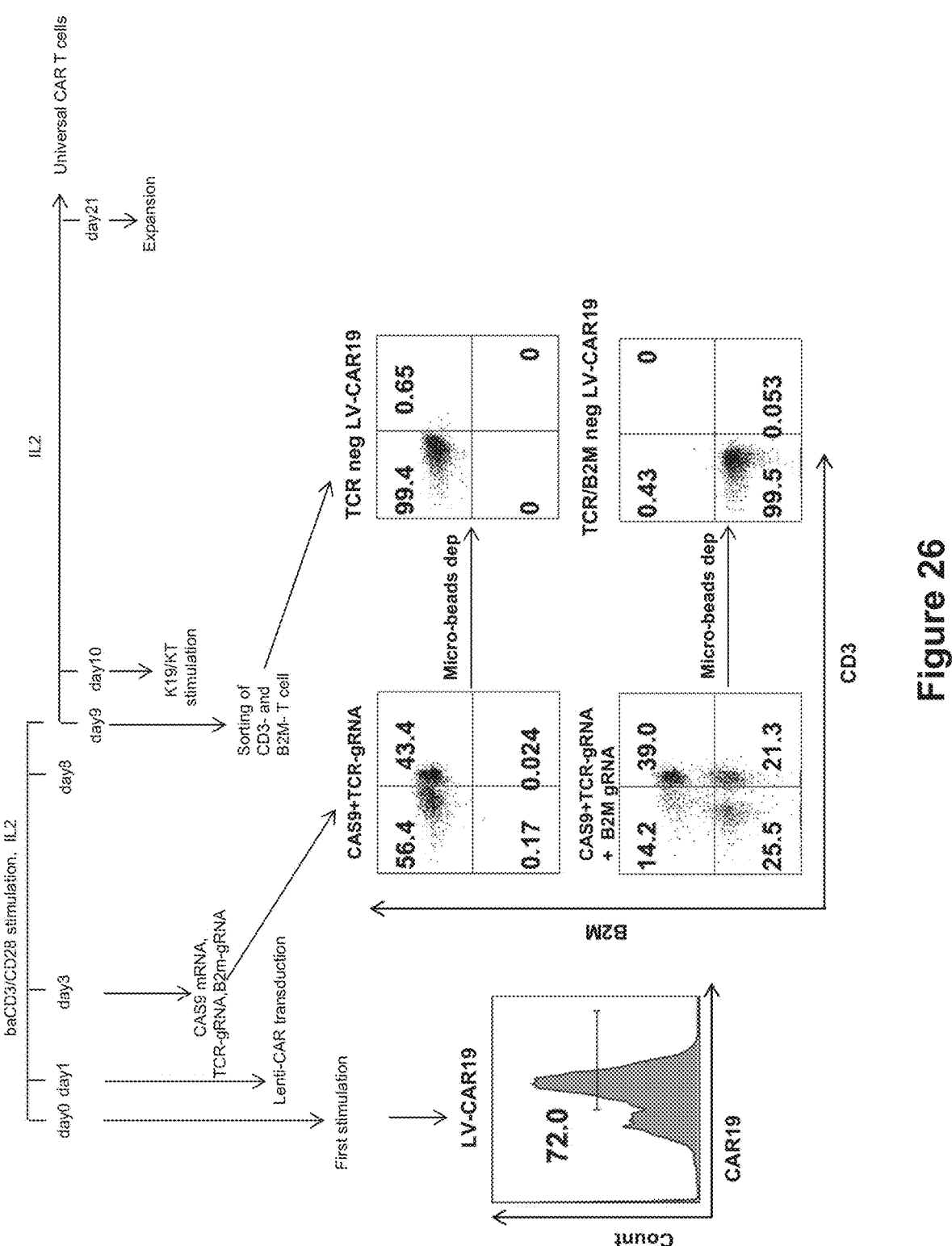
FIG. 26 is a panel of images showing the generation of universal CAR19 T cells. The top of the figure is an illustration of the protocol to generate the universal CAR19 T cells. The graph on the left shows the percentage of CAR19 positive T cells after lentiviral-CAR19 gene transduction. The right panel of graphs shows the percentage of TCR single negative and TCR/HLA-A double negative T cells before and after sorting.

Example 10: Universal CAR19 T Cells Generated by Combination of Lentiviral Transduction and Disruption of the TCR-CD3 Complex on T Cells Using CRISPR As shown in FIG. 26, primary T cell were stimulated with anti-CD3/anti-CD28 beads at day 0, and then transduced with *lenti*-CAR19. Over 70% of the cells were CAR19 positive as detected by flow cytometry. Since transient expression of CRISPR is sufficient to mediate gene knock-out, a "hit-and-run" delivery strategy was developed to transiently express CRISPR by utilizing electro-transfer of in vitro transcribed RNA encoding CAS9 and gRNAs targeting the constant regions of TCR α chain, TCR β chain, and beta-2 microglobulin gene on day 3. T cells were cultured for 24 hours at 32° C. after electrotransfer, then returned to normal condition.

To measure TCR expression, a monoclonal antibody specific for CD3 was used. CD3 was chosen as CD3 is only present on the cell surface when TCRs are expressed. CRISPR constructs were electroporated into primary T cells (FIG. 26). TCR single negative and TCR/HLA-A double negative cells were expanded by exposure to CD19 presenting K562 cells, which resulted in >100 fold expansion (FIG. 27).

Figures 28A, 28B:
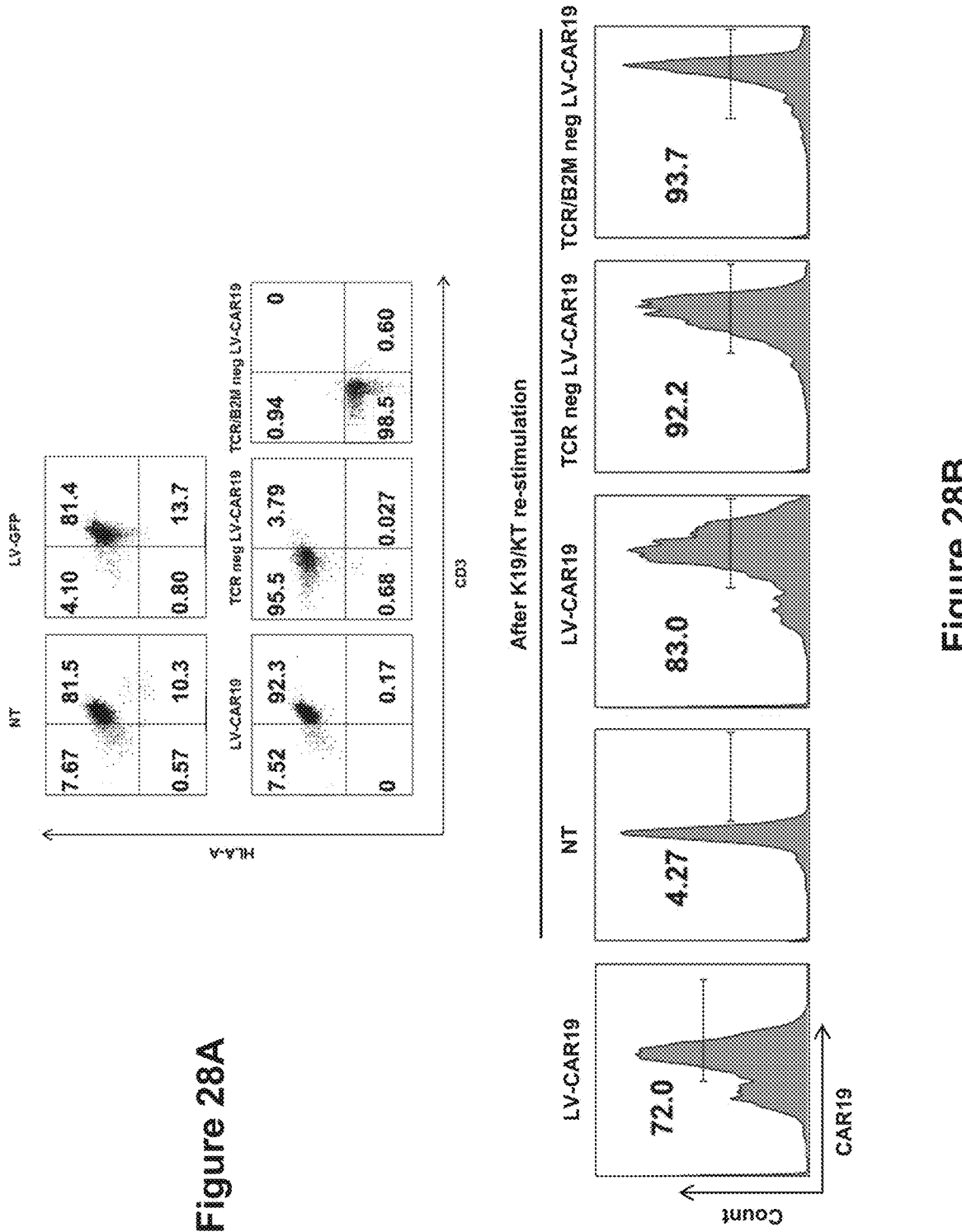
FIG. 28A is a panel of graphs showing the endogenous and transgenic gene expression of K562-CD19 expanded cells.
FIG. 28B is a panel of graphs showing that endogenous TCR expression remained negative in TCR single negative cells, while TCR and HLA-A expression remained negative in TCR/HLA-A double negative T cells after K562-CD19 stimulated expansion

After expansion, the cells remained TCR single negative or TCR/HLA-A double negative, and the CAR19 positive population was enriched. Endogenous TCR expression remained negative in TCR single negative cells, while TCR and HLA-A expression remained negative in TCR/HLA-A double negative T cells after K562-CD19 stimulated expansion (FIG. 28A). CAR19 positive cells were enriched by K562-CD19 stimulated expansion (FIG. 28B).

Figures 29A, 29B:
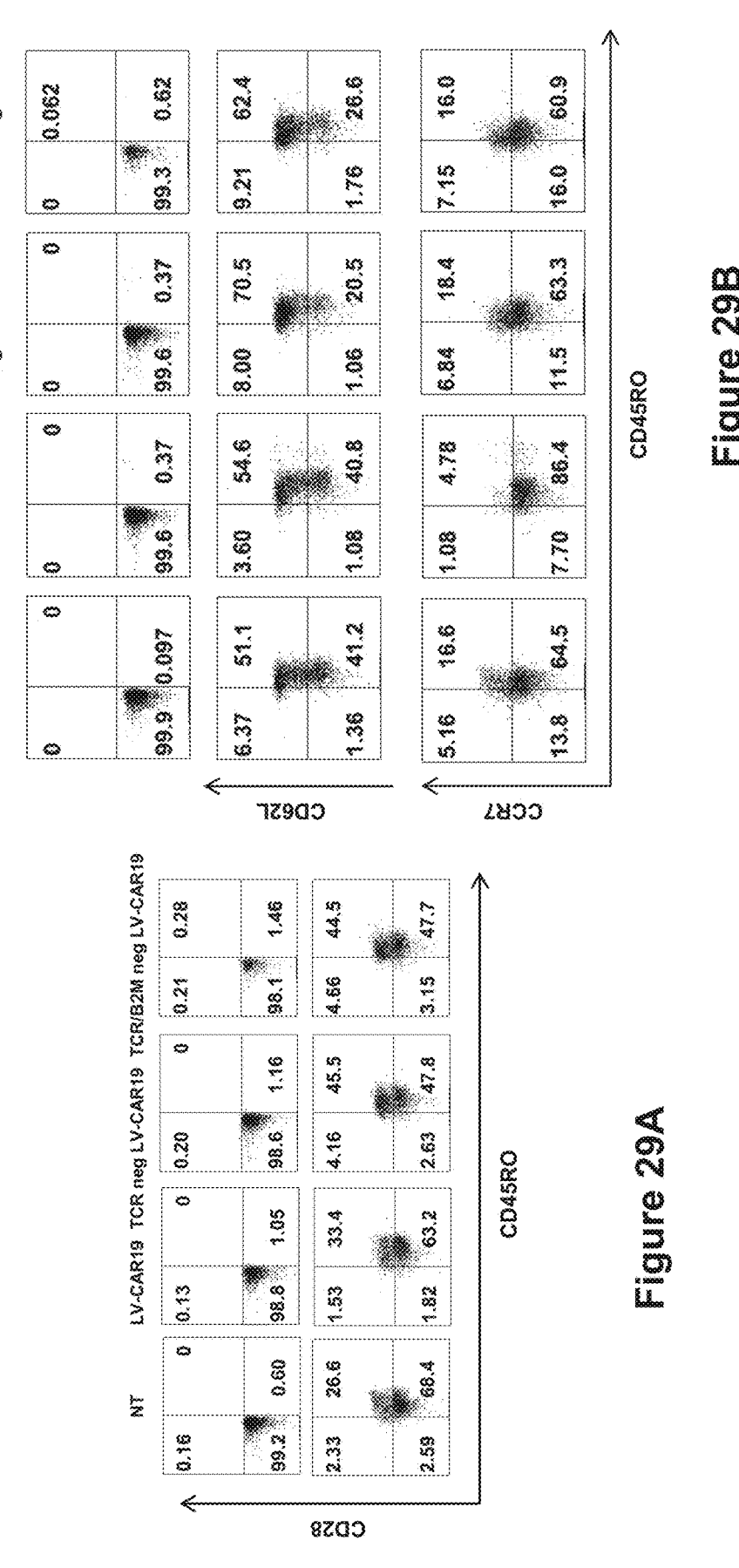
FIG. 29A is a panel of graphs showing that the majority of expanded universal CAR19 T cells are CD45RO positive and expressed medium levels of CD28 expression.
FIG. 29B is a panel of graphs showing that the majority of expanded universal CAR19 T cells retained high levels of CD62L expression and low levels of CCR7 expression.

The majority of expanded universal T cells were CD45RO positive (FIG. 29A) and retained high levels of CD62L expression (FIG. 29B), medium levels of CD28 expression (FIG. 29A) and low levels of CCR7 expression (FIG. 29B).

Figures 30A, 30B:
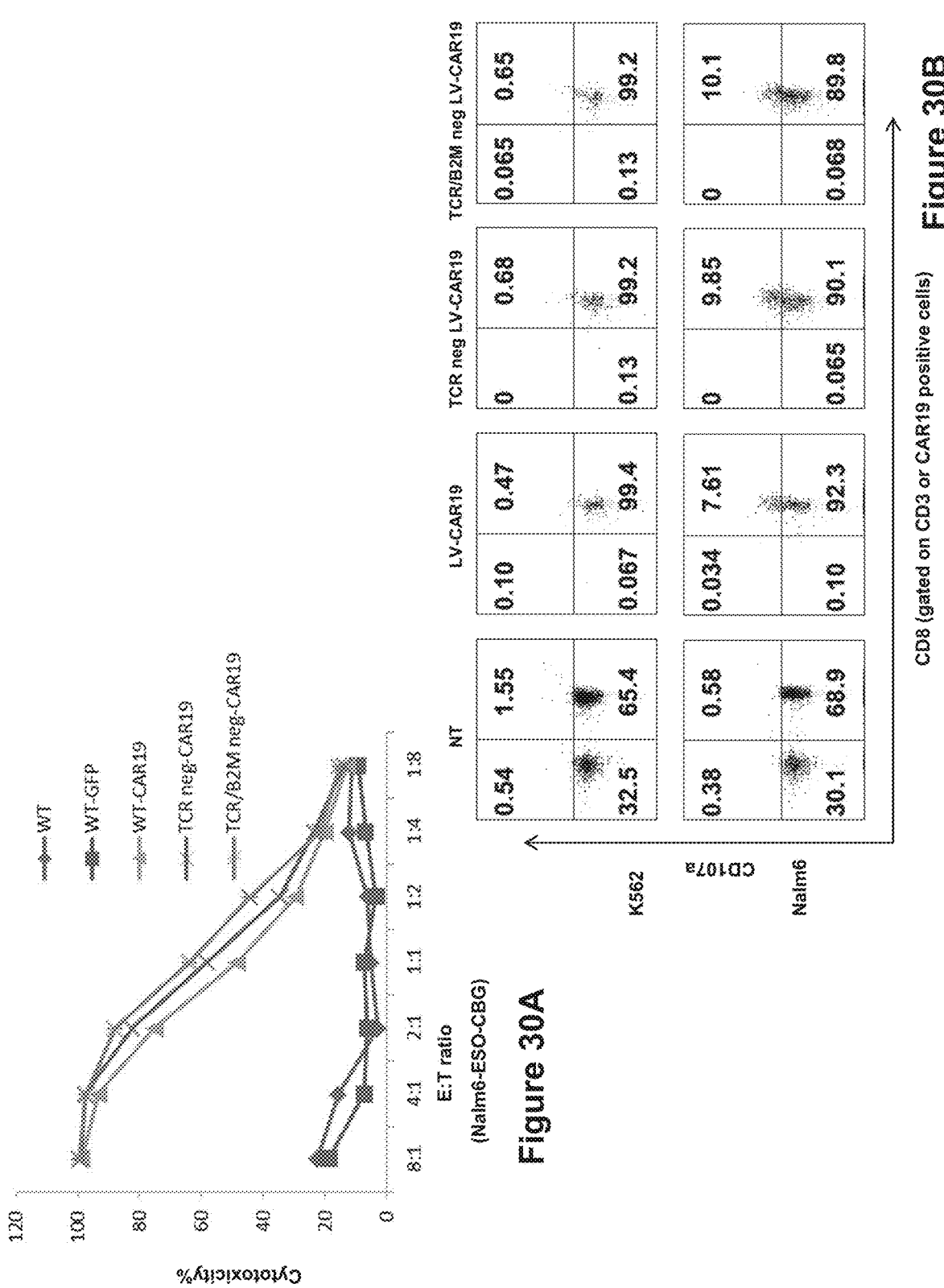
FIG. 30A is a graph showing that CRISPR gene editing did not affect the anti-tumor activity of universal CAR19 T cells in vitro.
FIG. 30B is a panel of graphs showing that the TCR single and TCR/HLA-A double negative CAR19 T cells showed robust lytic capacity when challenged with Nalm6 tumor cells.
Figures 30C, 30D:
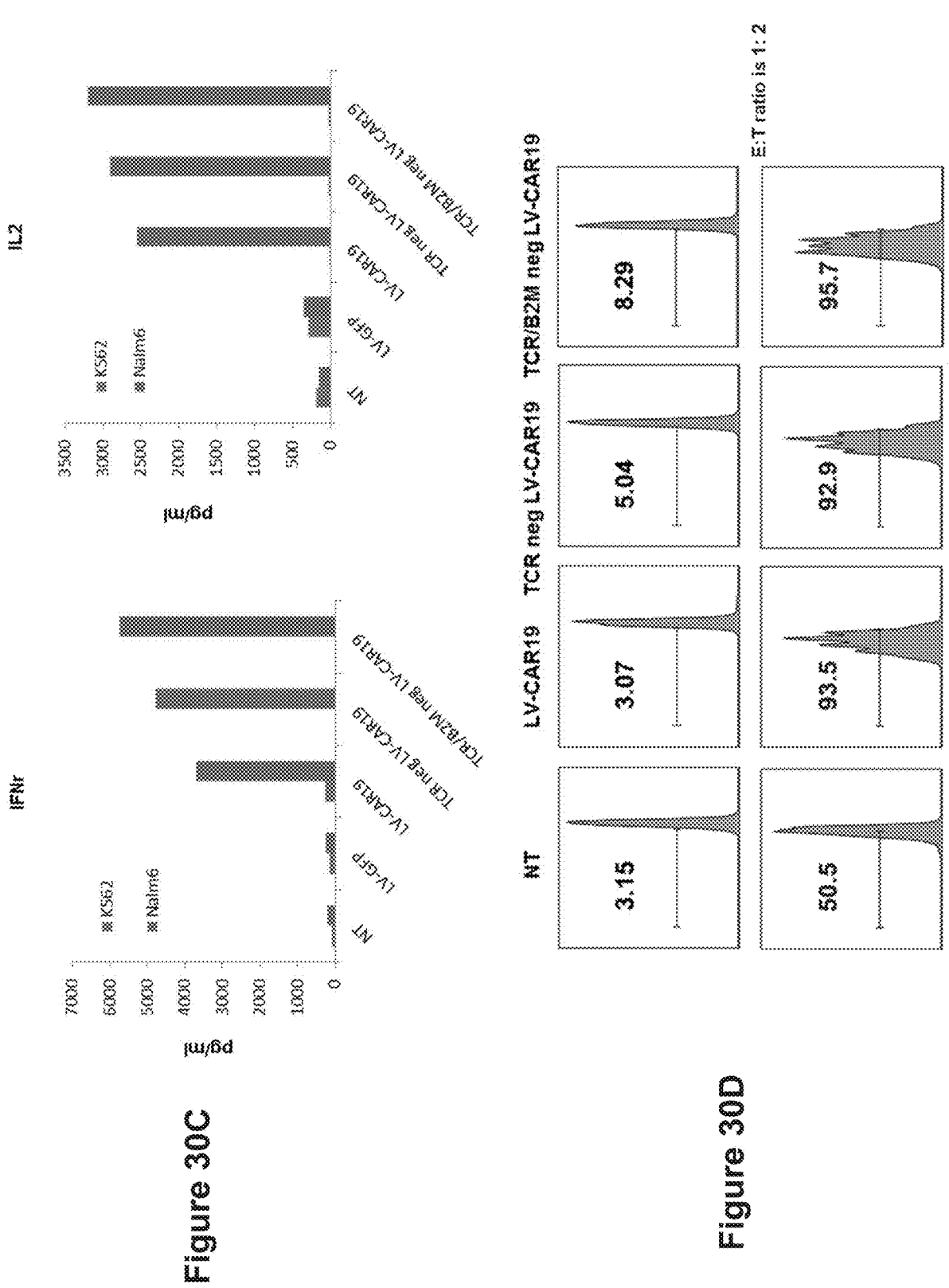
FIG. 30C is a panel of graphs showing cytokine secretion as part of the potent anti-tumor activity of these cells.
FIG. 30D is a panel of graphs showing TCR single ablation or TCR and HLA-A double ablation in CAR19 T cells that exhibited similar proliferation kinetics after challenge with Nalm6 tumor cells.
Figure 31:
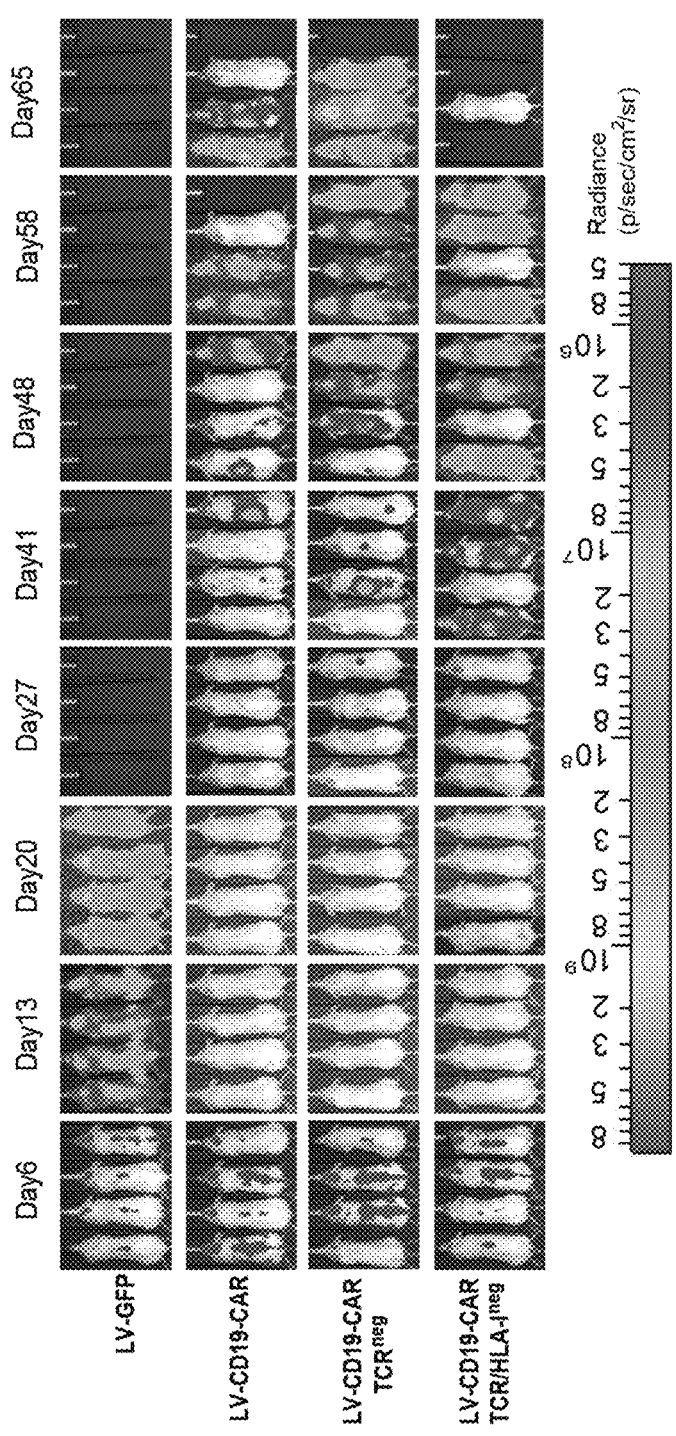
FIG. 31 is a panel of images showing that CRISPR gene editing did not affect the anti-tumor activity of universal CAR19 T cells in vivo. All the mice receiving unmanipulated T cells and mice infused with lentiviral GFP transduced wild type T cells died within 3 weeks after tumor cell infusion. Objective tumor regression was observed for mice receiving CAR19 T cells. CRISPR edited TCR single or TCR/HLA-A double negative universal CAR19 T cells showed the same anti-tumor activity.

CRISPR gene editing did not affect the anti-tumor activity of universal CAR19 T cells in vitro (FIG. 30A). Depletion of TCR or TCR/HLA-A had minimal effect on CAR19 expression and anti-tumor activity (FIGS. 30B and 30C). TCR single and TCR/HLA-A double negative CAR19 T showed robust lytic capacity when challenged with Nalm6 tumor cells (FIG. 30B). CD107a release and cytokine secretion also showed potent anti-tumor activity in the universal cells (FIG. 30C). TCR single ablation or TCR and HLA-A double ablation CAR19 T cells exhibited similar proliferation kinetics after challenge with CD19 expressing cells (FIG. 30D).

Figure 6A:
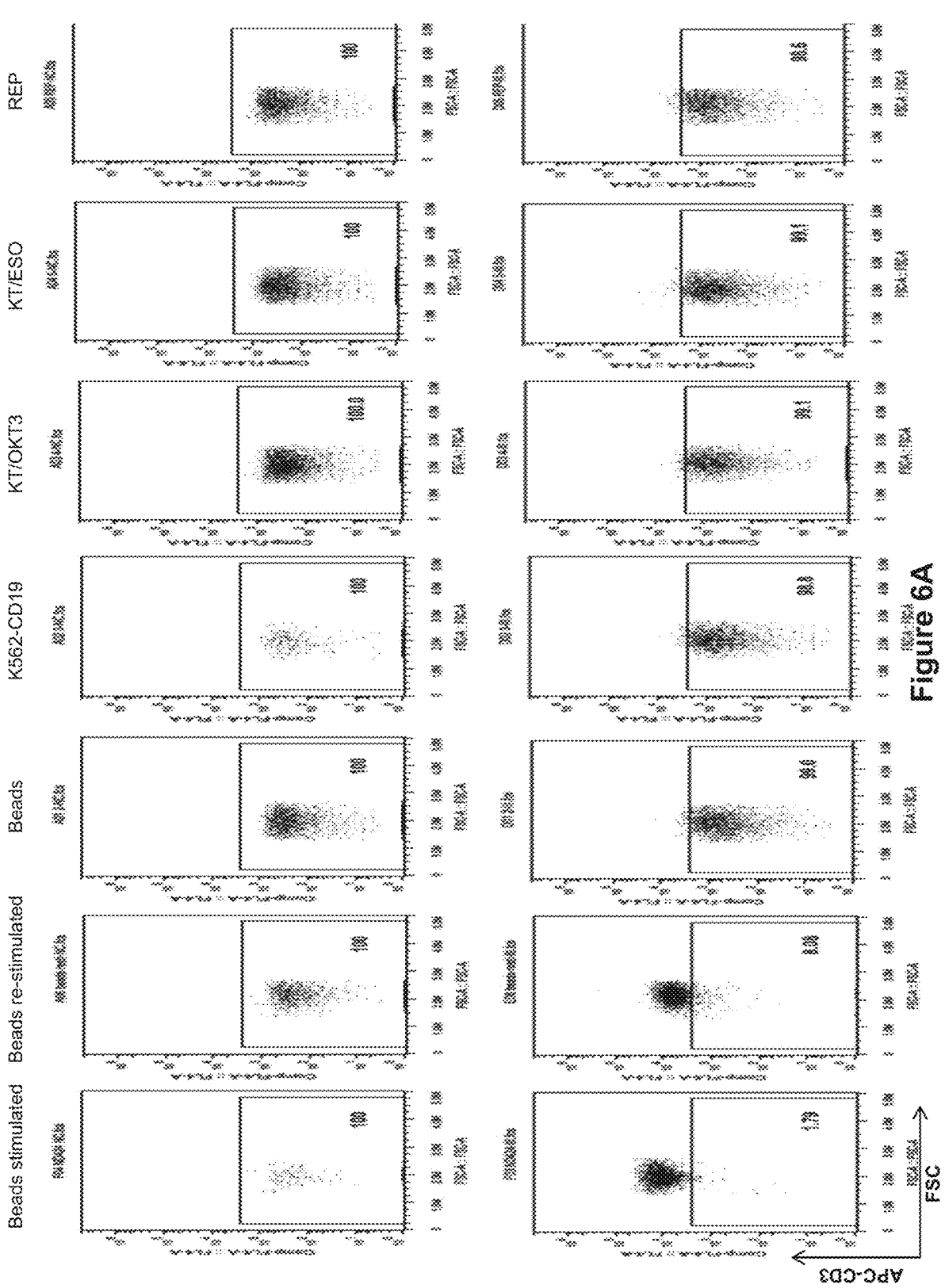
FIGS. 6A and 6B, shows TCR$^{neg}$ T cell characteristics after expansion under different conditions.
Figure 6B:
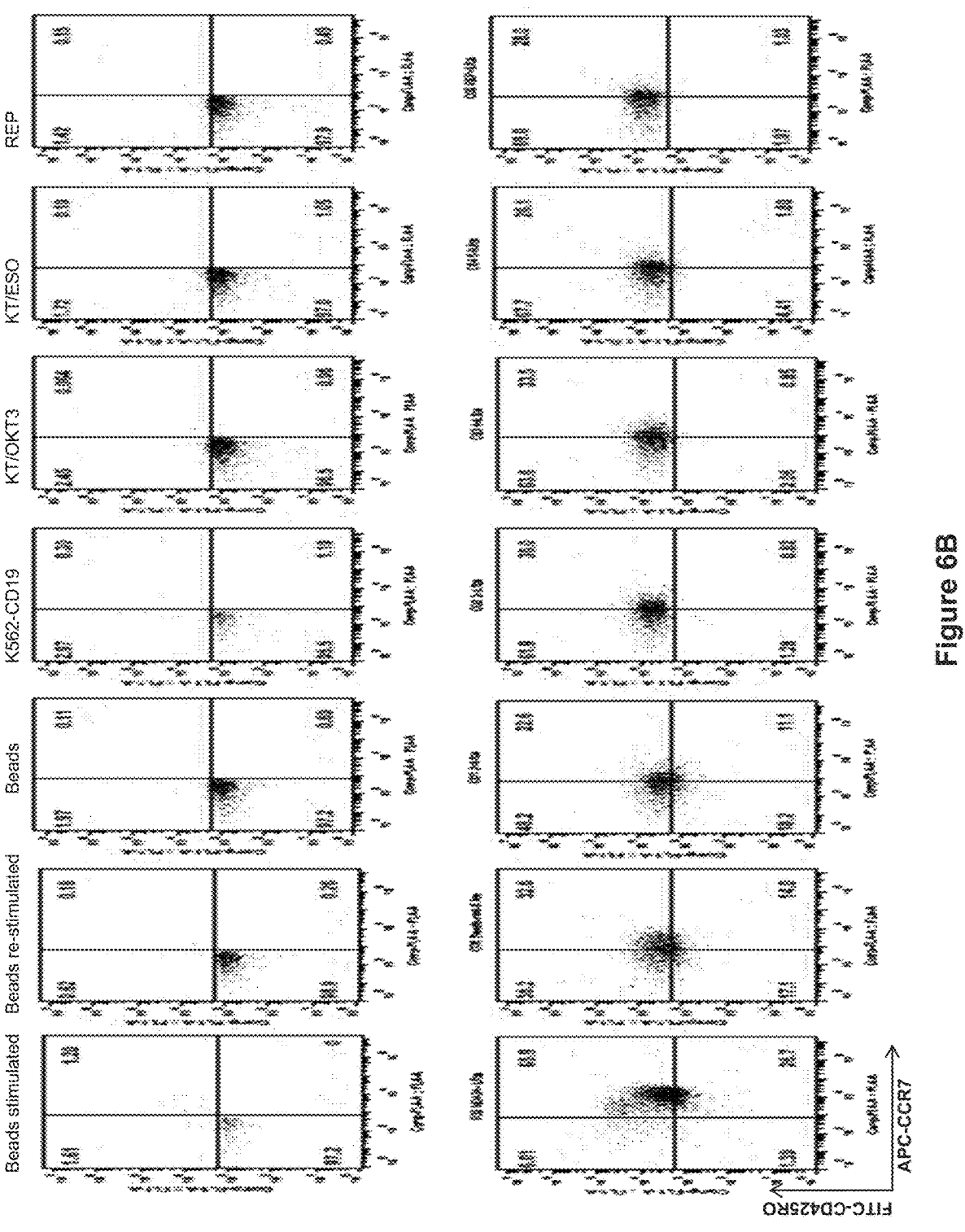

To test the anti-tumor activity of CRISPR/CAS9 edited CAR19 T cells, TCR single negative, TCR and HLA-A double negative CAR19 T were infused into NSG mice bearing Nalm6 tumor cells. All the mice receiving unmanipulated T cells and mice infused with lentiviral GFP transduced wild type T cells died within 3 weeks after tumor cell infusion. Objective tumor regression was observed for mice receiving CAR19 T cells (FIG. 6). CRISPR/CAS9 was found to not affect the in vivo tumor killing activity of CAR19 T cells, thus, confirming the advantage of combining lentiviral gene transfer and CRISPR/CAS9 for T cell therapy.

Figures 32A, 32B, 32C:
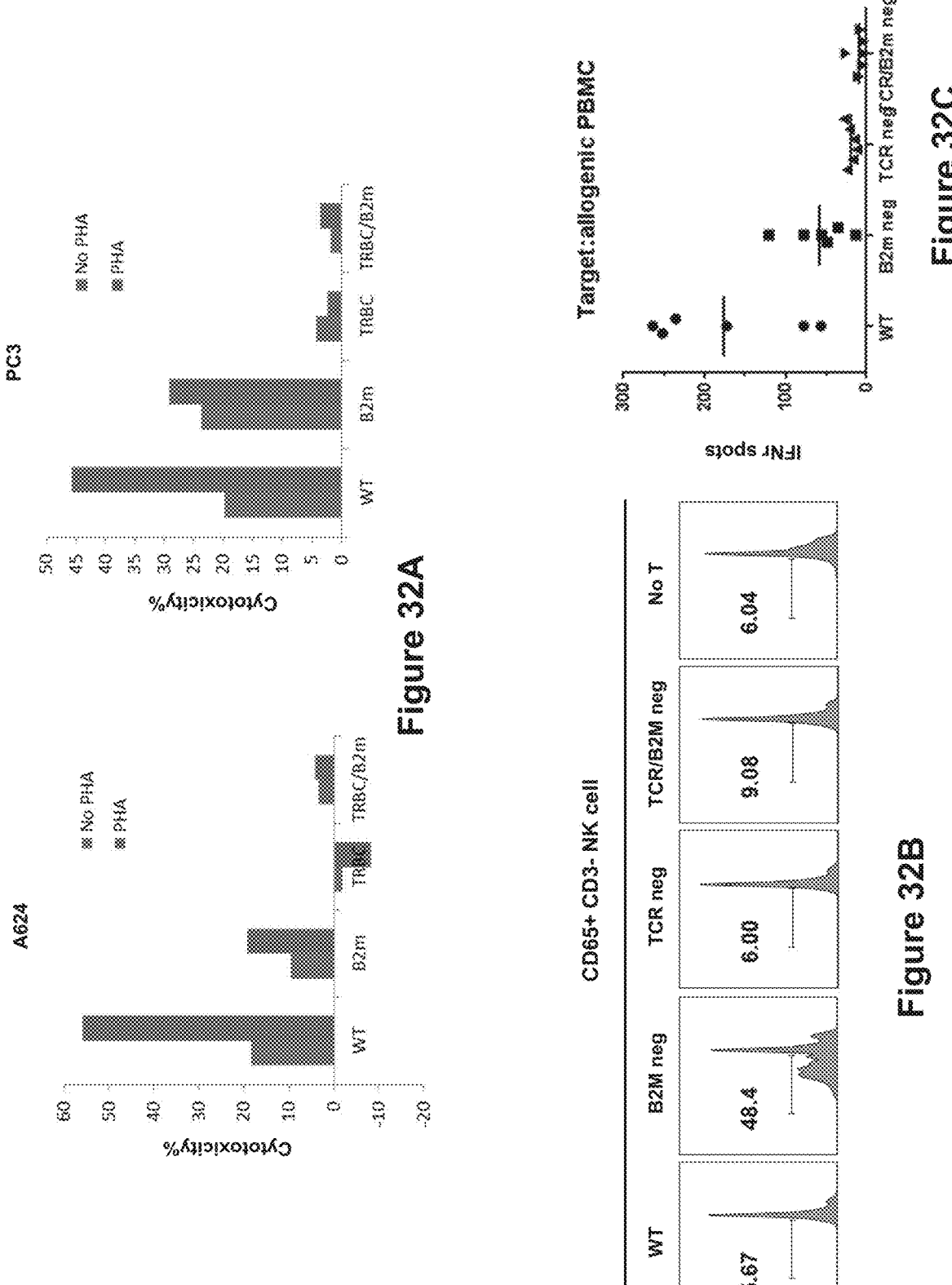
FIG. 32A is a panel of graphs showing TCR single or TCR and HLA-A double ablation in T cells sharply reduced alloreactivity.
FIG. 32B is a panel of graphs showing elimination of HLA-A molecule activated NK cells with a long period of co-culture (5 days).
FIG. 32C is a graph showing that no off-target activity was observed when the cells were challenged by allogeneic whole blood PBMC for 24 hours in an IFNr Eispot assay.

Full ablation of TCR α and β chains and HLA-A molecule on T cells completely abrogated non-specific killing when the cells were challenged with HLA unmatched tumor cell lines (FIG. 32A). Elimination of HLA-A molecules activated NK cells after a long period of co-culture (5 days). No off-target activity was observed when these cells were challenged by allogeneic whole blood PBMC after 24 hours in an IFNr Elispot assay. The lack of off-target activity suggests T cells may play a dominant role in acute immune responses after encountering allogeneic cells. All of the results suggest that CRISPR/CAS9 edited TCR α and β chains and HLA-A molecules (triple negative) T cells could serve as a source of universal effector donor cells.

Figure 33:
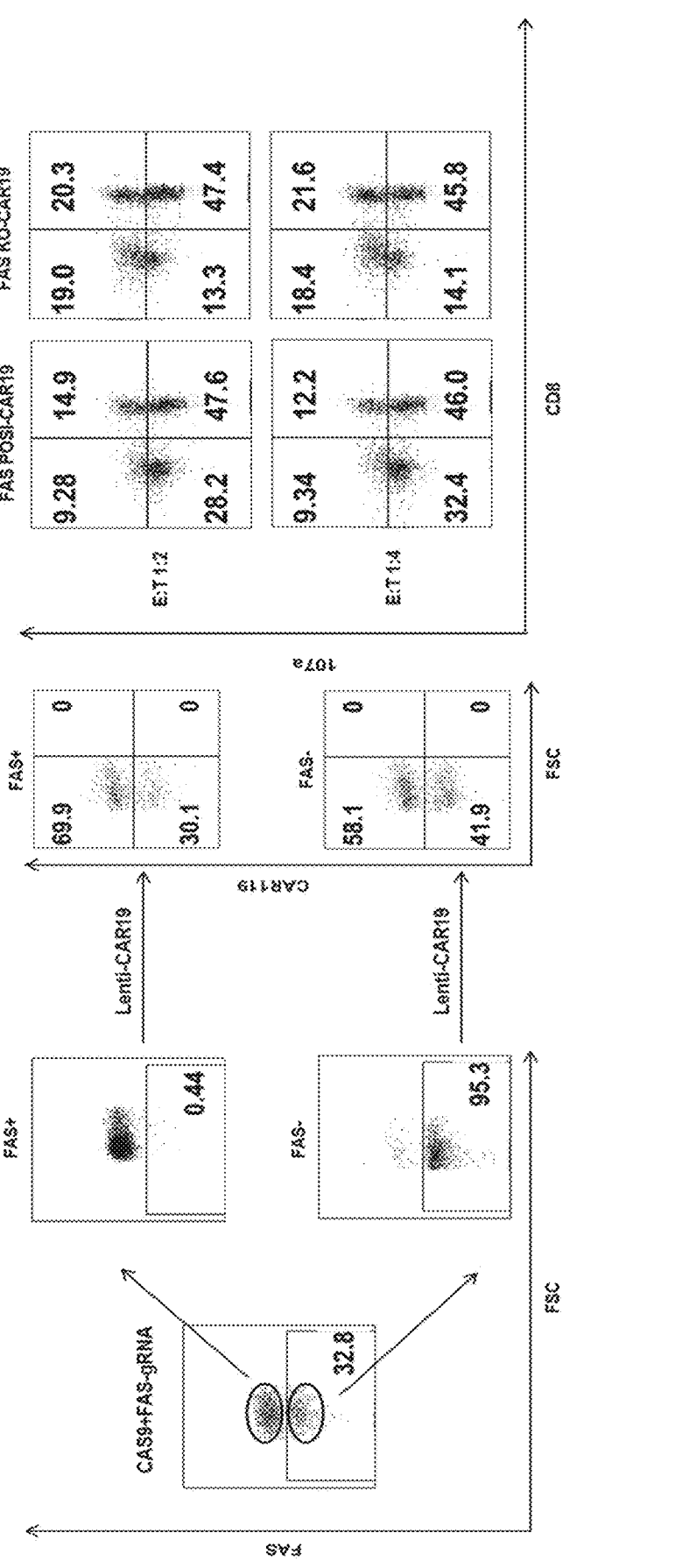
FIG. 33 is a panel of graphs showing that FAS ablation enhanced the anti-tumor activity of CAR19 T cells. FAS negative CAR19 T cells were generated. FAS ablation was confirmed by flow cytometry analysis. CAR19 gene expression of FASneg T cells was comparable to the wild type. Even after incubation with Nalm6 tumor cells for a short period of 4 hours, CD107a expression was greatly enhanced in FASneg CAR19 T cells compared the wild type counterpart.

CAS9 and different gRNAs targeting FAS were electro-transferred into T cells. FASneg cells were sorted and then transduced with lentiviral CAR19. Flow cytometry and Sanger sequencing data showed that FAS had been modified by the CRISPRs (FIG. 33). CAR19 gene expression of FASneg T cells was comparable to the wild type. Even after a short period of incubation with Nalm6 tumor cells, CD107a expression was greatly enhanced in FASneg CAR19 T cells compared to wild type counterpart cells even within 4 hours of co-culture.

Figures 34A, 34B:
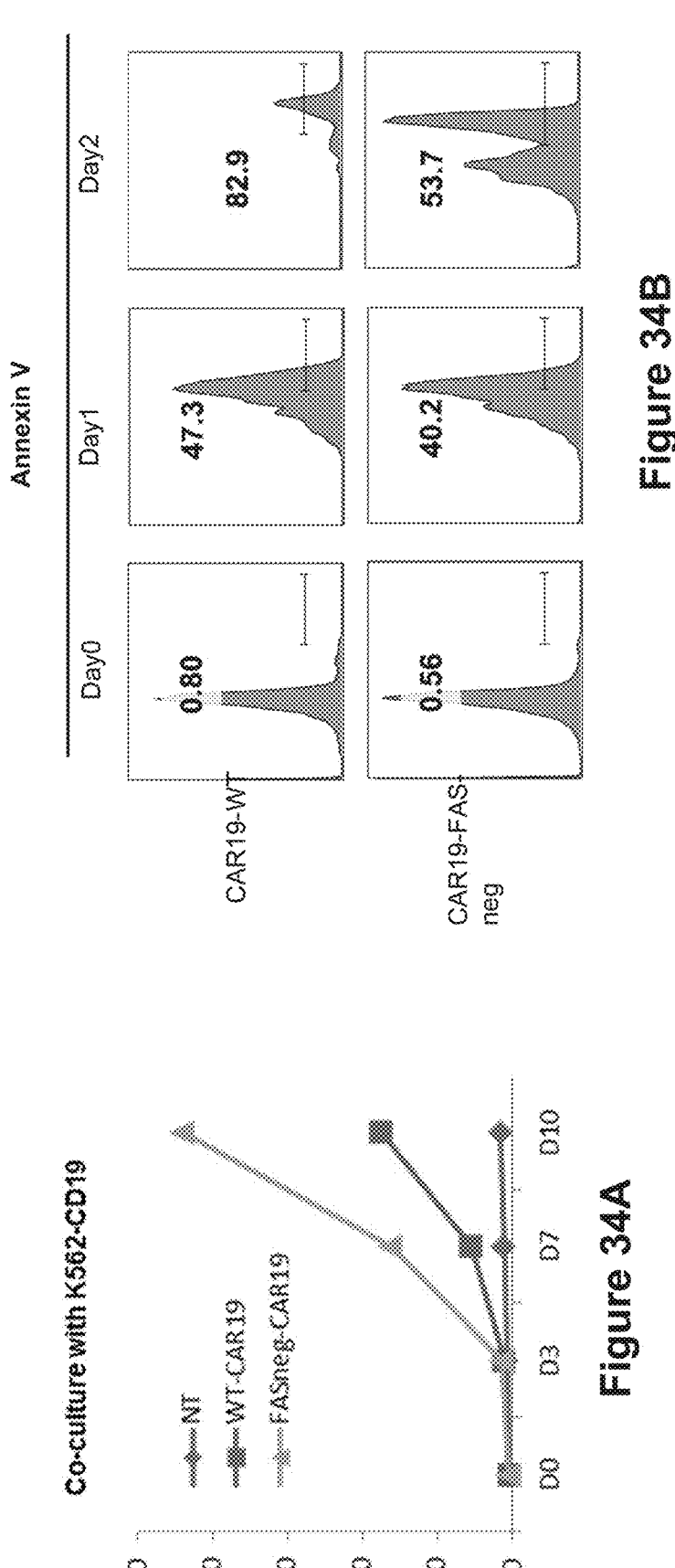
FIG. 34A is a graph showing that FAS ablation in CAR19 T cells enhanced CART cell survival and proliferation under in vitro antigenic conditions. FASneg CAR19 T cells expanded faster than wild type CAR19 T cells when the cells were stimulated with high levels of CD19+K562 cells.
FIG. 34B is a panel of graphs showing FASneg CAR19 T cells had reduced apoptosis levels as measured by Annexin V staining.

Some reports showed that even weak antigenic stimuli can trigger FAS activation to promote T cell proliferation (Rethi, et al, Blood, vol. 112(4):1195-1204, 2008). Interestingly, FASneg CAR19 T cells expanded much quicker than the wild type CAR19 T cells when the cells were stimulated by high levels of CD19+K562 cells. This suggests that FAS/FASL triggered apoptosis instead of activation under high level antigenic conditions (FIG. 34A). FASneg CAR19 T cells further showed reduced apoptosis levels as measured by Annexin V staining (FIG. 34B).

Figures 35A, 35B, 35C:
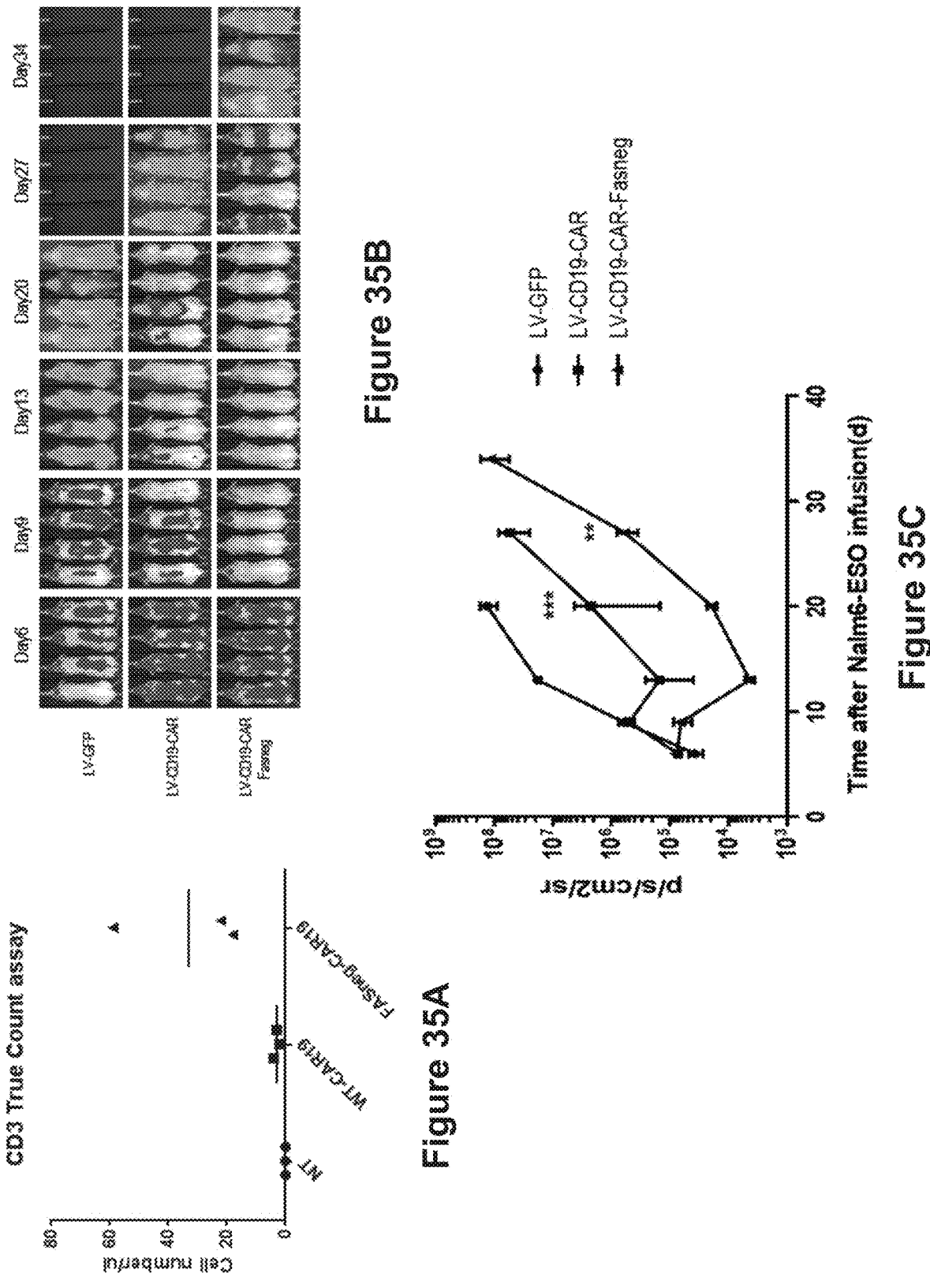
FIG. 35A is a graph showing that FAS ablation in CAR19 T cells enhanced CART cell function in an animal model. As had been observed in vitro, FASneg T cells showed enhanced proliferation as compared to the wild type T cells.
FIG. 35B is a panel of images showing FASneg CAR19 group demonstrated superior anti-tumor activity when compared to wild type group.
FIG. 35C is a graph showing significant differences in bioluminescence data between FASneg CAR19 group and wild type group.

As had been observed in vitro, FASneg T cell showed enhanced proliferation as compared to wild type T cells. Similar proliferation results were observed when a True Count assay of CAR19 T cells was performed after infusion of the cells into Nalm6 bearing mice. The FASneg CAR19 group showed superior anti-tumor activity when compared to the wild type group (FIG. 35B). This difference is illustrated in the graph of FIG. 35C showing the bioilluminescence data between those two groups. These data indicate that FAS ablation in CART cells enhanced its anti-tumor activity.

Figure 36:
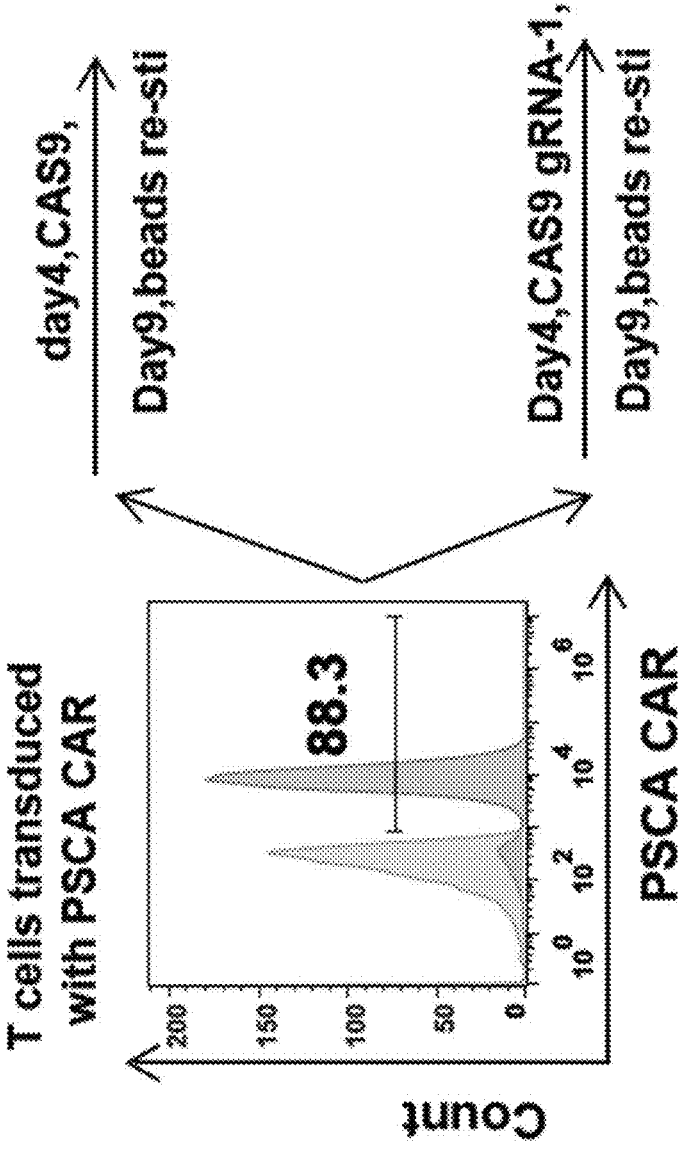
FIG. 36 is a panel of graphs showing the generation of PD1 negative PSCA-CAR T cells. PD1 ablation was confirmed by flow cytometric analysis. PD1 negative cells were enriched by microbead depletion. Wild type or PD1 negative PSCA-CAR T cells were expanded by stimulation with irradiated PSCA antigen presenting PC3 tumor cells. PSCA-CAR positive cells were enriched after expansion.
Figure 37:
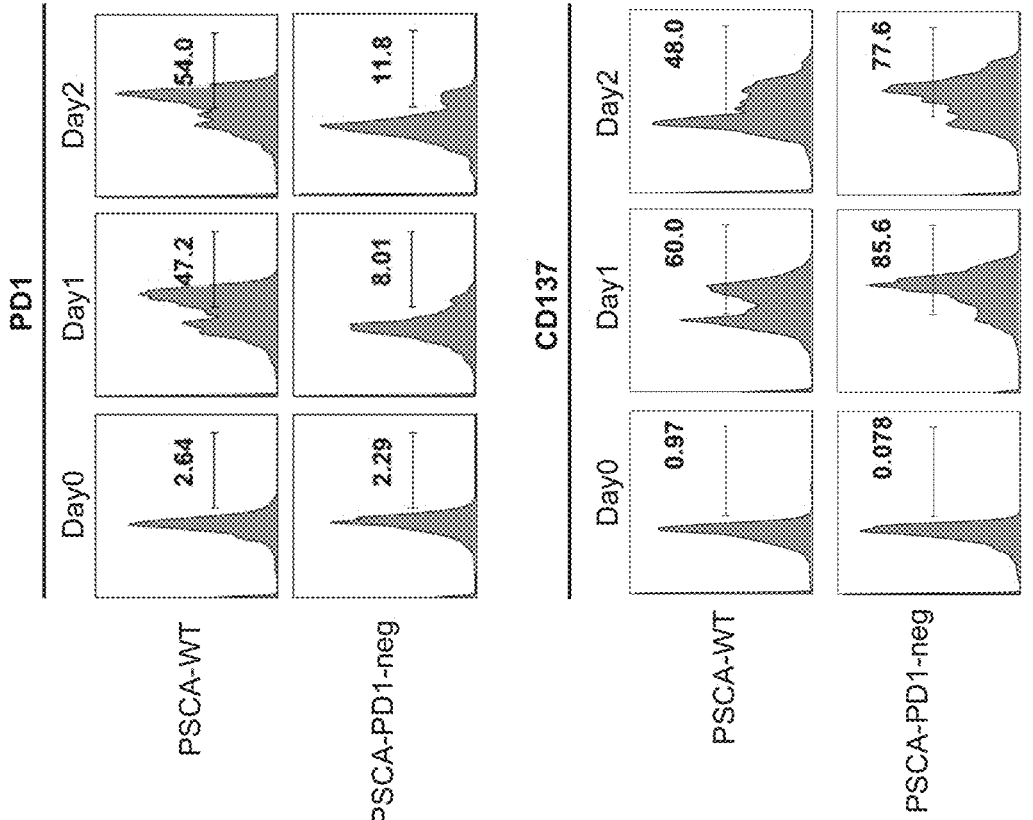
FIG. 37 is a panel of graphs showing that PD1 ablation and CD137 expression in PSCA-CAR T cells enhanced CART cell activation under in vitro antigenic conditions.

CAS9 and different gRNAs targeting PD1 were electro-transferred into T cells after lentiviral transduction with PSCA-CAR. PD1 knock out cells were confirmed by surface PD1 expression after CD3/CD28 bead stimulation (FIG. 36). PD1 negative cells were enriched by microbead depletion and then stimulated with PSCA antigen presenting PC3 tumor cells. PSCA-CAR positive cells were enriched both in the wild type and the PD1 negative groups. After incubation with PC3-PSCA-PDL1 tumor cells, PD1 expression was quickly upregulated on the surface of wild type PSCA-CAR T cells, with very low levels of PD1 expression detected on PD1 negative PSCA-CAR T cells (FIG. 37). PD1 negative PSCA-CAR T cells also showed greatly enhanced and sustained high levels of CD137 expression (FIG. 37), a marker of T cell activation, indicating that the PD1/PDL1 inhibitory signaling pathway was blocked.

Figures 38A, 38B:
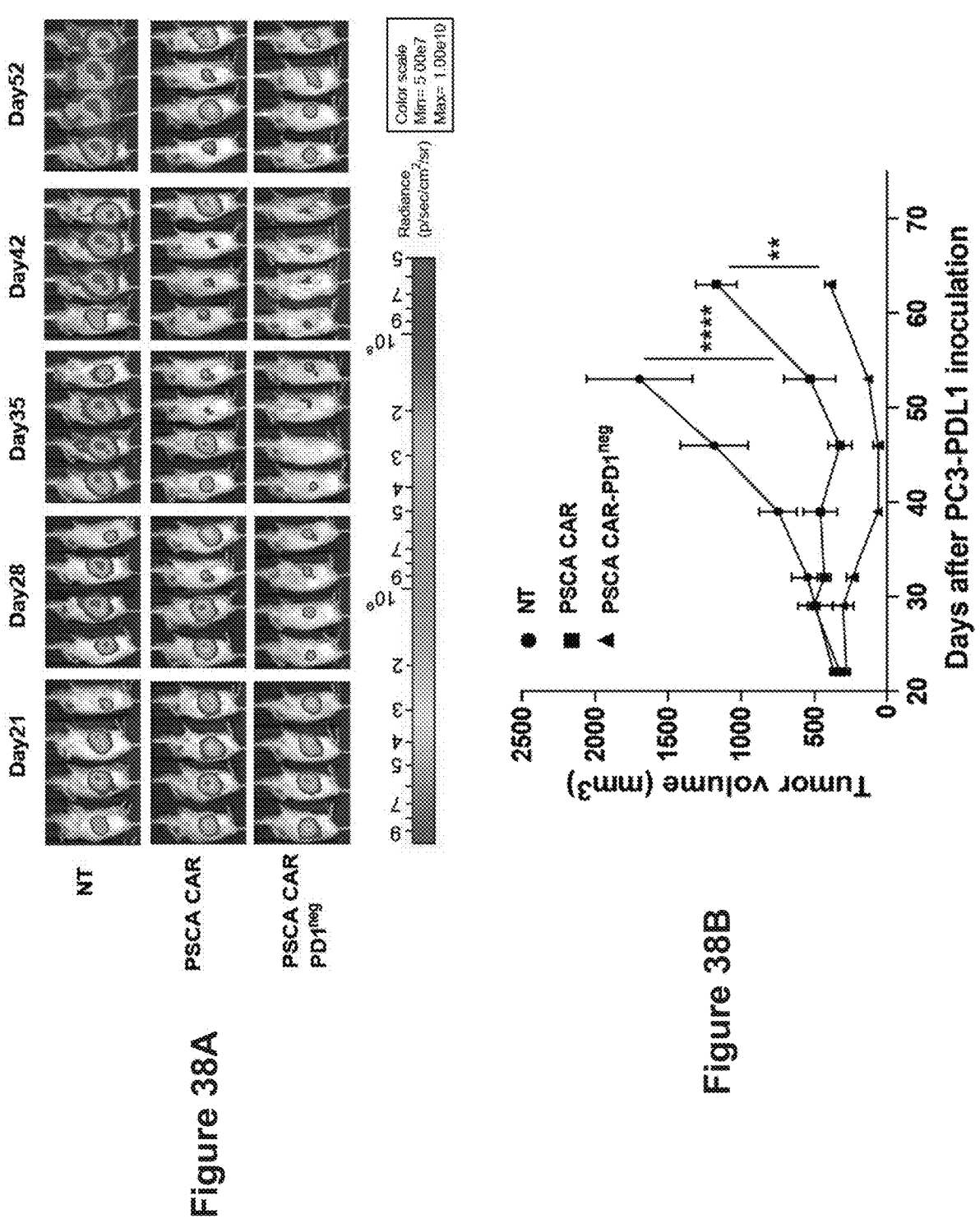
FIG. 38A is a panel of images showing PD1 ablation in an in vivo PC3-PSCA-PDL1 NSG model. The PSCA-CAR T cells demonstrated enhanced CART cell in vivo anti-tumor activity as compared to wild type group.
FIG. 38B is a graph showing the difference in tumor burden between the PD1 negative and the wild type group.

When tested in an in vivo PC3-PSCA-PDL1 NSG model, significant enhanced anti-tumor activity was detected in the PD1 negative PSCA-CAR T cell group compared to the wild type group (FIGS. 38A and 38B) suggesting a therapeutic value of PD1 ablation for CART cell therapy.

Figure 39:
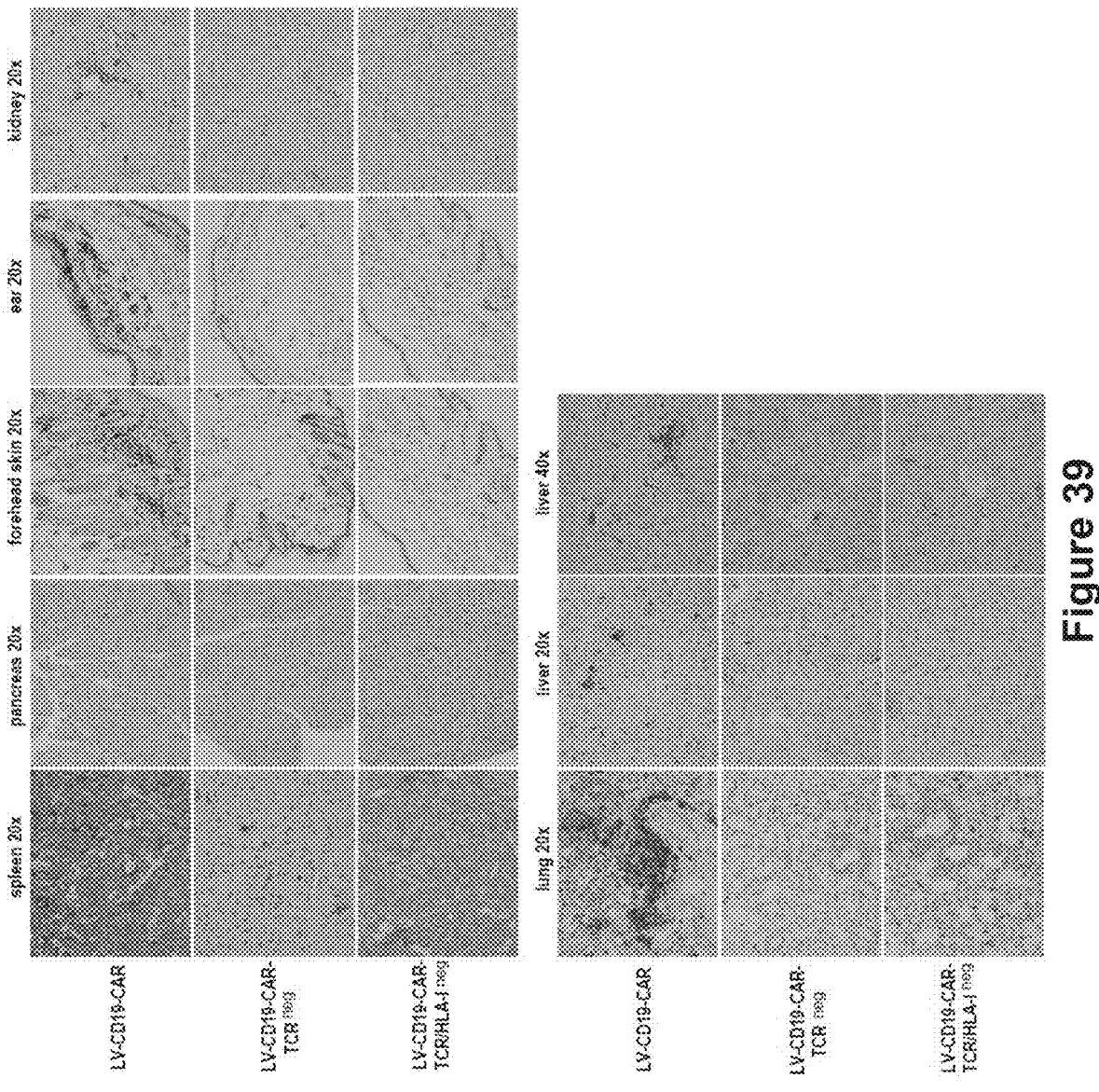
FIG. 39 is a panel of histological images showing that T cells with TCR or TCR/HLA-I ablated did not cause graft versus host disease (GVHD). The mice treated with the double or triple knock out CART cells did not develop any signs of GVHD. By contrast, 3 out of 4 mice from the wild-type CD19 CART group developed GVHD by day 65, which was confirmed by histological examination of different organs.

To test the graft vs host disease (GVHD) effect of CRISPR engineered universal CART cells, a high T cell dose was given to NSG mice with Nalm6 leukemia. The mice were treated with double or triple knock out CART cells and did not show any signs of developing GVHD. By contrast, 3 out of 4 mice from the wild-type CD19 CART group developed GVHD by day 65, which was confirmed by histological examination of different organs (FIG. 39).

Figures 40A, 40B:
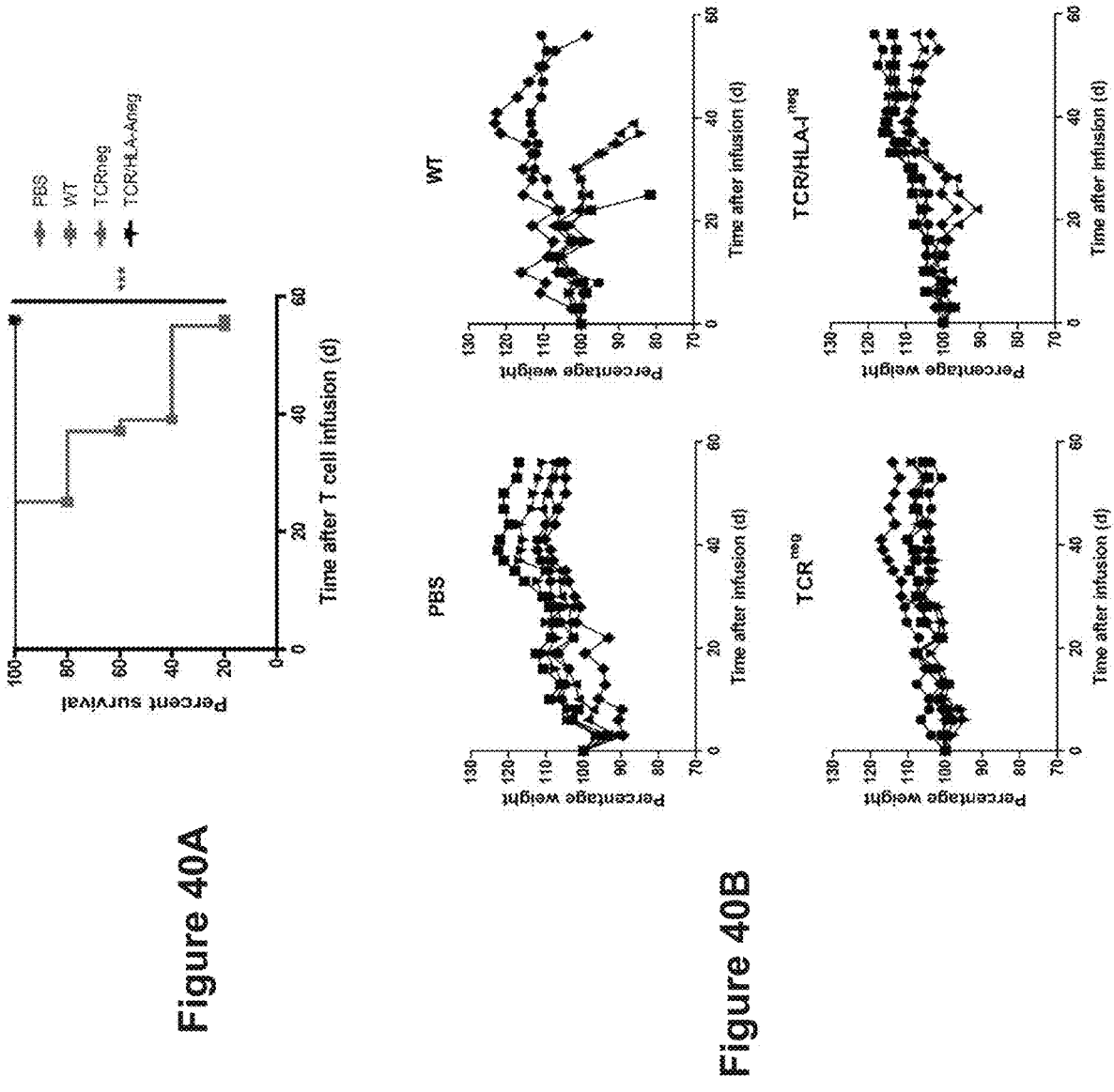
FIG. 40A is a graph showing the percent survival of animals injected with T cells with TCR or TCR/HLA-I ablated. Mice were sub-lethally irradiated and injected. Four out 5 mice receiving wild type T cells died of GVHD during the 60 day study. PBS treated, TCR single and TCR/HLA-I double ablated T cell treated groups did not show any signs of GVHD.
FIG. 40B is a panel of graphs showing the body weight of mice receiving wild type T cells, PBS treated, TCR single or TCR/HLA-I double-ablated T cells.

In another experiment, the cells were resuspended in FBS and infused intravenously into mice after a sub-lethal irradiation. Clinical GVHD was monitored 2 to 3 times per week. Four out 5 mice receiving wild type T cells died during the 60 day study, while PBS treated, TCR single and TCR/HLA-I double ablated T cell treated groups did not show any signs of GVHD. Mice receiving wild type T cells underwent body weight loss. However, PBS treated, TCR single and TCR/HLA-I double ablated T cell treated groups slightly gained weight during the study (FIGS. 40A and 40B).

Figures 41A, 41B:
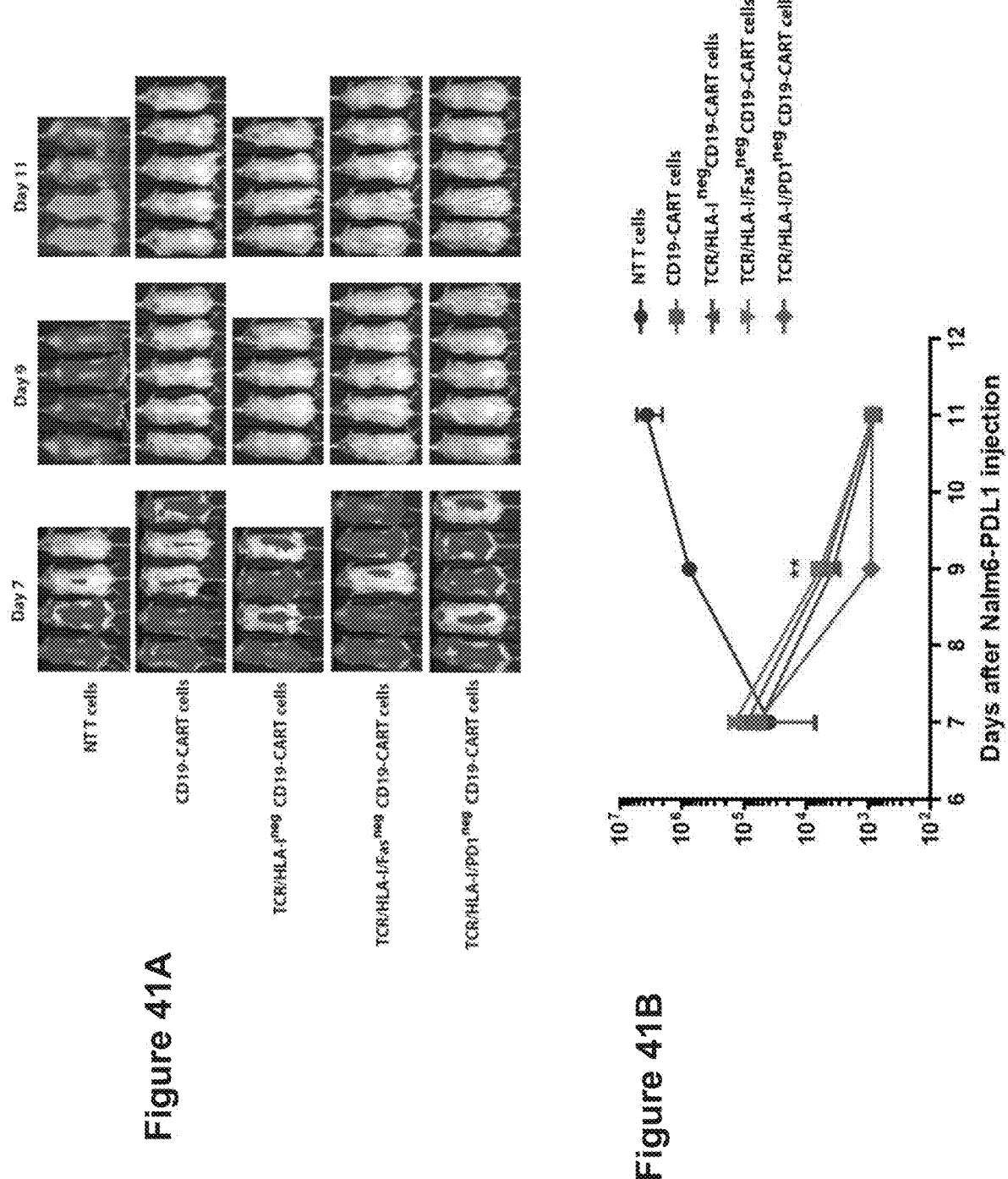
FIG. 41A is a panel of images showing improved anti-tumor activity of universal CART cells after blocking PD1 and Fas pathways with CRISPR/Cas9. Superior anti-tumor activity was detected in PD1 knock out universal CD19-CART cells when injected into Nalm6-PDL1 bearing mice.
FIG. 41B is a graph showing quantitative biolumines-cence data of mice receiving different CRISPR/Cas9 edited T cells.

T cells were treated with Cas9 and gRNAs targeting CD3, B2M and PD1 or Fas after lentiviral CD19-CAR transduction. Triple knock out universal CART cells were injected into mice bearing Nalm6-PDL1 tumors. Superior anti-tumor activity was observed in mice receiving PD1/CD3/HLA-I triple knock out cells as compared to CD3/HLA-I double knock out cells, further indicating the therapeutic value of blocking the PD1 signaling pathway (FIGS. 41A and 41B). These data supply a way to enhance the treatment of universal CART cells with CRISPR/Cas9.

Figure 42:
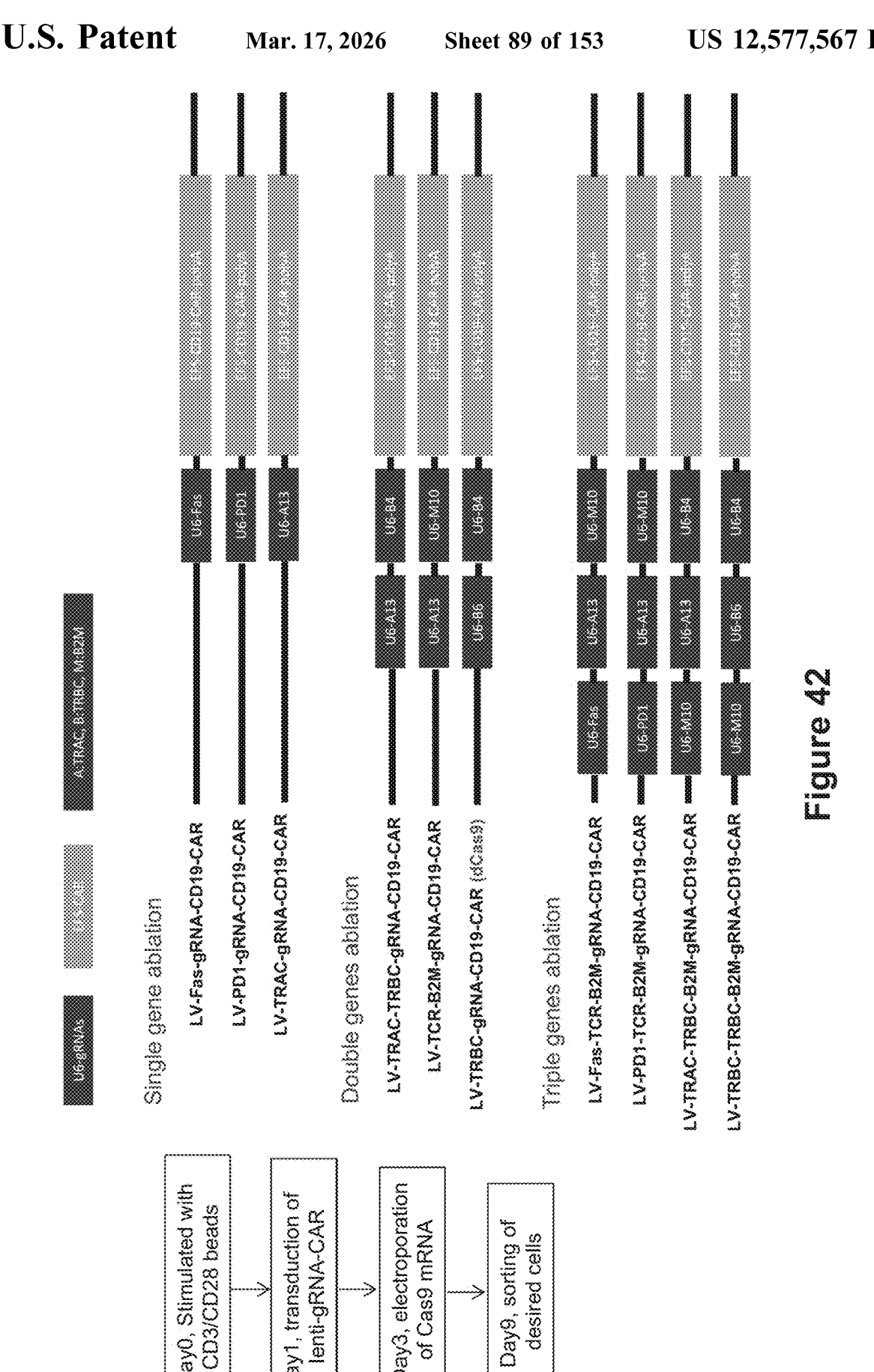
FIG. 42 is a panel of illustrations showing a one-shot system to generate universal CART cells. As gRNAs are prone to degrade, a simplified one-shot method was developed to constitutively express gRNAs together with CAR in a single lentiviral vector.
Figure 43:
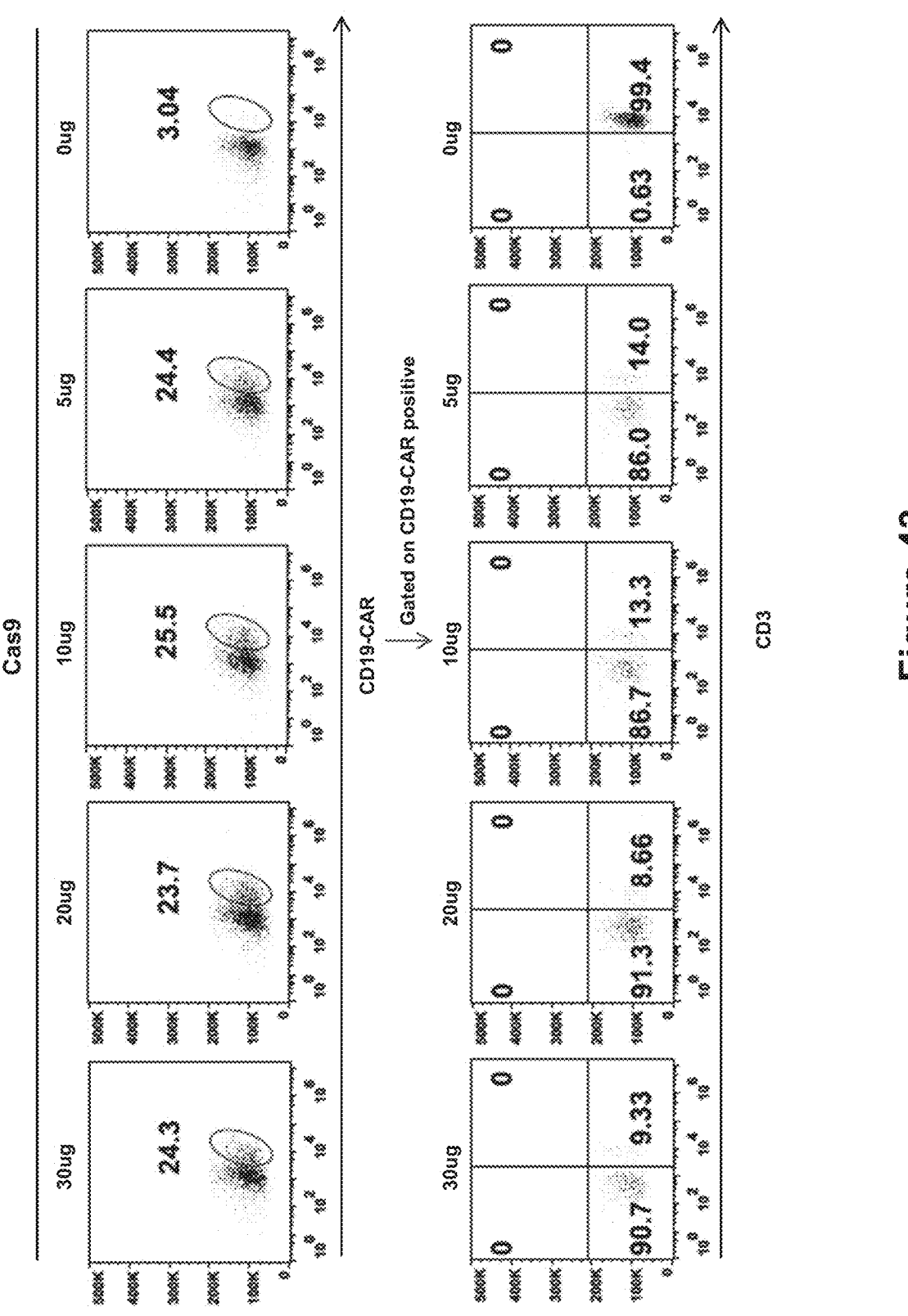
FIG. 43 is a panel of graphs showing efficient gene ablation with the one-shot system. Different amounts of CD3 ablation were observed after electro-transfer of Cas9 mRNA.

As gRNAs are prone to degrade, a simplified one-shot method was developed to generate universal CART cells. gRNAs were constitutively expressed together with CARs in a single lentiviral vector. Naïve T cells were transduced by lentivirus encoding gRNAs and CARs one day after stimulation with CD3/CD28 Dynabeads. The cells were electroporated with Cas9 mRNA at day 3 (FIG. 42). This system allows the manipulation of several genes with one vector (FIG. 42). CD3 expression was confirmed by flow cytometry at day 6. T cells treated with the one-shot system showed consistent gene ablation as high as 90% in each of the different Cas9 mRNA groups (FIG. 43).

Progress in adoptive T-cell therapy for cancer and infectious diseases has been hampered by the lack of readily available antigen-specific human T lymphocytes. Pluripotent stem cells could provide an unlimited source of T lymphocytes. To address this issue, expression of FAS, PD1, CTLA4, and PPP2r2d was disrupted in primary cells and T cells.

Sendai virus was used to reprogram primary cells and T cells. There are multiple methods available for the generation of iPSCs, including virus-mediated gene transduction and chemical induction. While lentiviral and retroviral vectors require integration into host chromosomes to express reprogramming genes, DNA-based vectors, such as adenovirus, adeno-associated virus, and plasmid vectors, exist episomally and do not require integration, however, they may still be integrated into host chromosomes at certain frequencies, and the reprogramming efficiency is relatively low. Likewise, mRNA based reprogramming is complicated and has proven to be extremely inefficient.

In contrast, Sendai virus does not integrate into the host genome or alter the genetic information of the host cell. Sendai virus also has reprogramming potential comparable to lentiviral- and retroviral-based gene transduction.

Each well in a 24 well plate was seeded with 0.1 million wild type, FASneg, CD3neg TCR alpha and beta chain knock-out T cells. The cells were stimulated with CD3/CD28 beads. At day 3 post stimulation, the beads were removed, the cells were resuspended in 1 mL of pre-warmed T cell complete medium, and then incubated with a calculated volume of CytoTune Sendai virus comprising a polycistronic vector for expression of hKlf4, hOct3/4 and hSox2 in the cells (Lifetechnologies, Carlsbad, CA). Treated T cells were seeded in 24 well plates, and centrifuged at 2250 rpm for 90 minutes at room temperature. An additional 1 mL of complete T cell medium was added to each well and the plate was incubated overnight at 37° C. in a humidified atmosphere of 5% CO2.

On the day after transduction, Sendai virus was removed by washing the T cells with fresh complete medium and culturing the cells for 2 days. Media was half changed every day. On day 3 after infection, cells were transferred to MEF feeder plates and cultured in T cell medium without any cytokines. Four days after infection, the cells were cultured in standard hES medium. Media was changed every day. ES-like colonies were observed around day 7. The cells were cultured in conditioned hES medium from day 15 and cultures continued for an additional 10 days. Colonies were picked at around 25 to 30 days after transduction.

Figures 44A, 44B:
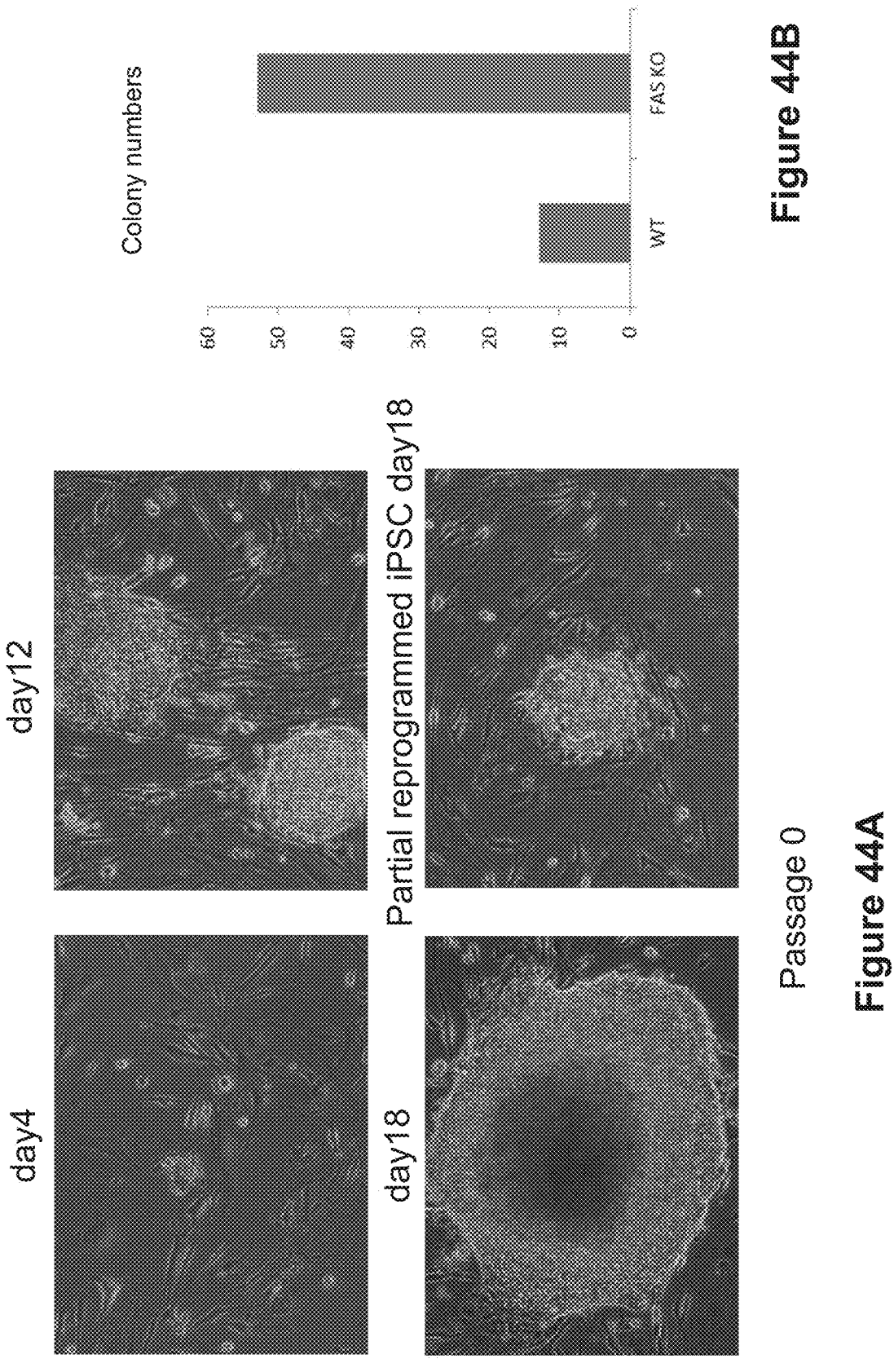
FIG. 44A is a panel of images showing the morphological changes during the process of reprogramming of iPSCs from Fas knock out T cells. Typical embryonic stem cell mor-phology formation indicating FASneg Tcells can be induced to pluripotent state.
FIG. 44B is a graph showing FASneg T cells repro-grammed to iPSCs at an efficiency of about 5 times of the wild type counterparts. p53 deficient cell lines have been reported as easier to reprogram due to the hindrance of the apoptosis pathway. FAS knock out may facilitate the repro-gramming process using a similar mechanism.

Around day 4, cell clumps were formed on feeder cells, indicating the initiation of the reprogramming process. T cells went through dramatic morphological changes during the reprogramming process to iPSCs (FIG. 44A). Around day 12, large cell clumps with loose edges began to emerge. Around day 18, T cells were transformed to typical ES-like colonies with well-defined edges. FASneg T cells were reprogrammed to iPSCs at an efficiency of about 5 times of the wild type counterparts (FIG. 44B). p53 deficient cell lines have been reported as easier to reprogram due to the hindrance of the apoptosis pathway. FAS knock out may facilitate the reprogramming process using a similar mechanism.

Figures 45A, 45B, 45C:
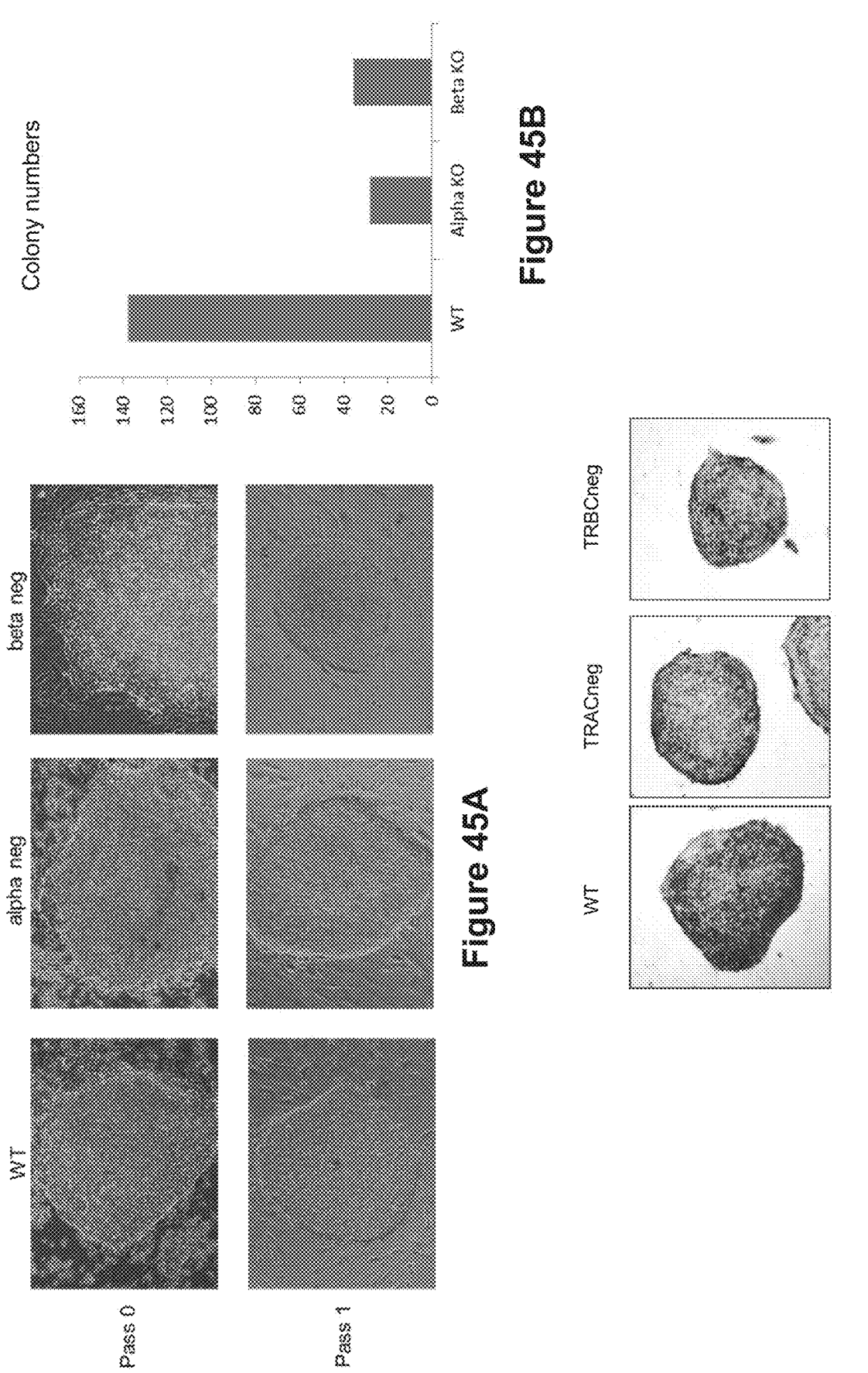
FIG. 45A is a panel of images showing the ES-like morphology of iPSCs from CD3neg TCR alpha or beta chain knock out T cells under defined reprogramming conditions. The morphology remained constant after several passages.
FIG. 45B is a graph showing that reprogramming of CD3neg T cells was about 5 times less efficient than the wild type counterparts, suggesting that TCR knock-out may play a role in the process of T cell reprogramming or affect the cell viability after Sendai virus infection.
FIG. 45C is a panel of images showing phosphatase staining of CD3neg iPSC cells.

ES-like morphology of iPSCs reprogrammed from CD3neg TCR alpha or beta chain knock out T cells was observed (FIG. 45A). The morphology remained constant after several passages. Reprogramming of CD3neg T cells was about 5 times less efficient than the wild type counterparts (FIG. 45B), suggesting that TCR knock-out may play a role in the process of T cell reprogramming or affect the cell viability after Sendai virus infection. FIG. 45C is a panel of images showing phosphatase staining of CD3neg iPSC cells.

Typical embryonic stem cell morphology was observed indicating that the FASneg, CD3neg TCR alpha and beta chain knock-out T cells were induced to a pluripotent state under defined reprogramming conditions. While loss of TCR expression makes T cells less healthy, the data described herein suggests that apoptosis plays an important role in the process of reprogramming.

Figure 46:
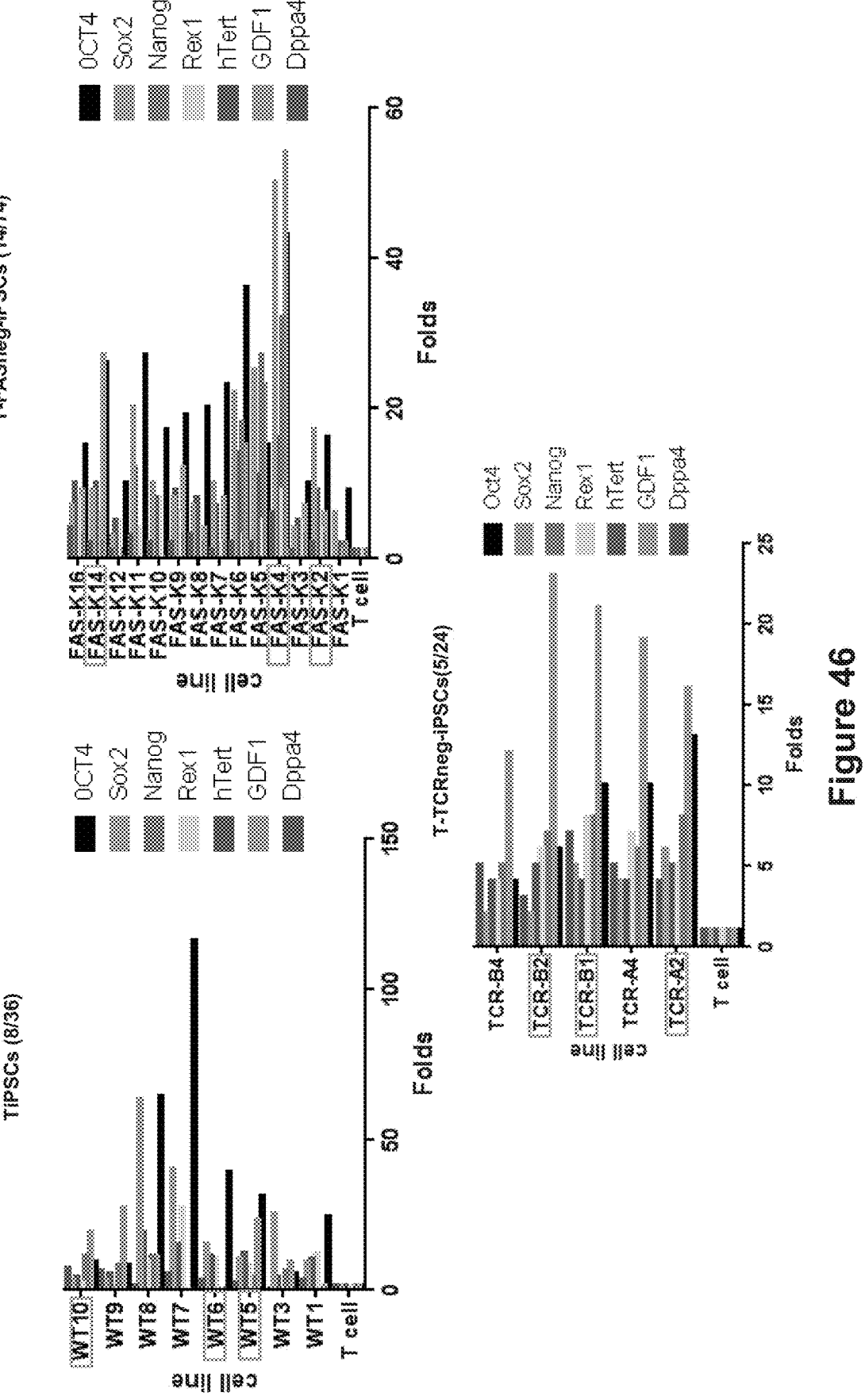
FIG. 46 is a panel of graphs showing induction of endogenous pluripotent stem cell genes in different T-iPSC cell lines.
Figure 47A:
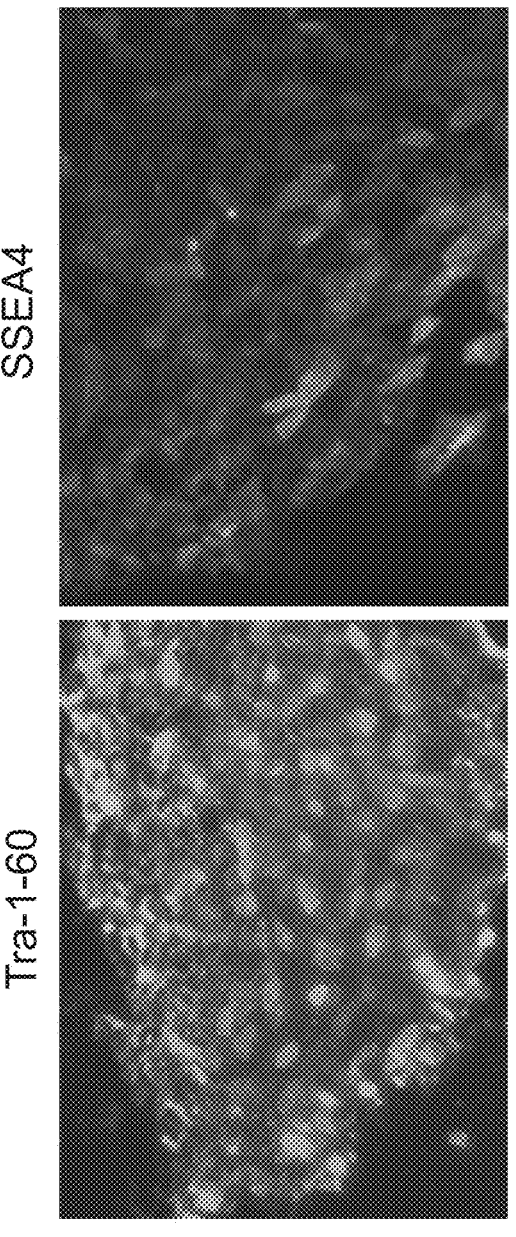
FIG. 47A is a panel of images showing immunostaining for Tra-1-60 and SSEA4 expression.
Figure 47B:
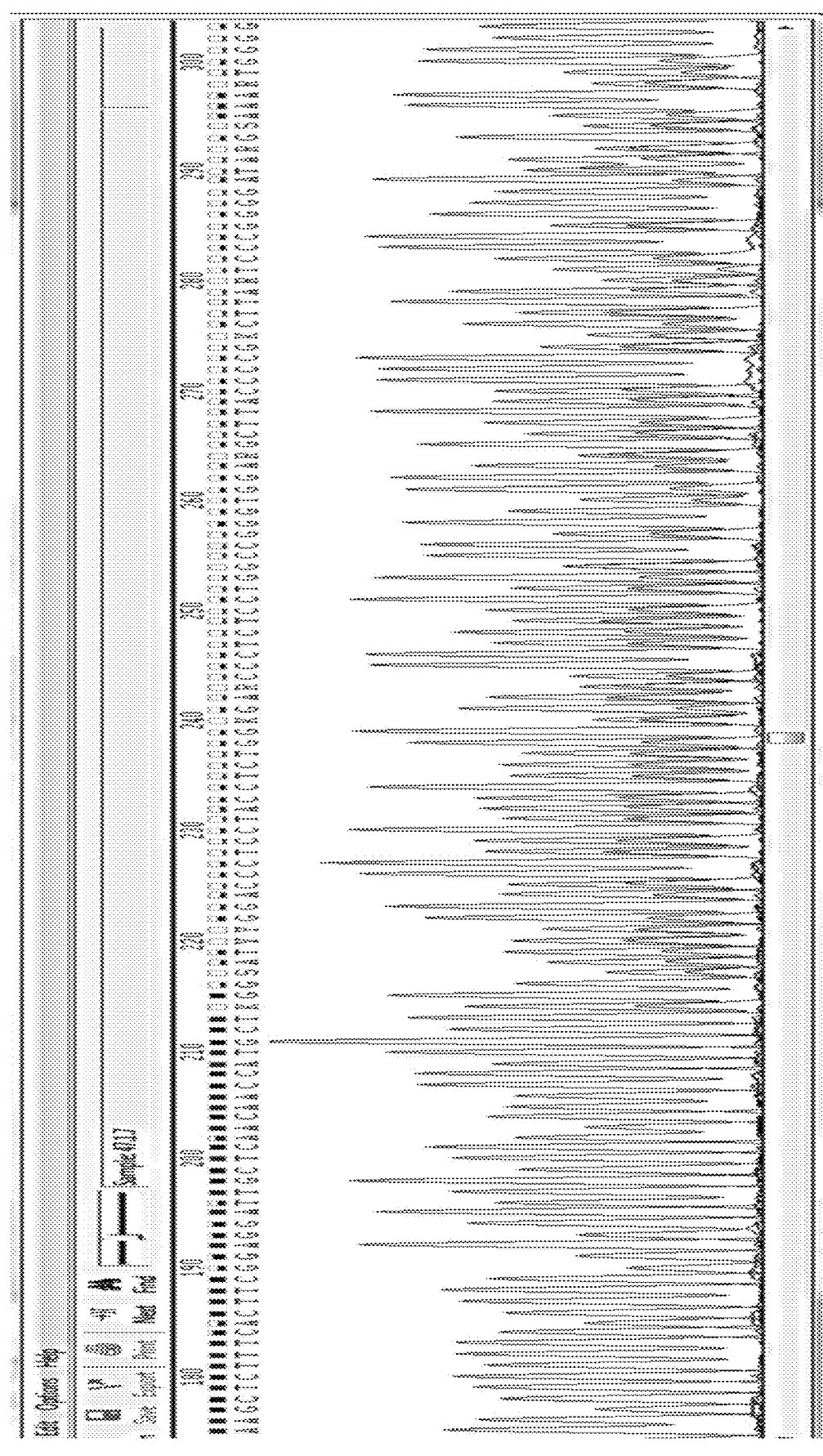
FIG. 47B is an image showing the confirmation of Fas knock out of T-iPSC by Sanger sequencing (SEQ ID NO: 92).
Figure 48A:
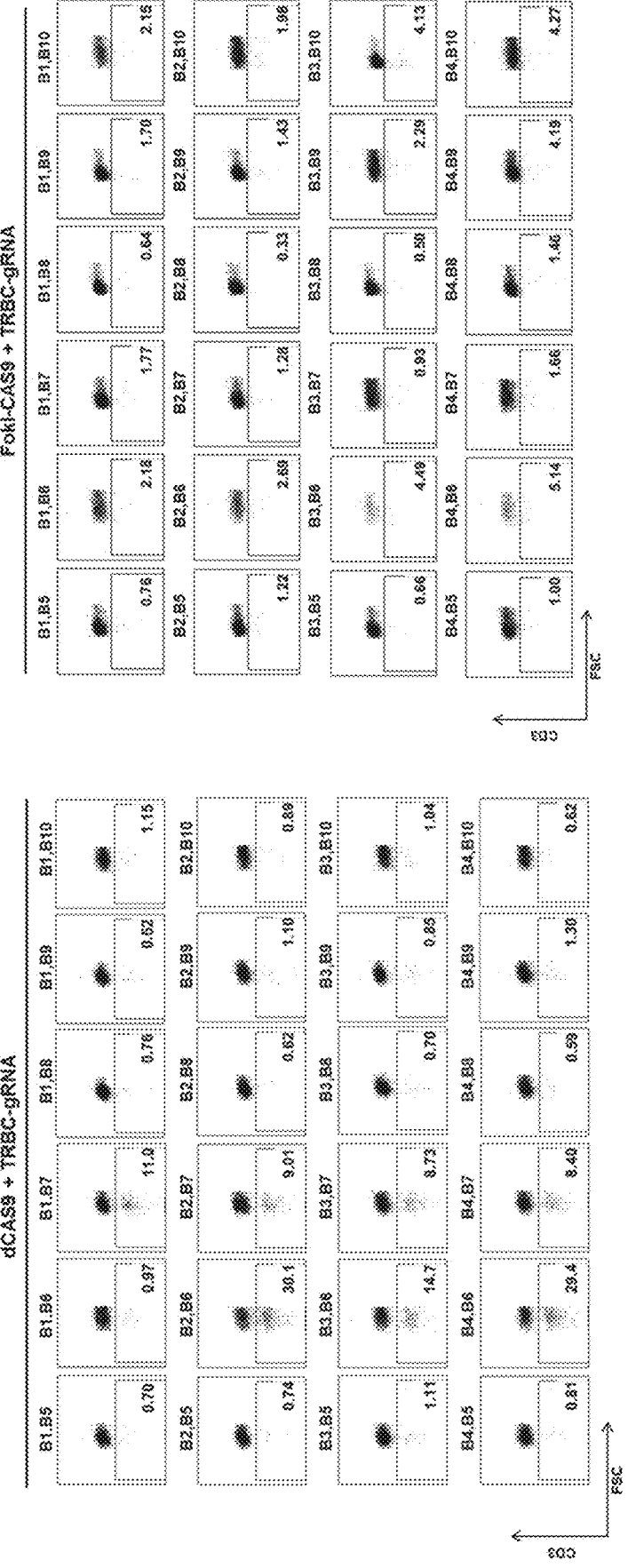
FIG. 48A is a panel of graphs showing gene ablation in naïve T cells with a different version of Cas9. CD3 was knocked out with dCas9 and FokI-Cas9.
Figure 48C:
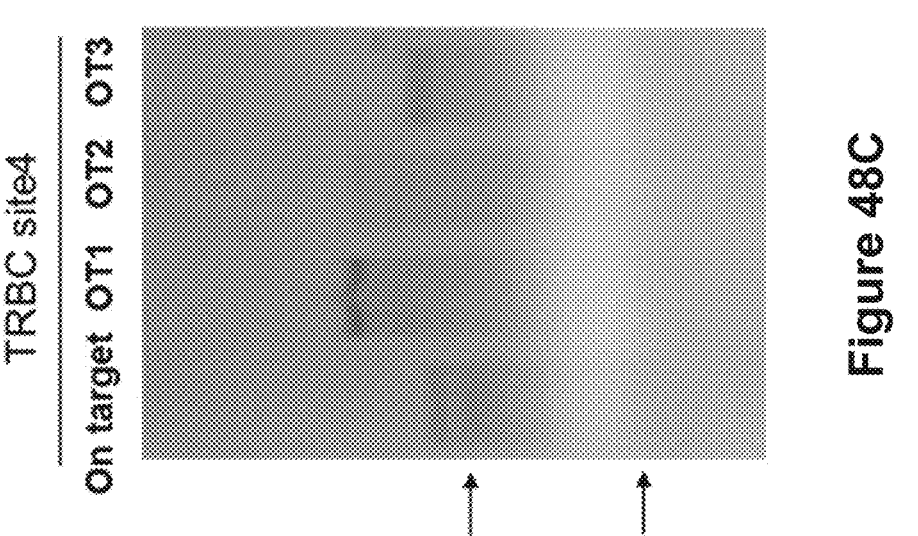
FIG. 48C is in image showing rare off-target events in gene modified T cells with CRISPR/cas9.
Figure 48B:
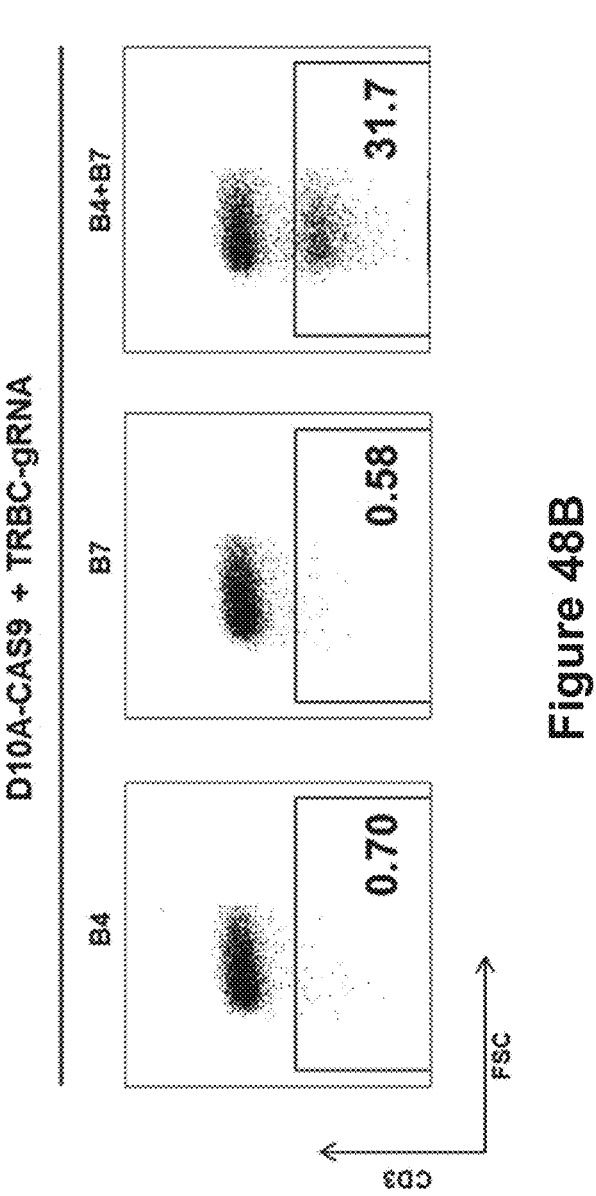
FIG. 48B is a panel of graphs showing that two gRNAs were needed for gene ablation of dCas9 and FokI-Cas9.

Induction of endogenous pluripotent stem cell genes was also detected in the different T-iPSC cell lines (FIG. 46). Immunostainings for Tra-1-60 and SSEA4 expression further indicated the stem cell phenotype of the T-iPSC cells (FIG. 47A). Fas knock out was confirmed in the T-iPSCs by Sanger sequencing (FIG. 47B).

dCas9 and FokI-Cas9 were reported to have less off-target activity. T cells were evaluated if they could be edited by a modified version of the CRISPR/dCAS9 and CRISPR/FokI-CAS9 system (FIG. 48A). Flow cytometric data showed primary T cells were edited by both CRISPR/dCAS9 and CRISPR/FokI-CAS9 (FIG. 48B). The CRISPR/dCAS9 gene knock out system exhibited enhanced specificity with at least one pair of gRNAs, rendering the knock out event more precise and more specific.

To test the off-target events of CRISPR/CAS9 in T cells, a surveyor assay was performed at off target sites. For the genes tested, no obvious cleavage was observed at the genomic loci (FIG. 48C).

Example 11: Multiplex Genome Editing

CART cells were generated by using a CRISPR/Cas9 system to simultaneously disrupt multiple genomic loci. The CART cells were deficient in the expression of endogenous TCR and HLA class I (HLA-I) molecules for use as allogeneic universal CART cells. T cell receptor (TCR) α chain, TCR β chain and beta-2 microglobulin (B2M) genes were disrupted with high efficiency through the co-electroporation of mRNA encoding Cas9 with gRNAs targeting these genes. Universal TCR or CART cells were generated by combining lentiviral (LV) delivery of CAR and CRISPR RNA electroporation to disrupt endogenous TCR and B2M genes simultaneously. In addition, disruption of endogenous PD1 enhanced the efficacy of CAR therapy in a solid tumor model.

Multiple Deliveries of gRNAs Disrupts Genes in Human Primary T Cells with High Efficiency without Impairing Effector Function Efficient multiplex genomic editing is required to generate universal T cells that are deficient in TCR, HLA and other genes. CRISPR/gRNA RNA electroporation was optimized to achieve efficient gene disruption in T cells. First, Cas9 and gRNAs were co-electroporated with RNA generated using an in vitro transcription system (FIG. 49, left), and a "hit-and-run" delivery strategy was developed to transiently deliver the Cas9 mRNA and gRNAs to T cells by electroporation (FIG. 49, right).

Figure 50A:
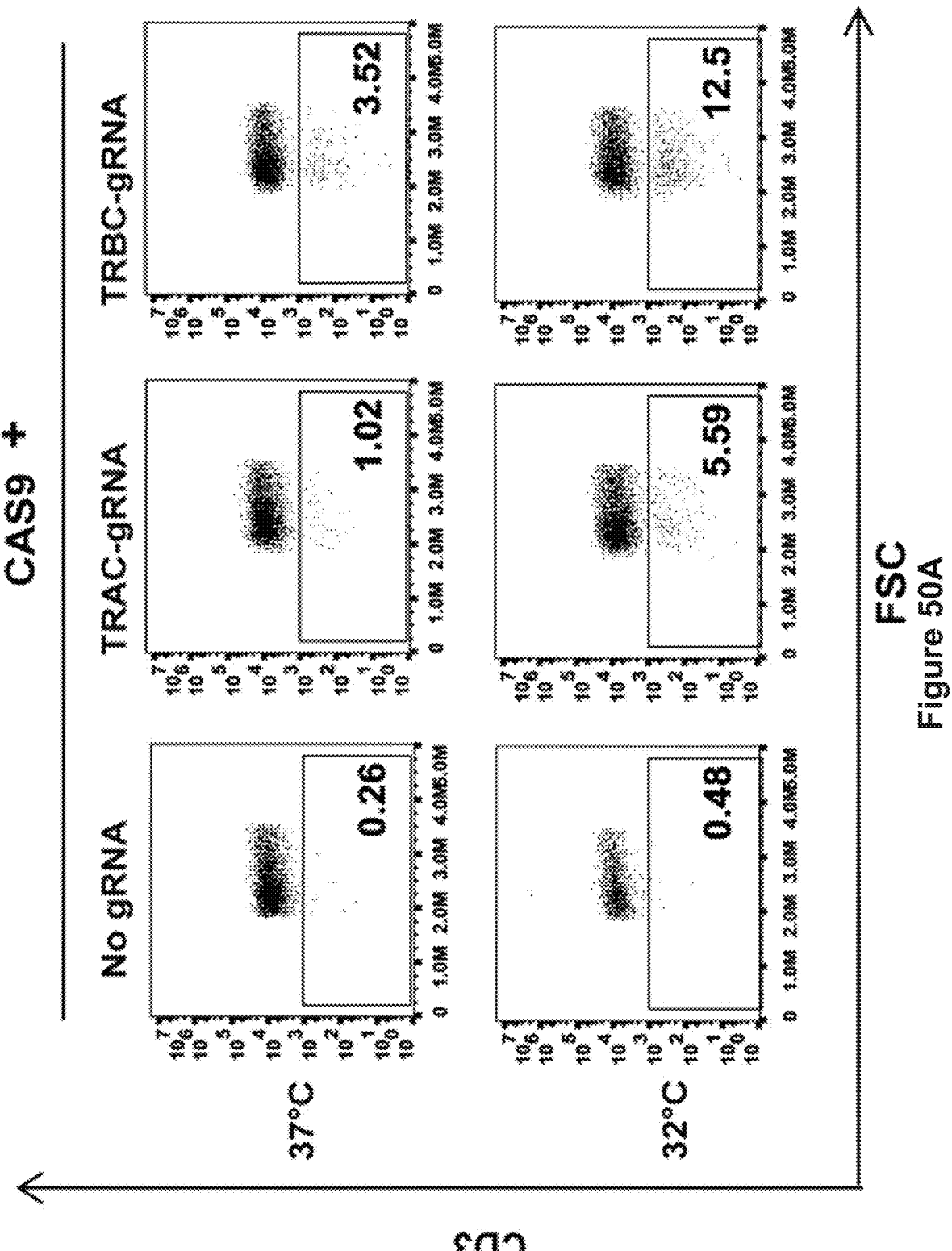
FIG. 50A is a panel of graphs showing CRISPR/Cas9 mediated efficient TCR disruption in T cells. CD3 expres-sion of CRISPR/Cas9 edited T cells cultured at 37° C. or 32° C.
Figure 51A:
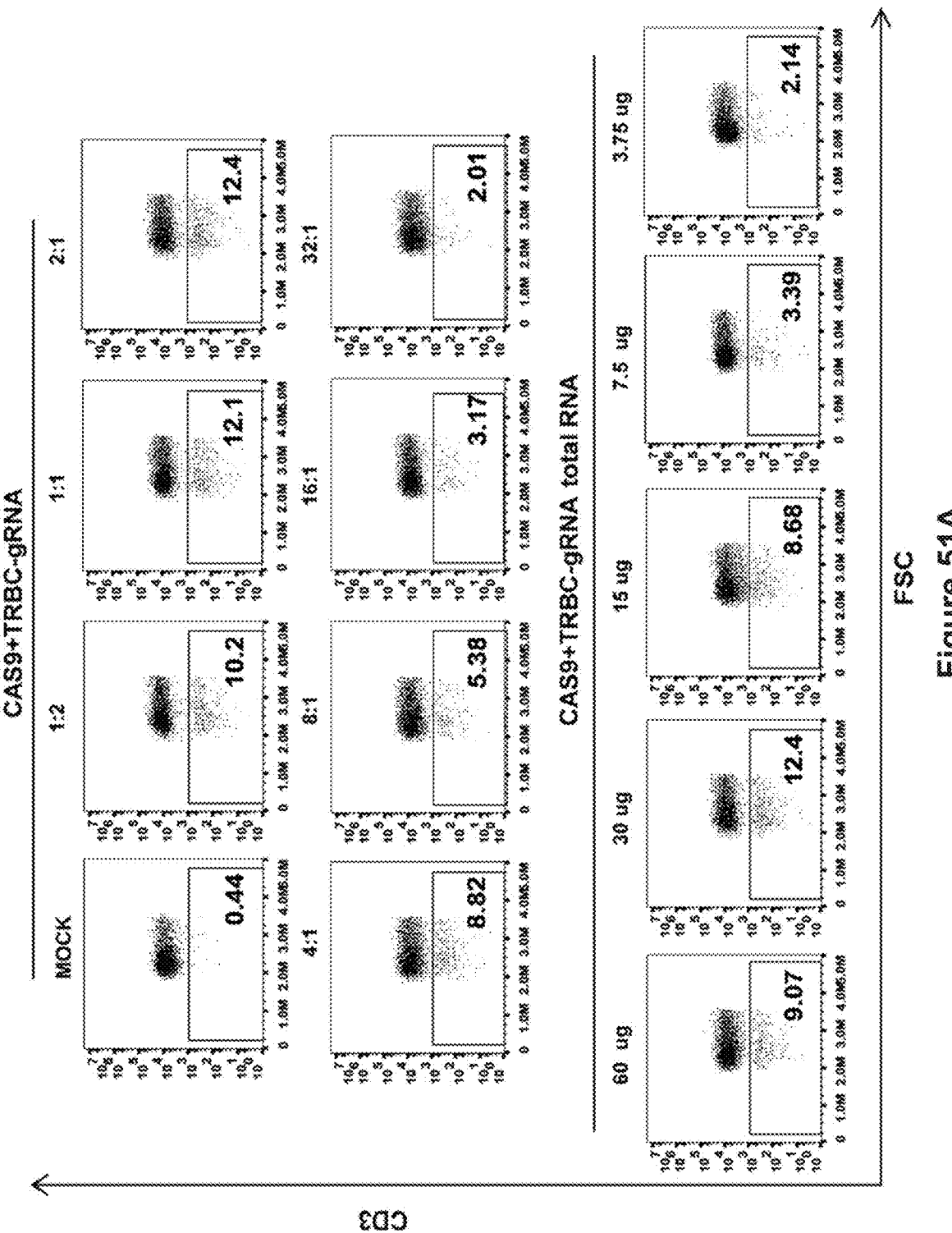
FIG. 51A is a panel of graphs showing the efficient CRISPR gene disruption that occurred in T cells. CD3 expression of T cells transferred with CRISPR using differ-ent Cas9:gRNA ratios (upper and middle panel) and amount of total CRISPR RNA (lower panel).

An initial experiment targeting the TCR β constant region (TRAC) or □ constant region (TRBC) with single electroporation resulted in 1% to 3% CD3-negative (CD3$^{neg}$) T cells, respectively, (FIG. 50A, upper graphs). To determine if transient exposure to mild hypothermia allowed more efficient gene disruption, cells were edited at 37° C. or 32° C. CRISPR-mediated disruption of TRAC and TRB was increased up to 4-fold when T cells were cultured for 24 h at 32° C. after Cas9/gRNA co-electroporation (FIG. 50A, lower graphs). The optimal molecular ratio of Cas9:gRNA for maximum disruption efficiency was 1:1 to 2:1, and the gene disruption efficiency was correlated with the amount of electro-transferred mRNA (FIG. 51A).

Figure 50B:
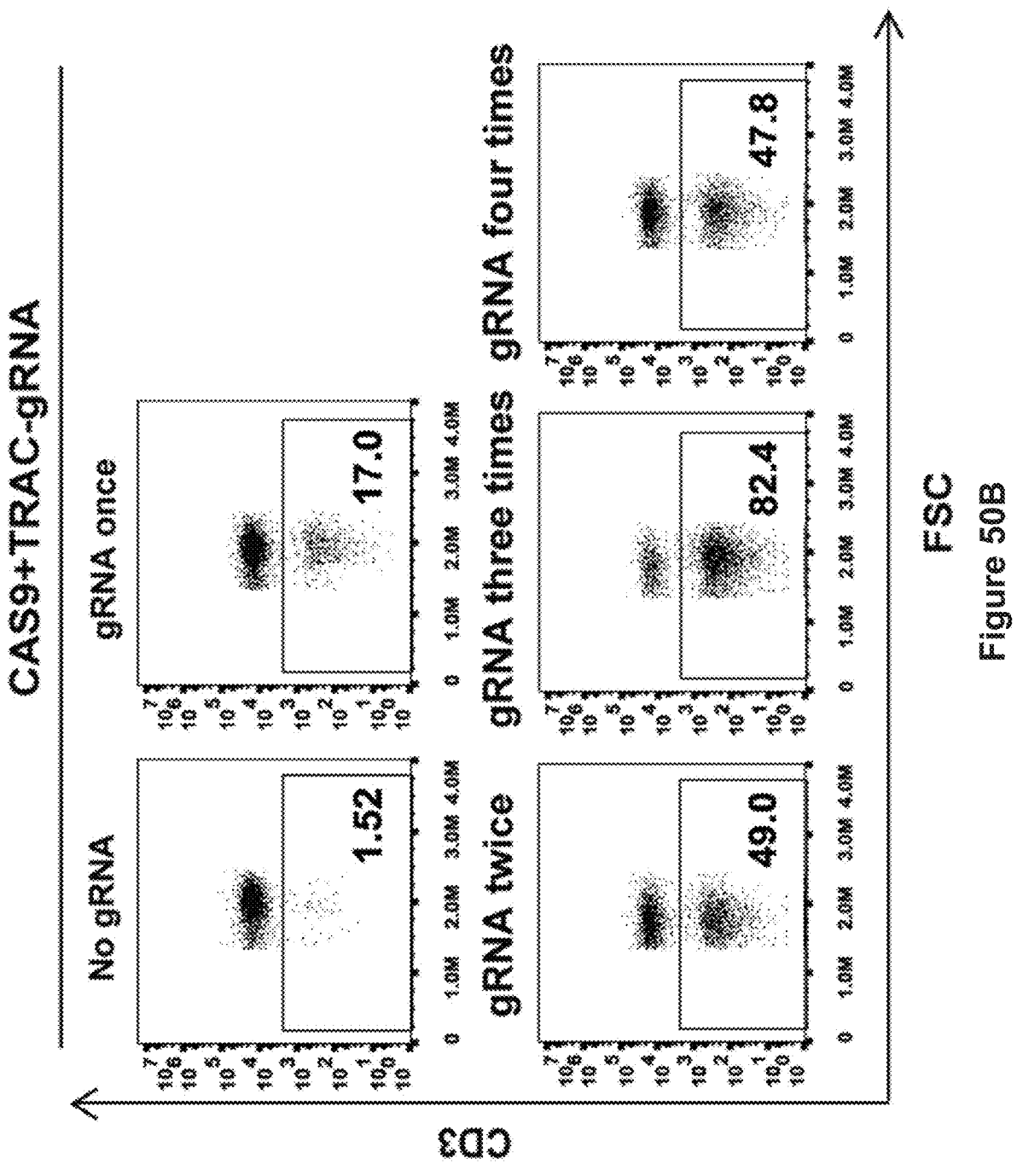
FIG. 50B is a panel of graphs showing CD3 expression of CRISPR/Cas9 edited T cells cultured after sequential CRISPR RNA electroporation.
Figure 52:
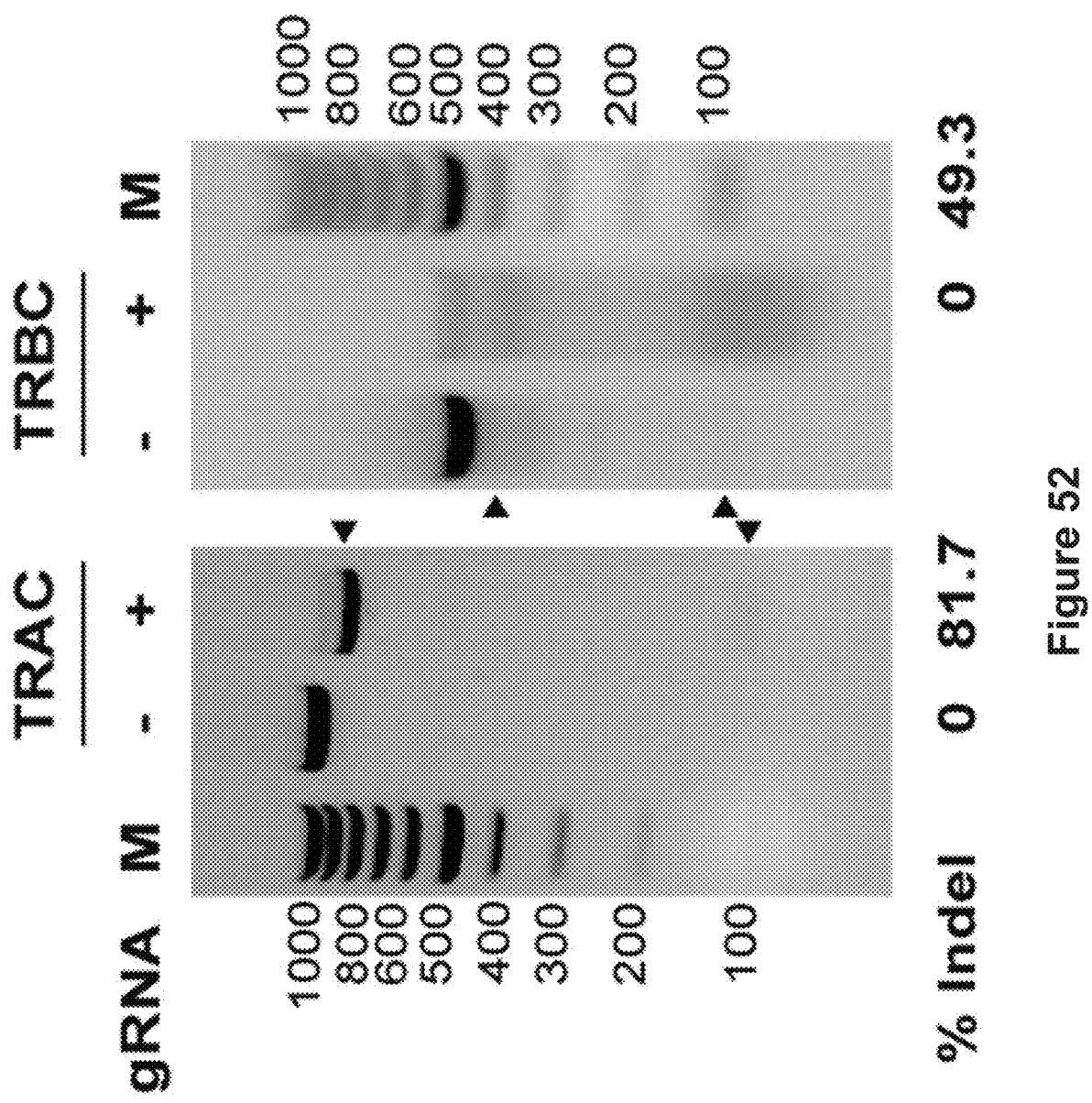
FIG. 52 is an image showing the amount of TCR-targeted gene disruption measured by a mismatch-selective T7 sur-veyor nuclease assay on DNA amplified from the cells. The calculated amount of targeted gene disruption in TRAC and TRBC is shown at the bottom. Arrows indicate expected bands.
Figure 53B:
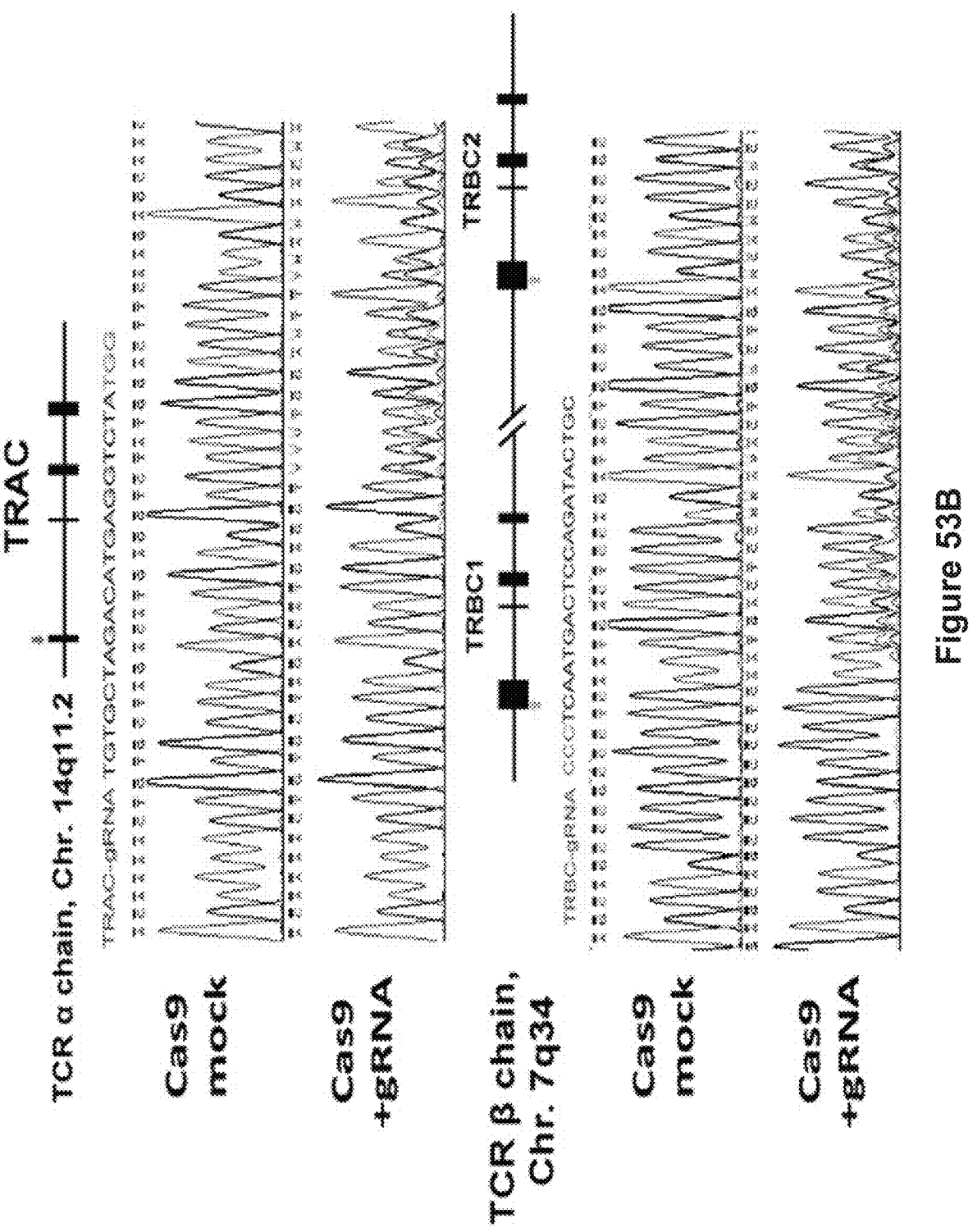
FIG. 53B is an image of a diagram of the human locus encoding the TCR α and β CRISPR gRNA targeting sites within the genomic locus of the TCR α and β constant region. Each exon is shown by a block. Arrow: sense strand gRNA targeting site, blue arrow: antisense strand gRNA targeting site. Multiple peaks in the Sanger sequencing results (SEQ ID NOs: 93-96) show the CRISPR-mediated events of NHEJ at the TRAC and TRBC genomic loci. TRAC-gRNA-5 and TRBC-gRNA-7 sequences are also shown (SEQ ID NOs: 15 and 16).
Figure 54:
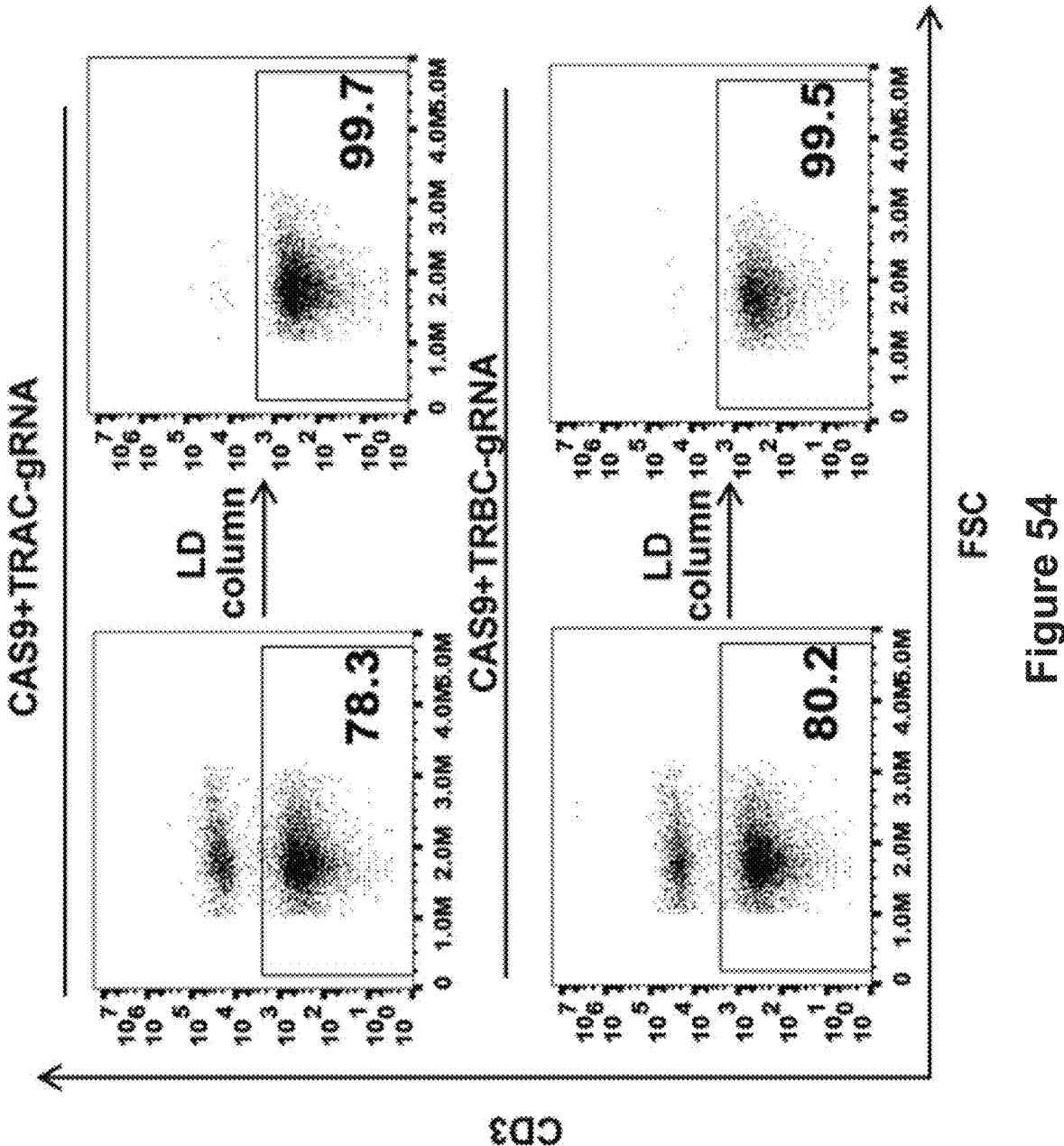
FIG. 54 is a panel of graphs showing CD3 expression in purified TCR$^{neg}$ cells.

Compared with mRNA, gRNAs are more prone to rapid degradation, which potentially limits the targeting efficiency. Thus, multiple, sequential electroporations of gRNA were tested after the initial Cas9/gRNA electroporation. There was a marked increase in disruption frequency at the protein level, as 82.4% of cells were CD3$^{neg}$ after the third gRNA electroporation (FIG. 50B). Clonal sequencing showed that the genomic targeting efficiency reached 89.4% after the third gRNA electroporation (FIG. 51B). A surveyor assay confirmed a cleavage rate of 81.7% and 49.3% at the genomic loci of TRAC and TRBC, respectively, after a third electroporation of gRNAs (FIG. 52). Multiple peaks in the Sanger sequencing data flanking the TRAC and TRBC target sites confirmed that the genomic reading frame shifted downstream of the target sites (FIG. 53A). The occurrence of insertions or deletions (indels) caused by the NHEJ mediated by CRISPR/Cas9 was confirmed by clonal sequencing (FIG. 53B). The TCR disrupted TCR/CD3$^{neg}$ population was enriched to over 99% (99.70±0.20%) by a single step of CD3 negative selection (FIG. 54).

Figure 55:
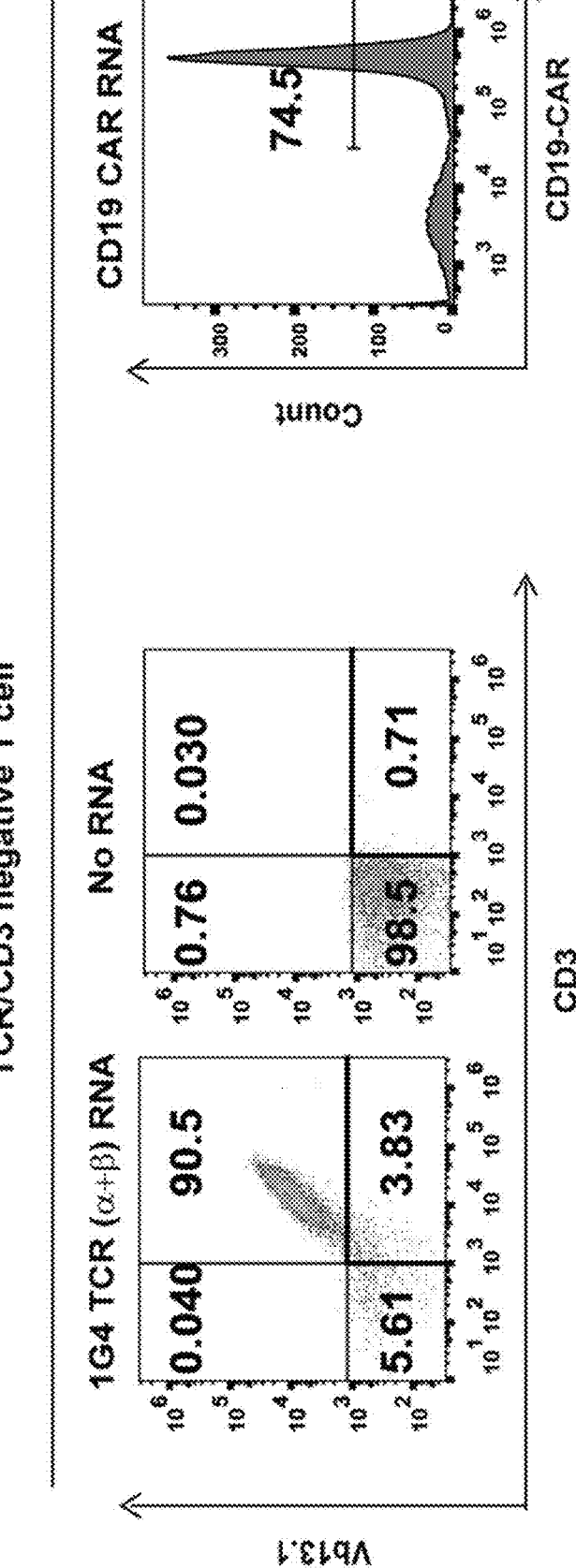
FIG. 55 is a panel of graphs showing redirection of TCR/CD3$^{neg}$ cells via the electrotransfer of 1G4 TCR (α and β) or CAR19 mRNA.
Figure 56:
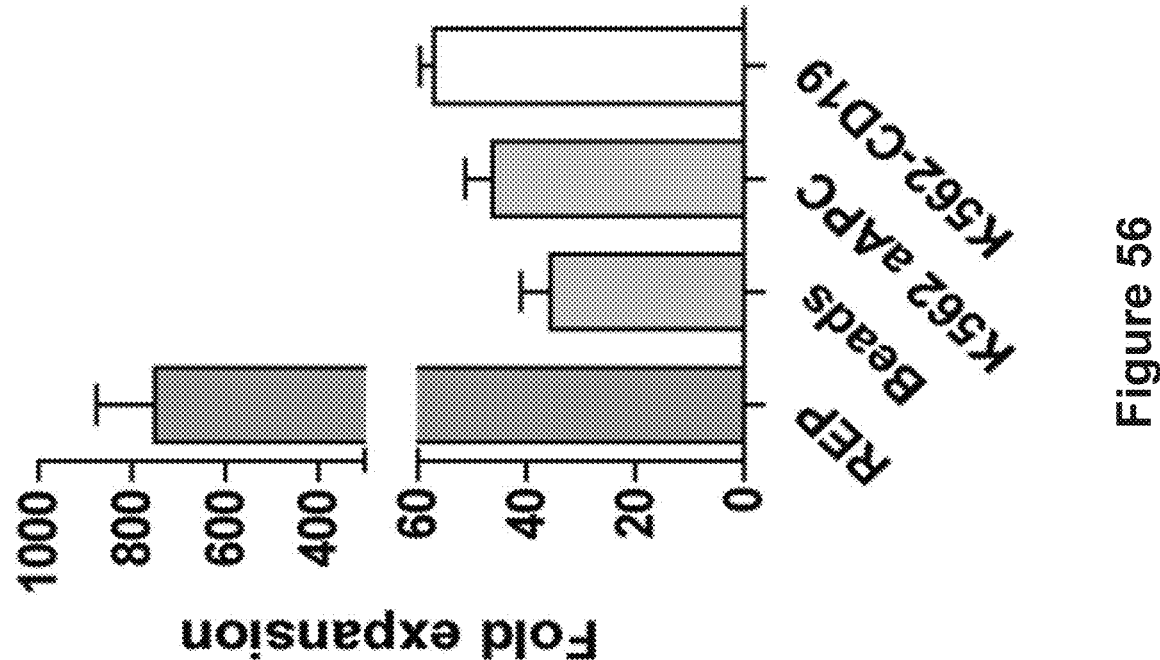
FIG. 56 is a graph showing TCR/CD3$^{neg}$ cell expansion after 10 days using different stimulation conditions.

To develop methods to expand the TCR/CD3$^{neg}$ T cells, TCR/CD3$^{neg}$ T cells were co-electroporated with the HLA-A2 restricted 1G4 NY-ESO-1 TCR (□□□) RNAs to restore CD3 expression (FIG. 55, left panel). Following T cell stimulation/expansion methods, the following were compared: 1) a rapid T cell expansion protocol (REP) using PBMC as feeder cells, 2) anti-CD3/CD28 Dynabeads (Beads), or 3) OKT3 loaded K562-based artificial antigen-presenting cells expressing ligands for CD28 and 4-1BB (K562 aAPC). TCR/CD3$^{neg}$ T cells were also electroporated with CD19 CAR RNA (FIG. 55, right panel) and then stimulated by irradiated K562 aAPC that expressed CD19 (K562-CD19). Fold expansion values of 751.0±217.1, 35.7±9.3, 46.3±8.5 and 57.5±5.0 were achieved for REP, Beads, K562 aAPC and K562-CD19, respectively, after a single stimulation for 10 days (FIG. 56).

Figure 57:
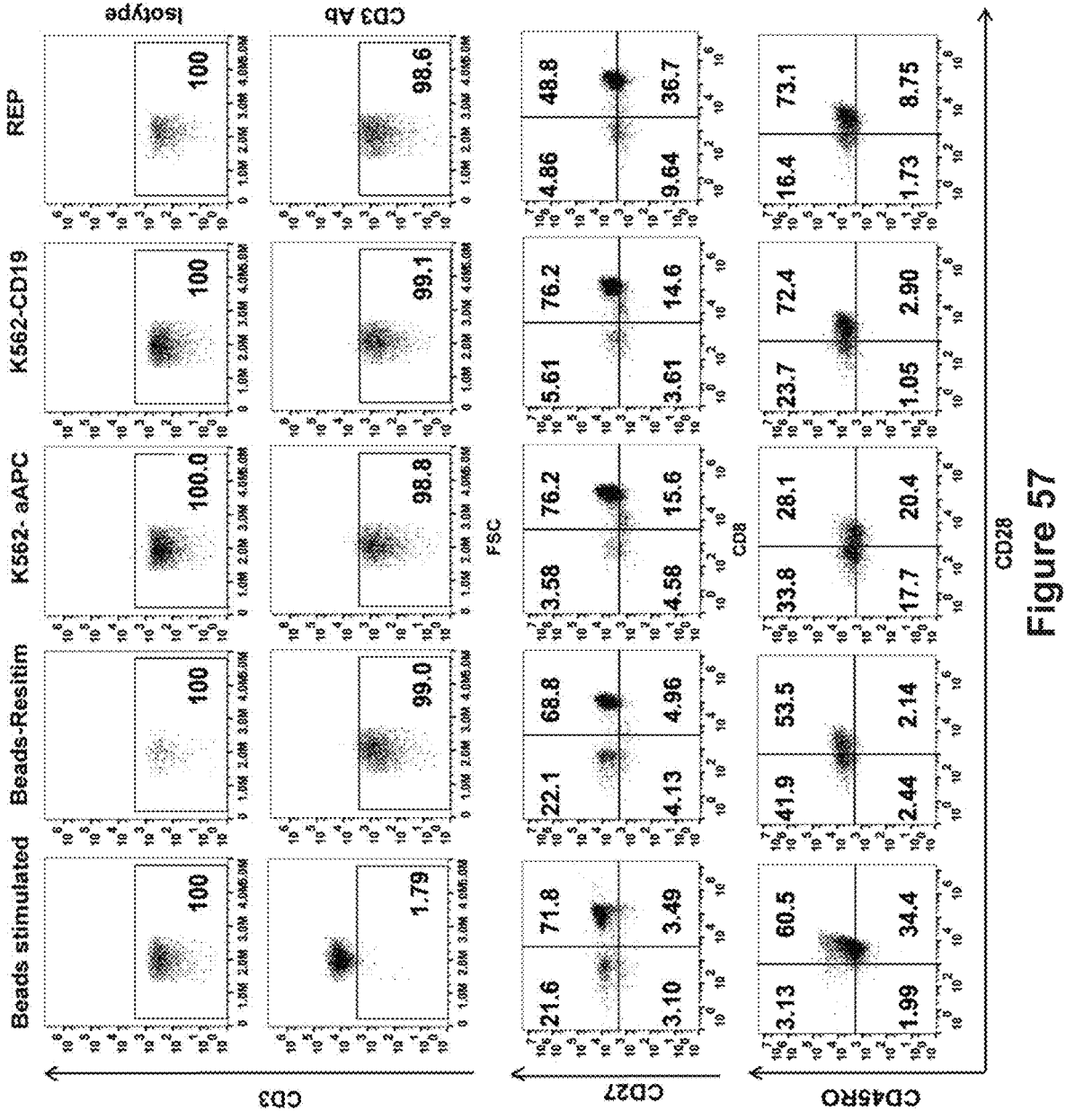
FIG. 57 is a panel of graphs showing that CRISPR/Cas9 editing did not impair antitumor efficacy of primary T cells. The phenotypes of TCR/CD3$^{neg}$ cells after the four different expansion techniques are shown.
Figures 58, 59A:
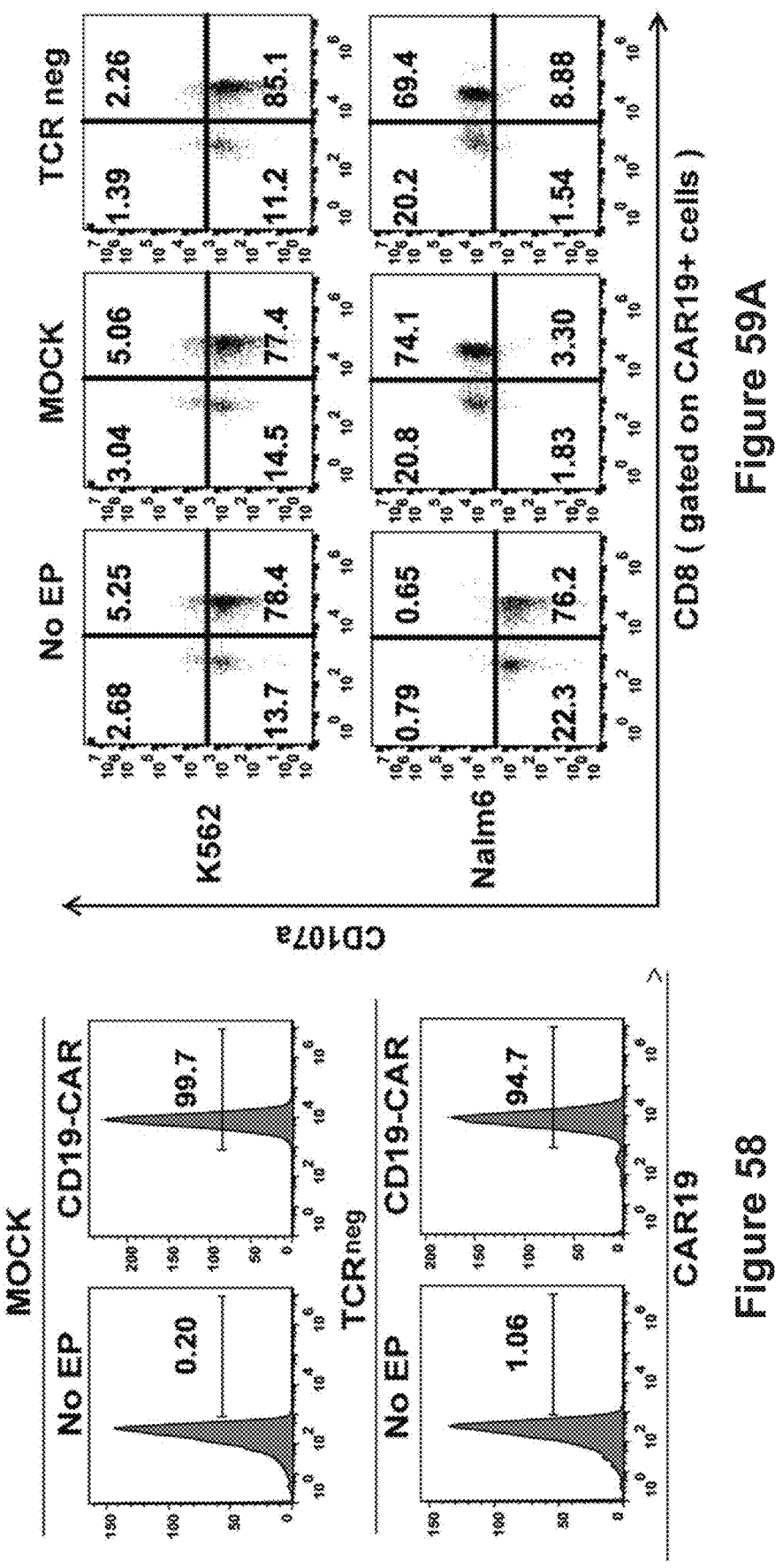
FIG. 58 is a panel of graphs showing the relative CD19-CAR expression after electrotransfer of CD19-CAR RNA into Cas9 MOCK and TCR/CD3$^{neg}$ cells.
FIG. 59A is a panel of graphs showing that no significant functional difference was observed between CD19-CAR redirected Cas9 MOCK and TCR/CD3$^{neg}$ cells as confirmed by CD107 release assay after incubation with Nalm6 target cells. Representative data from 3 independent experiments are shown. Bars, standard error.
Figures 59B, 59C:
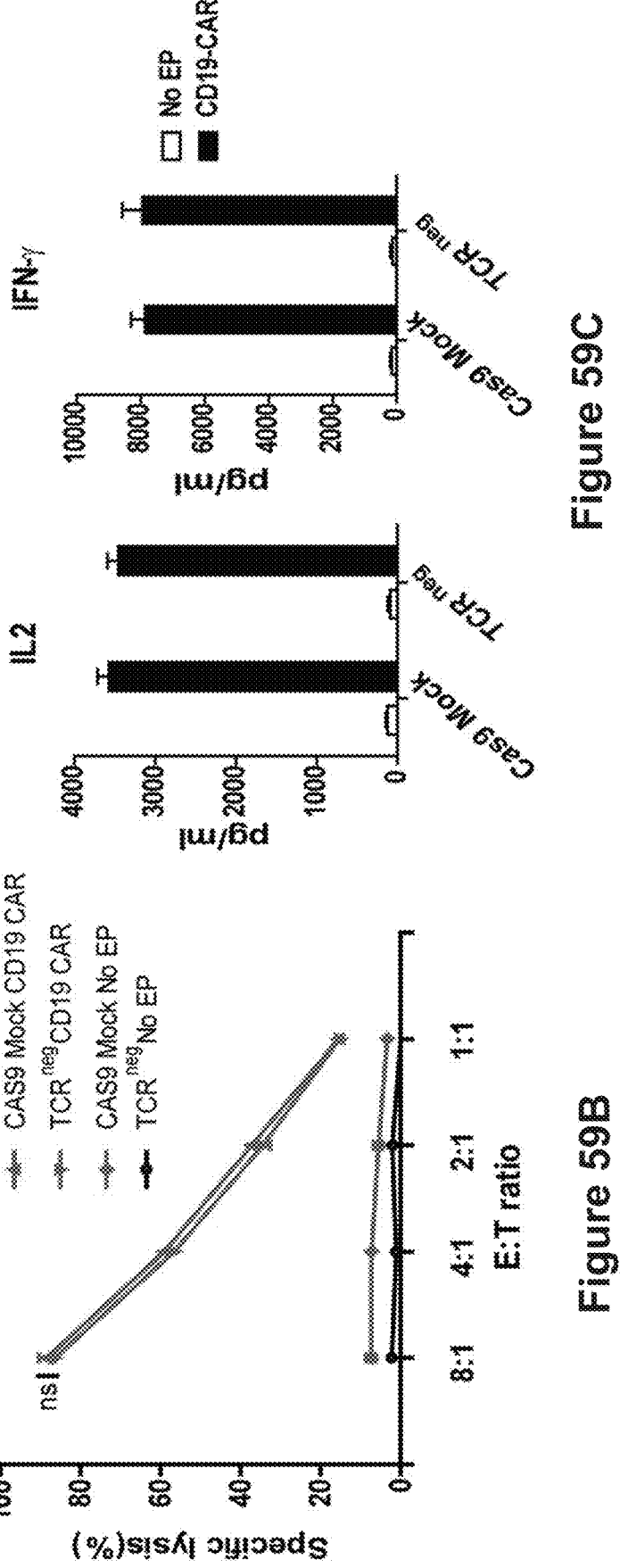
FIG. 59B is a graph showing that no significant functional difference was observed between CD19-CAR redirected Cas9 MOCK and TCR/CD3$^{neg}$ cells as confirmed by cyto-toxicity assay after incubation with Nalm6 target cells. Representative data from 3 independent experiments are shown. Bars, SE=standard error.
FIG. 59C is a panel of graphs showing that no significant functional difference was observed between CD19-CAR redirected Cas9 MOCK and TCR/CD3$^{neg}$ cells as confirmed by IL2 and IFNγ secretion after incubation with the Nalm6 target cells. Representative data from 3 independent experi-ments are shown. Bars, SE=standard error.
Figures 59D, 59E:
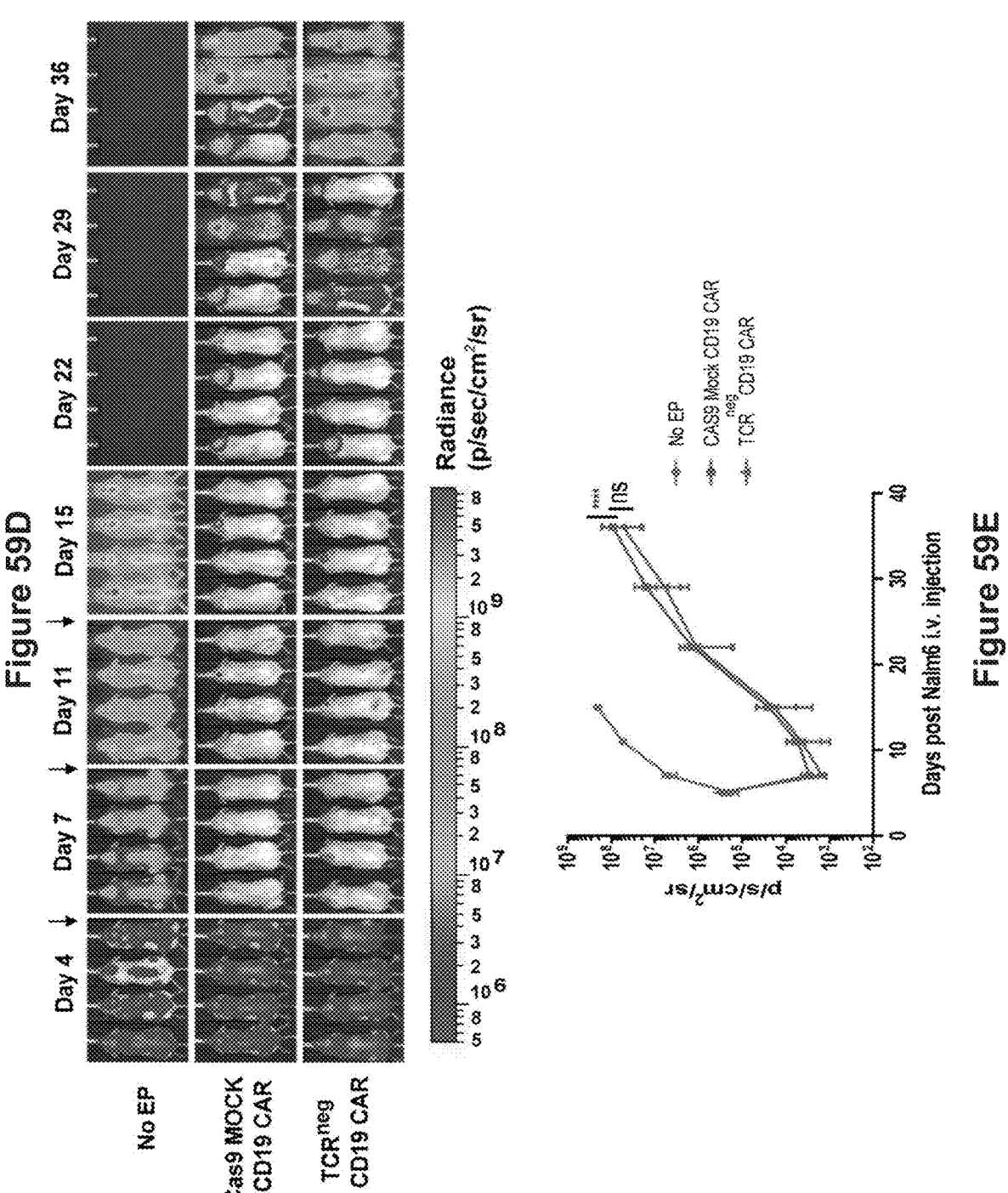
FIG. 59D is a panel of images of NOD/scid/γc(−/−) mice (n=12) injected with 1×10^6 Nalm6 tumor cells (i.v.) the mice were randomly sorted into three groups. Cas9 MOCK and TCR/CD3^{neg} T cells (10×10^6) expressing the CD19-CAR after electroporation were injected i.v. every 4 days for a total of three injections (arrows). Mice treated with T cells electroporated with no RNA served as controls. Images were obtained from the surviving animals as indicated. Imaging commenced 1 day before the start of T cell treatment. Bars, SE=standard error, EP=electroporation; E:T=effector to tumor ratio; arrow, time point of T cell infusion; ns, not significant. ****P<0.0001, ns by two-way ANOVA plus the Bonferroni post test.
FIG. 59E is a graph showing the radiance of the fluorescent cells.

To test whether CRISPR/Cas9 gene editing would affect the phenotype and function of the T cells, the phenotype of TCR/CD3$^{neg}$ T cells expanded by the different methods was examined and showed that all of the expanded cells remained CD3 negative and most retained a high level of CD27 (from 79.8% to 93.4%), consistent with a central memory cell phenotype (FIG. 57). The expanded TCR/CD3$^{neg}$ T cells were electroporated a second time with CD19 CAR mRNA to test their anti-tumor activities. The surface CAR expression of the TCR/CD3$^{neg}$ T cells was equal to that of the control group (FIG. 58). When the TCR/CD3$^{neg}$ CD19 CAR T cells were stimulated with CD19$^+$ Nalm6 leukemia cells, the CD107a up-regulation (FIG. 59A), cytokine secretion (FIG. 59C) and killing activity (FIG. 59B) of CD19 CAR$^+$ TCR/CD3$^{neg}$ T cells was equivalent to those of the wild-type control cells. The CD19 CAR TCR/CD3$^{neg}$ T cells were infused into Nalm6-bearing NSG mice to test their in vivo anti-tumor activity. Tumor regression was evident with an efficacy equivalent to that for the CART19 wild-type counterpart cells (FIGS. 59D and 59E). The results indicate that CRISPR/Cas9 editing of the endogenous TCR did not adversely affect the function of primary T cells for adoptive immunotherapy.

Reduced alloreactivity of TCR α, β and B2M triple-disrupted T cells.

Figure 60:
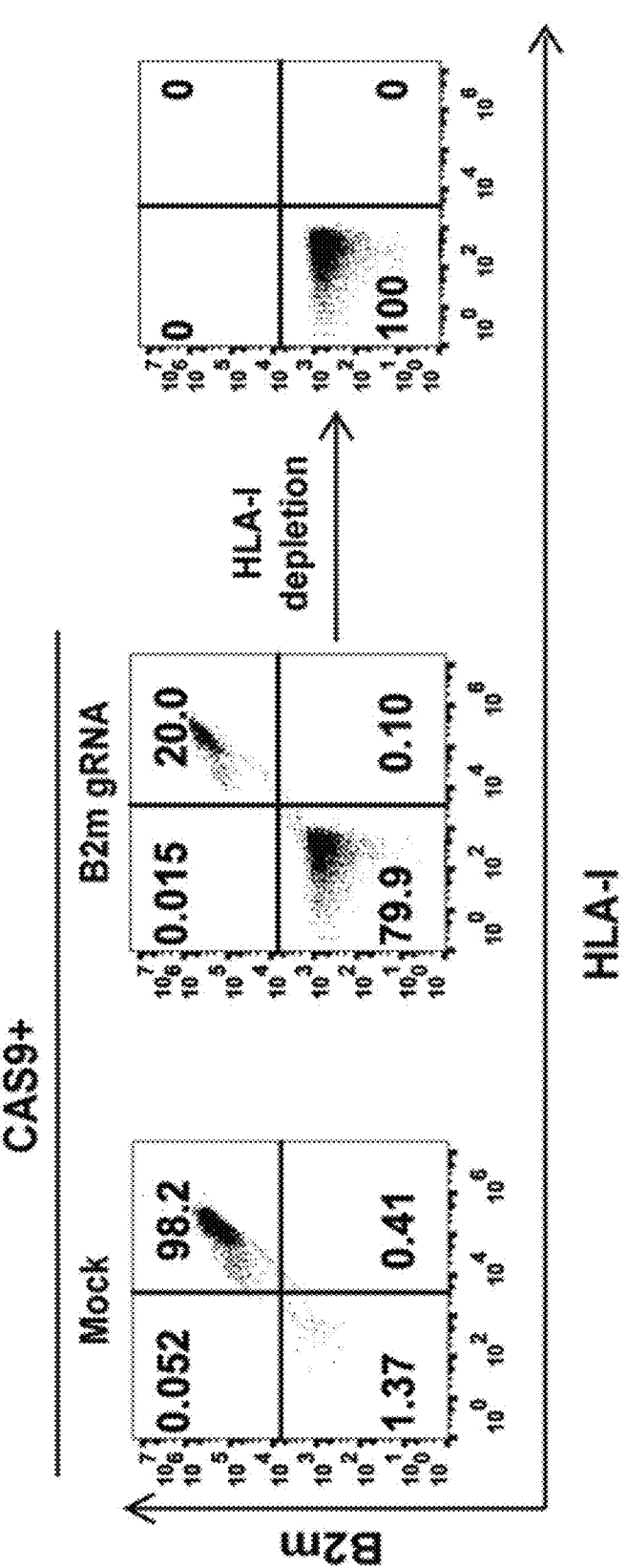
FIG. 60 is a panel of graphs showing double and triple gene ablation by CRISPR/Cas9 to generate universal effector cells. HLA-I disruption with gRNA targeting B2M.

Disrupting both TCR α and β chains is required to prevent TCR miss-pairing-associated toxicity for TCR-redirected T cell adoptive immunotherapy and B2M is essential for the assembly and expression of HLA-I complex. In view of this, TCR α and β chains and B2M triple disruption was developed to generate universal T cells. First, the ability of eliminating HLA-I expression on the T cells by disrupting B2M was tested. T cells were electroporated with B2M-targeting Cas9/gRNA RNA. This resulted in a B2M and HLA-I double-negative population of 79.9%. The HLA-I$^{neg}$ population could be further enriched by negative selection (FIG. 60).

Figure 61:
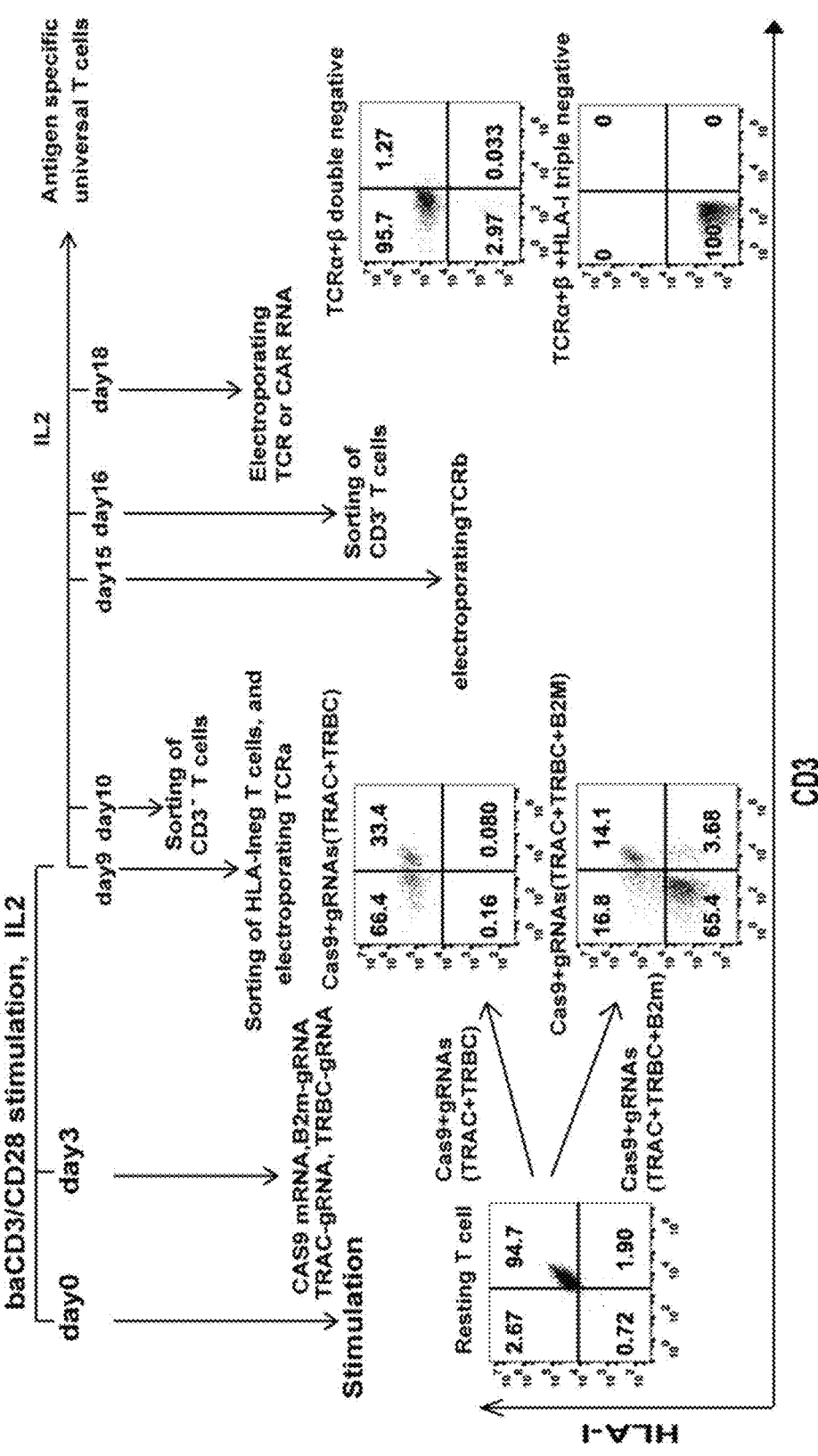
FIG. 61 is a flow chart of the protocol to generate universal effector cells as described herein.
Figures 62, 63:
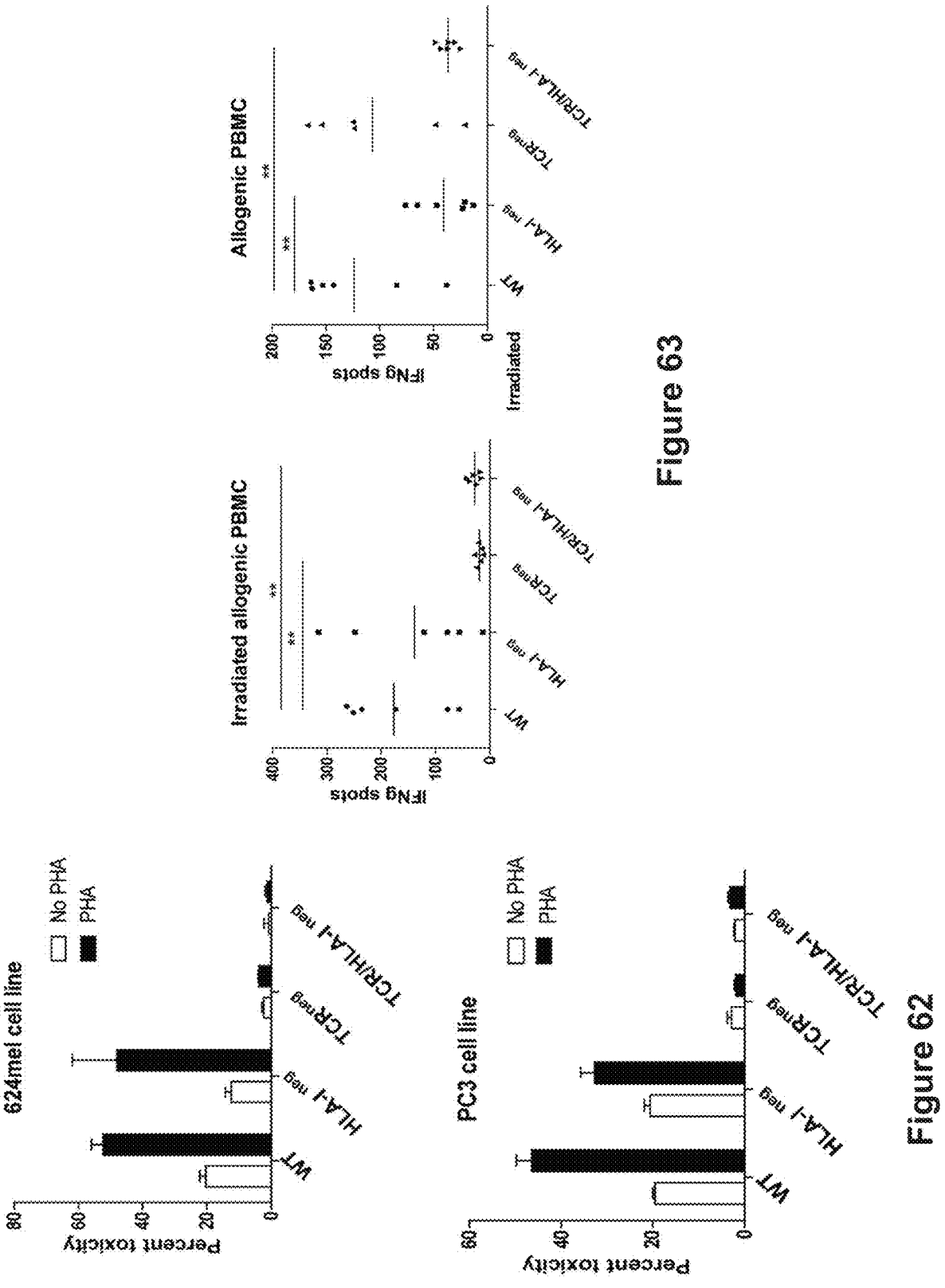
FIG. 62 is a panel of graphs showing that TCR ablation abrogated non-specific killing activity. 624mel-CBG and PC3-CBG tumor cell lines were incubated with T cells pre-treated with or without PHA at an effector to target ratio of 20.1 for 24 hours and cytotoxicity was calculated based on a luciferase assay. Data are the means±SD; n=3.
FIG. 63 is a panel of graphs showing an IFNγ Elispot assay to measure allo-reactivity of TCR and TCR/HLA disruption by challenging the gene-ablated T cells with irradiated allogenic PBMCs (left panel) or co-culturing allogenic PBMCs with irradiated gene-ablated T cells. Specific spots are shown on the y axis as the spots produced in the presence of stimulators minus the spots produced by the effectors alone. **P<0.01 by Mann-Whitney test.
Figure 64:
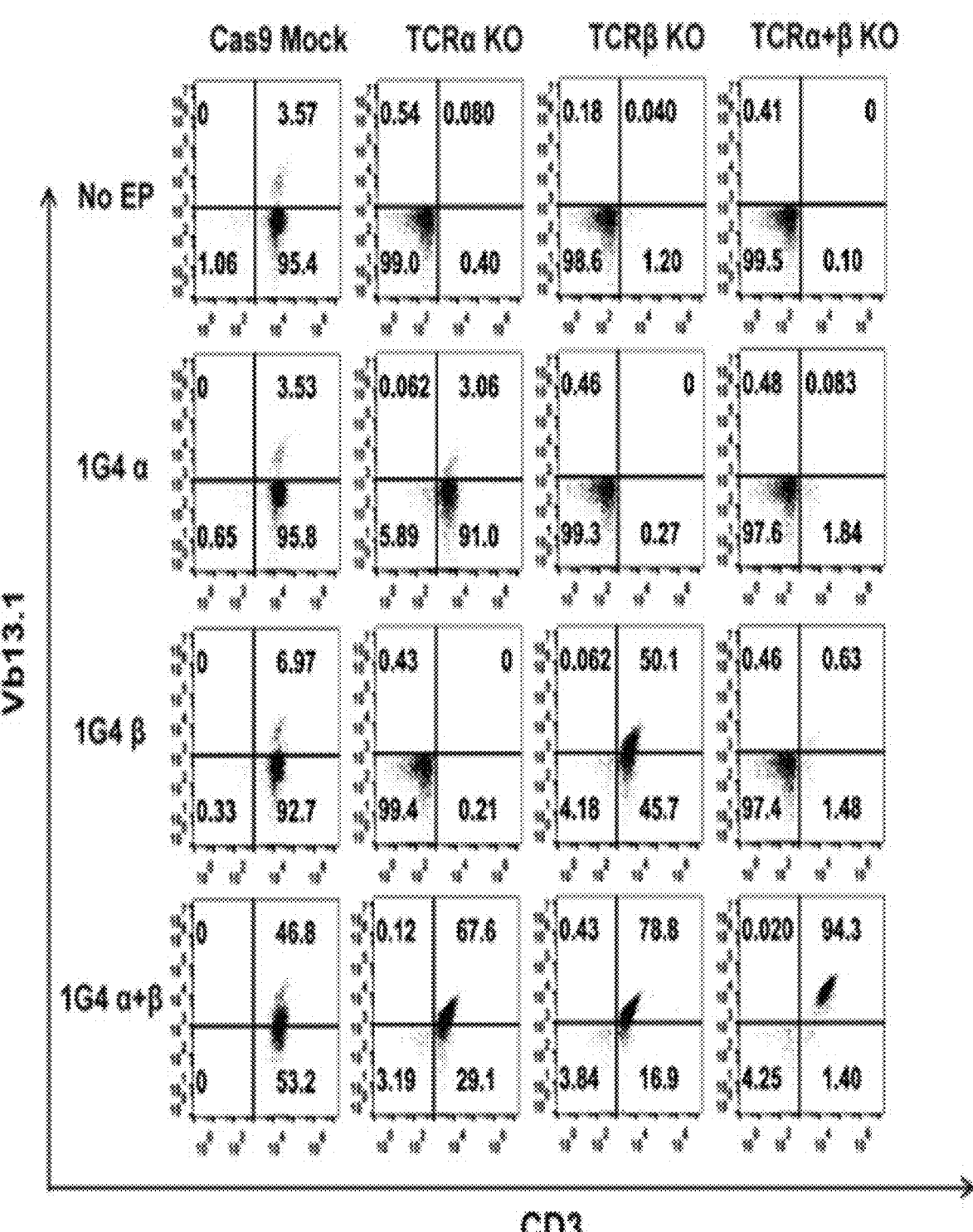
FIG. 64 is a panel of graphs showing that the disruption of the endogenous TCR by CRISPR/Cas9 improved TCR-redirected T cell function. Vb13.1 and CD3 expression is shown in T cells transfected with Cas9 mRNA alone (Cas9 Mock) or CD3^{neg} T cells with disrupted endogenous TCR α alone (α KO), β alone (β KO), α and β double (α+β KO) that were electroporated with NY-ESO-1 TCR α (1G4 α, 2 ug), β (1G4 β, 2 ug) or α+β RNA (1G4 α+β, 2+2 ug) RNA.

To generate triple-knockout T cells lacking the TCR α, β chains and B2M, Cas9 mRNA was co-electroporated with three different gRNAs targeting TRAC, TRBC and B2M. As a result, the CD3 and HLA-I double-negative cell population was 65.4% (FIG. 61). After enrichment of the double and triple knockout cells, the TCR α and β chains and B2M triple-knockout T cells abrogated the non-specific killing of HLA unmatched tumor cell lines (FIG. 62). No response was observed when these cells were challenged by allogeneic whole-blood irradiated PBMCs in an IFN□ Elispot assay (FIG. 63, left panel). The ablation of HLA-I molecules also sharply reduced the allo-reactivity, as confirmed by co-culture of allogenic PBMCs with irradiated B2M-disrupted cells (FIG. 63, right panel). The results above suggest that triple-negative T cells that lack TCR α and β chains and B2M could potentially serve as a source of universal T cells for adoptive immunotherapy, resisting rejection by the host immune system while unable to cause graft versus host disease.

Improved Anti-Tumor Activity of TCR Redirected, Endogenous TCR-Disrupted T Cells.

Figure 65A:
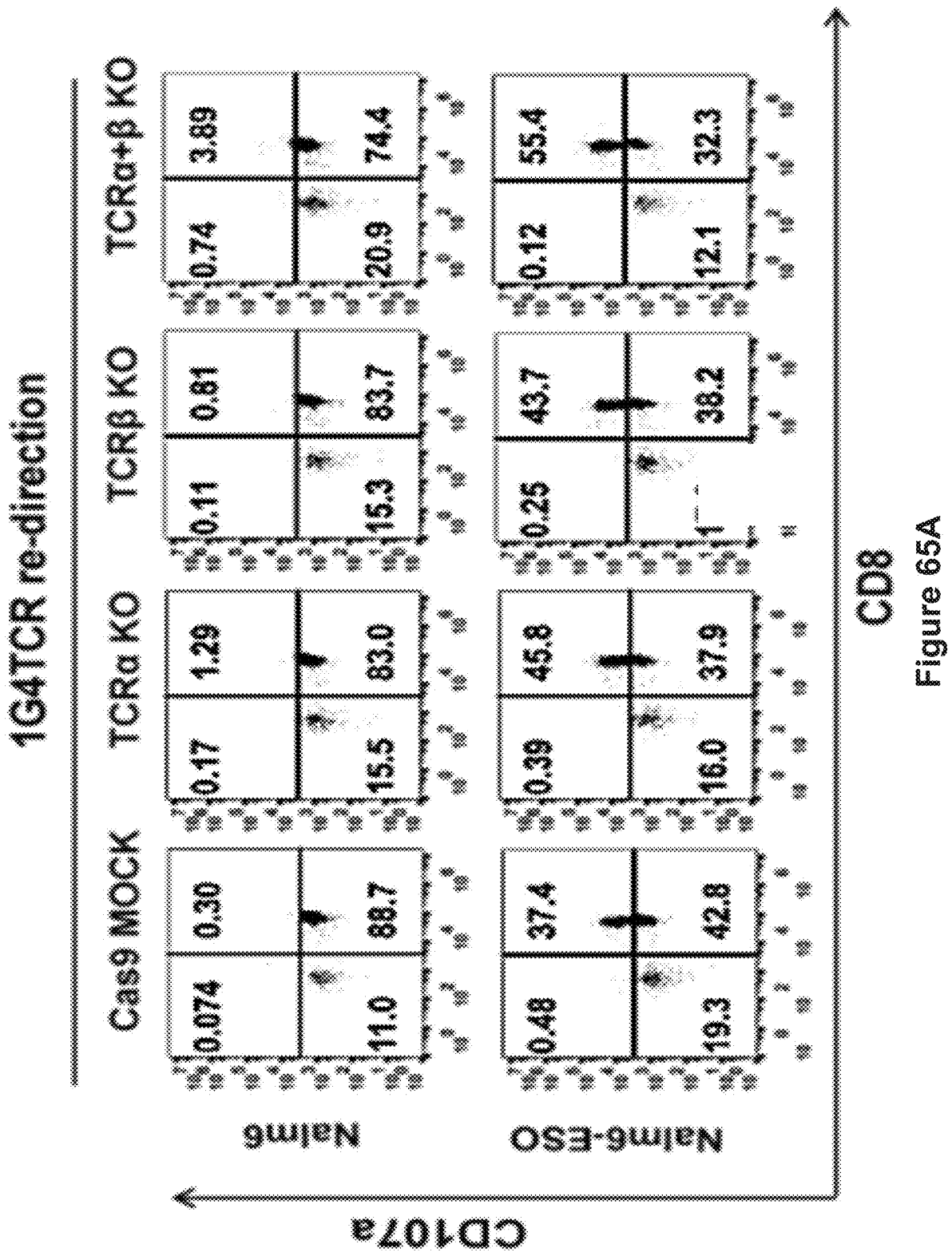
FIG. 65A is a panel of graphs showing CD107a up-regulation of the TCR (1G4) α/β RNA electroporated TCR α or β single knockout or α+β double knockout T cells stimulated with a HLA-A2/NY-ESO-1-positive cell line (Nalm6-ESO) or the control cell line Nalm6.
Figure 65B:
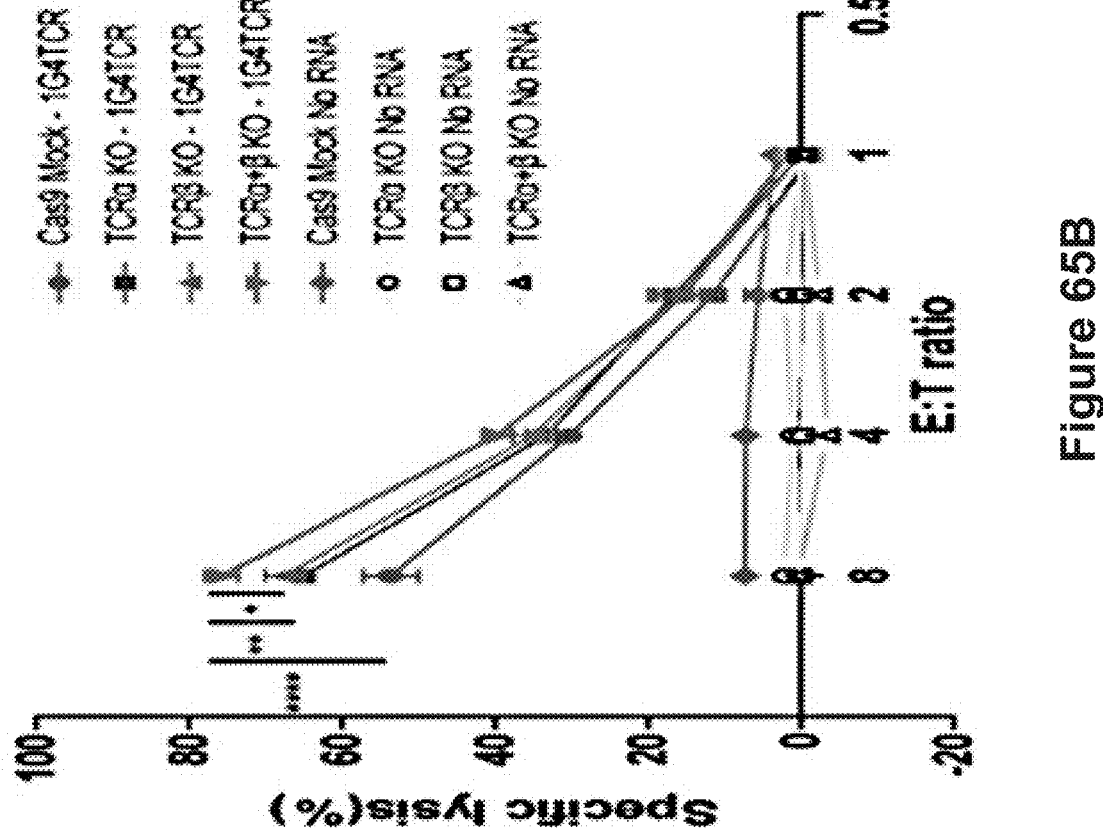
FIG. 65B is a graphs showing the lytic ability of TCR α+β RNA (1G4 TCR) electroporated TCR α or β single-knock-out or α+β double-knockout T cells shown in (a) in a luciferase-based CTL assay against Nalm6-ESO.

T cells with CRISPR/Cas9-disruption of TCR α and β chains showed elevated transgenic TCR expression on the cell surface after being redirected with an NY-ESO-1 TCR (1G4). Transgenic TCR expression was 67.6%, 78.8% or 94.3% for the TCR □ or □□□□ chain single knockout or the □□□□ double knockout, respectively, compared with 46.8% for wild-type T cells. The improved transgenic TCR expression led to enhanced T cell function, as evidenced by increased antigen-specific CD107a expression (FIG. 65A) and enhanced cytotoxicity (FIG. 65B), especially for the □□□ double-knockout T cells.

Figure 66:
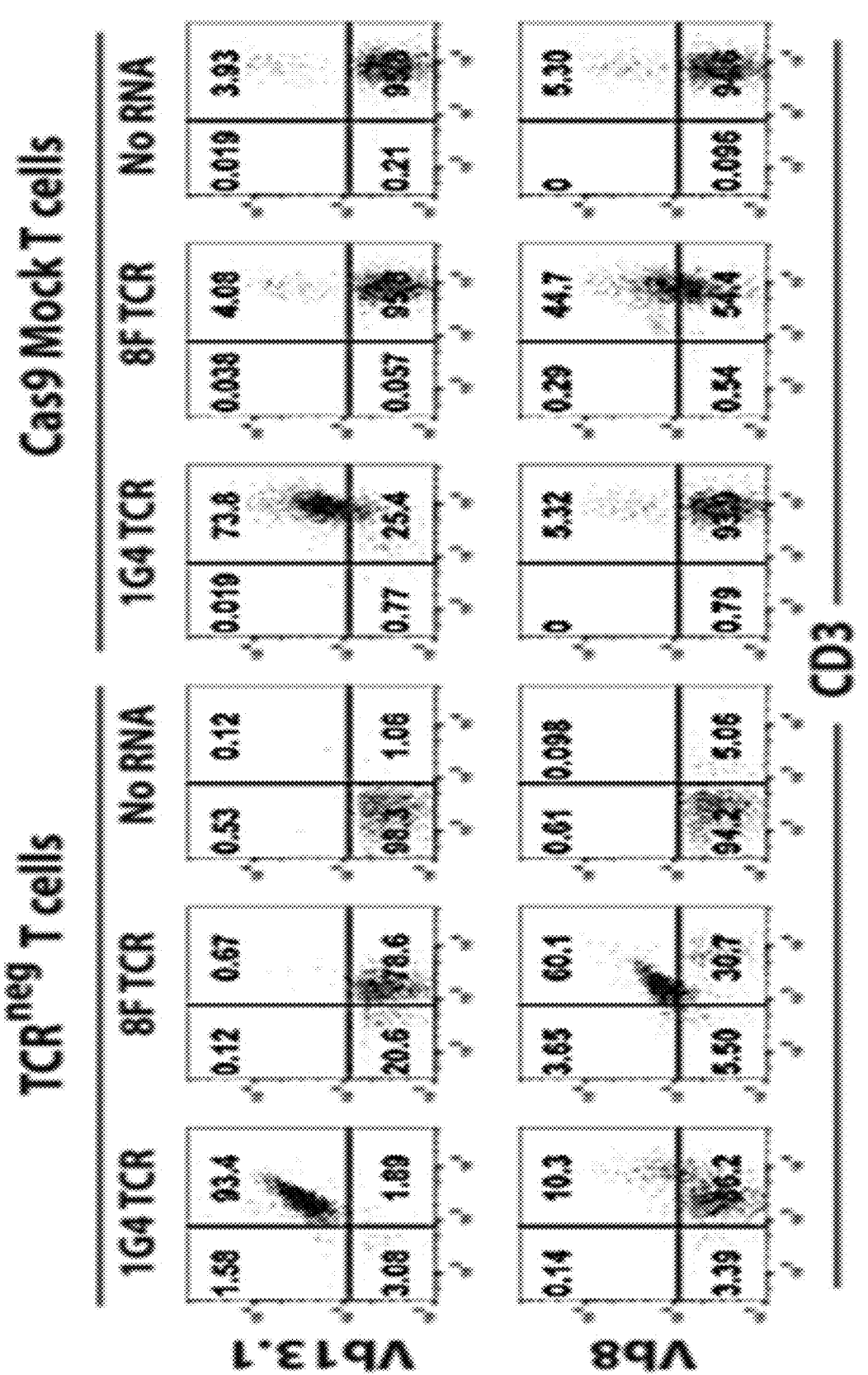
FIG. 66 is a panel of graphs showing Vbeta and CD3 expression in TCR α+β double-disrupted T cells (TCR^{neg} T cells) electroporated with two different NY-ESO-1 TCR RNA (1G4 TCR, 10 ug or 8F TCR, 10 ug) compared with control Cas9 Mock T cells.
Figure 67A:
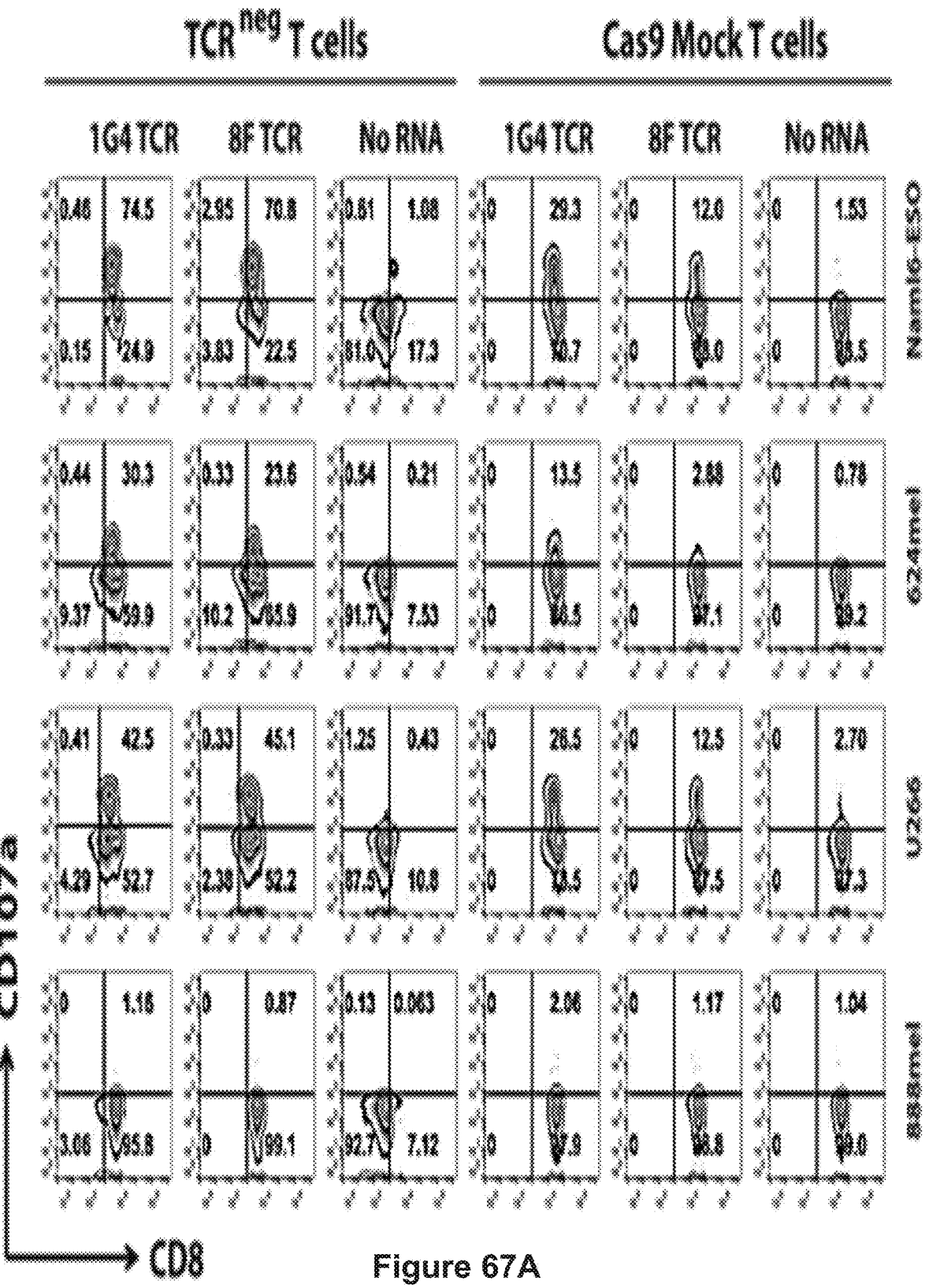
FIG. 67A is a panel of graphs showing CD107a up-regulation in NY-ESO-1 TCR (1G4 TCR or 8F TCR) RNA electroporated TCR double-knockout CD8^+ T cells stimulated with the HLA-A2/NY-ESO-1-positive cell lines Nalm6-ESO, 624-mel or U266. Nalm6 was used as the negative control.
Figure 67B:
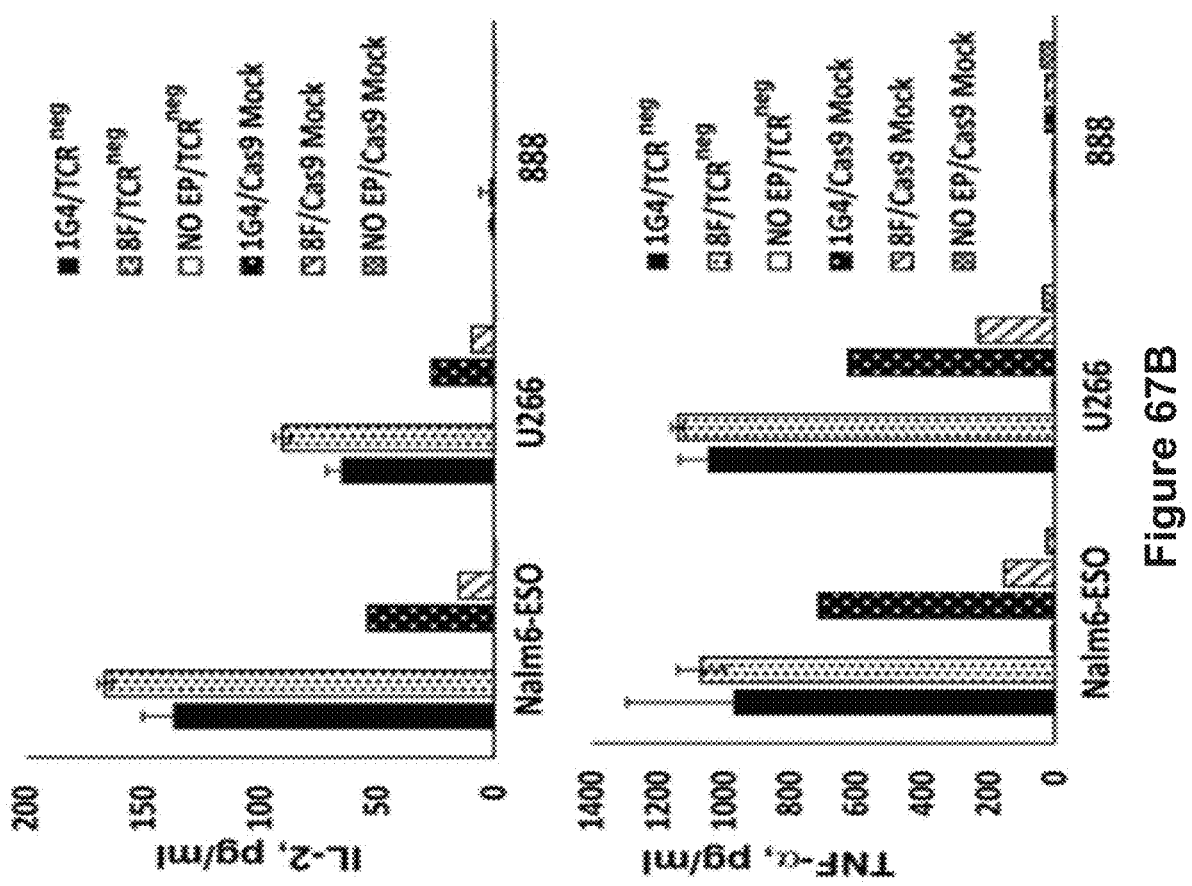
FIG. 67B is a panel of graphs showing cytokine production (IL-2 and TNF-α) of NY-ESO-1 TCR (1G4 TCR or 8F TCR) RNA electroporated TCR double-knockout T cells after stimulation with the HLA-A2/NY-ESO-1-positive cell lines Nalm6-ESO or U266; 888mel melanoma cells were used as a negative control. *P<0.05, P<0.01**P<0.0001, by two-way ANOVA plus the Bonferroni post test.

In a separate experiment, □□□ double-knockout T cells were transfected with a different NY-ESO-1 TCR (8F). Relative to 1G4 TCR, this 8F TCR exhibited a higher significant improvements in both transgenic TCR expression (FIG. 66; 60.1% for TCR/CD3$^{neg}$ versus 44.7% (with ~5% endogenous TCR Vβ8 background) for wild-type T cells (Cas9 Mock T cells)) and function (CD107a expression in FIG. 67A, and cytokine production in FIG. 67B). These results highlight the differential influence of endogenous TCR on transgenic TCR expression and function.

Universal CART Cells Retain Antitumor Efficacy and do not Cause GVHD.

Figure 68:
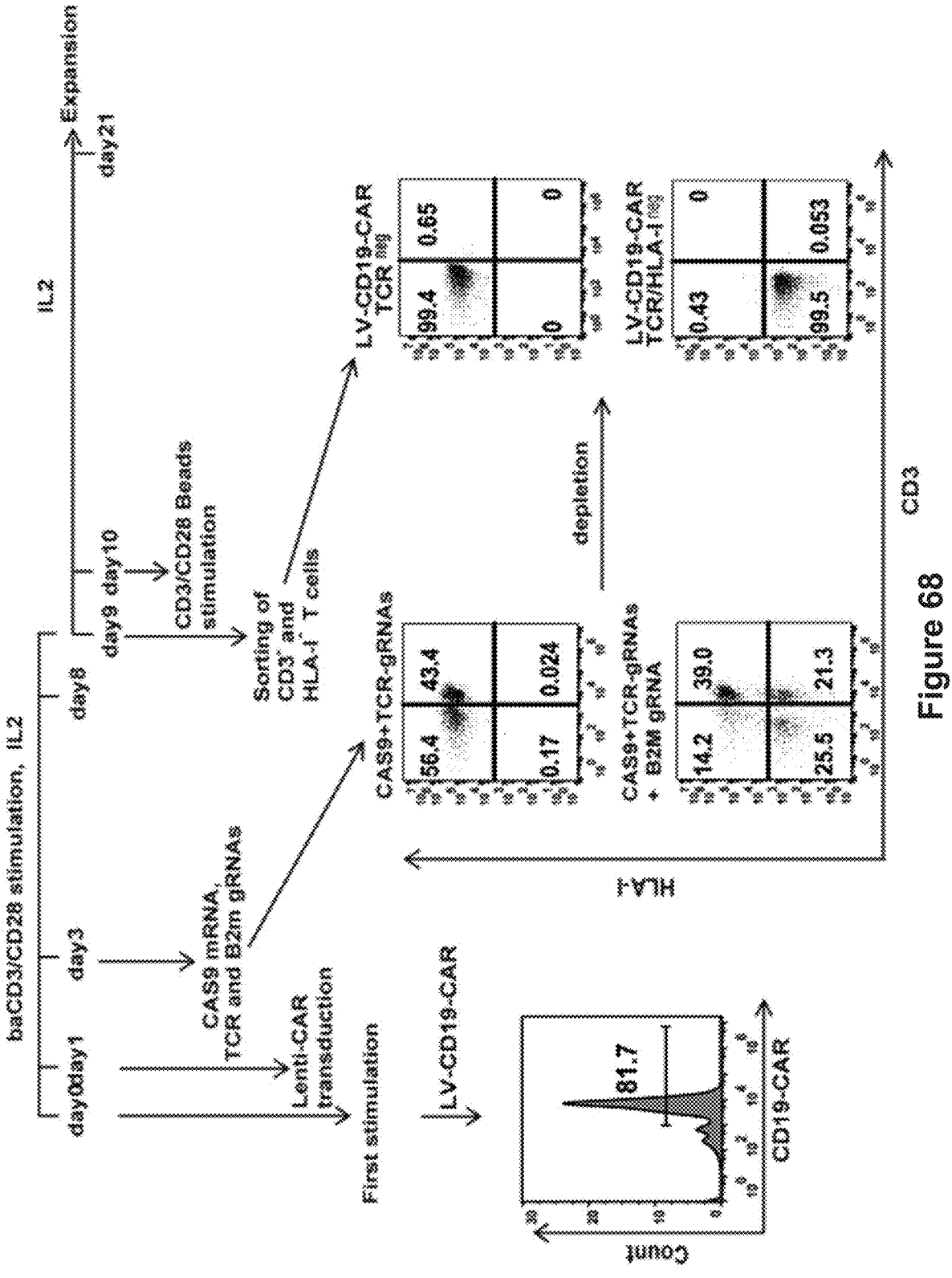
FIG. 68 is a panel of images showing the generation of universal CART cells with a combination of lentiviral gene transfer and CRISPR/Cas9 electroporation. A flow chart of the generation of universal CD19-CART cells is shown. T cells were transduced with lentiviral CD19-CAR on day 1 after stimulation, and Cas9 mRNA and gRNAs targeting the TCR α and TCR β chains and B2M were electroporated in the T cells 2 days later. The TCR and HLA-I double-negative cell population was enriched before re-simulation for expansion.
Figure 69:
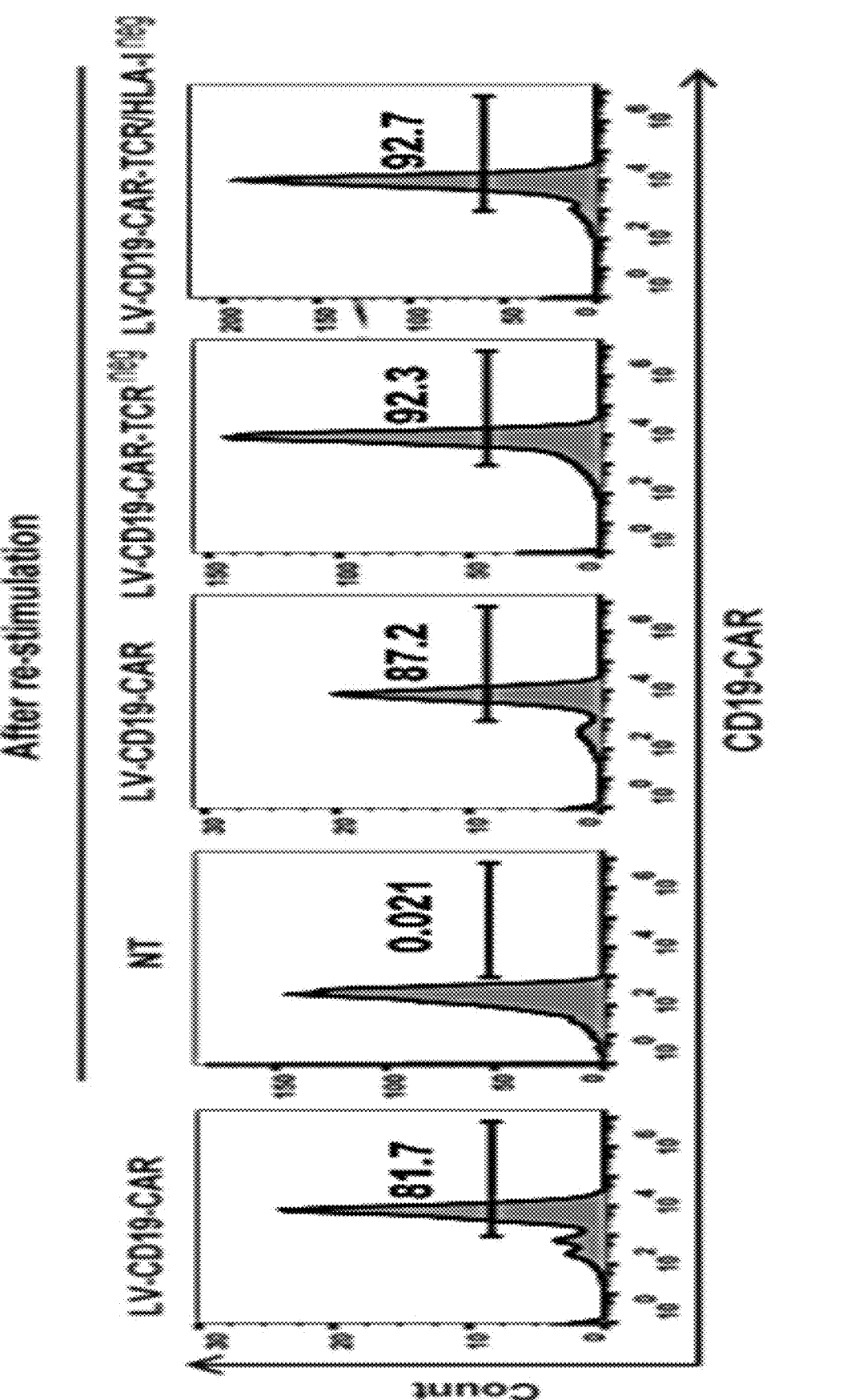
FIG. 69 is a panel of graphs showing CD19-CAR expression in gene-modified lenti-CD19-CAR T cells expanded by CD3/CD28 bead stimulation after 1G4 TCR electroporation.
Figure 70:
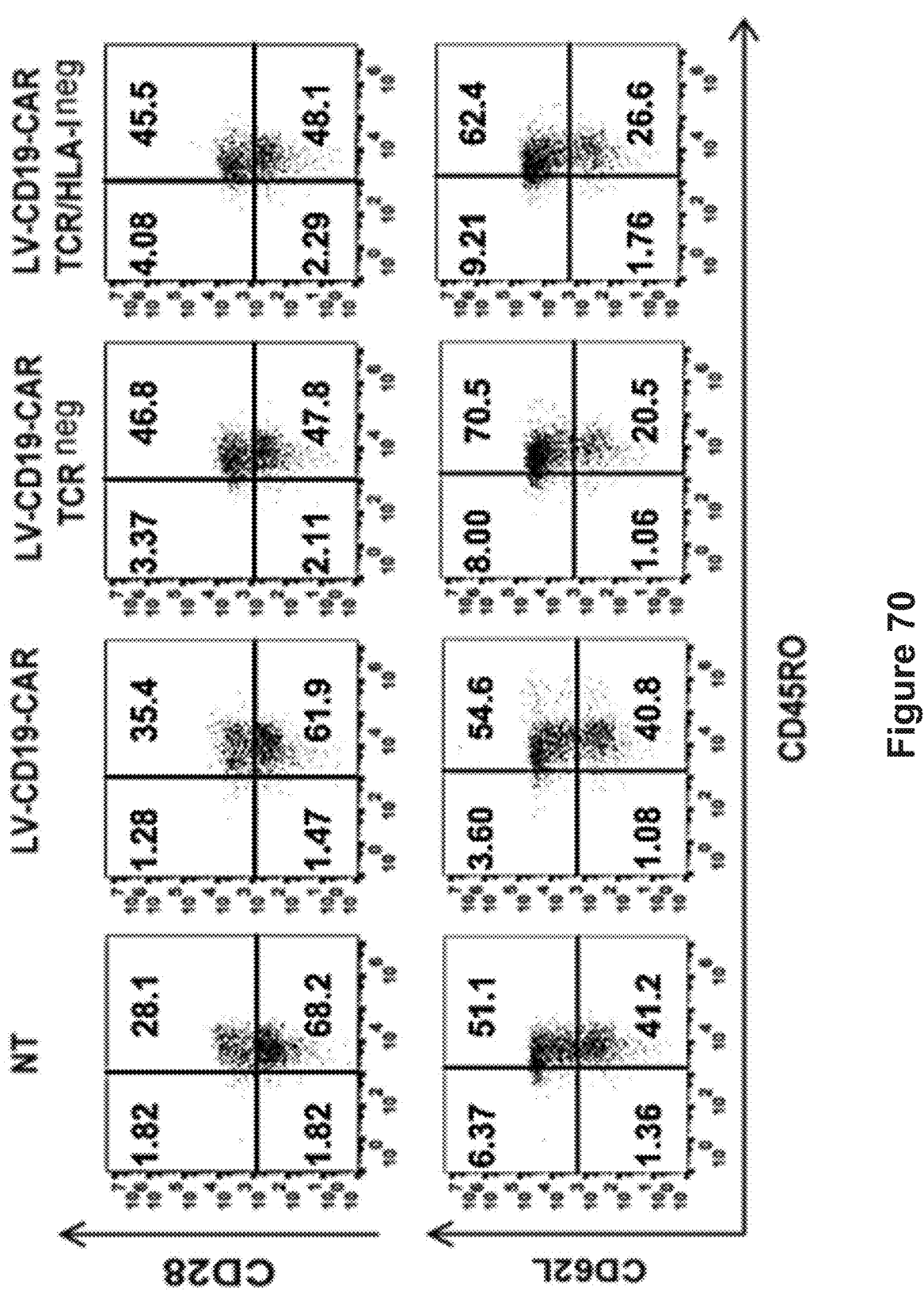
FIG. 70 is a panel of graphs showing the phenotype of CD19-CAR T cells.
Figure 71:
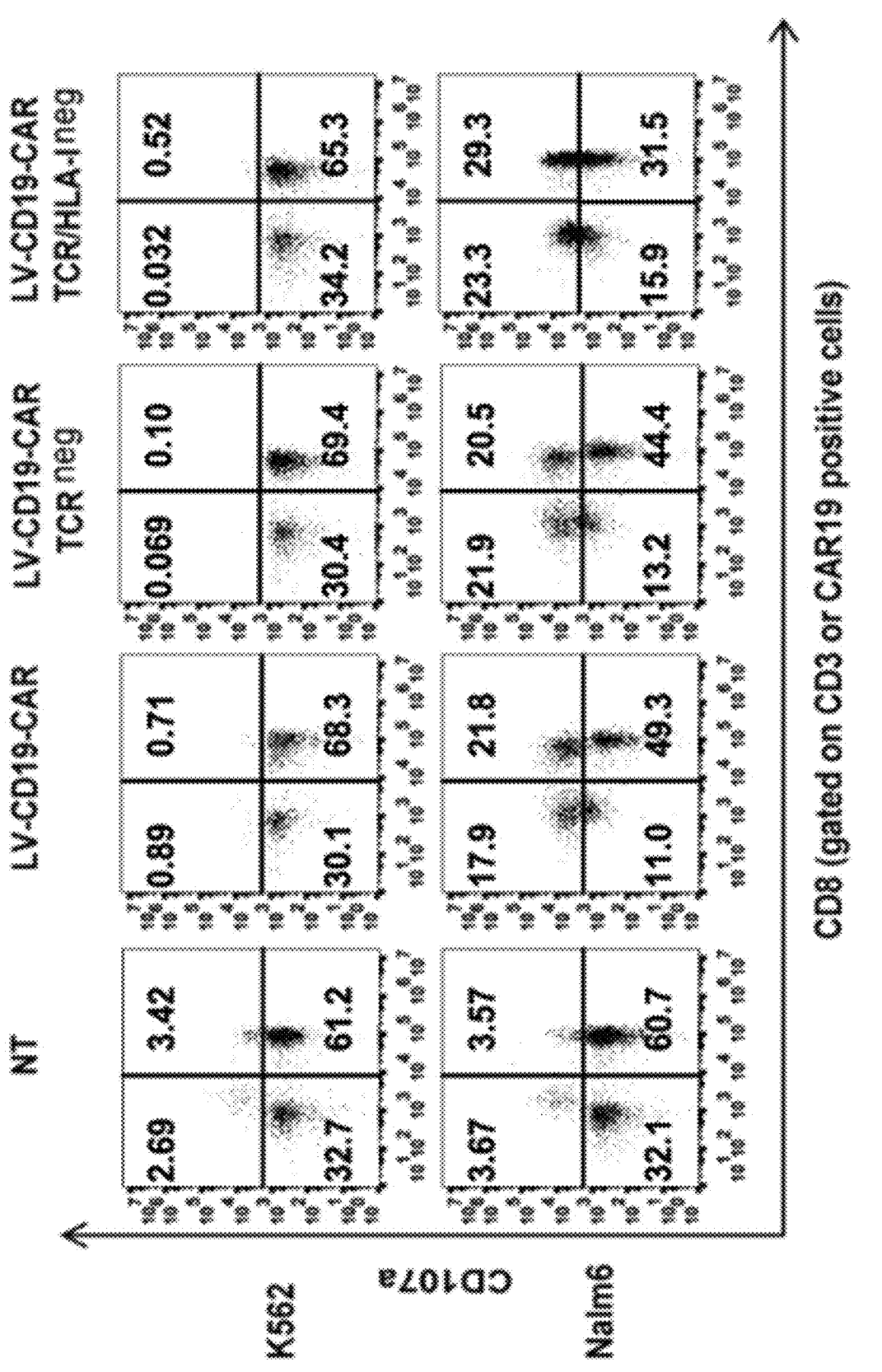
FIG. 71 is a graph showing CD107a release in TCR-negative and TCR/HLA-I double-negative CD19-CAR T cells. Representative data from 3 independent experiments are shown. Bars, SE=standard error.
Figure 72:
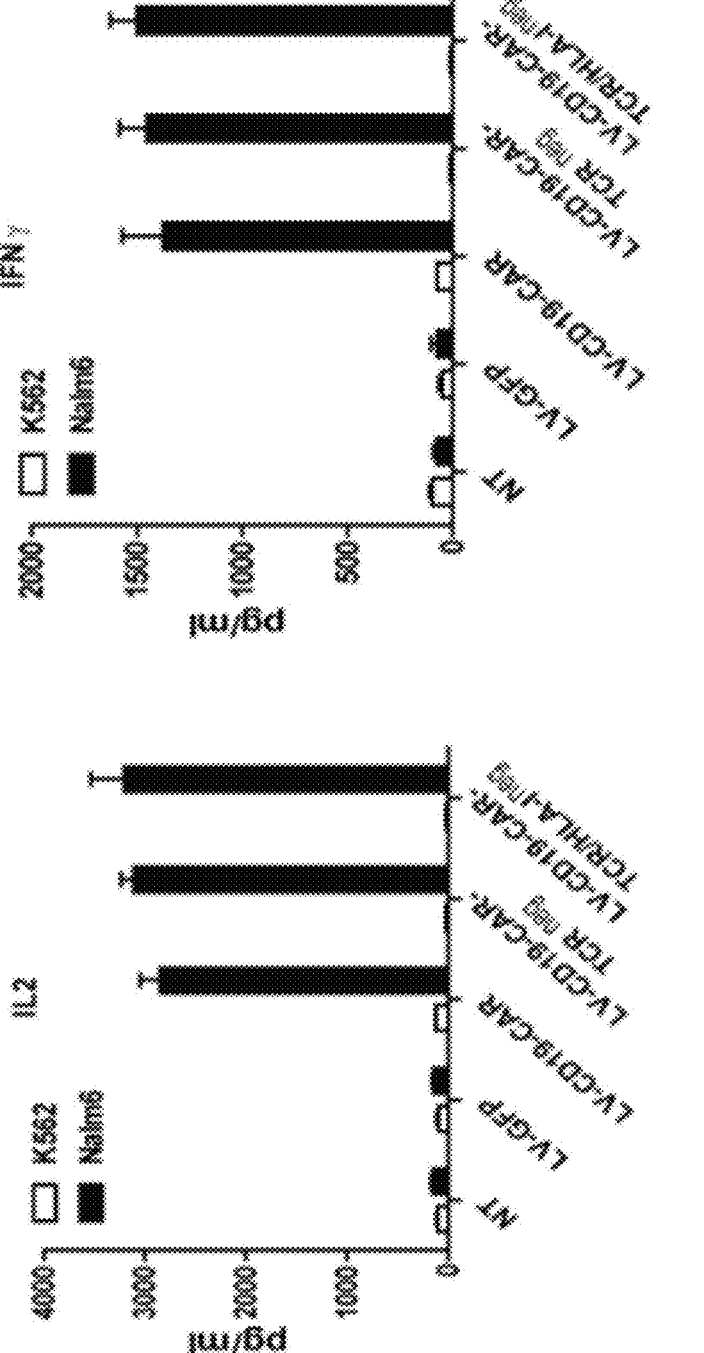
FIG. 72 is a panel of graphs showing cytokine secretion of TCR-negative and TCR/HLA-I double-negative CD19-CAR T cells. Representative data from 3 independent experiments are shown. Bars, SE=standard error.
Figure 73:
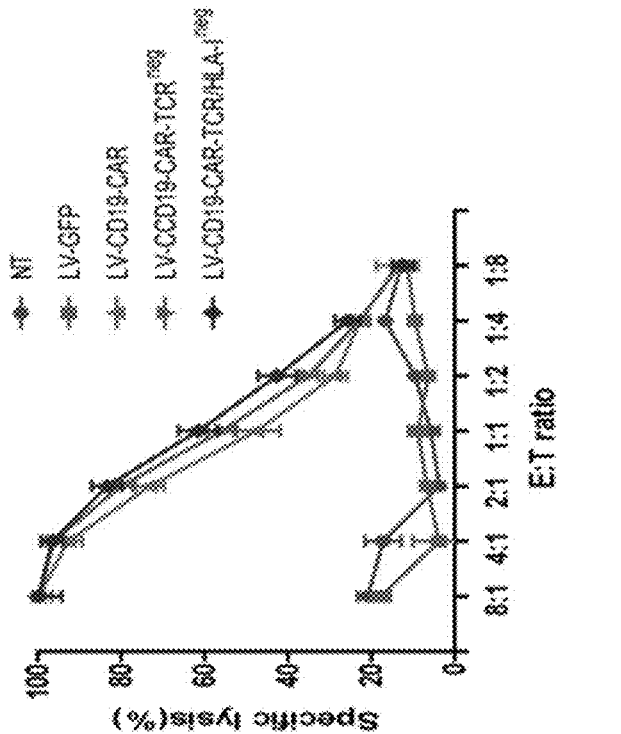
FIG. 73 is a graph showing tumor lytic capability of TCR-negative and TCR/HLA-I double-negative CD19-CAR T cells. Representative data from 3 independent experiments are shown. Bars, SE=standard error.
Figure 74:
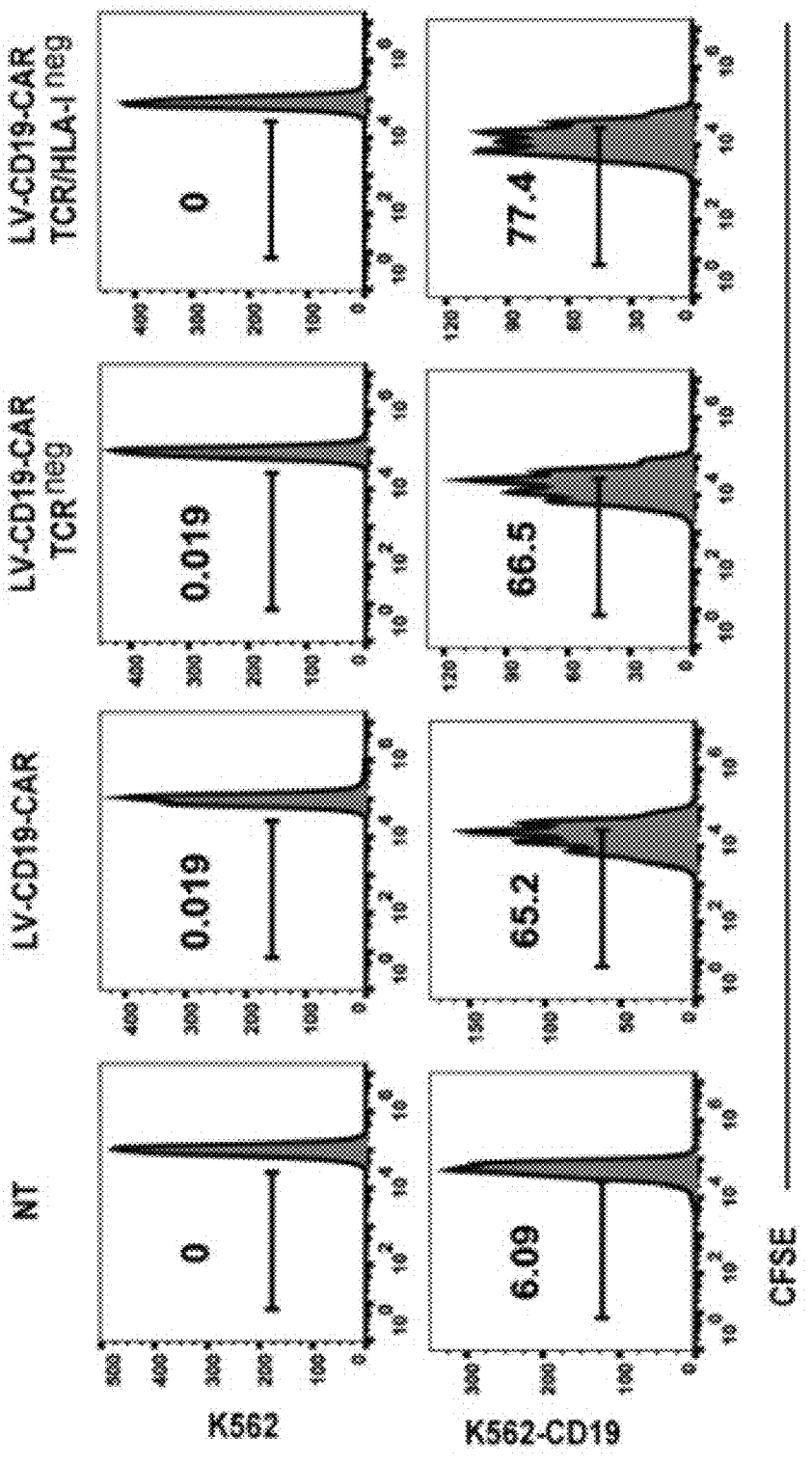
FIG. 74 a panel of graphs showing CFSE-labeled CD19-CAR and non-transduced T cells incubated with K562 and target K562-CD19 tumor cells at a ratio of 1 to 10 for 72 hours.

Universal CD19 CART cells were generated by combining LV transduction of CD19 CAR with RNA electroporation of Cas9/gRNAs (FIG. 68). The cells were expanded and the remaining CD3$^{neg}$ cells had high levels of CD19 CAR expression (FIG. 69). The majority of the expanded T cells were CD45RO positive and retained a high level of CD62L expression and a medium level of CD28 expression, consistent with a central memory cell status (FIG. 70). The expanded TCR/HLA-I double-negative CD19 CART showed robust in vitro anti-tumor activities, such as CD107a release (FIG. 71), cytokine secretion (FIG. 72), lytic capacity (FIG. 73), and proliferation (FIG. 74), that was as potent as those of the wild-type CD19 CART cells.

Figure 75A:
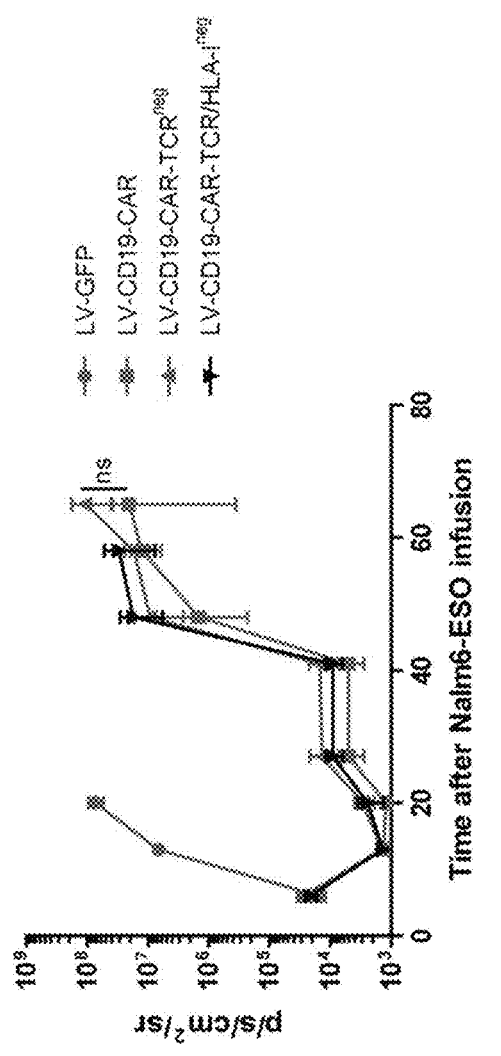
FIG. 75A is a graph showing BLI from mice treated with a single injection on day 7 expressing CD19-CAR and GFP using a lentiviral vector. ns, no difference by two-way ANOVA plus the Bonferroni post test. Tumors were established in NSG mice (n=4 per group) by i.v. injection of 1×10^6 Nalm6 cells. Beginning on day 7, T cells (1×10^7) expressing lentiviral (LV) transduced CD19-CAR were infused with a single injection. T cells expressing LV GFP protein were injected as controls.
Figure 75B:
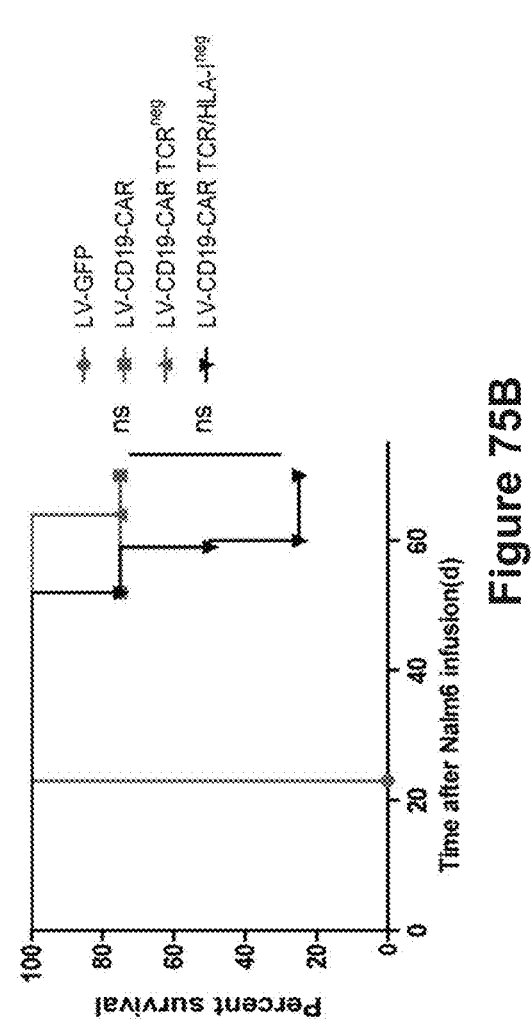
FIG. 75B is a graph showing the overall survival of mice receiving LV-GFP, LV-CD19-CAR, LV-CD19-CAR-TCR/CD3^{neg} and LV-CD19-CAR-TCR/HLA-I^{neg} T cells. ns, no difference by the log-rank Mantel-Cox test.

The T cells were infused into NSG mice bearing disseminated Nalm6 leukemia. Mice treated with CART cells with a disrupted endogenous TCR (LV-CD19 CAR TCR's) or with a simultaneous disruption of TCR and HLA-I (LV-CD19 CAR TCR/HLA-I$^{neg}$) exhibited tumor regression similar to that of mice treated with wild-type CD19 CART cells (LV-CD19 CAR) (FIGS. 75A and 75B), suggesting that the disruption of TCR alone or together with B2M did not affect CART cell anti-tumor activity.

Figure 76:
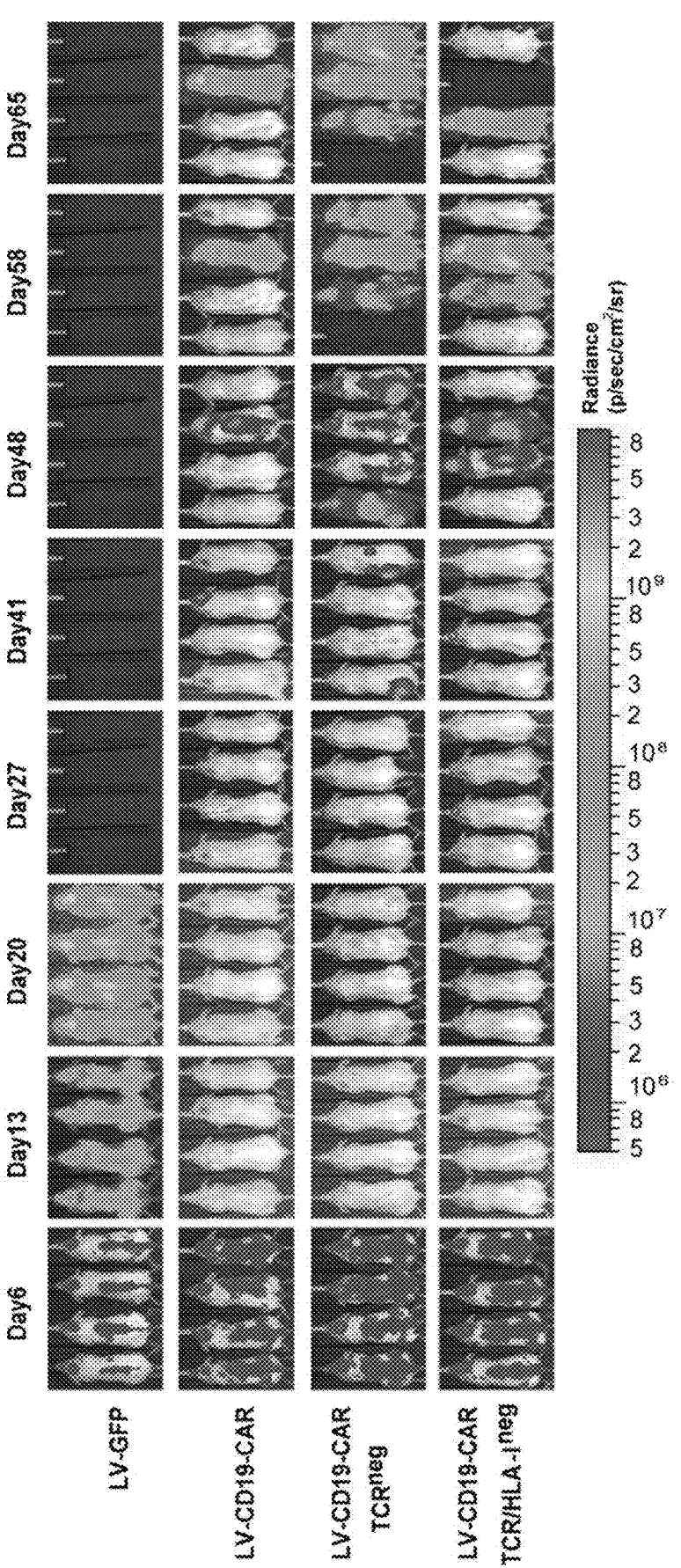
FIG. 76 is a panel of images showing that gene-modified CAR T cells retained antitumor efficacy and did not induce GVHD. Tumors were established in NSG mice (n=4 per group) by i.v. injection with 1×10^6 Nalm6 cells. Beginning on day 7, T cells (2×10^7) expressing LV-CD19-CAR were infused with a single injection. T cells expressing LV GFP protein were injected as controls. Imaging commenced 1 day before T cell treatment. Organs of randomly chosen mice from different treatment groups were collected on day 65 and used for CD3 immunohistochemistry staining.

To test the GVHD effect of the engineered T cells, a high T cell dose (20×10$^6$/mouse) was given to NSG mice with Nalm6 leukemia. As shown in FIG. 76, mice treated with CD19 CART cells with TCR disruption alone (LV-CD19 CAR TCR/CD3$^{neg}$) or the simultaneous disruption of TCR and B2M (LV-CD19 CAR TCR/HLA-I$^{neg}$) exhibited similar tumor regression compared with that of the wild-type CD19 CAR T cells (LV-CD19 CAR). Mice treated with the double or triple knock out CAR T cells did not develop any signs of GVHD. By contrast, 3 out of 4 mice from the wild-type CD19 CART (LV-CD19 CAR) group developed GVHD at day 65, which was confirmed by histological examination of different organs. Thus, the disruption of TCR alone or together with HLA-I did not affect the in vivo anti-tumor activity of CART cells while eliminating alloreactivity.

Adenoviral CRISPR Delivery into Primary T Cells.

Figure 77:
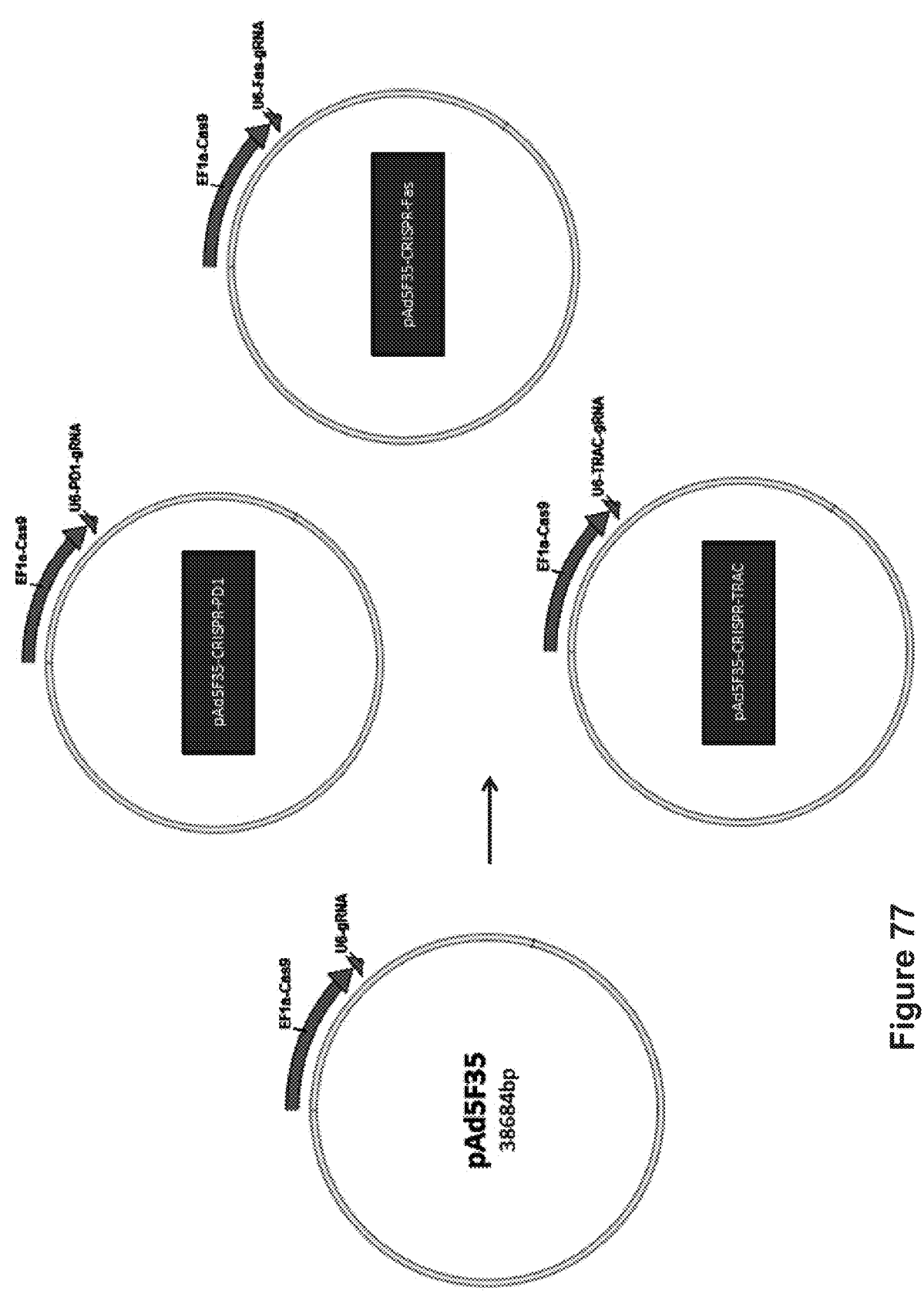
FIG. 77 is a series of schematics of vectors showing the design of pAd5F35-CRISPR targeting PD1, Fas and TCR alpha chain.
Figure 78:
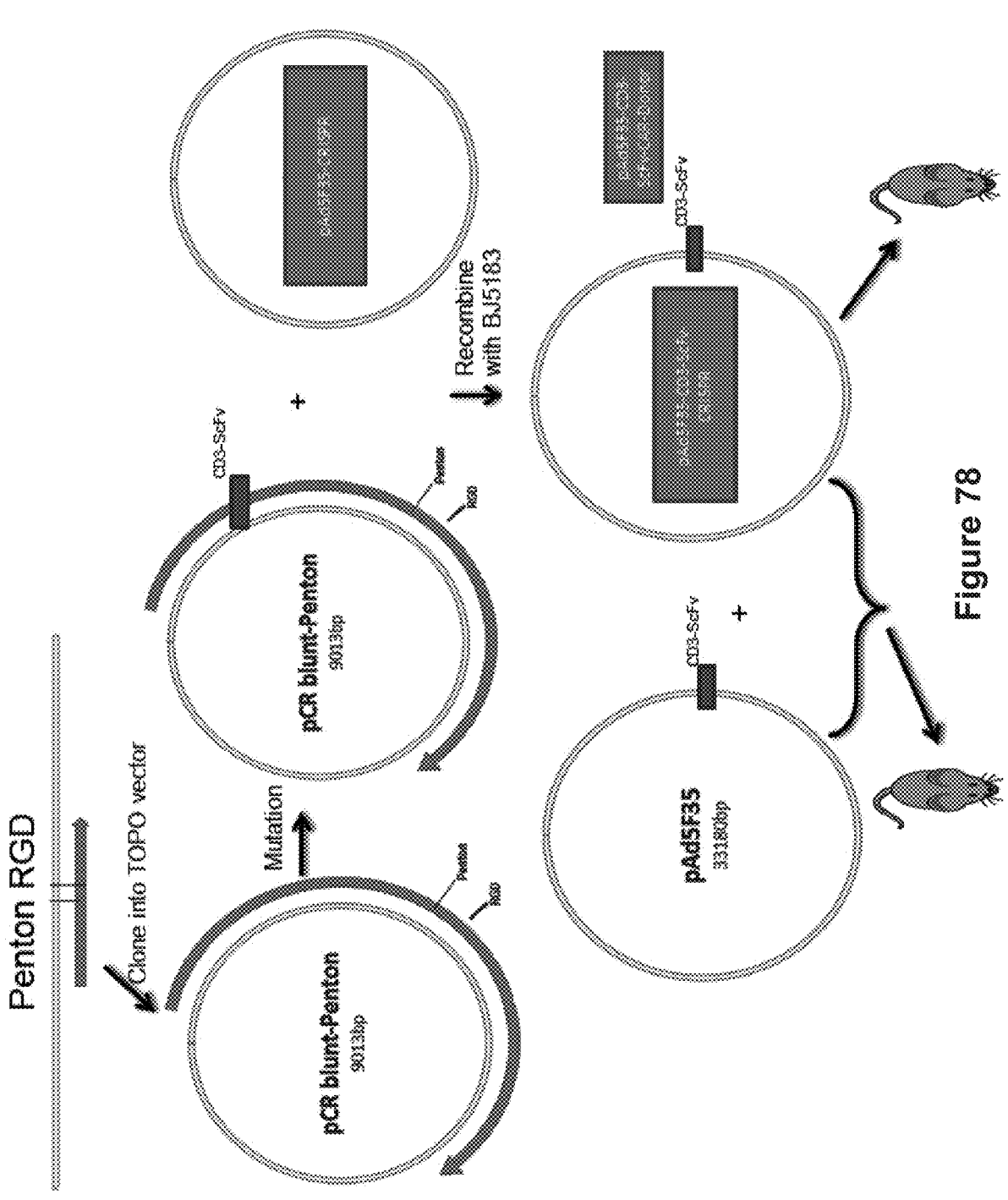
FIG. 78 is an illustration showing the design of penton modified pAd5F35-CRISPR with anti-CD3 ScFv, and schematic delivery of pAd5F35-CRISPR for knock in/out chimeric antigen receptor into T cells in vitro and in vivo.
Figure 79A:
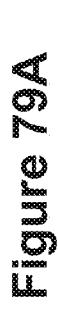
FIG. 79A is a graph showing Sanger sequencing (SEQ ID NO: 97) of PCR products flanking PD1-gRNA (SEQ ID NO: 64) targeting site. Adenoviral-pAd5F35-CRISPR-PD1 virus was transduced into MD231 cells. 3 days later, genomic DNA was extracted and performed PCR.

The CRISPR/Cas9 system are rapidly being harnessed for gene regulation and gene editing purposes in model organisms and cell lines. Viral vectors may be particularly fit to broaden the applicability of CRISPR to other cell types, including dividing and quiescent primary cells. Adenovirus, namely second-generation fiber-modified adenovirus encoding Cas9 and single guide RNA (gRNA) molecules, were used to bring Cas9 nuclease to the PD1, Fas and TRAC loci (FIG. 77). Adenoviral-mediated transduction of CRISPR into tumor cells (FIG. 78) yielded high rates of targeted mutagenesis of up to about 71% (FIGS. 79A and 79B). Adenovirus appears to constitute a valuable platform for introducing CRISPR into human T cells regardless of their quiescent status. This approach will aid investigating the potential for CRISPR gene regulation and editing in numerous experimental settings.

Electroporation Optimization.

CD3 and B2M knock-out efficiency and T cell expansion were assessed after Cas9 and gRNA electroporation (EP) in 4 mm cuvettes and 2 mm cuvettes. Standard EP conditions with a 2 mm cuvette (360 v/1 ms, $1^{st}$ EP-20 µg Cas9 RNA+10 µg gRNA/100 µl T cells, $2^{nd}$ EP 5 µg gRNA/100 µl T cells) showed the highest CD3 and B2M knockout percentages, 81.8% and 88.6%, respectively, with T cell expansion at about 2.7 fold (EP #1), compared with about 18.8 fold expansion of control EP T cells (EP #12). Decreasing the gRNA dose (EP #2-5) dramatically increased T cell expansion, but only slightly affected CD3 and B2M knockout efficiency. See FIG. 80. Standard EP conditions with a 4 mm cuvette resulted in dramatically decreased CD3 and B2M knockout efficiency (EP #8), suggesting that the EP conditions (voltage or/and pulse length) need to be further optimized for use with 4 mm cuvettes.

Compared with standard electroporation (EP) conditions in a 2 mm cuvette (EP #10-13) or 4 mm cuvette. High CD3/B2M knockout efficiency was observed with improved T cell fold expansion (EP #1 and 5). See FIG. 81.

To further optimize EP conditions to achieve maximum T cell fold expansion with CD3/B2M knockout efficiency over 60%, different EP conditions and RNA amounts were tested. The results showed that fold expansion was improved with relatively high CD3/B2M knockout efficiency (63.5% for CD3 and 84.8% for B2M) for EP #4 (400 v/2 ms/120 µg CAS9 RNA) for EP #1 and (500 v/1 ms/20 µg gRNA) for EP #2. See FIG. 82.

Additional experiments were performed to optimize EP conditions. Results showed that compared with the most favorable condition tested (EP #1 in FIG. 82), using 500 v/1 ms/120 µg CAS9 RNA (EP #1) and 500 v/1 ms/20 µg gRNA (EP #2) produced increased CD3/B2M knockout efficiency and T cell expansion (EP #3). See FIG. 83.

Large-Scale Electroporation and Expansion.

Experiments were performed to determine if large-scale electroporations could yield high knock-out and expansion efficiencies. On day 0, anti-CD3/anti-CD28 beads were used to stimulate T cells obtained from 3 donors ($100 \times 10^6$ cells/donor, concentrated to $0.5 \times 10^6$/ml). On day 1, stimulated T cells were transduced with CD19 CAR lentivirus. 50 mL ($25 \times 10^6$ cells) of T cells were reserved as unmodified T cells (Group 9). On Day 3, the beads were removed and the transduced T cells from each donor were separated into two groups, CART/mock EP (10 mL, $5 \times 10^6$) and CART/CRISPR (10 mL, $50 \times 10^6$). The cells were then electroporated with CAS9 RNA (1st EP) and Groups 1, 3, 5 and 7 cells were split. On day 4, the gRNA was electroporated into the T cells and the cells were cultured at $1 \times 10^6$ cells/mL. On days 5 and 7, the cells were split. On day 8, CD3+ cells were removed from Groups 2, 4 and 6. On day 11, the T cells were harvested and $25 \times 10^3$ cells from the three donors were sent for karyotyping.

TABLE 1

| Experimental groups. | | |
| --- | --- | --- |
| Group # | Donor | T cells |
| 1 | ND391 | CART/MOCK EP |
| 2 | ND391 | CART/CRISPR |
| 3 | ND463 | CART/MOCK EP |
| 4 | ND463 | CART/CRISPR |
| 5 | ND463 | UNMOD |
| 6 | ND469 | CART/MOCK EP |
| 7 | ND469 | CART/CRISPR |

Figure 87:
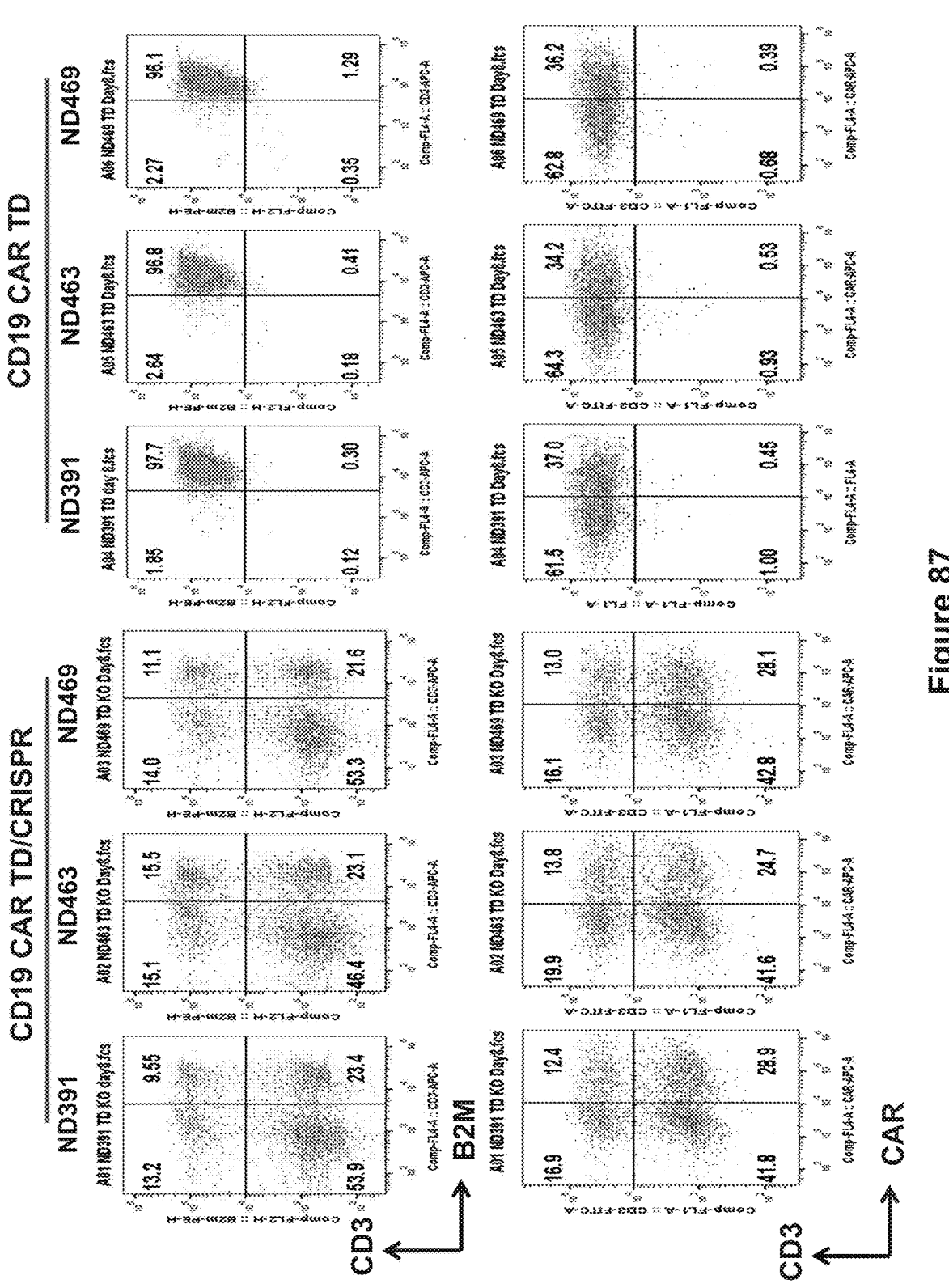
FIG. 87 is a panel of flow graphs showing CD3/B2M/CAR expression at day 8 of expanded T cells.

T cell numbers (upper chart of FIG. 85) and fold expansion (lower chart of FIG. 85) were assessed after the electroporation and culturing procedure. Fold expansion of the T cells transduced with CD19 CAR alone (TD alone) or transduced with CD19 CAR and edited with CRISPR (TD/KO) is shown in the left graph of FIG. 86 and fold expansion of the T cells on day 10 is shown in the right graph of FIG. 86. By optimizing electroporation conditions and CAS9/gRNA doses, approx. 60-70% CD3/B2M knock-down efficiency and approx. 30 fold T cell expansion was observed after 10 days (FIG. 87 shows CD3/B2M/CAR expression at day 10).

Figure 88:
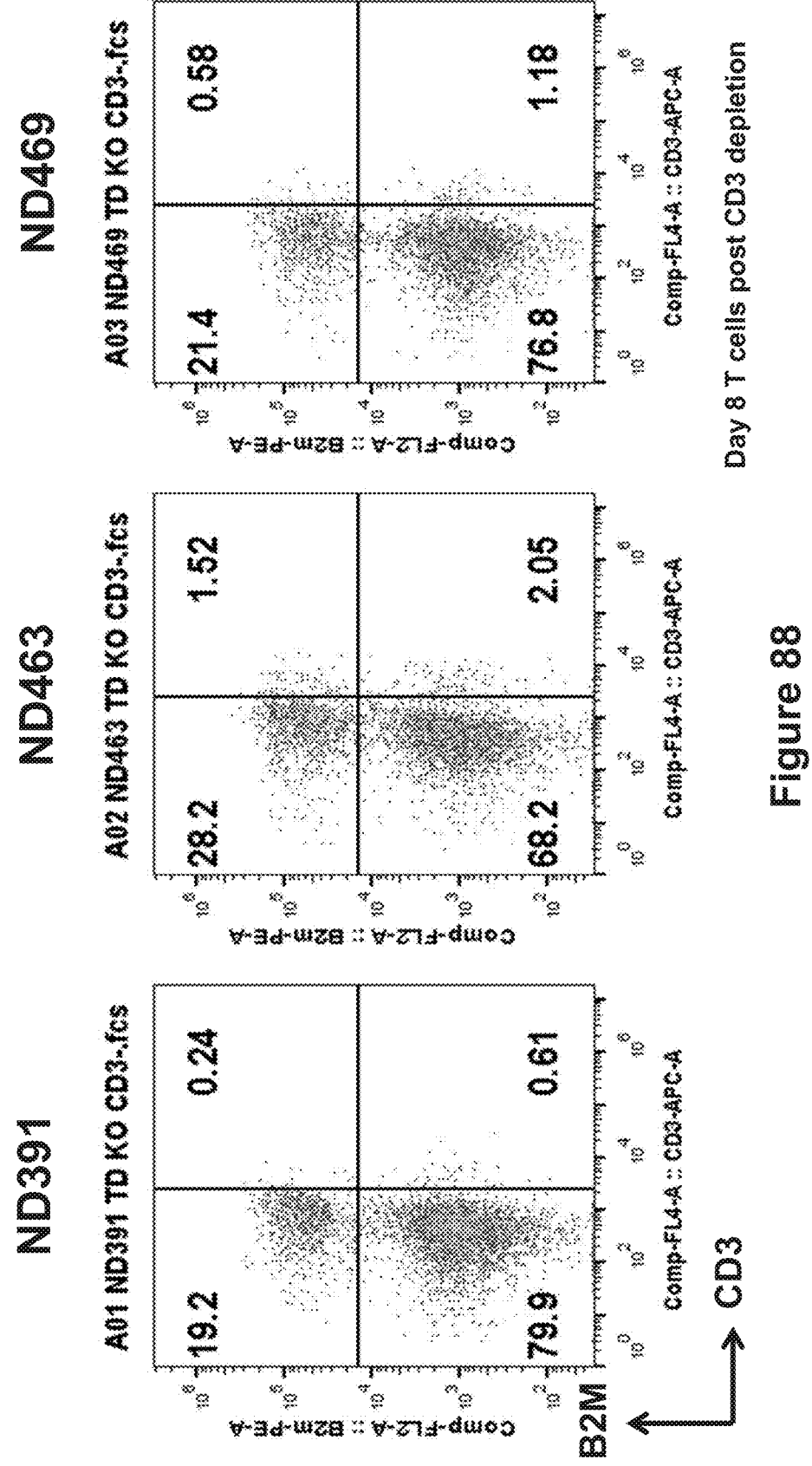
FIG. 88 is a panel of graphs showing CD3/B2M expression after CD3+ T cell depletion.

Eight days after CD3/CD28 bead stimulation and CRISPR RNA electroporation, CD3 positive T cells were removed. FIG. 88 shows CD3/B2M expression in the three donor populations at day 8. On day 11, T cells were subjected to FACS staining to detect CD3, B2M and CAR expression. ND463 non-transduced (NOTD) were used as a negative control. FIG. 89 shows CD3 and B2M expression in CD19 CAR TD (transduced)/CRISPR electroporated, CD3 depleted T cells; CD19 CAR TD/CRISPR electroporated T cells; and CD19 CAR TD T cells. FIG. 90 shows CAR expression in CD19 CAR TD/CRISPR electroporated, CD3 depleted T cells; CD19 CAR TD/CRISPR electroporated T cells; and CD19 CAR TD T cells. FIG. 91 shows CD3/B2M/CAR expression on day 11 in CD19 CAR TD (transduced)/CRISPR electroporated, CD3 depleted T cells; CD19 CAR TD/CRISPR electroporated T cells; and CD19 CAR TD T cells. FIG. 92 summarizes CD3/B2M/CAR expression in the different T cells groups.

On day 11 the different T cell groups, as indicated in FIG. 93, were stimulated by a CD19 positive cell lines, Raji or Nalm6. K562 was used as a CD19 negative control. After 4 hr of coculturing, CD107a up-regulation was detected in each of the T cell groups, except the negative controls.

On day 11, killing ability of the T cells, as indicated in FIG. 94, were tested using a luminescent cytotoxic lymphocyte (CTL) assay after coculturing the T cells with CD19 positive target cells, Nalm6-CBG. Also on day 11, cytokine production of the T cells was analyzed by stimulating the T cell groups with Nalm6 target cells, see FIG. 95.

The T cells were cultured in medium containing 100 U/ml of IL-2 for up to 26 days. The results shown in FIG. 96 indicate no abnormal T cell growth was observed for the CRISPR edited T cells from the three donors.

As one of most attractive applications of the CRISPR/Cas9 system, multiplex genome editing holds great promise for advancing T cell-based adoptive immunotherapy. However, the low targeting efficiency of DNA transfection limits the use of multiplex genome engineering in primary T cells. A "hit-and-run" delivery strategy was developed to introduce CRISPRs to T cells via the co-electroporation of Cas9 mRNA and gRNA. Through a combination of up to three rounds of gRNA electroporation with transient exposure to mild hypothermia, a targeting efficiency of >80% at the protein level was routinely achieved for a single gene disruption. More encouragingly, triple gene disruption of TRAC, TRBC and B2M yielded double negative CD3 and HLA-I at about 65% without any purification and selection. The results also demonstrate that enrichment to >99% purity of gene-disrupted T cells was easily achieved using clinically approved paramagnetic beads and that the purified T cells were expanded up to 500-fold in 10 days. The expanded T cells maintained their gene disruption phenotype and displayed features consistent with central memory T cells. The disrupted T cells did not cause GVHD, suggesting that they may be used as allogeneic CAR T cells. Importantly, the gene-edited T cells showed anti-tumor activities both in vitro and in different tumor mouse models that were as potent or more potent than non-gene edited T cells. Thus, the process described herein to generate synthetic cells could be easily translated into current GMP-compliant manufacturing procedures.

The data described herein demonstrates that CRISPR/Cas9 is a powerful multiplex genome editing tool in primary human T cells. Previous reports have shown that T cells can be genetically edited by ZFNs or TALEN to eliminate the expression of the endogenous TCR $\alpha$ and $\beta$ chains to avoid GVHD. Due to the complexity of the targeting strategies for manipulating multiple genes by zinc finger nucleases (ZFN) and TAL effector nuclease TALEN in T cells, previous studies have not been able to prevent GVHD and host-versus-graft reaction simultaneously in pre-clinical animal models. NK cell activation can also be aborted by the ablation of stimulatory NK ligands by CRISPR/Cas9 or by the expression of nonclassical HLA class I molecules such as HLA-E, which could potentially protect universal T cells from NK-cell-mediated rejection.

In summary clinical scale universal CART cells, with potent anti-tumor activity and reduced alloreactivity can be efficiently generated using multiplex CRISPR technology. This approach can be incorporated into current GMP-compliant manufacturing procedures and has a high potential for translation, given the successful translation of adoptive transfer therapy with ZFNs for HIV/AIDS. It is possible that universal CAR and TCR T cells will provide an alternative to autologous T cells. Indeed, it is conceivable that universal CAR and TCR T cells with disabled checkpoint molecules may be more efficacious and have wider use than current CART therapy using autologous T cells against cancers and infectious diseases.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a condition associated with enhanced immunity in a subject, comprising administering to the subject a therapeutically effective amount of a pharmaceutical composition comprising a CRISPR-modified T cell, wherein the CRISPR-modified T cell comprises:

(a) a CRISPR-mediated insertion or deletion in an endogenous gene locus causing a downregulation of the endogenous gene expression, wherein the endogenous gene is selected from the group consisting of TCR α chain (TRAC), TCR β chain (TRBC), beta-2 microglobulin (B2M), a HLA molecule, CTLA-4, PD1, and FAS;

wherein the CRISPR-mediated insertion or deletion is within:

(i) the TCR α chain gene locus and the TCR β chain gene locus, causing the downregulation of the TCR α chain gene expression and the TCR β chain gene expression, and wherein the CRISPR-mediated insertion or deletion in the TCR α chain gene locus is within a TCR α chain nucleotide sequence comprising SEQ ID NO: 1; and (ii) the beta-2 microglobulin (B2M) gene locus, causing the downregulation of the B2M gene expression; and wherein the CRISPR-mediated insertion or deletion is within a B2M gene nucleotide sequence comprising SEQ ID NO: 3, 44, 77, or 78; and (b) a nucleic acid encoding an exogenous T cell receptor (TCR) having an affinity for a surface antigen on a target cell, wherein the exogenous TCR comprises a TCR alpha chain and TCR beta chain.

2. The method of claim 1, wherein the condition associated with enhanced immunity is an autoimmune disease.

3. The method of claim 2, wherein the autoimmune disease is selected from the group consisting of Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenia purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo, Wegener's granulomatosis, and any combination thereof.

4. The method of claim 1, wherein the condition associated with enhanced immunity is a cancer.

5. The method of claim 4, wherein the cancer is selected from the group consisting of breast cancer, prostate cancer, ovarian cancer, cervical cancer, skin cancer, pancreatic cancer, colorectal cancer, renal cancer, liver cancer, brain cancer, lymphoma, leukemia, lung cancer, and any combination thereof.

6. The method of claim 1, wherein the exogenous TCR is selected from the group consisting of a wild-type TCR, a modified TCR, and a chimeric TCR.

7. The method of claim 6, wherein the modified TCR comprises:

(a) a TCR alpha chain and a TCR beta chain;

(b) a TCR alpha chain and a TCR beta chain and a co-stimulatory signaling domain at a C terminus of at least one of the TCR alpha chain and a TCR beta chain; or (c) at least one murine constant region.

8. The method of claim 7, wherein the co-stimulatory signaling domain is (i) selected from CD27, CD28, 4-1BB, OX40, CD30, CD40, PD-1, ICOS, lymphocyte function-associated antigen-1 (LFA-1), CD2, CD7, LIGHT, NKG2C, or B7-H3 co-stimulatory signaling domain; or (ii) a 4-1BB co-stimulatory signaling domain.

9. The method of claim 6, wherein the TCR beta chain or the TCR alpha chain of the modified TCR comprises at least one N-deglycosylation.

10. The method of claim 6, wherein the modified TCR has higher affinity for the target cell surface antigen when compared with the affinity of a wild-type TCR for the target cell surface antigen.

11. The method of claim 6, wherein the modified TCR is a modified NY-ESO-1 TCR, optionally an 8F TCR.

12. The method of claim 6, wherein the modified TCR comprises at least one disulfide bond.

13. The method of claim 1, wherein the target cell surface antigen is selected from the group consisting of viral antigen, bacterial antigen, parasitic antigen, tumor cell associated antigen (TAA), disease cell associated antigen, and any fragment thereof.

14. The method of claim 1, wherein the target cell surface antigen is a tumor cell associated antigen (TAA), or an NY-ESO-1 tumor associated antigen.

15. The method of claim 1, wherein the CRISPR-modified T cell further comprising an exogenous nucleic acid encoding a costimulatory molecule, wherein the costimulatory molecule is selected from the group consisting of CD3, CD27, CD28, CD83, CD86, CD127, 4-1BB, 4-1BBL, PD1 and PD1L.

16. The method of claim 15, wherein the CD3 comprises at least two different CD3 chains; or the CD3 comprises a CD3 zeta chain and CD3 epsilon chain.

17. The method of claim 1, wherein the CRISPR-modified T cell further comprises a CRISPR-mediated insertion or deletion in:

(a) the PD1 gene locus, causing the downregulation of the PD1 gene expression;

(b) the FAS gene locus, causing the downregulation of the FAS gene expression; or (c) the HLA molecule gene locus, causing the downregulation of the HLA molecule gene expression; or (d) the CTLA-4 gene locus, causing the downregulation of the CTLA-4 gene expression.

18. A method of treating a condition associated with enhanced immunity in a subject, comprising administering to the subject a therapeutically effective amount of a pharmaceutical composition comprising:

(a) a CRISPR-modified T cell, wherein the CRISPR-modified T cell comprises:

(i) a CRISPR-mediated insertion or deletion in an endogenous TCR α chain (TRAC) gene locus and an endogenous TCR β chain (TRBC) gene locus, causing downregulation of the endogenous TCR α chain (TRAC) and TCR β chain (TRBC) genes expression, wherein the CRISPR-mediated insertion or deletion in the TRAC gene locus is are within a TRAC nucleotide sequence comprising SEQ ID NO: 1; and (ii) a CRISPR-mediated insertion or deletion in an endogenous beta-2 microglobulin (B2M) gene locus, causing downregulation of the B2M gene expression; and wherein the CRISPR-mediated insertion or deletion is within a B2M nucleotide sequence comprising SEQ ID NO: 3, 44, 77, or 78; and (b) a nucleic acid encoding a modified T cell receptor (TCR) having an affinity for NY-ESO-1 on a target cell.

19. The method of claim 17, wherein the CRISPR-mediated insertion or deletion is within:

(a) a PD1 gene nucleotide sequence comprising SEQ ID NO: 4, 46, or 64;

(b) a FAS gene nucleotide sequence comprising SEQ ID NO: 5, or 45; or (c) a CTLA-4 gene nucleotide sequence comprising SEQ ID NO: 47.

* * * * *

SEQUENCE LISTING

```
<160> NUMBER OF SEQ ID NOS: 97

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1
tgtgctagac atgaggtcta                                                20

<210> SEQ ID NO 2
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 2
gcagtatctg gagtcattga                                                20

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 3
cgcgagcaca gctaaggcca                                                20
```

```
<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 4
ggcgccctgg ccagtcgtct                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 5
gagggtccag atgcccagca                                              20

<210> SEQ ID NO 6
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 6
tcatgtccta accctgatcc tctt                                         24

<210> SEQ ID NO 7
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 7
ttggactttt cccagctgac aga                                          23

<210> SEQ ID NO 8
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 8
taccaggacc agacagctct taga                                         24

<210> SEQ ID NO 9
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 9
tctcacctaa tctcctccag gcat                                         24

<210> SEQ ID NO 10
<211> LENGTH: 27
<212> TYPE: RNA
<213> ORGANISM: Artificial Sequence
<220> FEATURE:
```

-continued

<223> OTHER INFORMATION: Synthetic Sequence

<400> SEQUENCE: 10
aggaggauuc ggaacccaau cacugac                                         27

<210> SEQ ID NO 11
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_RNA
<222> LOCATION: (1)..(23)

<400> SEQUENCE: 11
cagugauugg guuccgaauc cucct                                           25

<210> SEQ ID NO 12
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 12
accuccuucc cauucaccca ccagcuc                                         27

<210> SEQ ID NO 13
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_RNA
<222> LOCATION: (1)..(23)

<400> SEQUENCE: 13
gcuggugggu gaaugggaag gaggt                                           25

<210> SEQ ID NO 14
<211> LENGTH: 122
<212> TYPE: DNA
<213> ORGANISM: Artificial Sequence
<220> FEATURE:
<223> OTHER INFORMATION: Synthetic Sequence

<400> SEQUENCE: 14
ttaatacgac tcactatagg caccaaagct gcccttaccg ttttagagct agaaatagca     60
agttaaaata aggctagtcc gttatcaact tgaaaaagtg gcaccgagtc ggtgcttttt    120
tt                                                                   122

<210> SEQ ID NO 15
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 15
tgtgctagac atgaggtcta tgg                                             23

<210> SEQ ID NO 16
<211> LENGTH: 23

```
<212> TYPE: DNA
<213> ORGANISM: Artificial Sequence
<220> FEATURE:
<223> OTHER INFORMATION: Synthetic Sequence

<400> SEQUENCE: 16
ccctcaatga ctccagatac tgc                                            23

<210> SEQ ID NO 17
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 17
tgggctggcg gccaggatgg ttcttggtag gtaggtgg                            38

<210> SEQ ID NO 18
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 18
tgggctggcg gccaggatgg ttcttagggg taggtggg                            38

<210> SEQ ID NO 19
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 19
tatatcacag acaaaactgt gctagacatg aggtctatgg acttcaagag caacagtgct    60
gtggcct                                                             67

<210> SEQ ID NO 20
<211> LENGTH: 66
<212> TYPE: DNA
<213> ORGANISM: Artificial Sequence
<220> FEATURE:
<223> OTHER INFORMATION: Synthetic Sequence

<400> SEQUENCE: 20
tatatcacag acaaaactgt gctagacatg agtctatgga cttcaagagc aacagtgctg    60
tggcct                                                              66

<210> SEQ ID NO 21
<211> LENGTH: 65
<212> TYPE: DNA
<213> ORGANISM: Artificial Sequence
<220> FEATURE:
<223> OTHER INFORMATION: Synthetic Sequence

<400> SEQUENCE: 21
tatatcacag acaaaactgt gctagacatg gtctatggac ttcaagagca acagtgctgt    60
ggcct                                                               65

<210> SEQ ID NO 22
<211> LENGTH: 66
<212> TYPE: DNA
```

-continued

```
<213> ORGANISM: Artificial Sequence
<220> FEATURE:
<223> OTHER INFORMATION: Synthetic Sequence

<400> SEQUENCE: 22
tatatcacag acaaaactgt gctagacatg agtctatgga cttcaagagc aacagtgctg    60
tggcct                                                               66

<210> SEQ ID NO 23
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 23
tatatcacag acaaaactgt gctagacatg tctatggact tcaagagcaa cagtgctgtg    60
gcct                                                                 64

<210> SEQ ID NO 24
<211> LENGTH: 66
<212> TYPE: DNA
<213> ORGANISM: Artificial Sequence
<220> FEATURE:
<223> OTHER INFORMATION: Synthetic Sequence

<400> SEQUENCE: 24
tatatcacag acaaaactgt gctagactga ggtctatgga cttcaagagc aacagtgctg    60
tggcct                                                               66

<210> SEQ ID NO 25
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 25
tatatcacag acaaaactgt gctagtgagg tctatggact tcaagagcaa cagtgctgtg    60
gcct                                                                 64

<210> SEQ ID NO 26
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 26
tatatcacag acaaaactgt gcttgaggtc tatggacttc aagagcaaca gtgctgtggc    60
ct                                                                   62

<210> SEQ ID NO 27
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 27
tatatcacag acaaaactgt gctagacatg aggttctatg gacttcaaga gcaacagtgc    60
tgtggcc                                                              67
```

-continued

```
<210> SEQ ID NO 28
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 28
tatatcacag acaaaactgt gctagacatg agggtctatg gacttcaaga gcaacagtgc      60
tgtggcc                                                               67

<210> SEQ ID NO 29
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 29
agcagcccgc cctcaatgac tccagatact gcctgagcag ccgcctgagg gtctcggcca      60
ccttctg                                                               67

<210> SEQ ID NO 30
<211> LENGTH: 66
<212> TYPE: DNA
<213> ORGANISM: Artificial Sequence
<220> FEATURE:
<223> OTHER INFORMATION: Synthetic Sequence

<400> SEQUENCE: 30
agcagcccgc cctcatgact ccagatactg cctgagcagc cgcctgaggg tctcggccac      60
cttctg                                                                66

<210> SEQ ID NO 31
<211> LENGTH: 66
<212> TYPE: DNA
<213> ORGANISM: Artificial Sequence
<220> FEATURE:
<223> OTHER INFORMATION: Synthetic Sequence

<400> SEQUENCE: 31
agcagcccgc ctcaatgact ccagatactg cctgagcagc cgcctgaggg tctcggccac      60
cttctg                                                                66

<210> SEQ ID NO 32
<211> LENGTH: 66
<212> TYPE: DNA
<213> ORGANISM: Artificial Sequence
<220> FEATURE:
<223> OTHER INFORMATION: Synthetic Sequence

<400> SEQUENCE: 32
agcagcccgc cctcaatgac tcagatactg cctgagcagc cgcctgaggg tctcggccac      60
cttctg                                                                66

<210> SEQ ID NO 33
<211> LENGTH: 65
<212> TYPE: DNA
<213> ORGANISM: Artificial Sequence
<220> FEATURE:
<223> OTHER INFORMATION: Synthetic Sequence
```

-continued

<400> SEQUENCE: 33
agcagcccgc cctcaatgac tagatactgc ctgagcagcc gcctgagggt ctcggccacc        60
ttctg                                                                     65

<210> SEQ ID NO 34
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 34
agcagcccgc ccgactccag atactgcctg agcagccgcc tgagggtctc ggccaccttc        60
tg                                                                        62

<210> SEQ ID NO 35
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 35
agcagcccgc cctcaaatga ctccagatac tgcctgagca gccgcctgag ggtctcggcc        60
accttct                                                                   67

<210> SEQ ID NO 36
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 36
agcagcccgc cctcaatgac tcccagatac tgcctgagca gccgcctgag ggtctcggcc        60
accttct                                                                   67

<210> SEQ ID NO 37
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 37
agcagcccgc cctcaatgac tccagatact gcctgagcag ccgcctgagg gtctcggcca        60
ccttctg                                                                   67

<210> SEQ ID NO 38
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 38
agcagcccgc cctcaatgac agatactgcc tgagcagccg cctgagggtc tcggccacct        60
tctg                                                                      64

<210> SEQ ID NO 39
<211> LENGTH: 66

-continued

```
<212> TYPE: DNA
<213> ORGANISM: Artificial Sequence
<220> FEATURE:
<223> OTHER INFORMATION: Synthetic Sequence

<400> SEQUENCE: 39
agcagcccgc cctcaatgac tcagatactg cctgagcagc cgcctgaggg tctcggccac      60
cttctg                                                                  66

<210> SEQ ID NO 40
<211> LENGTH: 55
<212> TYPE: DNA
<213> ORGANISM: Artificial Sequence
<220> FEATURE:
<223> OTHER INFORMATION: Synthetic Sequence

<400> SEQUENCE: 40
agcagcccgc cctcaactgc ctgagcagcc gcctgagggt ctcggccacc ttctg           55

<210> SEQ ID NO 41
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 41
agcagcccgc ctcatgactc agatactgct gagcagccgc ctgagggtct cggccacctt      60
ct                                                                      62

<210> SEQ ID NO 42
<211> LENGTH: 46
<212> TYPE: DNA
<213> ORGANISM: Artificial Sequence
<220> FEATURE:
<223> OTHER INFORMATION: Synthetic Sequence

<400> SEQUENCE: 42
agcagccact gcgtgagcag ccgcgtgagg gtctcggcca ccttct                     46

<210> SEQ ID NO 43
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 43
agcagcccgc cctcaatgac tccgagatac tgcctgagca gccgcctgag ggtctcggcc      60
accttct                                                                 67

<210> SEQ ID NO 44
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 44
ccgtggcctt agctgtgctc gcg                                               23

<210> SEQ ID NO 45
<211> LENGTH: 23
<212> TYPE: DNA
```

-continued

```
<213> ORGANISM: Artificial Sequence
<220> FEATURE:
<223> OTHER INFORMATION: Synthetic Sequence

<400> SEQUENCE: 45
ccatgctggg catctggacc ctc                                              23

<210> SEQ ID NO 46
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 46
gggcggtgct acaactgggc tgg                                              23

<210> SEQ ID NO 47
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 47
cataaagcca tggcttgcct tgg                                              23

<210> SEQ ID NO 48
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 48
aacaccgctc ccataaagcc atggcttgcc ttggatttca gcggcacaag gctcagctga       60
acct                                                                   64

<210> SEQ ID NO 49
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 49
aacaccgctc ccataatggc ttgccttgga tttcagcggc acaaggctca gctgaacct        59

<210> SEQ ID NO 50
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 50
aacaccgctc ccataaccat ggcttgcctt ggatttcagc ggcacaaggc tcagctgaac       60
ct                                                                     62

<210> SEQ ID NO 51
<211> LENGTH: 62
<212> TYPE: DNA
<213> ORGANISM: Artificial Sequence
<220> FEATURE:
<223> OTHER INFORMATION: Synthetic Sequence
```

<400> SEQUENCE: 51
aacaccgctc ccataaccat ggcttgcctt ggatttcagc ggcacaaggc tcagctgaac        60
ct                                                                        62

<210> SEQ ID NO 52
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 52
aacaccgctc ccataaagtc catggcttgc cttggatttc agcggcacaa ggctcagctg        60
aacc                                                                      64

<210> SEQ ID NO 53
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 53
aacaccgctc ccataaacca tggcttgcct tggatttcag cggcacaagg ctcagctgaa        60
cct                                                                       63

<210> SEQ ID NO 54
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 54
aacaccgctc ccataaaggg atttcagcgg cacaaggctc agctgaacct                    50

<210> SEQ ID NO 55
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 55
aacaccgctc ccataatggc ttgccttgga tttcagcggc acaaggctca gctgaacct         59

<210> SEQ ID NO 56
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 56
aacaccgctc ccataatggc ttgccttgga tttcagcggc acaaggctca gctgaacct         59

<210> SEQ ID NO 57
<211> LENGTH: 63
<212> TYPE: DNA
<213> ORGANISM: Artificial Sequence
<220> FEATURE:
<223> OTHER INFORMATION: Synthetic Sequence -continued

```
<400> SEQUENCE: 57
aacaccgctc ccataaacca tggcttgcct tggatttcag cggcacaagg ctcagctgaa      60
cct                                                                    63

<210> SEQ ID NO 58
<211> LENGTH: 61
<212> TYPE: DNA
<213> ORGANISM: Artificial Sequence
<220> FEATURE:
<223> OTHER INFORMATION: Synthetic Sequence

<400> SEQUENCE: 58
aacaccgctc ccataccatg gcttgccttg gatttcagcg gcacaaggct cagctgaacc      60
t                                                                      61

<210> SEQ ID NO 59
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 59
aacaccgctc ccataatggc ttgccttgga tttcagcggc acaaggctca gctgaacct       59

<210> SEQ ID NO 60
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 60
aacaccgctc ccataaagcc atggcttgcc ttggatttca gcggcacaag gctcagctga      60
acct                                                                   64

<210> SEQ ID NO 61
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 61
ggacatcaag cctgctaaca tgg                                              23

<210> SEQ ID NO 62
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 62
catcaagcct gctaacatgg agg                                              23

<210> SEQ ID NO 63
<211> LENGTH: 122
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
```

-continued

```
<222> LOCATION: (19)..(39)
<223> OTHER INFORMATION: n is a, c, g, or t

<400> SEQUENCE: 63
taatacgact cactatagnn nnnnnnnnnn nnnnnnnnng ttttagagct agaaatagca      60
agttaaaata aggctagtcc gttatcaact tgaaaaagtg gcaccgagtc ggtgcttttt     120
tt                                                                    122

<210> SEQ ID NO 64
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 64
ggccaggatg gttcttaggt                                                  20

<210> SEQ ID NO 65
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 65
tgggctggcg gccaggatgg ttcttaggta ggtggggt                              38

<210> SEQ ID NO 66
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 66
tgggctggcg gccaggatgg taggtaggtg gggt                                  34

<210> SEQ ID NO 67
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 67
tgggctggcg gccaggatgg ttttaggtag gtggggt                               37

<210> SEQ ID NO 68
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 68
tgggctggcg gccaggatgg taggtaggtg gggt                                  34

<210> SEQ ID NO 69
<211> LENGTH: 114
<212> TYPE: DNA
<213> ORGANISM: Artificial Sequence
<220> FEATURE:
<223> OTHER INFORMATION: Synthetic Sequence
```

-continued

```
<400> SEQUENCE: 69
ctgtgctaga catgaggtct atggacttca agagcaacag tgctgtggcc tggagcaaca      60
aatctgactt tgcatgtgca aacgccttca acaacagcat tattccagaa gaca          114

<210> SEQ ID NO 70
<211> LENGTH: 98
<212> TYPE: DNA
<213> ORGANISM: Artificial Sequence
<220> FEATURE:
<223> OTHER INFORMATION: Synthetic Sequence

<400> SEQUENCE: 70
gatgtgtata tcacagacaa aactgtgcta gacatgaggt ctatggactt caagagcaac      60
agtgctgtgg cctggagcaa caaatctgac tttgcatg                             98

<210> SEQ ID NO 71
<211> LENGTH: 108
<212> TYPE: DNA
<213> ORGANISM: Artificial Sequence
<220> FEATURE:
<223> OTHER INFORMATION: Synthetic Sequence

<400> SEQUENCE: 71
acccctcttc cctttccaga ggacctgaac aaggtgttcc cacccgaggt cgctgtgttt      60
gagccatcag aagcagagat ctcccacacc caaaaggcca cactggtg                 108

<210> SEQ ID NO 72
<211> LENGTH: 111
<212> TYPE: DNA
<213> ORGANISM: Artificial Sequence
<220> FEATURE:
<223> OTHER INFORMATION: Synthetic Sequence

<400> SEQUENCE: 72
gacccgcagc ccctcaagga gcagcccgcc ctcaatgact ccagatactg cctgagcagc      60
cgcctgaggg tctcggccac cttctggcag aaccccgca accacttccg c              111

<210> SEQ ID NO 73
<211> LENGTH: 75
<212> TYPE: DNA
<213> ORGANISM: Artificial Sequence
<220> FEATURE:
<223> OTHER INFORMATION: Synthetic Sequence

<400> SEQUENCE: 73
gattctgatg tgtatatcac agacaaaact gtgctagaca tgaggtctat ggacttcaag      60
agcaacagtg ctgtg                                                      75

<210> SEQ ID NO 74
<211> LENGTH: 74
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (47)..(49)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
```

-continued

```
<222> LOCATION: (57)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 74
gattctgatg tgtatatcac agacaaaact gtgctagaca tgaggtnnnt gganttnnan      60
aacnacngtg gtgg                                                        74

<210> SEQ ID NO 75
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 75
ccctcaagga gcagcccgcc ctcaatgact ccagatactg cctgagcagc cgcctgaggg      60
tctc                                                                  64

<210> SEQ ID NO 76
<211> LENGTH: 64
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 76
ccctcaagga gcagcccgcc ctcaatgact ccnnanactg nctgancanc cncctgangg      60
tctc                                                                  64

<210> SEQ ID NO 77
```

<211> LENGTH: 82
<212> TYPE: DNA
<213> ORGANISM: Artificial Sequence
<220> FEATURE:
<223> OTHER INFORMATION: Synthetic Sequence

<400> SEQUENCE: 77
gagctgacag cattcgggcc gagatgtctc gctccgtggc cttagctgtg ctcgcgctac        60
tctctctttt ctggcctgga gg                                                 82

<210> SEQ ID NO 78
<211> LENGTH: 120
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t

<400> SEQUENCE: 78
attcgggccg agatgtctcg ctccgtggcc ttagntgtgc tcncnctnct ctctctttcn        60
ggcctggagg ctatccagcg tgagtctctc ctaccctccc gctctggncc ttcctctccc       120

<210> SEQ ID NO 79
<211> LENGTH: 105
<212> TYPE: DNA
<213> ORGANISM: Artificial Sequence
<220> FEATURE:
<223> OTHER INFORMATION: Synthetic Sequence

<400> SEQUENCE: 79
gctcaacaac catgctgggc atctggaccc tcctacctct ggtgagccct ctcctgcccg        60
ggtggaggct taccccgtct tagtcccggg gataggcaaa gtggg                       105

<210> SEQ ID NO 80
<211> LENGTH: 94
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(41)
<223> OTHER INFORMATION: n is a, c, g, or t

```
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(52)
<223> OTHER INFORMATION: n is a, c, g, or t
<220> FEATURE:
<221> NAME/KEY: misc_feature
<222> LOCATION: (54)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 80
ttcacttcgg aggattgctc aacaaccatg ctnggnnnnn ngnnccnncn nncnnnnggn      60
ganccctctc cggcccggng gaaggcttac cccn                                 94

<210> SEQ ID NO 81
<211> LENGTH: 85
<212> TYPE: DNA
<213> ORGANISM: Artificial Sequence
<220> FEATURE:
<223> OTHER INFORMATION: Synthetic Sequence

<400> SEQUENCE: 81
gccagtcgtc tgggcggtgc tacaactggg ctggcggcca ggatggttct taggtaggtg      60
gggtcggcgg tcaggtgtcc cagag                                          85

<210> SEQ ID NO 82
<211> LENGTH: 91
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t

<400> SEQUENCE: 82
```

-continued

```
cctggccagt cgtctgggcg gtgctacaac tgggnnggcg gccaggatgg ttnttaggta        60
ggnggggtcg gcggtcaggt gtcccanagc c                                       91

<210> SEQ ID NO 83
<211> LENGTH: 90
<212> TYPE: DNA
<213> ORGANISM: Artificial Sequence
<220> FEATURE:
<223> OTHER INFORMATION: Synthetic Sequence

<400> SEQUENCE: 83
ggttttgctc tacttcctga agacctgaac accgctccca taaagccatg gcttgccttg        60
gatttcagcg gcacaaggct cagctgaacc                                         90

<210> SEQ ID NO 84
<211> LENGTH: 114
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t

<400> SEQUENCE: 84
cttcctgaag acctgaacac cgctcccata angntgngtc gtgtagtatt tcggcnccac        60
gntgatctga tcatgctgac tacgacgtgc tgctcctgtc ttctgctgtt tctt            114

<210> SEQ ID NO 85
<211> LENGTH: 80
<212> TYPE: DNA
<213> ORGANISM: Artificial Sequence
<220> FEATURE:
<223> OTHER INFORMATION: Synthetic Sequence

<400> SEQUENCE: 85
cgagttccac ccgcaccagt gcaacgtgtt cgtctacagc agtagcaaag ggaccatccg        60
cctgtgtgac atgcgctcct                                                    80

<210> SEQ ID NO 86
<211> LENGTH: 93
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (43)..(45)
<223> OTHER INFORMATION: n is a, c, g, or t
<220> FEATURE:
<221> NAME/KEY: misc_feature
```

-continued

```
<222> LOCATION: (62)..(62)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t

<400> SEQUENCE: 86
taaccatgca ctcccagaca tcgtggacat caagcctgct aannnggagg aactaaccaa      60
antcatccct gcnnccaatt tccacccccca cca                                  93

<210> SEQ ID NO 87
<211> LENGTH: 93
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (66)..(68)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t

<400> SEQUENCE: 87
tgcactccca gacatcgtgg acatcaagcc tgctaacatg ganganctga ncgaantcnt      60
cnctgnnncc nanttccacc cgcaccagtg caa                                   93

<210> SEQ ID NO 88
<211> LENGTH: 92
<212> TYPE: DNA
<213> ORGANISM: Artificial Sequence
<220> FEATURE:
<223> OTHER INFORMATION: Synthetic Sequence

<400> SEQUENCE: 88
gattctgatg tgtatatcac agacaaaact gtgctagaca tgaggtctat ggacttcaag      60
agcaacagtg ctgtggcctg gagcaacaaa tc                                    92

<210> SEQ ID NO 89
```

```
<211> LENGTH: 92
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (47)..(49)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 89
gattctgatg tgtatatcac agacaaaact gtgctagaca tgaggtnnnt gganttnnan        60
aacnacngtg gtggggcctg gaacaacaaa tc                                      92

<210> SEQ ID NO 90
<211> LENGTH: 79
<212> TYPE: DNA
<213> ORGANISM: Artificial Sequence
<220> FEATURE:
<223> OTHER INFORMATION: Synthetic Sequence

<400> SEQUENCE: 90
ccctcaagga gcagcccgcc ctcaatgact ccagatactg cctgagcagc cgcctgaggg        60
tctcggccac cttctggca                                                     79

<210> SEQ ID NO 91
<211> LENGTH: 79
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
```

-continued

```
<222> LOCATION: (52)..(52)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t

<400> SEQUENCE: 91
ccctcaagga gcagcccgcc ctcaatgact ccnnanactg nctgancanc cncctgangg      60
tctcggccnc cttntggca                                                  79

<210> SEQ ID NO 92
<211> LENGTH: 129
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t

<400> SEQUENCE: 92
aagctctttc acttcggagg attgctcaac aaccatgctn ggnatnngga ccctcctacc      60
tctggnganc cctctcctgg ccgggtggan gcttaccccg ncttantccc ggggatangn     120
```

-continued aaantgggg                                                               129

<210> SEQ ID NO 93
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 93
acaaaactgt gctagacatg aggtctatgg acttcaagag caac                         44

<210> SEQ ID NO 94
<211> LENGTH: 43
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 94
acaaaactgt gctagacatg aggtnnntgg anttnnanaa cna                          43

<210> SEQ ID NO 95
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 95
agcagcccgc cctcaatgac tccagatact gcctgagcag ccgc                         44

<210> SEQ ID NO 96
<211> LENGTH: 45
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature -continued

```
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 96
gagcagcccg ccctcaatga ctccnnanac tgnctgnncn nccnc                    45

<210> SEQ ID NO 97
<211> LENGTH: 86
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (66)..(66)
<223> OTHER INFORMATION: n is a, c, g, or t

<400> SEQUENCE: 97
caactgggct ggcggccagg atggttctta ggtaggtggg gtcggcggtc aggtgtccca    60
gagccngggg tctggaggga ccttcc                                        86
```